US009049849B2

(12) United States Patent
Dohrmann et al.

(10) Patent No.: US 9,049,849 B2

(45) Date of Patent: Jun. 9, 2015

(54) SCREENING METHODS FOR COMPOUNDS USEFUL FOR TREATING PANCREATIC DYSFUNCTION

(75) Inventors: Cord Dohrmann, Goettingen (DE); Matthias Austen, Goettingen (DE)

(73) Assignee: EVOTEC INTERNATIONAL GMBH, Hamburg (DE)

( * ) Notice: Subject to any disclaimer, the term of this patent is extended or adjusted under 35 U.S.C. 154(b) by 0 days.

(21) Appl. No.: 13/031,095

(22) Filed: Feb. 18, 2011

(65) Prior Publication Data

US 2011/0277045 A1 Nov. 10, 2011

Related U.S. Application Data

(63) Continuation of application No. 10/998,197, filed on Jan. 29, 2004, now abandoned, which is a continuation-in-part of application No. PCT/EP03/05700, filed on May 30, 2003.

(30) Foreign Application Priority Data

Sep. 17, 2001 (EP) .................................... 02020829
May 29, 2002 (EP) .................................... 02011963

(51) Int. Cl.

| | |
|---|---|
| ***C40B 30/04*** | (2006.01) |
| ***C40B 30/06*** | (2006.01) |
| ***A61K 38/17*** | (2006.01) |
| ***A61K 35/39*** | (2006.01) |
| ***A01K 67/027*** | (2006.01) |
| ***C07K 14/47*** | (2006.01) |

(52) U.S. Cl.

CPC ......... *A01K 67/0276* (2013.01); *A01K 2217/05* (2013.01); *A01K 2217/075* (2013.01); *A01K 2227/105* (2013.01); *A01K 2227/40* (2013.01); *A01K 2267/03* (2013.01); *C07K 14/47* (2013.01); *G01N 2800/042* (2013.01)

(58) Field of Classification Search

None

See application file for complete search history.

(56) References Cited

U.S. PATENT DOCUMENTS

| | | | | |
|---|---|---|---|---|
| 5,739,307 | A * | 4/1998 | Johnson et al. | 536/23.51 |
| 6,090,778 | A | 7/2000 | Johnson, Jr. et al. | |
| 6,274,554 | B1 | 8/2001 | Magal et al. | |
| 6,743,628 | B1 | 6/2004 | Johnson, Jr. et al. | |
| 8,399,408 | B2 | 3/2013 | Austen et al. | |
| 2002/0122829 | A1 | 9/2002 | Kishino et al. | |
| 2003/0166537 | A1 | 9/2003 | Hanke et al. | |
| 2004/0142418 | A1 * | 7/2004 | Sah et al. | 435/69.1 |
| 2005/0054102 | A1 | 3/2005 | Wobus et al. | |
| 2008/0241106 | A1 | 10/2008 | Austen et al. | |
| 2009/0258829 | A1 | 10/2009 | Harder et al. | |
| 2011/0003741 | A1 | 1/2011 | Austen et al. | |
| 2011/0256113 | A1 | 10/2011 | Austen et al. | |

FOREIGN PATENT DOCUMENTS

| | | | |
|---|---|---|---|
| EP | 1 010 432 | A | 6/2000 |
| WO | WO 97/08196 | A1 | 8/1996 |
| WO | WO 97/08196 | A | 3/1997 |
| WO | WO 99/06064 | A | 2/1999 |
| WO | WO 00/17360 | A1 | 3/2000 |
| WO | WO 00/18922 | A2 | 4/2000 |
| WO | WO 00/68386 | | 11/2000 |
| WO | WO 01/57272 | A2 | 8/2001 |
| WO | WO 01/75067 | A2 | 10/2001 |
| WO | WO 02/086107 | | 10/2002 |
| WO | WO 2004/093804 | A1 | 11/2004 |
| WO | WO 2005/501415 | A1 | 6/2005 |
| WO | WO 2008/000447 | A1 | 1/2008 |
| WO | WO 2009/059755 | A2 | 5/2009 |

OTHER PUBLICATIONS

Kim et al., Cold Spring Harbor Symposia on Quantitative Biology, 62:377-383, 1997.*

Stoffers et al., Nature Genetics, 17(2):138-139 Oct. 1997.*

Marabotti and Facchiano, Trends in Biochemical Sciences 34(3):98-99, 2009.*

Marabotti and Facchiano Bioinformatics, 26(19):2498, Aug. 2010.*

Airaksinen et al., "The GDNF Family: Signalling, Biological Functions and Therapeutic Value," Nature Reviews, vol. 3, pp. 383-394 (2002).

Atkinson et al., "The NOD mouse model of type 1 diabetes: As good as it gets?," Nature Medicine, vol. 5(6), pp. 601-604 (1999).

Banks, William A., "Characteristics of compounds that cross the blood-brain barrier," BMC Neurology, vol. 9 (Suppl 1): S3, pp. 1-5 (2009).

Benjamin et al., "A plasticity window for blood vessel remodelling is defined by pericyte coverage of the preformed endothelial network and is regulated by PDGF-B and VEGF," Development, vol. 125(9), pp. 1591-1598 (1998).

Bernard-Kargar et al., "Endocrine Pancreas Plasticity under Physiological and Pathological Conditions," Diabetes, vol. 50, Supplement 1, pp. S30-S35 (2001).

Boado, R. J. et al., "Blood-Brain Barrier and New Approaches to Brain Drug Delivery," Conferences and Reviews, The Western Journal of Medicine, vol. 156(3), pp. 281-286 (1992).

Bonner-Weir et al., "The pancreatic ductal epithelium serves as a potential pool of progenitor cells," Pediatric Diabetes, vol. 5, pp. 16-22 (2004).

(Continued)

*Primary Examiner* — Daniel E Kolker

*Assistant Examiner* — Stacey N MacFarlane

(74) *Attorney, Agent, or Firm* — Ropes & Gray LLP

(57) ABSTRACT

The present invention discloses polynucleotides which identify and encode DP119, DP444, DP810, DP685, WE474, DP160, RA977, or RA770 as well as novel functions for these proteins of the inventions. The invention provides for compositions for disorders associated with the expression of the proteins of the invention, such as for the treatment, alleviation and/or prevention of pancreatic dysfunction (for example diabetes, hyperglycemia, and impaired glucose tolerance), and related disorders, and other disease and disorders.

17 Claims, 60 Drawing Sheets

(56) References Cited

OTHER PUBLICATIONS

Bork et al., "Go hunting in sequence databases but watch out for the traps," Trends Genet. vol. 12(10), pp. 425-427 (1996).
Bork, P., "Powers and pitfalls in sequence analysis: the 70% hurdle," Genome Res., vol. 10(4), pp. 398-400 (2000).
Bouwens et al., "Regulation of Pancreatic Beta-Cell Mass," Physiol. Rev., vol. 85, pp. 1255-1270 (2005).
Brun et al., "The Dianetes-linked Transcription factor Pax4 is Expressed in Human Pancreatic Islets and is Activated by Mitogens and GLP-1," Human Molecular Genetics, vol. 17(4), pp. 478-469 (2008).
Carlsten et al., "GDNF and Neurturin Treatment Reverse Deficits in Diabetic Neuropathy," 2001 Neuroscience Meeting Planner, San Diego, CA, Program No. 138.17: Society for Neuroscience, 2001 [Online]. Retrieved on Apr. 21, 2010.
Carlsten, J.A., et al., "GDNF and neurturin treatment reverse deficits in diabetic neuropathy," Society for Neuroscience Abstracts (2001), vol. 27(1), pp. 361; 31st Annual Meeting of the Society for Neuroscience, San Diego, California, USA, Nov. 10-15, 2001, XP008022799, abstract.
Chen et al., "Reversine Increases the Plasticity of Lineage-committed Mammalian Cells," PNAS, vol. 104(25), pp, 10482-10487 (2007).
Chen et al., "Exploring Stern Cell Biology With Small Molecules," Mol. BioSyst., vol. 2, pp. 18-24 (2006).
Christianson et al., "Restorative Effects of Neurotrophin Treatment on Diabetic-Induced Cutaneous Axon Loss in Mice," Experimental Neurology, vol. 179(2), pp. 188-199 (2003).
D'Amour et al., "Production of Pancreatic Hormone-Expressing Endocrine Cells from Human Embryonic Stem Cells," Nature Biotechnology, vol. 24(11), pp. 1392-1401 (2006).
Doerks et al., "Protein annotation: detective work for function prediction," Trends Genet. vol. 14(6), pp. 248-250 (1998).
Dohrman et al., "Identification of novel differentiation factors for stem-cell based diabetes therapy," 2385-PO, Diabetes, New York, NY, US, vol. 52, No. Suppl 1, XP009042336, p. A550 (2003) abstract.
Dor et al., "Adult pancreatic β-cells are formed by self-duplication rather than stem-cell differentiation," Nature, vol. 429, pp. 41-46 (2004).
Dor et al., "Facultative Endocrine Progenitor Cells in the Adult Pancreas," Cell, pp. 183-184 (2008).
Edlund, "Pancreatic Organogenesis—Developmental Mechanisms and Implications for Therapy," Nature Reviews, vol. 3. pp. 574-532 (2002).
Guo at al., "Stem Cells to Pancreatic β-Cells: New Sources for Diabetes Cell Therapy," Endocrine Reviews, vol. 30(3), pp. 214-227 (2009).
Hitchcock, S.A. et al., "Structure—Brain Exposure Relationships," Journal of Medicinal Chemistry, vol. 49(26), pp. 7559-7583 (2006).
Ito et al., "Expression of glial cell line-derived neurotrophic factor family members and their receptors in pancreatic cancers," Surgery, vol. 138(4), pp. 788-794 (2005).
Jing et al., "GFRa-3 Are Two New Receptors for Ligands of the GDNF Family," Journal of Biological Chemistry, vol. 272(52), pp. 33111-33117 (1997).
Jomary et al., "Epitope-tagged recombinant AAV vectors for expressing neurturin and its receptor in retinal cells," Molecular Vision, SN, Atlanta, US, vol. 7, pp. 36-41 XP0023250051SSN: 1090-0535 (2001).
Karaca et al., "Exploring Functional β-Cell Heterogeneity In Vivo Using PSA NCAM as a Specific Marker," PLoS One, vol. 4(5) pp. e5555 (2009).
Kotzbauer et al., "Neurturin, a relative of glial-cell-derived neurotrophic factor," Nature, vol. 384, pp. 467-470, XP002092404ISSN: 0028-0836 (1996).
Kroon et al., "Pancreatic Endoderm Derived From Human Embrytonic Stem Cells Generates Glucose-Responsive Insulin-Secreting Cells in vivo," Nature Biotechnology, vol. 26(4), pp, 443-452 (2008).
Liew et al., "PAX4 Enhances Beta-Cell Differentiation of Human Embryonic Stem Cells", PloS One, vol. 3, issue 3, pp. 1-11 (2008).
Lin et al.. "Enhancement of Insulin-producing Cell Differentiation from Embryonic Stem Cells Using Pax-4-nucleofection Method," World Journal of Gastroenterology, vol. 13(11), pp. 1672-1679 (2007).
Lu et al., "Pax4 Paired Domain Mediates Direct Protein Transduction into Mammalian Cells," Endocrinology, vol. 148(11) pp. 5558-5565 (2007).
Mannucci et al.,"Fasting plasma glucose and glycated haemoglobin in the screening of diabetes and impaired glucose tolerance," Acta Diabetol, vol. 40(4), pp. 181-186 (2003).
Masure et al., "Enovin a Member of the Glial Cell-Line-Derived Neurotrophic Factor (GDNF) Family with Growth Promoting Activity on Neuronal Cells," European Journal of Biochemistry, vol. 266(3), pp. 892-902, XP0008829816ISSN: 0014-2956 (1999).
Moore, A., "Advances in beta-cell imaging," European Journal of Radiology, vol. 70(2) pp. 254-257 (2009).
Murray et al., "Differentiation of Embryonic Stem Cells to Clinically Relevant Populations: Lessons from Embryonic Development," Cell, vol. 132, pp. 661-680 (2008).
Mussman et al., "Inhibition of GSK3 Promotes Replication and Survival of Pancreatic Beta Cells," The Journal of Biological Chemistry, vol. 282(16), pp. 12030-12037 (2007).
Noguchi et al., "PDX-1 Protein Containing Its Own Antennapedia-Like Protein Transduction Domain Can Transduce Pancreatic Duct and Islet Cells," Diabetes, vol. 52, pp. 1732-1737 (2003).
Oiwa et al., "Dopaminergic Neuroprotection and Regeneration by Neurturin Assessed by Using Behavioral, Biochemical and Histochemical Measurements in a Model of Progressive Parkinson's Disease," Brain Research, vol. 947, pp. 271-283, XP008056645 (2002).
Oliver-Krasinski et al., "On the origin of the β-cell," Genes & Development, vol. 22, pp. 1998-2021 (2008).
Parkash et al., "The Structure of the Glial Cell Line-derived Neurotrophic Factor-Coreceptor Complex," The Journal of Biological Chemistry, vol. 283(50), pp. 35164-35172 (2008).
Prince et al. "Recent advances in pancreas development: from embryonic pathways to programming renewable sources of beta cells," F1000 Biol Rep. vol. 2(17) pp. 1-4. doi:10.3410/B2-17 (2010).
Risbud and Bhonde, "Models of pancreatic regeneration in diabetes," Diabetes Res Clin Pract., vol. 58, pp. 155-165 (2002).
Rosenblad et al., "Protection and Regulation of Nigral Dopaminergic Neurons by Neurturin or GDNF in a Partial Lesion Model of Parkinson's Disease After Administration into the Striatum or the Laternal Ventricle," European Journal of Neuroscience, vol. 11(5), pp. 1554-1566, XP008055970ISSN: 0953-816X (1999).
Rossi et al., "Parasympathetic Innervation and Function of Endocrine Pancreas Requires the Glial Cell Line-Derived Factor Family Receptor α2 (GFR α2)," Diabetes, vol. 54(5), pp. 1324-1330 (2005).
Sariola et al., "Novel functions and signalling pathways for GDNF," Journal of Cell Science, vol. 116, pp. 3855-3862 (2003).
Shi et al., "A Combined Chemical and Genetic Approach for the Generation of Induced Pluripotent Stem Cells," Cell Stem Cell, vol. 2, pp. 525-528 (2008).
Sigmund C.D., "Viewpoint: Are studies in genetically altered mice out of control?", Arterioscler Thromb Vasc Biol., vol. 20, pp. 1425-1429 (2000).
Skolnick, J. et al., "From genes to protein structure and function: novel applications of computational approaches in the genomicera," Trends Biotechnol., vol. 18(1), pp. 34-39 (2000).
Slack et al., "Developmental biology of the pancreas," Development, vol. 121, pp. 1569-1580 (1995).
Sosa-Pineda et al., "The Pax4 gene is essential for differentiation of insulin-producing b cells in the mammalian pancreas," Nature, vol. 386, pp. 399-402 (1997).
Spence et al. "Translational Embryology: Using Embryonic Principles to Generate Pancreatic Endocrine Cells From Embryonic Stem Cells," Developmental Dynamics, vol. 236, pp. 3218-3227 (2007).
Takahasi et al., "Induction of Pluripotent Stem Cells from Mouse Embryonic and Adult Fibroblast Cultures by Defined Factors," Cell, vol. 126, pp. 663-676 (2006).

(56) References Cited

OTHER PUBLICATIONS

Tourrel et al., "Glucagon-Like Peptide-1 and Exendin-4 Stimulate β-Cell Neogenesis in Streptolotocin-treated newborn rats resulting in persistently improved glucose homeostasis at adult age," Diabetes, vol. 50, pp. 1562-1570 (2001).

Tsaniras et al., "Generating Pancreatic β-cells From Embryonic Stem Cells by Manipulating Signaling Pathways," Apr. 2010.

Vukicevic et al., "Induction of nephrogenic mesenchyme by osteogenic protein 1 (bone morphogenetic protein 7)," Proc Natl Acad Sci USA. vol. 93(17), pp. 9021-9026 (1996).

Winter, W.E. and Schatz, D., "Prevention strategies for type 1 diabetes mellitus," Biodrugs, vol. 17(1), pp. 39-64 (2003).

Xu et al., "β Cells Can Be Generated from Endogenous Progenitors in Injured Adult Mouse Pancreas," Cell, vol. 132, pp. 197-207 (2008).

Zhang et al., "The rat model of type 2 diabetic mellitus and its glycometabolism characters," Exp Anim, vol. 52(5), pp. 401-407 (2003).

Zhou et al., "Generation of Induced Pluripotent Stem Cells Using Recombinant Proteins, "Cell Stem Cell, vol. 4, pp. 381-384 (2009).

Tansey et al., "GFRα-Mediated Localization of RET to Lipid Rafts Is Required for Effective Downstream Signaling, Differentiation, and Neuronal Survival," Neuron, vol. 25: 611-623 (2000).

Worby et al., "Glial Cell Line-derived Neurotrophic Factor Signals through the RET Receptor and Activates Mitogen-activated Protein Kinase*," The Journal of Biological Chemistry, vol. 271(39): 23619-23622 (1996).

* cited by examiner

Fig. 1A-C. EXPRESSION OF DP119 IN THE DEVELOPING CHICKEN
DP119
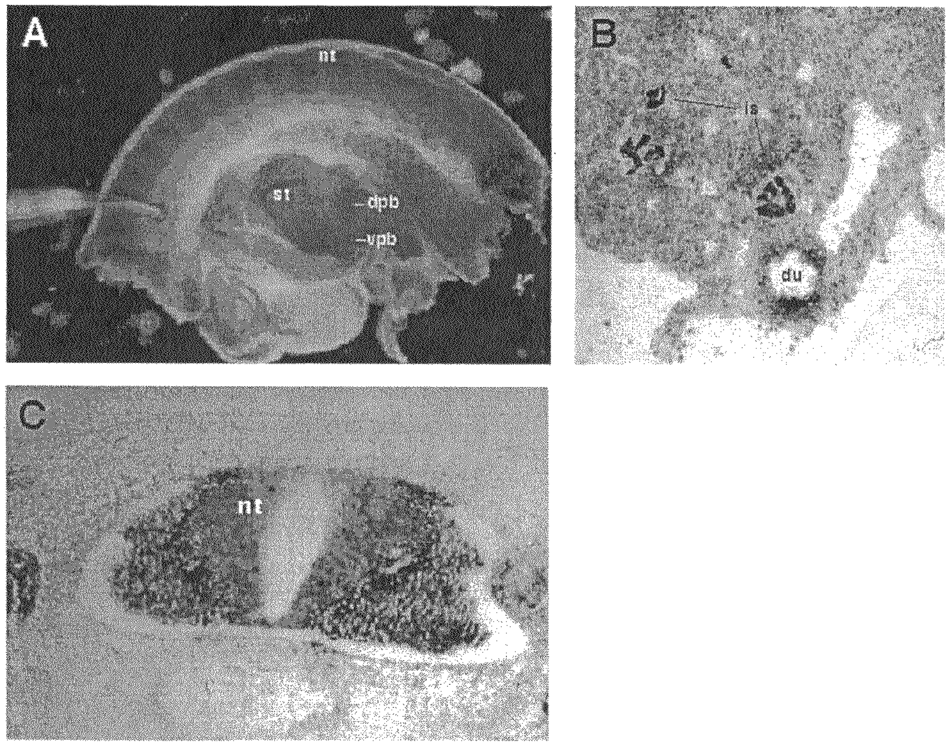

Fig. 1D. Expression of a human DP110 homolog.
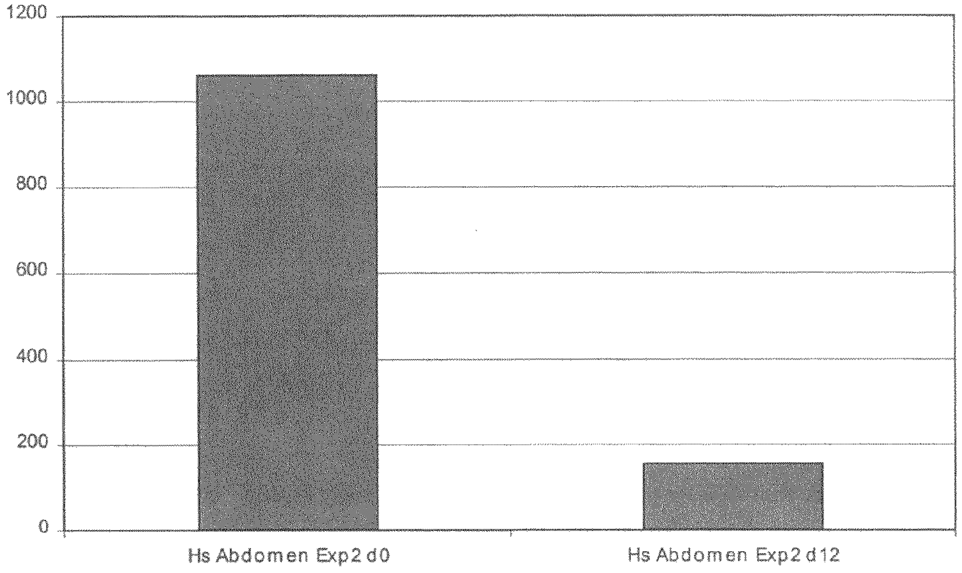

FIG. 2A: Nucleic acid sequence (SEQ ID NO:1) containing the 3′end of a chicken gene homologous to human DKFZp586L151. Underlined is the 3′-UTR.

ACGTCGTCTACAACGGGTCCTTCTACTACAACCGGGCCTTCACCCGCAACATCATCAAATACGAC
CTGAAGCAGCGGTACGTGGCCGCCTGGGCCATGCTGCACGACGTGGCCTACGAGGAGTCCACCCC
GTGGCGATGGCGCGGCCATTCCGATGTGGACTTCGCCGTGGACGAGAACGGCCTGTGGGTCATTT
ACCCGGCCATCAGCTACGAGGGCTTCAATCAGGAGGTGATCGTGCTGAGCAAGCTGAACGCAGCC
GACCTCAGCACCCAGAAAGAGACGACGTGGAGGACGGGCCTGCGGAAGAACTTCTATGGGAACTG
CTTCGTCATCTGCGGGGTCCTGTACGCGGTCGACAGCTACAACAAGAGGAACGCCAACATCTCCT
ACGCCTTTGACACGCACACCAACACTCAGATCATCCCCCGGCTGCTCTTTGAGAATGAGTACGCC
TACACCACGCAGATAGACTATAACCCCAAGGACCGCCTGCTCTACGCTTGGGACAATGGCCACCA
GGTCACCTACCACGTCATCTTTGCCTACTGAGCGCCCCGGGATGGGGCACTGCGAGCGAGGGGCC
ACCAGCACCTTTCATTGTTGTTATTTTTATTATTATTATTATTATTTTGTACAAATCAAAGA
GTACGTGATGGGTTTTTGTCTCAGGCTGTTTAGATGGCGGATTGTAGATCGATCCCCAGGCCAGG
ACCACCCCTTTGTCCCCGGTGTGACCTTGCCTCTGTGCTCGAGGGCAGTGCGGCGGGGCCCGTGG
CAGCAGGGCTGCTCCTTTGGGGGGACGCTGAGGAGGAGGTGGCCCTGACATAACCCTGCTGATGT
TTTTTTAGATGAAAGCCATCAGCGCTTAACCCCAGGCCCAGTGCAAAGCTGGCCTTTCTGCTGCA
GGCACCGGCTCCTGTGGCAGGACGGTGGTGTCCACCCGTCCCCGTGGAGGGGTGCATTGTCCCCT
CGGGGGGCCACCCTCCCACCCGACAGTCAGCGGGTGCTTGGGAGATCCTGCTGTACAACACGCAC
AGCCCCGGTGCTGGCACTTAGCTGAGGACTGTCCCCTCTCCCCCTGACTCTGCCCTTTGCAGCCT
GCCCTGGGGGCTCCATCTGGCCTGGGGGGGGGCTGTGGGTGCCGGGCTGGGTGCTGGCAGTGGGA
GGGGGGCACTGTAAATATGTGTAGATGACTTCTGTTTGTGCGTTTTGTAACCAAAATAGTCCCCA
TTTGGTATCTGCCTCGCGGAGGTCCCAGCCTCCGTCCCTCCAGCCTGGCACCGCCTTGTATTTAC
CCGCTGTTAATAATAAAAGATCAAGTACCTTTGCAAAAAAAAAAAAAAAA

FIG. 2B: Amino acid sequence of chicken DP119 (SEQ ID NO: 2)

VVYNGSFYYNRAFTRNIIKYDLKQRYVAAWAMLHDVAYEESTPWRWRGHSDVDFAVDENGLWVIY
PAISYEGFNQEVIVLSKLNAADLSTQKETTWRTGLRKNFYGNCFVICGVLYAVDSYNKRNANISY
AFDTHTNTQIIPRLLFENEYAYTTQIDYNPKDRLLYAWDNGHQVTYHVIFAY

FIG. 2C: Nucleic acid sequence (SEQ ID NO: 3) of human DKFZp586L151 (from clone DKFZp586L151); partial codon (GenBank Accession Number AL050137.1)

GTGAGTTTTTCAGCGGTGACAATGGAGTGGATTTGCTGATTGAAGATCAGCTCCTGAGACACAAC
GGCCTGATGACCAGTGTCACCCGGAGGCCTGCAGCCACCCGTCAGGGACACAGCACTGCTGTGAC
AAGCGACCTGAACGCTCGGACCGCACCCTGGTCCTCAGCACTGCCACAGCCCTCGACCTCAGATC
CCAGCATCGCCAACCATGCCTCAGTGGGACCAACACTCCAAACAACCTCGGTGTCTCCAGATCCC
ACAAGGGAGTCAGTCCTGCAGCCTTCTCCTCAGGTACCAGCCACCACTGTGGCCCACACAGCCAC
CCAGCAACCAGCAGCCCCAGCTCCTCCGGCAGTGTCTCCCAGGGAGGCATTGATGGAAGCTATGC
ACACAGTCCCAGTGCCTCCCACCACAGTCAGAACAGACTCGCTGGGGAAAGATGCTCCTGCTGGG
CGGGGAACAACCCCTGCCAGCCCCACGCTGAGCCCCGAAGAAGAAGATGACATCCGGAATGTCAT
AGGAAGGTGCAAGGACACTCTCTCCACAATCACGGGGCCGACCACCCAGAACACATATGGGCGGA
ATGAAGGGGCCTGGATGAAGGACCCCCTGGCCAAGGATGAGCGGATTTACGTAACCAACTATTAC
TACGGCAACACCCTGGTAGAGTTCCGGAACCTGGAGAACTTCAAACAAGGTCGCTGGAGCAATTC
CTACAAGCTCCCGTACAGCTGGATCGGCACAGGCCACGTGGTATACAATGGCGCCTTCTACTACA
ATCGCGCCTTCACCCGCAACATCATCAAGTACGACCTGAAGCAGCGCTACGTGGCTGCCTGGGCC
ATGCTGCATGACGTGGCCTACGAGGAGGCCACCCCCTGGCGATGGCAGGGCCACTCAGACGTGGA
CTTTGCTGTGGACGAGAATGGCCTATGGCTCATCTACCCGGCCCTGGACGATGAGGGCTTCAGCC
AGGAGGTCATTGTCCTGAGCAAGCTCAATGCCGCGGACCTGAGCACACAGAAGGAGACCACATGG
CGCACGGGGCTCCGGAGGAATTTCTACGGCAACTGCTTCGTCATCTGTGGGGTGCTGTATGCCGT
GGATAGCTACAACCAGCGGAATGCCAACATCTCCTACGCTTTCGACACCCACACCAACACACAGA
TCGTCCCCAGGCTGCTGTTCGAGAATGAGTATTCCTATACGACCCAGATAGACTACAACCCCAAG
GACCGCCTGCTCTATGCCTGGGACAATGGCCACCAGGTCACTTACCATGTCATCTTTGCCTACTG
ACACCCTTGTCCCCACAAGCAGAAGCACAGAGGGGTCACTAGCACCTTGTGTGTATGTGTGTGCG
TGCACGTGTGTGTAGGTGGGTATGTGTTGTTTAAAAATATATATTATTTTGTATAATATTGCAAA
TGTAAAATGACAATTTGGGTCTATTTTTTTATATGGATTGTAGATCAATCCATACGTGTATGTGC
TGGTCTCATCCTCCCCAGTTTATATTTTTGTGCAAATGAACTTCTCCTTTTGACCAGTAACCACC
TTCCTTCAAGCCTTCAGCCCCTCCAGCTCCAAGTCTCAGATCTCGACCATTGAAAAGGTTTCTTC
ATCTGGGTCTTGCAGGAGGCAGGCAACACCAGGAGCAGAAATGAAAGAGGCAAGAAAGAAGTGCT
ATGTGGCGAGAAAAAAAGTTTTAATGTATTGGAGAAGTTTTAAAAAACCCAGAAAAACGCTTTTT
TTTTTTTAATAAAGAAGAAATTTAAAATCAAAAAAAAAAAAAAAA

FIG. 2D. Amino acid sequence (partial) of human hypothetical protein (GenBank Accession Number CAB43286.1; SEQ ID NO: 4)

EFFSGDNGVDLLIEDQLLRHNGLMTSVTRRPAATRQGHSTAVTSDLNARTAPWSSALPQPSTSDP
SIANHASVGPTLQTTSVSPDPTRESVLQPSPQVPATTVAHTATQQPAAPAPPAVSPREALMEAMH
TVPVPPTTVRTDSLGKDAPAGRGTTPASPTLSPEEEDDIRNVIGRCKDTLSTITGPTTQNTYGRN
EGAWMKDPLAKDERIYVTNYYYGNTLVEFRNLENFKQGRWSNSYKLPYSWIGTGHVVYNGAFYYN
RAFTRNIIKYDLKQRYVAAWAMLHDVAYEEATPWRWQGHSDVDFAVDENGLWLIYPALDDEGFSQ
EVIVLSKLNAADLSTQKETTWRTGLRRNFYGNCFVICGVLYAVDSYNQRNANISYAFDTHTNTQI
VPRLLFENEYSYTTQIDYNPKDRLLYAWDNGHQVTYHVIFAY

FIG. 2E. Nucleic acid sequence of Mus musculus, Similar to DKFZP586L151 protein (GenBank Accession Number BC025654.1; SEQ ID NO: 5)

CCACGCGTCCGAGTGAAGCCGCCTTCCAGCCTGTCTTTGCTGAGACCTCCGACCCAAGGTGGTCT
CTGTAGGGACTAAAGTCCCTACTGTCGCATCTCTCATGGCCTATCCCCTGCCATTGGTTCTCTGC
TTTGCTCTGGTGGTGGCACAGGTCTGGGGGTCCACTACACCTCCCACAGGGACAAGCGAGCCCCC
TGATGTGCAAACAGTGGAGCCCACGGAAGATGACATTCTGCAAAACGAGGCGGACAACCAGGAGA
ACGTTTTATCTCAGCTGCTGGGAGACTATGACAAGGTCAAGGCTGTGTCTGAGGGCTCTGACTGT
CAGTGCAAATGTGTGGTGAGACCGCTGGGCCGAGATGCCTGCCAGAGGATCAACCAGGGGGCTTC
CAGGAAGGAAGACTTCTACACTGTGGAAACCATCACCTCGGGCTCATCCTGTAAATGTGCTTGTG
TTGCTCCTCCGTCTGCCGTCAATCCCTGTGAGGGAGACTTCAGGCTCCAGAAGCTTCGGGAGGCT
GACAGCCGAGATTTGAAGCTGTCTACAATTATAGACATGTTGGAAGGTGCTTTCTACGGCCTGGA
CCTCCTAAAGCTGCATTCGGTTACCACTAAACTCGTGGGGCGAGTGGATAAACTGGAGGAGGAAG
TCTCTAAGAACCTCACCAAGGAGAATGAGCAAATCAAAGAGGACGTGGAAGAAATCCGAACGGAG
CTGAACAAGCGAGGCAAGGAGAACTGCTCTGACAACACCCTAGAGAGCATGCCAGACATCCGCTC
AGCCCTGCAGAGGGATGCGGCTGCAGCCTACGCCCACCCAGAGTATGAAGAACGGTTTCTGCAGG
AGGAAACTGTGTCACAGCAGATCAACTCCATCGAACTCCTGAGGACGCAGCCACTGGTCCCTCCT
GCAGCGATGAAGCCGCAGCGGCCCCTGCAGAGACAGGTGCACCTGAGAGGTCGGCTGGCCTCCAA
GCCCACCGTCATCAGGGGAATCACCTACTATAAAGCCAAGGTCTCTGAGGAGGAAAATGACATAG
AAGAGCAGCACGATGAGCTTTTCAGTGGCGACAGTGGAGTGGACTTGCTGATAGAAGATCAGCTT
CTAAGACAGGAAGACCTACTGACAAGTGCCACCCGGAGGCCAGCAACCACTCGTCACACTGCTGC
TGTCACGACTGATGCGAGCATTCAGGCCGCAGCCTCATCCTCAGAGCCTGCACAGGCCTCTGCCT
CAGCATCCAGCTTTGTTGAGCCTGCTCCTCAGGCCTCCGATAGAGAGCTCTTGGCAACCCCACAG
ACTACCACAGTGTTTCCAGAGCCCACGGGGGTGATGCCTTCTACCCAAGTCTCACCCACCACCGT
GGCCCACACAGCTGTCCAGCCACTTCCAGCAATGGTTCCTGGGGACATATTTGTGGAAGCTCTAC
CCTTGGTCCCTCTGTTACCTGACACAGTTGGGACAGACATGCCAGAGGAAGAGGGGACTGCAGGG
CAGGAAGCAACCTCTGCTGGTCCCATCCTGAGCCCTGAAGAAGAAGATGACATTCGGAATGTGAT
AGGAAGGTGCAAGGACACCCTCTCTACAATCACAGGACCGACCACCCAGAACACATATGGACGGA
ATGAAGGGGCCTGGATGAAGGACCCCCTAGCCAAGGACGACCGCATTTACGTAACCAACTATTAC
TATGGCAACACACTGGTCGAGTTCCGAAACCTGGAGAACTTCAAACAAGGTCGCTGGAGCAATTC
CTACAAGCTTCCATACAGCTGGATCGGCACGGGTCACGTGGTCTACAACGGCGCCTTCTACTATA
ACCGGGCCTTCACCCGAAACATCATCAAGTATGACCTGAAGCAGCGTTATGTGGCTGCCTGGGCC
ATGCTGCACGATGTGGCCTATGAGGAGGCCACTCCTTGGCGGTGGCAGGGTCACTCGGATGTGGA
CTTTGCTGTGGATGAGAATGGCCTGTGGCTTATCTACCCAGCTCTGGATGATGAAGGTTTCAACC
AGGAGGTCATTGTCCTGAGCAAGCTCAATGCCGTGGACCTGAGCACGCAGAAGGAGACCACGTGG
CGCACTGGGCTCCGGAGGAATTTCTATGGCAACTGCTTTGTCATCTGTGGGGTACTATATGCTGT
GGACAGCTATAACCAGAGGAATGCCAACATCTCCTATGCCTTTGACACACACACCAACACACAGA
TTGTCCCTAGGCTGCTGTTTGAGAATGAATATTCGTACACCACCCAGATAGACTACAACCCCAAG
GACCGCCTCCTCTATGCCTGGGACAATGGCCACCAGGTCACCTACCATGTCATCTTTGCCTACTG
ACACACTTGACCCTGCAAAAAGAAGCACAGTGGGGCCACTAGCACCTTGTGTGTGTCTGTGTGCA
TGTCTGTCTGTGAGATTGTGCAGGTGGGTGTGTGTTGTTTTAAAATATATTATTTTGTATAATAT
TACAAGTGTAAAATGACAGTTTGGGTCTATTTTTTTTATATGGATTGTAGATCAATCCATATGTG
TATGTGCTGGTCTCATCCTTCACAATTTATATTTTTGTGCAAATGAACTTCTCCTTCTGACCAGT
AACTACCTTCTTTCGTGCTCTGAACCTCTGGCTCCTGAGGTCAAGGGCTGGAGGGTTTCTTCCTC
CAGGTCTTGCAGCCAGGAGCAGGAGTGTGGGGCTCAGGAAAAAGTGCTAAGTGGCGGCAAAGTTT
TTATGTATTAGAGAAGTTCTTAAAACTCAGAAAAAAATACTTTTTTTAAATAAAGGAGATATTTT
AAGACCCTTAAAAAAAAAAAAAAAAAAAAAAAAAAAAAAAAAAAAAAAAAAAAAAAAA
AAA

FIGURE 2F. Amino acid sequence of mouse protein similiar to DKFZP586L151 protein (GenBank Accession Number AAH25654.1; SEQ ID NO: 6)

MAYPLPLVLCFALVVAQVWGSTTPPTGTSEPPDVQTVEPTEDDILQNEADNQENVLSQLLGDYDK
VKAVSEGSDCQCKCVVRPLGRDACQRINQGASRKEDFYTVETITSGSSCKCACVAPPSAVNPCEG
DFRLQKLREADSRDLKLSTIIDMLEGAFYGLDLLKLHSVTTKLVGRVDKLEEEVSKNLTKENEQI
KEDVEEIRTELNKRGKENCSDNTLESMPDIRSALQRDAAAAYAHPEYEERFLQEETVSQQINSIE
LLRTQPLVPPAAMKPQRPLQRQVHLRGRLASKPTVIRGITYYKAKVSEEENDIEEQHDELFSGDS
GVDLLIEDQLLRQEDLLTSATRRPATTRHTAAVTTDASIQAAASSSEPAQASASASSFVEPAPQA
SDRELLATPQTTTVFPEPTGVMPSTQVSPTTVAHTAVQPLPAMVPGDIFVEALPLVPLLPDTVGT
DMPSEEGTAGQEATSAGPILSPEEEDDIRNVIGRCKDTLSTITGPTTQNTYGRNEGAWMKDPLAK
DDRIYVTNYYYGNTLVEFRNLENFKQGRWSNSYKLPYSWIGTGHVVYNGAFYYNRAFTRNIIKYD
LKQRYVAAWAMLHDVAYEEATPWRWQGHSDVDFAVDENGLWLIYPALDDEGFNQEVIVLSKLNAV
DLSTQKETTWRTGLRRNFYGNCFVICGVLYAVDSYNQRNANISYAFDTHTNTQIVPRLLFENEYS
YTTQIDYNPKDRLLYAWDNGHQVTYHVIFAY

FIGURE 2G. Aligment of DP119 from different species (Dr, zebrafish; Mm, mouse; Hs, Homo sapiens; Dr, Danio rerio; Gg, chicken)

```
10        20        30        40        50        60
                    ----:----|----:----|----:----|----:----|----:----|----:----|
NA73457 Dr          -----------------------------------------------------------I
NA12640 Dr          ------------------------------------MWRIVELVACLLPMSSHVSSQSKI
IPI00221918 Mm      ------------------------MEAAAVLPRYLQLRLLLVLLLLVLLRAGPVWPDSKV
FLJ90228 Hs         ------------------------MAAAALPP-----KPLLLLPLVLLLSGKPTRADSKV
DKFZP586L151-like Mm -MAYPLPLVLCFALVVAQVWGSTTPPTGTSEPPDVQTVEPTEDDILQNEADNQENVLSQL
CL18A-like Rn       -MAYPLFLVLCFALVVARVWGSSTPPTGTSEPPDVQTVAPTEDDVLQNEADNQENVLSQL
IPI00178517 Hs      -MAKPRLLVLYFALIVVPAWVSSIVLTGTSEPPDAQTVAPAEDETLQNEADNQENVLSQL
ctg11453 Dr         MTEMKIWCVLLMAFALTSAAPKENLRLEEKTK--------DNNDTLQVEIDNQEHILSQL
ctg30117 Dr         --MGLLLYIFCCVFCLTRAN---VEQQATDNT--------DNRATLSDEMDNQENILTQL
DP119 Gg            ------------------------------------------------------------

                             70        80        90       100       110       120
                    ----:----|----:----|----:----|----:----|----:----|----:----|
NA73457 Dr          FGEPEPVKMISEGSDCRCKCVMRPLSIEACSRLRDGSLRVDDFYTVETVSSGSDCK-CSC
NA12640 Dr          FGE-EQVRMTSEGSDCRCKCIMRPLTRDACARLRTGSVRVEDFYTVETVSSGADCK-CSC
IPI00221918 Mm      FSDLQQVRMTSEGSDCRCKCIMRPLSKDACSRVRSGRARVEDFYTVETVSSGADCR-CSC
FLJ90228 Hs         FGDLQQVRMTSEGSDCRCKCIMRPLSKDACSRVRSGRARVEDFYTVETVSSGTDCR-CSC
DKFZP586L151-like Mm LGDYDKVKAVSEGSDCQCKCVVRPLGRDACQRINQGASRKEDFYTVETITSGSSCK-CAC
CL18A-like Rn       LGDYDKVKAVSEGSDCQCKCVVRPLGRDACQRINRGASRKEDFYTVETITSGSSCK-CAC
IPI00178517 Hs      LGDYDKVKAMSEGSDCQCKCVVRPLGRDACQRINAGASRKEDFYTVETITSGSSCK-CAC
ctg11453 Dr         LGDYDKVKALSEGSDCGCKCVVRPLSASACQRIEEGHATPQDFYTVETITSGPHCK-CAC
ctg30117 Dr         IGDYDKVKTLSEGSDCQCKCVVRPHSRSACKRIEEAQAKIEDFYTVEPVTAGPHCKKCAC
DP119 Gg            ------------------------------------------------------------

                            130       140       150       160       170       180
                    ----:----|----:----|----:----|----:----|----:----|----:----|
NA73457 Dr          TAPPSSLNPCENEWRTEKLMKQAPELLKL-------------------------------
NA12640 Dr          TAPPSSLNPCENEWKREKLKKQAPELLKL-------------------------------
IPI00221918 Mm      TAPPSSLNPCENEWKMEKLKKQAPELLKL-------------------------------
FLJ90228 Hs         TAPPSSLNPCENEWKMEKLKKQAPELLK--------------------------------
DKFZP586L151-like Mm VAPPSAVNPCEGDFRLQKLREADSRDLK--------------------------------
CL18A-like Rn       VAPPSAVNPCEGDFRLQKLREADSRDLK--------------------------------
IPI00178517 Hs      VAPPSALNPCEGDFRLQKLREADSQDLKVGPGMGQCLGREGTFEIHKSGKAMVEDSKPFR
ctg11453 Dr         IAPPSALNPCEGDFRLKKLRQAGKDNIK--------------------------------
ctg30117 Dr         IAPPSALNPCEGDFRFKKLQKTGQYDIK--------------------------------
DP119 Gg            ------------------------------------------------------------

                            190       200       210       220       230       240
                    ----:----|----:----|----:----|----:----|----:----|----:----|
NA73457 Dr          --------------------------------------------------HSMVDLLEGT
NA12640 Dr          --------------------------------------------------QSMVDLLEGT
IPI00221918 Mm      --------------------------------------------------QSMVDLLEGA
FLJ90228 Hs         ------------------------------------------------------------
DKFZP586L151-like Mm -------------------------------------------------LSTIIDMLEGA
CL18A-like Rn       -------------------------------------------------LSTIIDMLEGA
IPI00178517 Hs      EGLSNFLTQTFRKAECTYTIVLAYIPVYTNVFLTATSQFLASGFPVEPPLSTIIDMLEGA
```

Fig. 2H

```
ctg11453 Dr              -------------------------------------------------LSTILELLEGS
ctg30117 Dr              -------------------------------------------------LSNIMDLLEGS
DP119 Gg                 ------------------------------------------------------------

                                   250       260       270       280       290       300
                         ----:----|----:----|----:----|----:----|----:----|----:----|
NA73457 Dr               LYSMDLMKVHAYMNKVVS------------------------------QMNTLEETIKTN
NA12640 Dr               LFSMDLLKVHSYINKVVS------------------------------QMNNLEE-----
IPI00221918 Mm           LYSMDLMKVHAYIQKVAS------------------------------QMNTLEESIKAN
FLJ90228 Hs              -------------------------------------------------------SIKAN
DKFZP586L151-like Mm     FYGLDLLKLHSVTTKLVG------------------------------RVDKLEEEVSKN
CL1BA-like Rn            FYGLDLLKLHSVTTKLVG------------------------------RVDKLEEEVSKN
IPI00178517 Hs           FYGLDLLKLHSVTTKLVGRVDKLEENLEGAFYGLDLLKLHSVTTKLVGRVDKLEEEVSKN
ctg11453 Dr              FYGMDLLKLHSVTTKILD------------------------------RMDTIEKMVLNN
ctg30117 Dr              FYGMDLLKLHSVTTKLLE------------------------------RVDNIEKSFSGN
DP119 Gg                 ------------------------------------------------------------

                                   310       320       330       340       350       360
                         ----:----|----:----|----:----|----:----|----:----|----:----|
NA73457 Dr               LTRENEFVRDSVVNLSNQLKRYENYSDIMVSIKKEISSLGLQLLQKDAA----------S
NA12640 Dr               ------------------------------------------------------------
IPI00221918 Mm           LSLENKVVKDSVHHLSEQLKSYENQSAIMNSIKKELSSLGLQLLQRDAAAVPATAPASSP
FLJ90228 Hs              LSRENEVVKDSVHHLSEQLRHYENHSAIMLGIKKELSRLGLQLLQKDAAAAPAT-PATGT
DKFZP586L151-like Mm     LTKENEQIKEDVEEIRTELNKRGKENCSDN--TLESNPDIRSALQRDAA-----------
CL1BA-like Rn            LTKENEQIKEDVEEIRTELNKRGKENCSDN--ILGNMPDIRSALQRDAA-----------
IPI00178517 Hs           LTKENEQIKEDMEEIRTEMNKRGKENCSEN--ILDSNPDIRSALQRDAA-----------
ctg11453 Dr              QTEEKLNTISTSPNP-----QLSTSS----------PTTLPSVIQEKS------------
ctg30117 Dr              LTNEKVSVKGEKGQG-----KGARSNQRQE--KKKRLSVLEPSLQKNAA-----------
DP119 Gg                 ------------------------------------------------------------

                                   370       380       390       400       410       420
                         ----:----|----:----|----:----|----:----|----:----|----:----|
NA73457 Dr               DSKAQGTESKKSKEAIKP-PNKKPPAVKPPPKQPKEKPVKPKKEAPAKAAKPAKPDPTTK
NA12640 Dr               ------------------------------------------------------------
IPI00221918 Mm           DSKAQDTAGGQGRDLNKYGSIQKSPSDKGLAKPPKEKLLKVEKLR-KESIKGRIPQPTAR
FLJ90228 Hs              GSKAQDTARGKGKDISKYGSVQKSFADKGLPKPPKEKLLQVEKLR-KESGKGSPLQPTAK
DKFZP586L151-like Mm     AAYAHP--EYEERFLQEETVSQQINSIELLRTQPLVPPAAMKPQRPLQRQVHLRGRLASK
CL1BA-like Rn            AAYAHPEEQYEERFLQEETVSQQINSIELLRTQPLAPPTVMKPRQPSQRQVHLRGRLASK
IPI00178517 Hs           AAYAHP--EYEERFLQEETVSQQINSIELLQTRPLALPEVVKSQRPLQRQVHLRGRPASQ
ctg11453 Dr              TSLEQQN-DKAAAPQHMESKYEEKFVGDILNSGSDLNKATTALQE--QEQQGRKKQP---
ctg30117 Dr              AAPANTE-VQMQQPIPDQRKYEEKFVGNQGPSKPVLKKSKSEGQE--EQNKPAKTKADAK
DP119 Gg                 ------------------------------------------------------------

                                   430       440       450       460       470       480
                         ----:----|----:----|----:----|----:----|----:----|----:----|
NA73457 Dr               TKTSVHQTGVIRGITYYKASKSE-------------------------------------
NA12640 Dr               ------------------------------------------------------------
IPI00221918 Mm           PRALAQQQAVIRGFTYYKAGRQEARQEARQEAPKAAADSTLKGTSHLEKLPPKIEAKLP-
FLJ90228 Hs              PRALAQQQAVIRGFTYYKAGKQ--------EVTEAVADNALQGTSWLEQLPPKVEGRSNS
DKFZP586L151-like Mm     -------PTVIRGITYYKAKVSEEENDIEEQNDELPSGDSGVDLLIEDQLLAQED--LLT
CL1BA-like Rn            -------PTVIRGITYYKAKVSEEENDIEEQNDELPSGDSGVDLLIEDQLLRQED--LLM
IPI00178517 Hs           -------PTVIRGITYYKAKVSEEENDIEEQQDEFPSGDNGVDLLIEDQLLRNNG--LMT
ctg11453 Dr              -------KITVRGITYYRSDPVDENDSEKNLKETSASSVTQTGALIKEHLKASTQSTLNT
```

Fig. 2I

```
ctg30117 Dr           ------NMSLASMTPYKANRMEDSEGES----------RMDLIIEDQLHKQG---LNT
DP119 Gg              ------------------------------------------------------------

                              490       500       510       520       530       540
                      ----:----|----:----|----:----|----:----|----:----|----:----|
NA73457 Dr            ------------------------------------------------------------
NA12640 Dr            ------------------------------------------------------------
IPI00221918 Mm        -EPNSAKGDDVRLQASEQGNLTPDITTTTTTSTSSSTTTTTTGTTSTTS----------TT
FLJ90228 Hs          AEPNSAEQDEAEPRSSKRVDLASGTTKLILPPHSLHHHSTPVLATPAPFHLQCHNKPVPS
DKFZP586L151-like Mm  SATRRPATTR--HTAAVTTDASIQAAASSSEPAQASASASSFVEPAPQASDRSLLATPQT
CL18A-like Rn         SATRRPATTR--HAAAVSTDASVQATALSSEPAQASASAPSLVDPASQAPDRQLLASPQT
IPI00178517 Hs        SVTRRPAATRQGHSTAVTSDLAARTAPWSEALPQPSTSDPSIANKASVGP------TLQT
ctg11453 Dr           LTPSPTSHSNALTVTESSVGINAHKGEVTTIVNTASVTGSKTDSVTDLTQLSPRVRETLT
ctg30117 Dr           PVTTPEAT---VTVTQSTT-INLNTQNPTTARMSNVTKQTQQQSVKANNSS------TIT
DP119 Gg              ------------------------------------------------------------

                              550       560       570       580       590       600
                      ----:----|----:----|----:----|----:----|----:----|----:----|
NA73457 Dr            ------------------------------------------------------------
NA12640 Dr            ------------------------------------------------------------
IPI00221918 Mm        STTSTTTPS---------------------------------------------------
FLJ90228 Hs          PRRNQTTPSRALPGRSNCRPRWRAGPTPQSPTPQSRMRLSPGPPSENTWLLAPHPNPCNH
DKFZP586L151-like Mm  TTVPPEPTG---VMPSTQVSPTTVAHTAVQP-----LPAMVPGDIFVEALPLVPLLPDTV
CL18A-like Rn         TTVSPETMS---VMPSTQVSPTTVAHTAIQP-----PPAMIPGDIFVEALSLVPMSPDTV
IPI00178517 Hs        TSVSPDPTRRSVLQPSPQVPATTVAHTATQQPAAPAPPAVSPREALMEAMHTVPVPPTTV
ctg11453 Dr           TTRTTTKTA---TTSQPVKRKYSISWDEEEE-------AVVP-EQVEEEKAVKPVVEDKV
ctg30117 Dr           TERPTMPTS---TTSTSTMTPGTNTTTIATP-------LVVP-KQLAR------------
DP119 Gg              ------------------------------------------------------------

                              610       620       630       640       650       660
                      ----:----|----:----|----:----|----:----|----:----|----:----|
NA73457 Dr            ------------------------------------------------------------
NA12640 Dr            ------------------------------------------------------------
IPI00221918 Mm        ----------PITTPWPTEPPLHPEVPSQGRED---------------------------
FLJ90228 Hs          HHRHPHPQPPTTSLLPTEPPSQPEVSSQGRRA----------------------------
DKFZP586L151-like Mm  GTDMPEEEGTAQQEATSAGPILSPEEEDDIRNVIG-------------------------
CL18A-like Rn         GTDMAEEESTARQEATSASPILSPEEEDDIRNVIGVPRCSEAPHISAAFLHGLKHSVGPS
IPI00178517 Hs        RTDSLGKDAPAGWGTTPASPTLSPEEEDDIRNVIG-------------------------
ctg11453 Dr           GEEPQRKPPTAHHQAKTISTVKQQIKPSLG------------------------------
ctg30117 Dr           ------------------------------------------------------------
DP119 Gg              ------------------------------------------------------------

                              670       680       690       700       710       720
                      ----:----|----:----|----:----|----:----|----:----|----:----|
NA73457 Dr            ------------------------------------------------------------
NA12640 Dr            ------------------------------------------------------------
IPI00221918 Mm        ----------------------------------------------------------SC
FLJ90228 Hs          ----------------------------------------------------------SC
DKFZP586L151-like Mm  ----------------------------------------------------------RC
CL18A-like Rn         VPWHHVEICLKIRVEVLLSLVWQGLPGYQAIPKRYPEENGWIPAPPRKTGVLKEALQLEC
IPI00178517 Hs        ----------------------------------------------------------RC
ctg11453 Dr           ----------------------------------------------------------MC
ctg30117 Dr           ----------------------------------------------------------IC
```

Fig. 2J

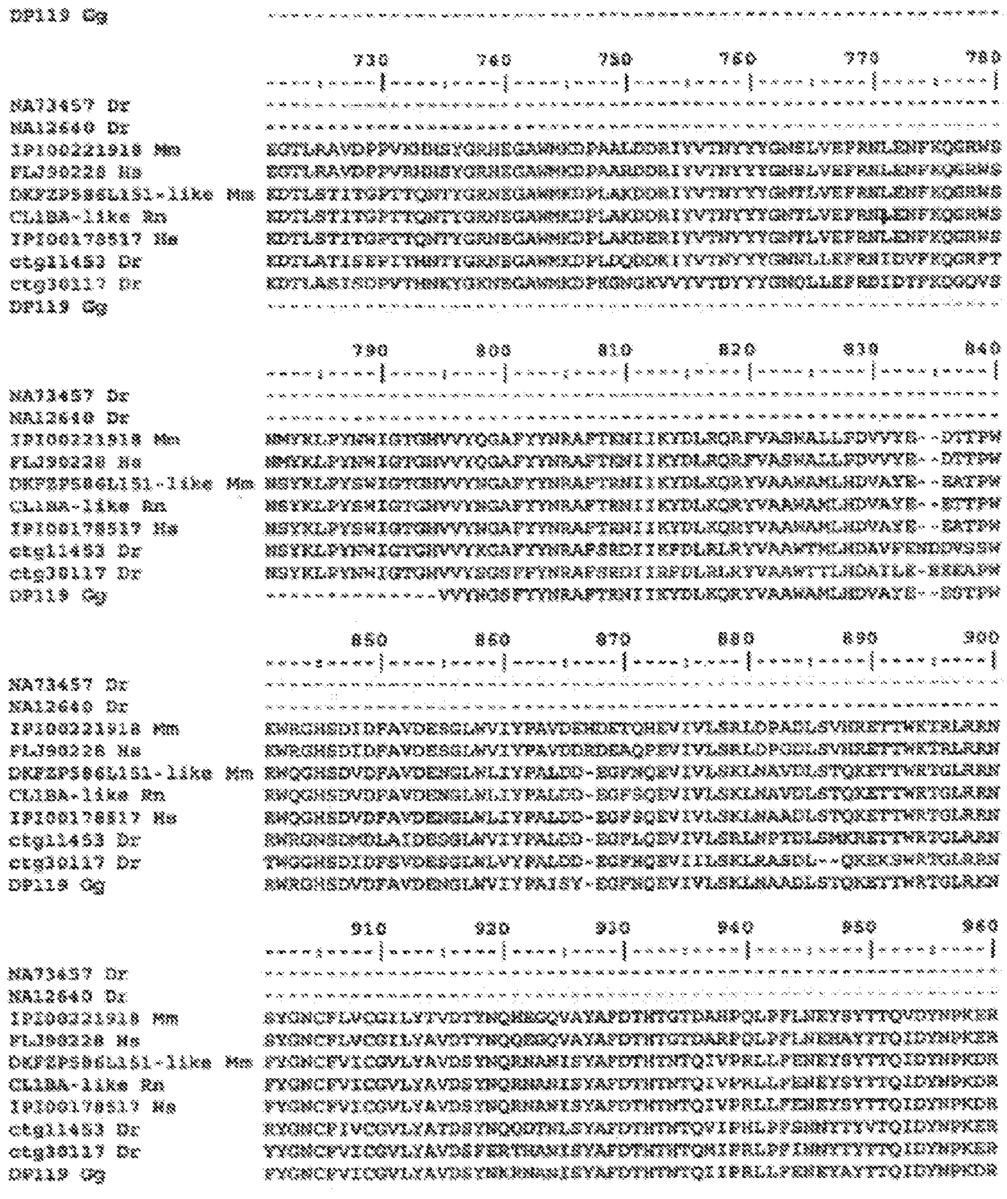

```
DP119 Gg                 ------------------------------------------------------------

                                730       740       750       760       770       780
                         ----:----|----:----|----:----|----:----|----:----|----:----|
NA73457 Dr               ------------------------------------------------------------
NA12640 Dr               ------------------------------------------------------------
IPI00221918 Mm           EGTLAAVDPPVHHHSYGRHSGAWNKDPAALDDRIYVTNYYYGNSLVEFRNLENFKQGRWS
FLJ90228 Hs              EGTLAAVDPPVHHHSYGRHSGAWNKDPAARDDRIYVTNYYYGNSLVEFRNLENFKQGRWS
DKFZP586L151-like Mm     KDTLSTITGPTTQNTYGRNSGAWNKDPLAKDDRIYVTNYYYGNTLVEFRNLENFKQGRWS
CL1BA-like Rn            KDTLSTITGPTTQNTYGRNSGAWNKDPLAKDDRIYVTNYYYGNTLVEFRNLENFKQGRWS
IPI00178517 Hs           KDTLSTITGPTTQNTYGRNSGAWNKDPLAKDERIYVTNYYYGNTLVEFRNLENFKQGRWS
ctg11453 Dr              KDTLATISEPITHNTYGRNSGAWNKDPLDQDDRIYVTNYYYGNNLLEFRNIDVFKQGRFT
ctg30117 Dr              KDTLASISDPVTHNKYGKNSGAWNKDPKGNGKVVYVTDYYYGNQLLEFRDIDTFKQGQVS
DP119 Gg                 ------------------------------------------------------------

                                790       800       810       820       830       840
                         ----:----|----:----|----:----|----:----|----:----|----:----|
NA73457 Dr               ------------------------------------------------------------
NA12640 Dr               ------------------------------------------------------------
IPI00221918 Mm           NMYKLPYNNIGTGNVVYQGAFYYNRAFTRNIIKYDLRQRFVASNALLPDVVYE--DTTPW
FLJ90228 Hs              NMYKLPYNNIGTGNVVYQGAFYYNRAFTRNIIKYDLRQRFVASNALLPDVVYE--DTTPW
DKFZP586L151-like Mm     NSYKLPYSNIGTGNVVYNGAFYYNRAFTRNIIKYDLKQRYVAAWAMLHDVAYE--EATPW
CL1BA-like Rn            NSYKLPYSNIGTGNVVYNGAFYYNRAFTRNIIKYDLKQRYVAAWAMLHDVAYE--ETTPW
IPI00178517 Hs           NSYKLPYSNIGTGNVVYNGAFYYNRAFTRNIIKYDLKQRYVAAWAMLHDVAYE--EATPW
ctg11453 Dr              NSYKLPYNNIGTGNVVYKGAFYYNRAFSRDIIKFDLRLRYVAAWTMLHDAVFENDDVSSW
ctg30117 Dr              NSYKLPYNNIGTGNVVYEGSFFYNRAFSRDIIRFDLRLRYVAAWTTLHDAILK-EEEAPW
DP119 Gg                 --------------VVYNGSFYYNRAFTRNIIKYDLKQRYVAAWAMLHDVAYE--ESTPW

                                850       860       870       880       890       900
                         ----:----|----:----|----:----|----:----|----:----|----:----|
NA73457 Dr               ------------------------------------------------------------
NA12640 Dr               ------------------------------------------------------------
IPI00221918 Mm           EWRGHSDIDFAVDESGLWVIYPAVDEHDETQHEVIVLSRLDPADLSVHRETTWKTRLRRN
FLJ90228 Hs              EWRGHSDIDFAVDESGLWVIYPAVDDRDEAQPEVIVLSRLDPGDLSVHRETTWKTRLRRN
DKFZP586L151-like Mm     EWQGHSDVDFAVDENGLWLIYPALDD-EGFNQEVIVLSKLNAVDLSTQKETTWRTGLRRN
CL1BA-like Rn            EWQGHSDVDFAVDENGLWLIYPALDD-EGFSQEVIVLSKLNAVDLSTQKETTWRTGLRRN
IPI00178517 Hs           EWQGHSDVDFAVDENGLWLIYPALDD-EGFSQEVIVLSKLNAADLSTQKETTWRTGLRRN
ctg11453 Dr              EWRGNSDMDLAIDESGLWVIYPALDD-EGFLQEVIVLSRLNPTDLSMKRETTWRTGLRRN
ctg30117 Dr              TWGGHSDIDFSVDESGLWLVYPALDD-EGFHQEVIILSKLRASDL--QKEKSWRTGLRRN
DP119 Gg                 EWRGHSDVDFAVDENGLWVIYPAISY-EGFNQEVIVLSKLNAADLSTQKETTWRTGLRKN

                                910       920       930       940       950       960
                         ----:----|----:----|----:----|----:----|----:----|----:----|
NA73457 Dr               ------------------------------------------------------------
NA12640 Dr               ------------------------------------------------------------
IPI00221918 Mm           SYGNCFLVCGILYTVDTYNQHEGQVAYAFDTHTGTDAHPQLPFLNEYSYTTQVDYNPKER
FLJ90228 Hs              SYGNCFLVCGILYAVDTYNQQEGQVAYAFDTHTGTDARPQLPFLNEHAYTTQIDYNPKER
DKFZP586L151-like Mm     FYGNCFVICGVLYAVDSYNQRNANISYAFDTHTNTQIVPRLLFENEYSYTTQIDYNPKDR
CL1BA-like Rn            FYGNCFVICGVLYAVDSYNQRNANISYAFDTHTNTQIVPRLLFENEYSYTTQIDYNPKDR
IPI00178517 Hs           FYGNCFVICGVLYAVDSYNQRNANISYAFDTHTNTQIVPRLLFENEYSYTTQIDYNPKDR
ctg11453 Dr              KYGNCFIVCGVLYATDSYNQQDTNLSYAFDTHTNTQVIPHLPFSNNYTYVTQIDYNPKER
ctg30117 Dr              YYGNCFVICGVLYAVDSFERTNANISYAFDTHTNTQNIPRLPFINNYTYTTQIDYNPKER
DP119 Gg                 FYGNCFVICGVLYAVDSYNKRNANISYAFDTHTNTQIIPRLLFENEYAYTTQIDYNPKDR
```

Fig. 2K

```
                                970       980       990       1000      1010      1020
                        ~~~~:~~~~|~~~~:~~~~|~~~~:~~~~|~~~~:~~~~|~~~~:~~~~|~~~~:~~~~|
NA73457 Dr              ~~~~~~~~~~~~~~~~~~~~
NA12640 Dr              ~~~~~~~~~~~~~~~~~~~~
IPI00221918 Mm          VLYAWDNGHQLTYTLHFVV
FLJ90228 Hs             VLYAWDNGHQLTYTLHFVV
DKFZP586L151-like Mm    LLYAWDNGHQVTYHVIFAY
CL1BA-like Rn           LLYAWDNGHQVTYHVIFAY
IPI00178517 Hs          LLYAWDNGHQVTYHVIFAY
ctg11453 Dr             VLYAWDNGHQVTYNVQFAY
ctg30117 Dr             MLYAWDNGHQVTYDVIF--
DP119 Gg                LLYAWDNGHQVTYHVIFAY
```

Fig. 3A-D. EXPRESSION OF DP444
DP0444
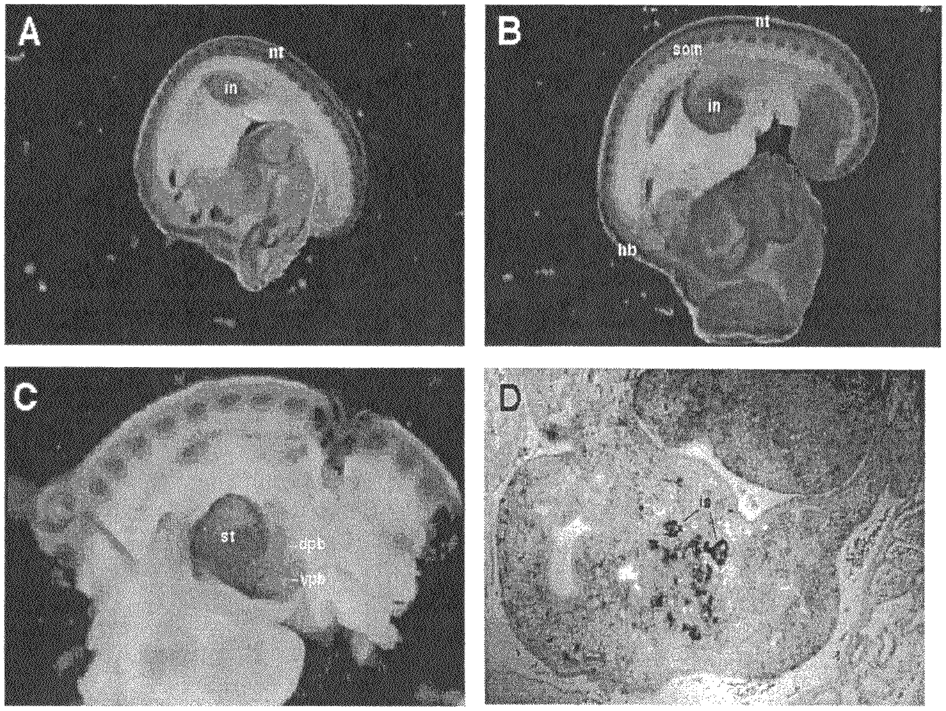

Fig. 3E: Loss of DP444 function leads to islet defects in zebrafish
a) 24hr old embryo injected with control antisense oligo
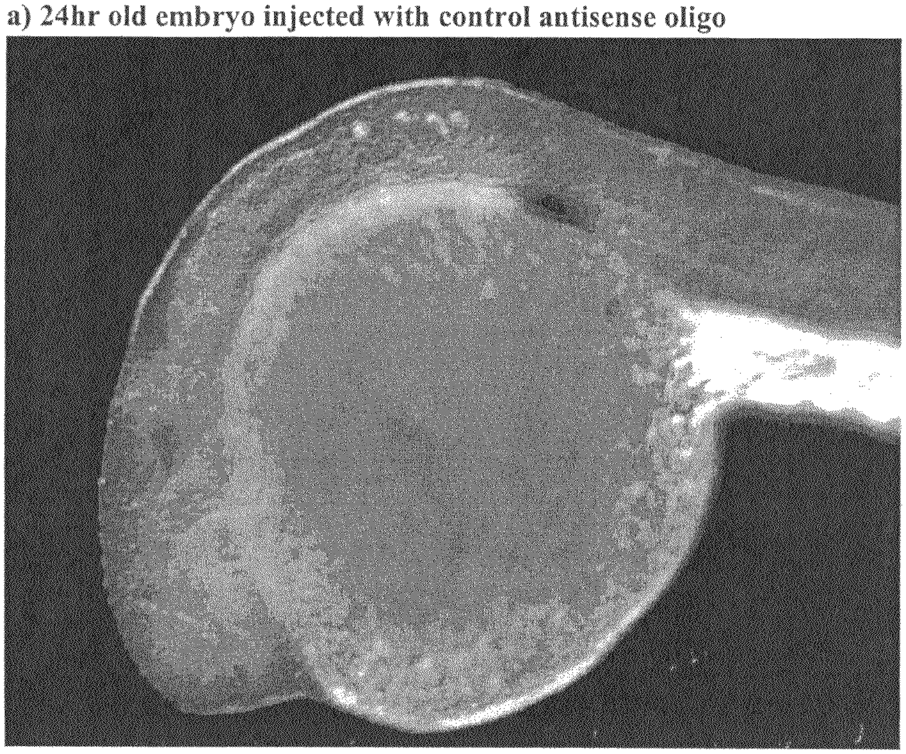
b) 24 hr old embryo injected with antisense oligo blocking the translation of DP444 (a + b: in situ hybridization, insulin expression stained purple)
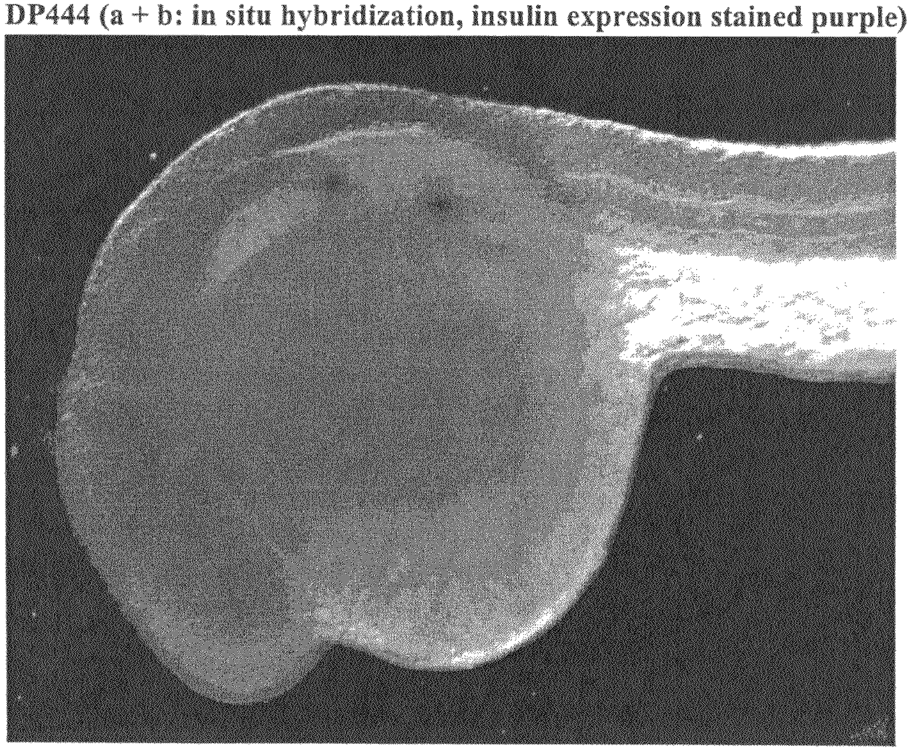

FIG. 4: DP444 sequences

FIG. 4A: Nucleic acid sequence (SEQ ID NO:7). The stop codon is in bold and the 3'UTR is underlined.

CCACGCGTCCGCCCACGCGTCCGGAAAGAGTTTTGGTAGAGAACAAGCTTCATGGACTTTCTCCA
GCTCTCTCTGAAGCCATCCAGAGCATTTCTCGCTGGGAACTTGTCCAGGCTGCGCTCCCACATGT
GCTACACTGCACTGCAACATTGCTCTCCAACCGAAACAAGCTAGGTCATCAGGATAAACTTGGAG
TAGCTGAAACAAAGCTTCTTCACACTCTTCACTGGATGCTGTTGGAGGCCCCTCAGGACTGCAGC
AATGACCGATTTGGAGGAGACAGAGGTTCTAGCTGGGGAGGGAGCAGTAGTGCCTTTATCCACCA
GGCTGAAAACCAGGGATCACCGGGACATCCCCGACCCAGCACCACGAATGATGAGGACGAGAACA
ACAGAAGGAAGTTCTTTCAGAACTCCATGGCCACCGTGGAGCTCTTTGTGTTCCTCTTTGCTCCT
CTGGTTCACAGGATTAAAGAATCTGACCTGACGTTTCGATTGGCTAGTGGCCTTGTTATTTGGCA
GCCTATGTGGGAACACAGGCAACCTGAAGTGTCTGCCTTCAATGCCCTCGTAAAACCAATCAGGA
ACATTGTTACAGCTAAAAGAAGTTCTCCTACCAACAATCAGAGTGTGACTTGTGAATCCCTAAAT
CTGGACAGTGGTCATACAGAGGGACTGCAGGTGGTCTGTGAGACGACCCTGCCCGATTCTGTACC
TTCAAAGCCCACTGTTTCAGCATGTCATCGTGGAAATTCCTTGGAAGGAAGCGTGTCCTCTCAAA
CCTCTCAGGAGAGAGGTACTCCACATCCCAGAGTGTCCATGGTGATCCCACCATGCCAGAAGTCT
CGCTATGCCACTTACTTTGATGTGGCAGTACTGCGCTGCTTGCTGCAGCCTCACTGGTCTGAGGA
GGGCACACAGTGGTCACTGATGTATTACCTGCAGAGACTGAGGCATATGCTACAGGAAAAGCCCG
AGAAACCACCTGAGCCAGAGATCACCCCTTTGCCAAGACTTCGCAGTAGCTCCATGGTGGCTGCT
GCACCCTCTCTGGTGAATACCCACAAAACTCAGGATCTCACAATGAAATGTAATGAGGAAGAAAA
ATCACTAAGCACAGAAGCGTTTTCCAAGGTTTCACTGACCAACTTGCGTAGGCCAGCGGTTCCAG
ATCTCTCCACAGATCTGGGGATGAACATCTTCAAAAAGTTTAAAAGCCGCAAAGAGGACAGAGAG
CGTGAACGCAAAGGGTCAATTCCTTTCCACCATACTGGGAAGAAGCGTCAACGGAGAATGGGGAT
GCCCTTCCTTCTCCATGAGGACCATTTGGATGTTTCACCCACTCGGAGCACTTTTTCATTTGGCA
GTTTTTCTGGCATTGGAGAGGACCGACGTGGCATTGAGAGAGGAGGATGGCAAACCACCATATTG
GGAAAGTTCACCAGACGGGGGAGCTCTGACACAGCAACGGAGATGGAAAGCCTGAGCGCTAGGCA
CTCACACTCTCACCACACTCTTGTCTCTGATATGCCAGACCACTCAAACAGCCATGGAGAGAACA
CAGTCAAAGAAGTTCGGTCCCAGATCTCTACCATCACTGTGGCCACCTTCAACACTACCCTGGCT
TCGTTCAATGTGGGCTATGCTGATTTCTTCAGTGAGCACATGAGGAAGCTTTGCAATCAGGTGCC
CATCCCTGAGATGCCCCACGAGCCTCTTGCGTGTGCCAACCTCCCACGGAGCCTGACAGACTCAT
GCATCAATTACAGTTGCTTGGAGGATACGGATCACATTGATGGAACCAACAACTTTGTCCACAAG
AACGGCATGCTGGATCTCTCGGTAAATGGCAAGGAATGAGGAAAGCCAGGTCCCTCTTCTGTCAA
TATAGTGGTACCATTGAGATCAGGGTGTTGATGGGCTTTTCCTCCACCTCTTTATATGACTTCTC
TCAGCAGTACATAAAGGTAGTCCTGAAGGCTGTTTACTTGGTCCTGAACCATGACATCAGCTCCA
GGATTTGTGATGTGGCACTGAACATTGTGGAGTGCTTGCTTCAGCTTGGAGTGGTGCCATCTGTA
GAGAAAGTCCGGAGGAAGAGCGAGAACAAAGAAAATGAAGCCCCTGAAAAGAGACCAAATGAGGG
ATCTTTTCAACTCAAAGCTTCTGGAGGTTCGGCTTGTGGATTTGGGCCTCCTCCAGTCAGTGGAA
CTGGAGATGGAGGAGAAGAAGGAGGCGGTGGAAGTGGTGGAGGAGGAAGCGATGGAGGTGGTGGA
GGAGGAGGGCCGTATGAGAAGAATGACAAAAAAAAAAAAAAA

FIG. 4B: Amino acid sequence of DP444 (SEQ ID NO:8)

TRPPTRPERVLVENKLHGLSPALSEAIQSISRWELVQAALPHVLHCTATLLSNRNKLGHQDKLGV
AETKLLHTLHWMLLEAPQDCSNDRFGGDRGSSWGGSSSAFIHQAENQGSPGHPRPSTTNDEDENN
RRKFFQNSMATVELFVFLFAPLVHRIKESDLTFRLASGLVIWQPMWEHRQPEVSAFNALVKPIRN
IVTAKRSSPTNNQSVTCESLNLDSGHTEGLQVVCETTLPDSVPSKPTVSACHRGNSLEGSVSSQT
SQERGTPHPRVSMVIPPCQKSRYATYFDVAVLRCLLQPHWSEEGTQWSLMYYLQRLRHMLQEKPE
KPPEPEITPLPRLRSSSMVAAAPSLVNTHKTQDLTMKCNEEEKSLSTEAFSKVSLTNLRRPAVPD
LSTDLGMNIFKKFKSRKEDRERERKGSIPFHHTGKKRQRRMGMPFLLHEDHLDVSPTRSTFSFGS
FSGIGEDRRGIERGGWQTTILGKFTRRGSSDTATEMESLSARHSHSHHTLVSDMPDHSNSHGENT
VKEVRSQISTITVATFNTTLASFNVGYADFFSEHMRKLCNQVPIPEMPHEPLACANLPRSLTDSC
INYSCLEDTDHIDGTNNFVHKNGMLDLSVNGKE

FIG. 4C. Nucleic acid sequence of the human homolog QV2-NN2006-230401-628-d06 NN2006 (SEQ ID NO:9, GenBank Accession Number BI035296)

GGAAATTGACCCGGCGAGGCAGTTCAGATGCAGCCACTGAGATGGAGAGTCTGAGCGCCAGGCAT
TCCCACTCCCATCACACCCTGGTAAGCGACCTGCCGGACCCCTCCGACAGCCATGGAGAAAACAC
CGTCAAGGAAGTGCGATCTCAGATCTCCACCATCACAGTTGCGACCTTCAATACCACTTTGGCGT
CATTCAACGTAGGCTATGCAGACTTTTTCAATGAGCATATGAGGAAACTCTGCAACCAGGTGCCT
ATCCCGGAGATGCCACATGAACCTCTGGCATGTGCTAACCTACCTCGAAGCCTCACAGACTCCTG
CATAAACTACAGCTACCTAGAGGACACAGAACATATTGACGGGACCAATAACTTTGTC

FIG. 4D: Amino acid sequence of the human homolog of DP444 (SEQ ID NO:10) (Translation of SEQ ID NO:9)

KLTRRGSSDAATEMESLSARHSHSHHTLVSDLPDPSDSHGENTVKEVRSQISTITVATFNTTLAS
FNVGYADFFNEHMRKLCNQVPIPEMPHEPLACANLPRSLTDSCINYSYLEDTEHIDGTNNFV

FIG. 4E: GenBank Accession Number BF951817 QV1-NN0228-091100-436-g05 NN0228 Homo sapiens, (SEQ ID NO:11)

TCGGTACCGGGTCAGTACGGATGTGAGGTCAGATTCCTTGATCCTGGTACCAGTGGAGCAAACAG
AAACACGAAGAGCTCCACAGTAGCCATGGAGTTCTGGAAGATCTTTCTTCGGTTGTTCTCTTCTT
CGTCATTAGAGCTGCTTTGGCAAGGCTGCCCTGGAGAACCCTGGTTTTCAACCTGGTGGATGAAA
GCACTGCTGCTTCCACCCCAGCTGGAGCCTCGGTCTGTACCCCCAAACCGCTCATTGTTGCAGTC
CTGGGGGGCCTCCAGAAGCATCCAGTGTAGAGTGTGAAGGAGCTTTGTCTCAGCAACACCCAATT
TATCCTGGTGGCCTAGCTTGTTTCGGTTTGAAAGCAGGGTTGCAGTGCAGTGGAGGACATGAGGC
AAAGCAGCTTGCACCAGTTCCCATCCGGAAATGCTCTGGATGGCTTCAGAGAGAGCTGGAGAGAG
GCCATGCAGCTTGTTTTCTACCAACACTCGCTCAAAGGACACACAAGAAGCTTCATATTGCTTCC
CCAGTTTGGGCCTCAAAAATGCACTGGTTTGCCGGCACAGGAAGGTCTGGATGGGCAGGGGGATG
CCGCGGGC

FIG. 4F: GenBank Accession Number AI214480.1; qg69c12.x1 Soares_NFL_T_GBC_S1 Homo sapiens, (SEQ ID NO:12)

TGCCCATCCAGACCTTCCTGTGGCGGCAAACCAGTCCTTTGAGCGAGTGTTGGTAGAAAACAAGC
TGCATGGCCTCTCTCCAGCTCTCTCTGAAGCCATCCAGAGCATTTCCAGATGGGAACTGGTGCAA
GCTGCTTTGCCTCATGTCCTCCACTGCACTGCAACCCTGCTTTCAAACCGAAACAAGCTAGGCCA
CCAGGATAAATTGGGTGTTGCTGAGACAAAGCTCCTTCACACTCTACACTGGATGCTTCTGGAGG
CCCCCCAGGACTGCAACAATGAGCGGTTTGGGGGTACAGACCGAGGCTCCAGCTGGGGTGGAAGC
AGCAGTGCTTTCATCCACCAGGTTGAAAACCAGGGTTCTCCAGGGCAGCCTTGCCAAAGCAGCTC
TAATGACGAAGAAGAGAACAACCGAAGA

FIG. 4G: GenBank Accession Number Hs2_5191_28_4_1 predicted mRNA, (SEQ ID NO:13)

ATGGTGAAGAGGAAGAGCTCCGAGGGCCAGGAGCAGGACGGCGGCCGCGGCATCCCCCTG
CCCATCCAGACCTTCCTGTGGCGGCAAACCAGTTTTTATTATGACTGTACACGCCACCAG
GATAAATTGGGTGTTGCTGAGACAAAGCTCCTTCACACTCTACACTGGATGCTTCTGGAG
GCCCCCCAGGACTGCAACAATGAGCGGTTTGGGGGTACAGACCGAGGCTCCAGCTGGGGT
GGAAGCAGCAGTGCTTTCATCCACCAGGTTGAAAACCAGGGTTCTCCAGGGCAGCCTTGC
CAAAGCAGCTCTAATGACGAAGAAGAGAACAACCGAAGAAAGATCTTCCAGAACTCCATG
GCTACTGTGGAGCTCTTCGTGTTTCTGTTTGCTCCCCTGGTACACAGGATCAAGGAATCT
GACCTCACCTTCCGTCTGGCCAGTGGGCTTGTTATATGGCAGCCCATGTGGGAACACAGA
CAGCCCGGAGTCTCTGGCTTTACCGCACTGGTGAAGCCCATCAGGAACATCATTACAGCT
AAGAGAAGTTCTCCTATCAACAGTCAAAGCCGGACCTGTGAATCACCAAATCAAGATGCA
AGACACTTAGAGGTACTACTAACCTGGTGCTTCTATTTTAGCCTCATGCTTCTATTCAGT
TCACCTCTGTATGATGAATTCTTGATGTGTAACTCTCCTATAGATACTGGGTATGGAGAT
GAAAAAGAAAATAATTAA

FIG. 4H: GenBank Accession Number Hs2_5191_28_4_1 predicted protein, (SEQ ID NO:14)

```
MVKRKSSEGQEQDGGRGIPLPIQTFLWRQTSFYYDCTRHQDKLGVAETKLLHTLHWMLLE
APQDCNNERFGGTDRGSSWGGSSSAFIHQVENQGSPGQPCQSSSNDEEENNRRKIFQNSM
ATVELFVFLFAPLVHRIKESDLTFRLASGLVIWQPMWEHRQPGVSGFTALVKPIRNIITA
KRSSPINSQSRTCESPNQDARHLEVLLTWCFYFSLMLLFSSPLYDEFLMCNSPIDTGYGD
EKENN
```

FIG. 4I: GenBank Accession Number Hs2_5191_28_4_3 predicted mRNA, (SEQ ID NO:15)

ATGCTGTGCTGCCCCTCTGAAAGCTTGATTGTCAGTATAATTATCTTCTTTCTGCCATGG
AACAGGGCCTCTCTTGTGATACCTCCGTGCCAAAGGTCCCGCTATGCCACCTACTTTGAC
GTTGCTGTTCTGCGCTGCCTACTTCAGCCCCATTGGTCTGAGGAAGGCACTCAGTGGTCT
CTGATGTACTATCTACAAAGGCTGCGACACATGTTGGAAGAGAAGCCAGAAAAGCCTCCG
GAGCCAGATATTCCTCTCCTGCCCAGACCCAGGAGTAGCTCCATGGTGGCAGCAGCTCCC
TCACTAGTGAACACCCACAAAACCCAAGATCTCACCATGAAGTGTAACGAGGAGGAAAAA
TCTCTTAGCTCTGAGGCCTTTTCCAAGGTTTCACTGACCAATCTGCGTAGATCTGCAGTC
CCAGATCTTTCTTCAGACCTGGGCATGAATATTTTTAAAAAGTTCAAGAGCCGCAAAGAA
GACCGAGAGAGGAAAGGCTCCATTCCATTCCACCACACAGGCAAGAGGAGGCCACGGAGA
ATGGGAGTGCCCTTCCTGCTTCACGAGGACCACCTGGATGTGTCCCCCACGCGCAGCACA
TTCTCCTTTGGAAGTTTCTCTGGGCTGGGAGAAGACAGGCGAGGAATTGAGAAAGGAGGC
TGGCAAACCACCATTTTAGGGAAATTGACCCGGCGAGGCAGTTCAGATGCAGCCACTGAG
ATGGAGAGTCTGAGCGCCAGGCATTCCCACTCCCATCACACCCTGGTAAGCGACCTGCCG
GACCCCTCCAACAGCCATGGAGAAAACACCGTCAAGGAAGTGCGATCTCAGATCTCCACC
ATCACAGTTGCGACCTTCAATACCACTTTGGCGTCATTCAACGTAGGCTATGCAGACTTT
TTCAATGAGCATATGAGGAAACTCTGCAACCAGGTGCCTATCCCGGAGATGCCACATGAA
CCTCTGGCATGTGCTAACCTACCTCGAAGCCTCACAGACTCCTGCATAAACTACAGCTAC
CTAGAGGACACAGAACATATTGACGGGACCAATAACTTTGTCCACAAGAATGGAATGCTT
GATCTTTCTGTAGTTCTGAAGGCTGTTTATCTTGTCCTTAATCATGACATCAGCTCTCGT
ATCTGTGACGTGGCGCTAAACATTGTGGAATGCTTGCTTCAACTTGGTGTGGTGCCCTGT
GTAGAAAAGAATAGAAAGAAGAGTGAAAACAAGGAAAATGAGACCTTGGAAAAGAGGCCA
AGTGAGGGAGCTTTCCAATTCAAAGGAGTATCTGGAAGTTCCACCTGTGGATTCGGAGGC
CCTGCTGATGAAAGTACACCTGTAAGCAACCATAGGCTTGCTCTAACAATGCTCATCAAA
ATAGTGAAGTCTTTGGGATGTGCCTATGGTTGTGGTGAAGGACACCGAGGGCTCTCTGGA
GATCGTCTGAGACACCAGGTATTCCGAGAGAATGCCCAGAACTGCCTCACTAAGCTATAC
AAGCTAGATAAGATGCAGTTCCGACAAACCATGAGGGACTATGTGAACAAGGACTCTCTC
AATAATGTAGTGGACTTCTTGCATGCTTTGCTAGGATTTTGTATGGAGCCGGTCACTGAC
AACAAGGCTGGGTTTGGAAATAACTTCACCACAGTGGACAACAAATCCACAGCCCAAAAT
GTGGAAGGCATTATCGTCAGCGCCATGTTTAAATCCCTCATCACACGCTGCGCTTCAACC
ACACATGAATTGCACAGCCCTGAGAATCTGGGACTGTATTGTGACATTCGTCAGCTGGTC
CAGTTTATCAAAGAGGCTCATGGGAATGTCTTCAGGAGAGTGGCCCTCAGCGCTCTGCTT
GACAGTGCCGAGAAGTTAGCACCAGGGAAAAAGGTGGAGGAGAATGAACAGGAATCTAAG
CCTGCAGGCAGTAAAAGCGATGAACAAATGCAAGGAGCCAACTTGGGGCGGAAAGATTTC
TGGCGTAAGATGTTCAAGTCCCAGAGTGCAGCAAGTGACACCAGCAGCCAGTCTGAACAG
GACACTTCAGAATGCACGACTGCCCACTCAGGGACCACCTCTGACCGACGTGCCCGCTCA

Fig. 4J

CGATCCCGCAGAATTTCCCTCCGAAAGAAGCTTAAACTCCCCATAGGGAACTGGCTGAAG
AGATCATCCCTCTCAGGCCTGGCAGATGGTGTGGAGGACCTCCTGGACATTAGCTCTGTG
GACCGACTCTCTTTCATCAGGCAAAGCTCCAAGGTCAAATTCACTAGTGCTGTGAAGCTT
TCTGAAGGTGGGCCAGGAAGTGGCATGGAAAATGGAAGAGATGAAGAGGAGAATTTCTTC
AAGCGTCTTGGTTGCCACAGTTTTGATGATCATCTCTCTCCCAACCAAGATGGTGGAAAA
AGCAAAAACGTGGTGAATCTTGGAGCAATCCGACAAGGCATGAAACGCTTCCAATTTCTG
TTAAACTGCTGTGAGCCAGGGACAATTCCTGATGCCTCCATCCTAGCAGCTGCCTTGGAT
CTAGAAGCCCCTGTGGTGGCCAGAGCAGCCTTGTTCCTGGAATGTGCTCGTTTTGTTCAC
CGCTGCAACCGTGGCAACTGGCCAGAGTGGATGAAAGGGCACCACGTGAACATCACCAAG
AAAGGACTTTCCCGGGGACGCTCTCCCATTGTGGGCAACAAGCGAAACCAGAAGCTGCAG
TGGAATGCAGCCAAGCTCTTCTACCAATGGGGAGACGCAATTGGCGTCCGATTGAATGAG
CTGTGCCACGGGGAAAGTGAGAGCCCAGCCAACCTGCTGGGTCTCATTTACGATGAAGAG
ACCAAGAGGAGACTTAGAAAGGAGGATGAGGAGGAAGACTTTTTAGATGACAGTAAGGAG
ACTCCCTTTACTACAAGAACCCCTGCTTGTACTGTGAACCCCTCTAAATGCGGTTGCCCC
TTTGCCTTGAAGATGGCAGCATGTCAGCTTCTTCTGGAGATTACCACCTTCCTGCGAGAG
ACCTTTTCTTGCCTGCCCAGACCTCGCACTGAGCCTCTGGTGGACTTGGAGAGCTGCAGA
CTTCGTTTGGATCCCGAGTTGGACCGGCACAGATATGAGAGGAAGATCAGCTTTGCTGGG
GTCCTGGACGAAAATGAAGACTCAAAAGATTCTCTCCACAGCAGCAGCCACACTCTCAAA
TCAGATGCAGGAGTCGAGGAGAAGAAAGTTCCCAGCAGGAAGATCAGGATAGGAGGTTCT
CGCCTGCTCCAGATTAAAGGAACCCGCAGTTTCCAGGTGAAGAAGGGGGGTTCCTTGTCC
AGCATTCGCCGGGTCGGCAGCTTAAAGAGCAGCAAGTTATCACGGCAGGACTCAGAGTCT
GAGGCTGAGGAGCTGCAGCTGTCCCAGAGCAGGGACACTGTCACTGACCTAGAAGGGAGT
CCTTGGAGTGCAAGCGAGCCCAGCATTGAGCCAGAGGGAATGAGTAATGCCGGCGCGGAG
GAGAATTACCACAGAAACATGTCGTGGCTTCATGTGATGATCTTGCTGTGCAATCAGCAG
AGTTTCATCTGCACTCACGTTGACTACTGCCATCCCCACTGCTACCTGCACCACAGCCGC
TCCTGTGCCCGACTGGTCAGAGCCATCAAGCTACTCTATGGAGACAGTGTGGACTCCCTG
AGGGAAAGCAGCAACATCAGCAGTGTGGCTCTCCGGGGCAAGAAACAGAAAGAATGCTCA
GATAAGTCATGCCTGAGGACACCTTCTCTAAAGAAGAGAGTTTCAGATGCCAATCTGGAA
GGAAAAAAAGATTCCGGAATGCTGAAGTACATCAGACTTCAGGTATTGTTACCTGGATCA
GAAGGATTCATGGAACTTTTAACAGGGAGGGGACTCCAGACAGCCTATTTACTAATGTTT
GGGACATACAACATCAGTTGGTACAGTGTTGGCATAAAGCCCCTTCAGTTGGTGATGAGC
TTGTCGCCTGCTCCCTTATCTCTGTTAATCAAGGCAGCACCAATTCTGACAGAGGAGATG
TACGGAGACATCCAGCCAGCTGCCTGGGAGCTCCTGCTCAGCATGGATGAGCACATGGCA
GGGGCAGCAGTGAAGGTGCCTGAGGCCGTGTCCGACATGCTGATGTCAGAGTTCCACCAC
CCGGAGACTGTGCAGAGGCTGAACGCTGTCCTCAAGTTCCACACGCTCTGGAGGTTTCGC
TATCAGGTCTGGCCCCGGATGGAGGAAGGGGCACAGCAGATTTTTAAGAAATCCTTTTCA
GCCCGGGCTGTGTCCCGCTCCCATCAAAGGGCAGAACACATCTTAAAGAACTTGCAGCAG
GAGGAAGAAAAGAAACGACTTGGTAGAGAAGCCAGCCTCATCACTGCCATCCCCATCACC
CAGGAGGCTTGCTATGAGCCCACATGCACGCCCAACTCAGAACCGGAAGAAGAAGTAGAA
GAAGTCACCAATCTGGCATCCCGTCGACTGTCTGTGAGTCCATCCTGCACCTCCAGCACT
TCCCACAGGAATTATTCCTTCCGCCGCGGGTCAGTCTGGTCAGTGCGTTCAGCCGTCAGT
GCTGAAGATGAGGAACATACCACTGAACACACGCCGAACCACCATGTGCCTCAGCCCCCA

Fig. 4K

CAAGCAGTGTTCCCAGCATGCATCTGTGCAGCAGTACTTCCCATTGTTCATCTGATGGAG
GATGGTGAGGTGCGGGAAGATGGAGTAGCAGTGAGTGCTGTGGCTCAACAAGTCTTATGG
AACTGTCTAATTGAAGATCCATCAACGGTTCTTCGACATTTTCTGGAAAAACTGACCATC
AGCAATAGACAAGATGAGTTAATGTACATGCTGCGCAAACTTCTCTTGAATATTGGAGAC
TTTCCTGCTCAGACATCTCACATCCTATTCAACTATTTGGTAGGATTAATCATGTACTTT
GTGCGGACCCCCTGCGAGTGGGGGATGGATGCCATTTCAGCCACCCTGACATTCCTGTGG
GAGGTGGTGGGTTACGTGGAGGGCCTCTTCTTCAAGGATCTCAAGCAGACGATGAAGAAG
GAGCAGTGTGAGGTGAAGCTCCTGGTGACCGCTTCAATGCCAGGTACTAAAACCTTGGTA
GTTCATGGACAGAATGAGTGCGATATCCCAACCCAGTTACCAGTCCATGAAGACACTCAA
TTTGAAGCCCTGTTGAAGGAGTGTCTGGAGTTTTTTAATATCCCAGAATCCCAGTCAACA
CATTATTTTCTTATGGATAAACGATGGAACCTTATCCACTACAATAAGACCTATGTTCGA
GATATTTATCCTTTCCGGAGGTCAGTATCTCCCCAGCTGAATCTTGTACATATGCATCCA
GAGAAGGGACAGGAGCTCATTCAGAAACAGGTGTTCACCCGAAAGCTGGAAGAAGTAGGG
CGGGTGTTGTTTCTCATCTCCCTAACCCAGAAGATCCCCACAGCCCACAAACAGTCCCAC
GTCTCCATGCTTCAGGAAGACCTCCTCCGCCTGCCCTCATTCCCTCGTAGTGCTATTGAT
GCTGAGTTTTCACTCTTCAGTGATCCTCAAGCTGGAAAGGAACTGTTTGGCCTCGACACT
CTTCAGAAAAGCTTGTGGATCCAGCTGCTGGAGGAAATGTTCCTGGGCATGCCGAGCGAG
TTTCCATGGGGAGACGAAATCATGCTTTTCCTCAACGTTTTTAACGGGGCTCTGATCCTC
CACCCGGAAGACAGTGCCCTGCTCAGGCAGTATGCTGCCACCGTCATCAACACCGCGGTG
CACTTCAACCACCTCTTCTCTCTCAGCGGCTACCAGTGGATTCTCCCCACCATGCTGCAG
GTGTACTCCGACTATGAAAGCAATCCCCAGCTGCGTCAAGCCATCGAATTTGCCTGTCAC
CAGTTCTATATTCTACACCGGAAGCCCTTTGTGCTCCAGCTGTTTGCTAGTGTGGCCCCT
CTCCTGGAATTTCCTGATGCTGCCAATAATGGGCCCAGCAAAGGTGTGTCAGCTCAGTGC
CTGTTTGACTTGCTGCAGTCCCTAGAGGGAGAGACCACCGACATATTAGACATCTTAGAG
CTGGTCAAAGCTGAGAAGCCTCTCAAGTCATTAGATTTCTGCTATGGAAACGAAGATCTG
ACATTTTCTATCAGTGAAGCCATTAAGCTCTGTGTCACTGTGGTGGCGTATGCTCCCGAA
TCATTCAGAAGTCTTCAGATGCTGATGGTCTTAGAAGCCTTAGTTCCATGTTACCTACAA
AAGCTAAAGAGGCAGACATCACAGGTGGAGACAGTACCTGCTGCCCGAGAGGAGATTGCG
GCCACTGCTGCTCTTGCGACGTCCCTACAGGCCCTTTTGTACAGTGTAGAGGTCCTCACC
AGGGAAAACCTTCATTTACTGGAGGAAGGGCAAGGCATTCCCAGAGAGGAACTGGATGAA
CGAATTGCTCGGGAAGAGTTCAGAAGACCCCGGGAGTCCTTACTGAATATTTGCACTGAG
TTCTATAAGCACTGTGGGCCACGGCTGAAGATCTTGCAAAATCTGGCTGGGGAGCCTCGG
GTCATTGCCTTGGAACTGCTGGATGTGAAGTCTCACATGAGTGTGCTAGGGAAAGGCCCC
AGAATTACTTCCCTGTGCACTCGTATTTCGTCTTCCTACAGAGATGCCATTTCACTTGAA
ATTCATGCTAAAGGCCGTATTTGTGTTTCAAAAGGAACGTGA

Fig. 4L GenBank Accession Number Hs2_5191_28_4_3 predicted protein, (SEQ ID NO:16)

MLCCPSESLIVSIIIFFLPWNRASLVIPPCQRSRYATYFDVAVLRCLLQPHWSEEGTQWS
LMYYLQRLRHMLESKPEKPPEPDIPLLPRPRSSSMVAAAPSLVNTHKTQDLTMKCNEEEK

SLSSEAFSKVSLTNLRRSAVPDLSSDLGMNIFKKFKSRKEDRERKGSIPFHHTGKRRFRR
MGVPFLLHEDHLDVSPTRSTFSFGSFSGLGEDRRGIEKGGWQTTILGKLTRRGSSDAATE
MESLSARHSHSHHTLVSDLPDPSNSHGENTVKEVRSQISTITVATFNTTLASFNVGYADF
FNEHMRKLCNQVPIPEMPHEPLACANLPRSLTDSCINYSYLEDTEHIDGTNNFVHKNGML
DLSVVLKAVYLVLNHDISSRICDVALNIVECLLQLGVVPCVEKNRKKSENKENETLEKRP
SEGAFQFKGVSGSSTCGFGGPADESTPVSNHRLALTMLIKIVKSLGCAYGCGEGHRGLSG
DRLRHQVFRENAQNCLTKLYKLDKMQFRQTMRDYVNKDSLNNVVDFLHALLGFCMEPVTD
NKAGFGNNFTTVDNKSTAQNVEGIIVSAMFKSLITRCASTTHELHSPENLGLYCDIRQLV
QFIKEAHGNVFRRVALSALLDSAEKLAPGKKVEENEQESKPAGSKSDEQMQGANLGRKDF
WRKMFKSQSAASDTSSQSEQDTSECTTAHSGTTSDRRARSRSRRISLRKKLKLPIGNWLK
RSSLSGLADGVEDLLDISSVDRLSFIRQSSKVKFTSAVKLSEGGPGSGMENGRDEEENFF
KRLGCHSFDDHLSPNQDGGKSKNVVNLGAIRQGMKRFQFLLNCCEPGTIPDASILAAALD
LEAPVVARAALFLECARFVHRCNRGNWPEWMKGHHVNITKKGLSRGRSPIVGNKRNQKLQ
WNAAKLFYQWGDAIGVRLNELCHGESESPANLLGLIYDEETKRRLRKEDEEEDFLDDSKE
TPFTTRTPACTVNPSKCGCPFALKMAACQLLLEITTFLRETFSCLPRPRTEPLVDLESCR
LRLDPELDRHRYERKISFAGVLDENEDSKDSLHSSSHTLKSDAGVEEKKVPSRKIRIGSS
RLLQIKGTRSFQVKKGGSLSSIRRVGSLKSSKLSRQDSESEAEELQLSQSRDTVTDLEGS
PWSASEPSIEPEGMSNAGAEENYHRNMSWLHVMILLCNQQSFICTHVDYCHPHCYLHHSR
SCARLVRAIKLLYGDSVDSLRESSNISSVALRGKKQKECSDKSCLRTPSLKKRVSDANLE
GKKDSGMLKYIRLQVLLPGSEGFMELLTGRGLQTAYLLMFGTYNISWYSVGIKFLQLVMS
LSPAPLSLLIKAAPILTEEMYGDIQPAAWELLLSMDEHMAGAAVKVPEAVSDMLMSEFHH
PETVQRLNAVLKFHTLWRFRYQVWPRMEEGAQQIFKKSFSARAVSRSHQRAEHILKNLQQ
EEEKKRLGREASLITAIPITQEACYEPTCTPNSEPEEEVEEVTNLASRRLSVSPSCTSST
SHRNYSFRRGSVWSVRSAVSAEDEEHTTEHTPNHHVPQPPQAVFPACICAAVLPIVHLMS
DGEVREDGVAVSAVAQQVLWNCLIEDPSTVLRHFLEKLTISNRQDELMYMLRKLLLNIGD
FPAQTSHILFNYLVGLIMYFVRTPCEWGMDAISATLTFLWEVVGYVEGLFFKDLKQTMKK
EQCEVKLLVTASMPGTKTLVVHGQNECDIPTQLPVHEDTQFEALLKECLEFFNIPESQST
HYFLMDKRWNLIHYNKTYVRDIYPFRRSVSPQLNLVHMHPEKGQELIQKQVFTRKLEEVG
RVLFLISLTQKIPTAHKQSHVSMLQEDLLRLPSFPRSAIDAEFSLFSDPQAGKELFGLDT
LQKSLWIQLLEEMFLGMPSEFPWGDEIMLFLNVFNGALILHPEDSALLRQYAATVINTAV
HFNHLFSLSGYQWILPTMLQVYSDYESNPQLRQAIEFACHQFYILHRKPFVLQLFASVAP
LLEFPDAANNGPSKGVSAQCLFDLLQSLEGETTDILDILELVKAEKPLKSLDFCYGNEDL
TFSISEAIKLCVTVVAYAPESFRSLQMLMVLEALVPCYLQKLKRQTSQVETVPAAREEIA
ATAALATSLQALLYSVEVLTRENLHLLEEGQGIPREELDERIAREEFRRPRESLLNICTE
FYKHCGPRLKILQNLAGEPRVIALELLDVKSHMSVLGKGPRITSLCTRISSSYRDAISLE
IHAKGRICVSKGT

Fig. 4M Alignment of DP444 human amino acid sequence with sequences from other species (mouse, DP444 Mm; chicken, DP444 Gg; Zebrafish, DP444 Dr).

```
                   10        20        30        40        50        60
           ----:----|----:----|----:----|----:----|----:----|----:----|
DP444 Hs   MVKRKSSEGQEQDGGRGIPLPIQTFLWRQTSAFLRPKLGKQYEASCVSFERVLVENKLHG
DP444 Mm   MVKRKSSEGQEQDGGRGIPLPIQTFLWRQTSAFLRPKLGKQYEASCVSFERVLVENKLHG
DP444 Gg   ------------------------------TRPFTRP------------ERVLVENKLHG
DP444 Dr   MVKRKSLDDSDQENCRGIPFPIQTFLWRQTSAFLRPKLGKQYEASCVSFERVLVENKLHG

                   70        80        90       100       110       120
           ----:----|----:----|----:----|----:----|----:----|----:----|
DP444 Hs   LSPALSEAIQSISRWELVQAALPHVLHCTATLLSNRNKLGHQDKLGVAETKLLHTLHWML
DP444 Mm   LSPALSEAIQSISRWELVQAALPHVLHCTATLLSNRNKLGHQDKLGVAETKLLHTLHWML
DP444 Gg   LSPALSEAIQSISRWELVQAALPHVLHCTATLLSNRNKLGHQDKLGVAETKLLHTLHWML
DP444 Dr   LSPALTEAIQSISRWELVQAALPHVLHCTSILLSNRNKLGHQDKLGVAETKLLHTLHWML

                  130       140       150       160       170       180
           ----:----|----:----|----:----|----:----|----:----|----:----|
DP444 Hs   LEAPQDCNNER--PGGTDRGSSWGGSSSAFIHQVENQGSPGQPCQSSSNDSEENNRRKIF
DP444 Mm   LEAPQDCNNDQ--PGGTDRGSSWGGSSSAFIHQIENQGSPGQPCRSSSHDSEENNRRKTF
DP444 Gg   LEAPQDCSNDR--PGG-DRGSSWGGSSSAFIHQAENQGSPGHPRPSTTNDSDENNRRKPF
DP444 Dr   LEAAQECHQEPGLIHGWSGGS--SGSGSAYLQPHGNQGLTDRN--GSTPEETKYARAKLY

                  190       200       210       220       230       240
           ----:----|----:----|----:----|----:----|----:----|----:----|
DP444 Hs   QNSMATVELFVFLFAPLVHRIKESDLTFRLASGLVIWQPMWEHRQPGVSGFTALVKPIRN
DP444 Mm   QNSMATVELFVFLFAPLVHRIKESDLTFRLASGLVIWQPMWEHRQPEVSGFTALVKPIRN
DP444 Gg   QNSMATVELFVFLFAPLVHRIKESDLTFRLASGLVIWQPMWEHRQPEVSAFNALVKPIRN
DP444 Dr   HKNMATVELFVFLFAPLIHRIKESDLTFRLAQGLVIWQPMWEHRQPDVPAFSALIKPLRN

                  250       260       270       280       290       300
           ----:----|----:----|----:----|----:----|----:----|----:----|
DP444 Hs   IITAKRSSPINSQSRTCESPNQDAR-HLEGLQVVCETFQSDSIS-PKATISGCHRGNSFD
DP444 Mm   IITAKRSSPINSQSQTCESPNQDTRQQGEGLQVVSEALQSDSIS-PKATISGCHQGNSFD
DP444 Gg   IVTAKRSSPTNNQSVTCESLNLDSG-HTEGLQVVCETTLPDSVP-SKPTVSACHRGNSLE
DP444 Dr   IITAKRNSQMNNQCSPHDSSN------PCPAVVCESALSDSSSSPSNTGQSCRRGNSLE

                  310       320       330       340       350       360
           ----:----|----:----|----:----|----:----|----:----|----:----|
DP444 Hs   GSLSSQTSQERGPSHSRASLVIPPCQRSRYATYFDVAVLRCLLQPHWSEEGTQWSLMYYL
DP444 Mm   GSLSSQTSQERGPSHSRASLVIPPCQRSRYATYFDVAVLRCLLQPHWSEEGTQWSLMYYL
DP444 Gg   GSVSSQTSQERGTPHPRVSMVIPPCQKSRYATYFDVAVLRCLLQPHWSEEGTQWSLMYYL
DP444 Dr   M------------------------QRARYATYFDVAVLRCLMQPHWTEEGVHWALIYYL

                  370       380       390       400       410       420
           ----:----|----:----|----:----|----:----|----:----|----:----|
DP444 Hs   QRLRHMLEEKPEKPP--------EPDIP---------LLPRPRSSSMVAAAPSLVNTHKT
DP444 Mm   QRLRHMLEEKPEKTP--------DPDIP---------LLPRPRSSSMVAAAPSLVNTHKT
DP444 Gg   QRLRHMLQEKPEKPP--------EPEIT---------PLPRLRSSSMVAAAPSLVNTHKT
```

Fig. 4N

```
DP444 Dr   QRLRQILQITPLPRPRSSSMVAATPSLVNTHKTQPKNPPTRPRSSSMVAATPSLVNTHKT

                   430       440       450       460       470       480
           ----:----|----:----|----:----|----:----|----:----|----:----|
DP444 Hs   QDLTMKCNEEEKSLSSEAPSKVSLTNLRRSAVPDLSSDLGMNIFKKFKSRKEDRER--KG
DP444 Mm   QDLTMKCNEEEKSLSPEAPSKVSLTNLRRSAVPDLSSDLGMNIFKKFKSRKEDRER--KG
DP444 Gg   QDLTMKCNEEEKSLSTEAPSKVSLTNLRRPAVPDLSTDLGMNIFKKFKSRKEDRERERKG
DP444 Dr   QDMTLKCNEESRSLSSETPSKVSVTNLRRQAVPDLSSEMGMNIFKKFKNRREDRER--KG

                   490       500       510       520       530       540
           ----:----|----:----|----:----|----:----|----:----|----:----|
DP444 Hs   SIPFHHTGKKRPRRMGVPFLLHEDHLDVSPTRSTFSFGSFSGLGEDRRGIEKGGWQTTIL
DP444 Mm   SIPFHHTGKRRPRRMGVPFLLHEDHLDVSPTRSTFSFGSFSGLGEDRRGIEKGGWQTTIL
DP444 Gg   SIPFHHTGKKRQRRMGMPFLLHEDHLDVSPTRSTFSFGSFSGIGEDRRGIERGGWQTTIL
DP444 Dr   SIPFHHTGKKRQRRMGVPFLMHEDHLDVSPTRSTFSFGSFSGLGDDRRTLDRGGWPSTIN

                   550       560       570       580       590       600
           ----:----|----:----|----:----|----:----|----:----|----:----|
DP444 Hs   GKLTRRGSSDAATEMESLSARHSHSHHTLVSDLPDPSNSHGENTVKE-VRSQISTITVAT
DP444 Mm   GKLTRRGSSDAATEMESLSARHSHSHHTLVSDLPDHSNSHGENTVKE-VRSQISTITVAT
DP444 Gg   GKFTRRGSSDTATEMESLSARHSHSHHTLVSDMPDHSNSHGENTVKE-VRSQISTITVAT
DP444 Dr   GKLTRRGSSDTTGDVDSLGAKHFHSHH---NLPEHSNSHSENTIKEGVRSQISTITMAT

                   610       620       630       640       650       660
           ----:----|----:----|----:----|----:----|----:----|----:----|
DP444 Hs   FNTTLASFNVGYADFFNEHMRKLCNQVPIPEMPHEPLACANLPRSLTDSCINYSYLEDTE
DP444 Mm   FNTTLASFNVGYADFFSEHMRKLCSQVPIPEMPHEPLACANLPRSLTDSCINYSYLEDTE
DP444 Gg   FNTTLASFNVGYADFFSEHMRKLCNQVPIPEMPHEPLACANLPRSLTDSCINYSCLEDTD
DP444 Dr   FNTTVASFNVGYTDFFTEHIKKLCNPIPIPEMPCEPLACSNLPRSLTDSCINYTSLEDRD

                   670       680       690       700       710       720
           ----:----|----:----|----:----|----:----|----:----|----:----|
DP444 Hs   HIDGTNNFVHKNGMLDLSVVLKAVYLVLNRDISSRICDVALNIVECLLQLGVVPCVEKNR
DP444 Mm   HIDGTNNFVHKNGMLDLSVVLKAVYLVLNRDISSRICDVALNIVECLLQLGVVPCVEKNR
DP444 Gg   HIDGTNNFVHKNGMLDLSVNGKE-------------------------------------
DP444 Dr   TIEGTNNFILKNGMLDLAVRGKNYNRETIKE-----------------------------

                   730       740       750       760       770       780
           ----:----|----:----|----:----|----:----|----:----|----:----|
DP444 Hs   KKS
DP444 Mm   KKS
DP444 Gg   ---
DP444 Dr   ---
```

Fig. 5A-D. EXPRESSION OF DP810
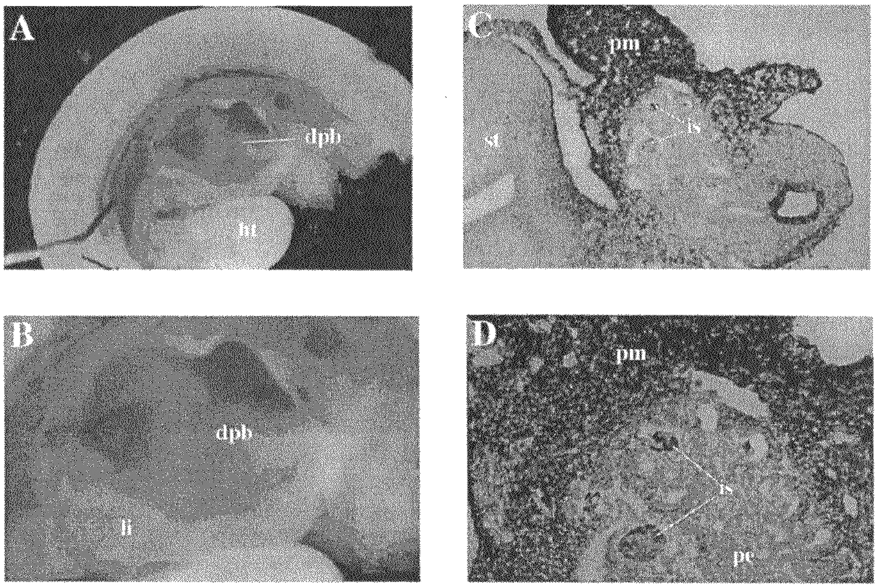

FIG. 6A: Nucleic acid sequence (SEQ ID NO: 17) encoding the polydom-like protein of chicken. The 3` untranslated region is underlined and the stop codon is in bold font.

GAATTCGGCACGAGGATCACCCACGTCATAGTACTCGGGGACAACTTCAACTGTGAGCACAAACA
TCACTTTGTCATGTGTAGAAGGCTACACTCTGGTGGGAGCAAGCACATCCACGTGCAAGGAGAGT
GGCGTTTGGATGCCAGAGTTTTCTGATGACATTTGCATTCCTGTGTCATGTGGGATCCCAGAATC
TCCAGAGCACGGATTTGTGGTTGGCACCAAATTCAGTTACAAAGATGTGGTTCTTTATAAATGTG
ATCCTGGCTACGAACTACAAGGTGATACAGAACGGACTTGCCAAGAAGACAAGCTTTGGAGTGGC
TCAGTGCCAACATGCAGAAGAGTATCTTGTGGCCCCCAGAGGTGATCGAAAATGGATCTGTTCA
AGGAGAAGAGTTCCTGTTTGGCAGCGAGGCTTTTTACAGCTGTGACCCTGGTTTCGAACTGCAGG
GACCAAGCCGAAGAATTTGCCACGTTGACAAGAAGTGGAGCCCCTCTGCTCCTGTGTGTAGGCGA
ATTACTTGCGGGCTGCCTCCTTCAATAGAAAAGCAGAGGCCATTTCTACAGGAAACACATACAA
AAGTAATGTAACCTTTGTGTGCAGCTCTGGTTACCACCTTGTTGGACCGCAGAATATCACATGTC
TTGCCAATGGGAGCTGGAGTAAGCCATTACCACTGTGTGAAGAGACCAGATGCAAACTGCCACTT
TCTTTGCTGAATGGGAAGGCAATTTATGAAAATAATACAGTTGGCAGTACTGTAGCATATTTCTG
CAAGAGCGGATACAGTTTGGAAGGAGAACCTACAGCAGAGTGCACAAGGGANNNNNNNNNNNNN
NTCCTTTGCCTCTCTGTAAACCAAACCCTTGTCCCGTGCCTTTCATAATCCCAGAGAATGCCCTT
CTCTCTGAGGTGGATTTTTACGTCGGGCAGAATGTGTCCATCAGGTGCAGGGAAGGCTACCAGTT
GAAAGGGCAGGCTGTGATCACTTGTAATGCTGATGAGACTTGGACTCCAACAACAGCTAAGTGTG
AAAAGATATCTTGCGGGCCCCCAGCTCACATAGAGAATGCTTTCATCCGTGGTAGCTTCTATCAG
TATGGAGATATGATCACCTACTCATGCTACAGTGGTTATATGCTGGAGGGACCCCTGCGGAGCAT
TTGCTTAGAAAATGGAACGTGGACAACACCACCTACATGCAAAGCTGTCTGTCGGTTCCCATGTC
AGAATGGTGGAGTCTGTGAGCGACCAAATGCCTGCTCGTGTCCAGATGGCTGGATGGGTCGTCTC
TGTGAAGAGCCAATATGCATTTTGCCATGTCTCAATGGAGGTCGCTGTGTGGCTCCTTACAAGTG
TGACTGCCCCCCTGGATGGACTGGATCGCGGTGCCATACAGCTGTTTGCCAGTCACCTTGCTTAA
ATGGTGGGAAGTGCATACGACCAAATCGATGTTACTGTCCCTCATCATGGACTGGACATGATTGC
TCAAGAAAACGGAAGGCTGGATTCTACCACTTCTAACAGCAGAGCAACAGTTTTACACTCAGAAA
CCTTTCTTCAGCCTAGACAGCGGGGCTCAGAATCTAATGCATTGTAAATCACATCCATTGCTTCC
CTTCCCCCCACCTCCTTTGTTTTGTATTTTATTTTGTGATATATTTTTTCTATACCTTTCAATTT
TTAAAGAAAACCTCTGTATTTTCCATTTACAAAAGTATTATCAAATATATGCTGCTATATACACA
CCATACACATACAAAAGTGAAGATCCCTACTGTTCACTGAGAAAGTGGCTGTGTACGGTGAAGTC
CCTCCCATTTCTTACACCCGGTAAGCTAATTAAAACATGCTATACTGCCAGCCATGATTAAACMS
AMtGYKKCMGTTCTGCTTATCATCTGCCAAAGCATACTGAAATCCAGCAACTTAATGGTAAGGAA
TAATTATGTAAAGCTAATTGAACCACCGAACTTTGCATTGGGCTTGTGTCATGGTTGTATAAATT
AGAAGTACATCTGATAAAGTCCCAATTGTAGCCAGAGTTCCTGGTGGACGTAAGTAGATTCTGTA
ATGTTCATTATGTGACATTAACGTCATTGGAAAGCGACTTAGATGGAAGGCAGTGGCAAGAATTT
TAGCCATCAGTAAAATACTCAAAAGCATGAAAGAGTTGAGACAATGTCTAGGCAATAACAGCCTC
TGAGGATTTTTGGCATACAGGCATTTCAGGTGTCATGATCAGTCTGGATAATCCAGAATGCAGCA
GCGGACAGCACAGACCACTGAAAACTTCCCCCTGGTAATGGAACTCACCACTACTTGCCTGCAAC

Fig. 6B

CAGTAGCCCTTTCCTGTGTGATGATCAAATACACATCCAACATCCTCCTGCCAGGCAAATGTTTT
TGAGACATGGGGTTTGGGTCCCAATGtTTTGGCCCTGCAGTAGGGAGAGAAGGTGAAGCTTTGCT
GTTTGCTTGCAGAAGAGTGGTATTTATGTTATGCTGAACCCTCAGAGAACTGGAAAAGGCCTCTC
TTGTGTACATGCACAGGCAGAAATACCTAGCTGAGTAAGAAATGCTGAGAGCACACATGCTGTCC
GATTTCTCTTTCGCACATTGTTGATCCCAGTGCATCTGAGAGTCACACATGGTTGAGTGCCATCA
TTCAGTTGTGCTCTAATGAGCTGAGATGCTGAGATTTACCGATGGGTACGTGGTGTGGCGGAATT
ACAAGGTGGAAATCCCAGTCATGTGCTGAGGTCAAATGTTTGCTAATTATCATCAGATAGTAATG
AAGTCTAGTCTGTGAAAGAAGATTTTAGAGTGAGAACCATTGATCGGGAGCTCCATTTTTCCCAG
TAGCAGCAGAAAAGCATGACTGTCAGCCCACACTAGGAAAGAAGAAGGAATATGCTCTACACTCT
GCAGCATTACTGCGTAGTTACCCTCGGGGTCATGAGCGTGCACACGCTGCCCCCACCTCCCCCCT
TCCCTCTTTATAAATATACATTCCCTTTATGAATGCATGATAGGACAATAAAAGGAGCTAATGGA
GGGACTAGGGCGCTAGTGAAGACTGACACATAGCTAATGGCTGTTAACCCAAGACCAGAAATGGG
GAACAAACAAGTGAAGCTGTGAACCAGGAAAAGCTGGAAGAAAAACAAACAGGTGAAGAATATTT
GTCAAGGGACGAGCTGAATTCGAATGCAGATTCCTTCCCACTGGGAGCTGCAACCGGCTGAAGAG
TTGTTCTTTCAACTCCCGTAAATATATTTTTTCTGATGGATTCTGCTGACATGTACCAACAGCCA
TCAGTGTTTACAGCTTTGGTTCAAGTTAGCATTCAGTAAATAATAACACGTTTCAACCCACGGTC
ACTGCCATGTGTAGGCACTTTGTTCCCTGACTCCTGCTGCTGTGCACAGTGGGGTGTACAGATGC
TGTAGTGAGCAGCTCGGGATACCTGAAGGGAAAGAGTGCATCAGTGGGAGAAGTGGATTTTTATT
TATATGTCATTCTCATCTTTTACAAAGTAGTCCCATTTTCAGTGTGCTTCTCTGGTACGTGCCCT
CACAGCCCTGGCAATCTCCAGAGCAGAGCAGCAGTGCTTTGGAAGGCGAGCAGGGCTGGCAGGAG
ACTGCTGAGCCTTGGGGGCGAGGGCCGGCTTTTAGCACTGCAGCTTCACACTAGTGACTAGTACA
TGGAGTTTGGGGATATACTCAGTCAATACGTTTCATAAGCTGATGTGGTAGAAAGAGTAGCTGAA
ACTATAGGCTGTTATATTAGTGCTGTGTATGATGCTTTGATACTTGCTGGAATATTATCCCTTCC
CCATTCTGTGCGGTATTGTCATTTATGTCACTGCTTGTTGTGTGTTTTAAAGGACTTCTGTGTGA
TGCACTTTACACTGTAAATAAAGTTGCACCCTGTTTAGTACCWAAAAAAAAAAAAAAAAAAA

Fig. 6C Amino acid sequence of chicken DP810 (SEQ ID NO: 18).

YSGTTSTVSTNITLSCVEGYTLVGASTSTCKESGVWMPEFSDDICIPVSCGIPESPEHGFVVGTK
FSYKDVVLYKCDPGYELQGDTERTCQEDKLWSGSVPTCRRVSCGPPEVIENGSVQGEEFLFGSEA
FYSCDPGFELQGPSRRICHVDKKWSPSAPVCRRITCGLPPSIEKAEAISTGNTYKSNVTFVCSSG
YHLVGPQNITCLANGSWSKPLPLCEETRCKLPLSLLNGKAIYENNTVGSTVAYFCKSGYSLEGEP
TAECTRNNNNNNPLPLCKPNPCPVPFIIPENALLSEVDFYVGQNVSIRCREGYQLKGQAVITCNA
DETWTPTTAKCEKISCGPPAHIENAFIRGSFYQYGDMITYSCYSGYMLEGPLRSICLENGTWTTP
PTCKAVCRFPCQNGGVCERPNACSCPDGWMGRLCEEPICILPCLNGGRCVAPYKCDCPPGWTGSR
CHTAVCQSPCLNGGKCIRPNRCYCPSSWTGHDCSRKRKAGFYHF

Fig. 6D : Nucleic sequence of Homo sapiens likely ortholog of mouse polydom (POLYDOM), mRNA encoding a peptide homologous to amino acids 319-866 of mouse polydom (GenBank Accession Number NM_024500.1; SEQ ID NO: 19).

TATGAATGCACAGCTTGCCCATCGGGGACATACAAACCTGAAGCCTCACCAGGAGGAATCAGCAG
TTGCATTCCATGTCCCGATGAAAATCACACCTCTCCACCTGGAAGCACATCCCCTGAAGACTGTG
TCTGCAGAGAGGGATACAGGGCATCTGGCCAGACCTGTGAACTTGTCCACTGCCCTGCCCTGAAG
CCTCCCGAAAATGGTTACTTTATCCAAAACACTTGCAACAACCACTTCAATGCAGCCTGTGGGGT
CCGATGTCACCCTGGATTTGATCTTGTGGGAAGCAGCATCATCTTATGTCTACCCAATGGTTTGT
GGTCCGGTTCAGAGAGCTACTGCAGAGTAAGAACATGTCCTCATCTCCGCCAGCCGAAACATGGC
CACATCAGCTGTTCTACAAGGGAAATGTTATATAAGACAACATGTTTGGTTGCCTGTGATGAAGG
GTACAGACTAGAAGGCAGTGATAAGCTTACTTGTCAAGGAAACAGCCAGTGGGATGGGCCAGAAC
CCCGGTGTGTGGAGCGCCACTGTTCCACCTTTCAGATGCCCAAAGATGTCATCATATCCCCCCAC
AACTGTGGCAAGCAGCCAGCCAAATTTGGGACGATCTGCTATGTAAGTTGCCGCCAAGGGTTCAT
TTTATCTGGAGTCAAAGAAATGCTGAGATGTACCACTTCTGGAAAATGGAATGTCGGAGTTCAGG
CAGCTGTGTGTAAAGACGTGGAGGCTCCTCAAATCAACTGTCCTAAGGACATAGAGGCTAAGACT
CTGGAACAGCAAGATTCTGCCAATGTTACCTGGCAGATTCCAACAGCTAAAGACAACTCTGGTGA
AAAGGTGTCAGTCCGCGTTCATCCAGCTTTCACCCCACCTTACCTTTTCCCAATTGGAGATGTTG
CTATCGTATACACGGCAACTGACCTATCCGGCAACCAGGCCAGCTGCATTTTCCATATCAAGGTT
ATTGATGCAGAACCACCTGTCATAGACTGGTGCAGATCTCCACCTCCCGTCCAGGTCTCGGAGAA
GGTACATGCCGCAAGCTGGGATGAGCCTCAGTTCTCAGACAACTCAGGGGCTGAATTGGTCATTA
CCAGAAGTCATACACAAGGAGACCTTTTCCCTCAAGGGGAGACTATAGTACAGTATACAGCCACT
GACCCCTCAGGCAATAACAGGACATGTGATATCCATATTGTCATAAAAGGTTCTCCCTGTGAAAT
CCCATTCACACCTGTAAATGGGGATTTTATATGCACTCCAGATAATACTGGAGTCAACTGTACAT
TAACTTGCTTGGAGGGCTATGATTTCACAGAAGGGTCTACTGACAAGTATTATTGTGCTTATGAA
GATGGCGTCTGGAAACCAACATATACCACTGAATGGCCAGACTGTGCCAAAAAACGTTTTGCAAA
CCACGGGTTCAAGTCCTTTGAGATGTTCTACAAAGCAGCTCGTTGTGATGACACAGATCTGATGA
AGAAGTTTTCTGAAGCATTGGAGACGACCCTGGGAAAAATGGTCCCATCATTTTGTAGTGATGCA
GAGGACATTGACTGCAGACTGGAGGAGAACCTGACCAAAAAATATTGCCTAGAATATAATTATGA
CTATGAAAATGGCTTTGCAATTGGTAATTAAATTCTGTGGCATCGGTAGTTGGCAAGACTAATCT
GCAAAATAAGAATAATTCCAGAAAAGTGAGGCAAACTAGAAACATTAACTTCTATTAATTTATTC
ATCAAGTATTTTAGGATGGCTAAATAATTTGATAATGTGCTGAAAGATCATTAAGGTTATATCAA
ATTTTAGTAACAAATAAATTATTTAAAATTATTTGCCAGGATTCTTAAAAATGACAAAAACTAAG
AAAACTAAGTCACATATGCTGGTAAAATTCAAATGTTGATGTATCCTAAAAGAGAATAGTAATAA
AGTCCTAACAGCAACTTTT

Fig. 6E Amino acid sequence of the human likely ortholog of mouse polydom (GenBank Accession Number NP_078776.1; SEQ ID NO: 20)

MLYKTTCLVACDEGYRLEGSDKLTCQGNSQWDGPEPRCVERHCSTFQMPKDVIISPHNCGKQPAK
FGTICYVSCRQGFILSGVKEMLRCTTSGKWNVGVQAAVCKDVEAPQINCPKDIEAKTLEQQDSAN
VTWQIPTAKDNSGEKVSVRVHPAFTPPYLFPIGDVAIVYTATDLSGNQASCIFHIKVIDAEPPVI
DWCRSPPPVQVSEKVHAASWDEPQFSDNSGAELVITRSHTQGDLFPQGETIVQYTATDPSGNNRT
CDIHIVIKGSPCEIPFTPVNGDFICTPDNTGVNCTLTCLEGYDFTEGSTDKYYCAYEDGVWKPTY
TTEWPDCAKKRFANHGFKSFEMFYKAARCDDTDLMKKFSEALETTLGKMVPSFCSDAEDIDCRLE
ENLTKKYCLEYNYDYENGFAIGN

Fig. 7A-B. Expression of DP685/autotaxin
DP685
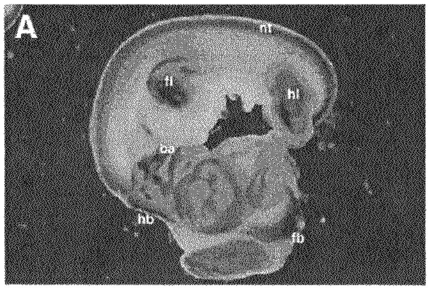
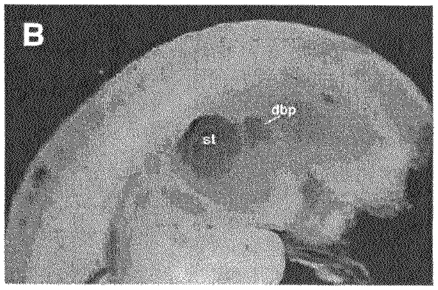

Fig. 7C. Quantitative analysis of DP685 expression in human abdominal adipocyte cells.
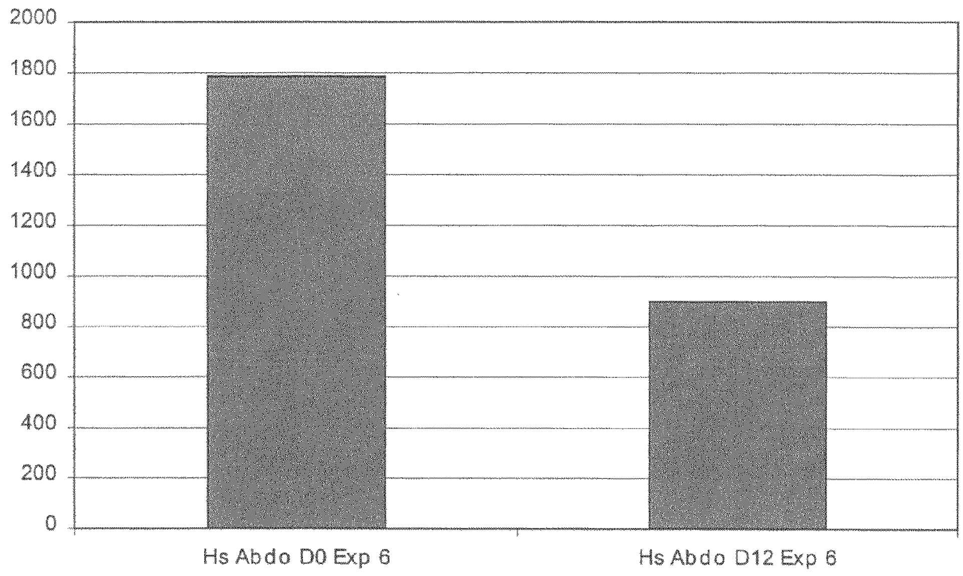

FIG. 8: DP685 sequence

FIG. 8A: Nucleic acid sequence (SEQ ID NO: 21) encoding the DP685-like protein of chicken.

CTTAAGTAGAGGAGACTGTTGCACTAATTACCAGGTCGTTTGCAAAGGAGAAACCCACTGGGTCG
ATGATGACTGTGAAGAGATAAAAACTCCTGAATGTCCAGCAGGCTTTGTTCGTCCTCCTTTGATC
ATCTTCTCTGTTGATGGTTTCCGTGCATCATATATGAAGAAAGGGAACAAGGTCATGCCCAATAT
TGAAAAGCTGAGATCTTGTGGAACACATTCTCCTTACATGAGGCCGGTCTACCCTACAAAAACCT
TCCCCAACTTGTACACCCTTGCTACTGGACTCTATCCTGAATCACATGGAATCGTTGGCAATTCA
ATGTATGACCCAGTGTTTGATGCCAGCTTCAGTCTTCGAGGGCGAGAGAAATTCAATCACAGATG
GTGGGGAGGTCAACCAATTTGGATTACTGCAGCCAAGCAAGGGGTGAAAGCTGGCACATTCTTCT
GGTCTGTTGTCATCCCCCACGAGCGTAGAATACTAACAATACTGCAGTGGCTGACCCTTCCGGAT
AACGAAAGGCCTTATGTTTATGCTTTCTACTCTGAGCAACCAGATGCTGCTGGCCACAGATATGG
TCCTTTCAACTCAGAGATGATGGTAAATCCCCTGAGAGAGATTGACAAGACAGTAGGACAACTAA
TGGATGGACTGAAACAGCTGAAACTGCATCGATGTGTCAATGTCATATTTGTTGGTGATCATGGG
ATGGAAGATACTACTTGTGAAAGAACTGAATTTTTGAGCAACTACCTGACCAACGTGGAAGATAT
CATTCTGCTGCCTGGATCTTTAGGGAGAATTCGCCCTAGGTCTAGCAATAACCTGAAATATGACC
CCAAAGTGATTGTTGCCAACCTTACATGCAGGAAGCCAGACCAGCACTTTAAGCCATACTTGAAG
CATCACCTTTCTAAACGCTTGCACTATGCTTACAATAGGCGAATTGAGGATGTCCATTTACTGGT
TGAGCGCAAGTGGCATGTAGCAAGGAAAGCTGTGGATGTTTACAAGAAACCAACAGGAAAGTGTT
TCTTCCATGGAGACCATGGCTATGACAACAAGATAAACAGCATGCAGACTGTCTTCATAGGTTAT
GGACCTACATTCAAATACAAGACCAAAGTACCGCCTTTTGAAAACATTGAACTTTACAATGTCAT
GTGTGATCTGCTTGGATTAAAGCCTGCTCCCAATAATGGTACCCACGGAAGTTTGAATCACCTGC
TAAGAGCCAATGTTTATAAACCAACTGTGCCAGATGAAGTTGCTAAGCCACTTTATCCTGTAGCA
CTACCTTCTGCATCAGATTTTGATATAGGATGTACATGTGATGATAAGAACAAGTTGGATGAACT
CAACAAGCGCTTTCATGTCAAGGGAACGGAAGAGAAGCATCTTCTGTACGGGCGCCCTGCAGTGC
TGTACCGCACGAAGTACAATATCTTGCACCACCATGACTTTGAAAGTGGCTACAGTGAAACATTC
CTGATGCCTCTCTGGACATCCTACACTATTTCCAAACAGGCAGAGGTATCCGGTGTCCCAGAACA
CCTGGCCAGCTGCGTCAGGCCCGATCTCCGCATATCTCCAGGAAACAGCCAGAGCTGCTCAGCCT
ACAGAGGTGACAAGCAGCTCTCCTACAGCTTCCTCTTCCCTCCTCAACTAAGTTCCTCTGCAGAA
GCAAAGTATGATGCTTTTCTAATAACAAATATCATTCCAATGTATCCTGCTTTCAAAAAGGTATG
GAACTATTTCCAAAGGGTTTTAGTGAAGAGATATGCCACTGAACGAAATGGAGTCAATGTTATAA
GTGGACCAATCTTTGACTATGACTATGATGGTTTACATGACACACCTGAAAAAATCAAACAGTTT
GTGGAAGGCAGTGCCATCCCTGTTCCTACTCATTACTATGCCATCATAACCAGCTGTTTAGATTT
CACTCAGCCAGCCGACAAGTGTGATGGACCACTCTCTGTTCTCTCGTACATCCTTCCCCACCGGC
CTGACAACGATGAGAGCTGCAATAGCATGGAAGATGAATCAAAGTGGGTTGAAGATCTTCTTAAG
ATGCACACTGCACGGGTGCGGGACATTGAGCAGCTCACAAGCTTGGACTTCTTCCGAAAGACGAG
TCGCAGCTACACAGAAATCCTCTCCCTAAAGACATACCTGCATACATTTGAAAGTGAAATTTAGC
TTTCTAACCTTGCTCAGTGCATTCTTTTATCAACTGGTGTATATTTTTATATTGGTTTTATATTT
ATTAATTTGAAACCAGGACATTAAAAATATTAGTATTTTAATCTTGTATCAAATCTTAAATATTA
AACCCTTGTGTCATTTGTTTTGTTTCTCTAATGTTTAATATAGGTATGTCTCTTGGTTTATTTAG
TAGCGCTTGTAATACTGCAGCTTAAGTCCTTACTCCAAGCTTTTATCTGGTGCTGCAGAATTTGA
TACGTGATTCGAGGAAATATTAATTTCCCATGCTCCTTTACCACACTTTTAGTCCTGTACTGTGT
ATCAAAATACTGAACATGTAAAATTACATTCATTTACTGTTGACTATGTGACAGACATATTTAAA
CCCTATAGACAAATAGCATCTTAAATATAATAAACCACACATTCAGTTTTNAAAAAAAAAAAAAA
AAAAAAAAAAAAAAAAAAAAAAAAAAA

FIG. 8B: Amino acid sequence of chicken DP683 (SEQ ID NO: 22).

LSRGDCCTNYQVVCKGETHWVDDDCEEIKTPECPAGFVRPPLIIFSVDGFRASYMKKGNKVMPNI
EKLRSCGTHSPYMRPVYPTKTFPNLYTLATGLYPESHGIVGNSMYDPVFDASFSLRGREKFNHRW
WGGQPIWITAAKQGVKAGTFFWSVVIPHERRILTILQWLTLPDNERPYVYAFYSEQPDAAGHRYG
PFNSEMMVNPLREIDKTVGQLMDGLKQLKLHRCVNVIFVGDHGMEDTTCERTEFLSNYLTNVEDI
ILLPGSLGRIRPRSSNNLKYDPKVIVANLTCRKPDQHFKPYLKHHLSKRLHYAYNRRIEDVHLLV
ERKWHVARKAVDVYKKPTGKCFFHGDHGYDNKINSMQTVFIGYGPTFKYKTKVPPFENIELYNVM
CDLLGLKPAPNNGTHGSLNHLLRANVYKPTVPDEVAKPLYPVALPSASDFDIGCTCDDKNKLDEL
NKRFHVKGTEEKHLLYGRPAVLYRTKYNILHHHDFESGYSETFLMPLWTSYTISKQAEVSGVPEH
LASCVRPDLRISPGNSQSCSAYRGDKQLSYSFLFPPQLSSSAEAKYDAFLITNIIPMYPAFKKVW
NYFQRVLVKRYATERNGVNVISGPIFDYDYDGLHDTPEKIKQFVEGSAIPVPTHYYAIITSCLDF
TQPADKCDGPLSVLSYILPHRPDNDESCNSMEDESKWVEDLLKMHTARVRDIEQLTSLDFFRKTS
RSYTEILSLKTYLHTFESEI

FIG. 8C: Nucleic sequence of Homo sapiens autotaxin-t (atx-t) gene (GenBank Accession Number L46720.1; SEQ ID NO: 23).

AGTGCACTCCGTGAAGGCAAAGAGAACACGCTGCAAAAGGCTTTCCAATAATCCTCGACATGGCA
AGGAGGAGCTCGTTCCAGTCGTGTCAGATAATATCCCTGTTCACTTTTGCCGTTGGAGTCAATAT
CTGCTTAGGATTCACTGCACATCGAATTAAGAGAGCAGAAGGATGGGAGGAAGGTCCTCCTACAG
TGCTATCAGACTCCCCCTGGACCAACATCTCCGGATCTTGCAAGGGCAGGTGCTTTGAACTTCAA
GAGGCTGGACCTCCTGATTGTCGCTGTGACAACTTGTGTAAGAGCTATACCAGTTGCTGCCATGA
CTTTGATGAGCTGTGTTTGAAGACAGCCCGTGCGTGGGAGTGTACTAAGGACAGATGTGGGGAAG
TCAGAAATGAAGAAAATGCCTGTCACTGCTCAGAGGACTGCTTGGCCAGGGGAGACTGCTGTACC
AATTACCAAGTGGTTTGCAAAGGAGAGTCGCATTGGGTTGATGATGACTGTGAGGAAATAAAGGC
CGCAGAATGCCCTGCAGGGTTTGTTCGCCCTCCATTAATCATCTTCTCCGTGGATGGCTTCCGTG
CATCATACATGAAGAAAGGCAGCAAAGTCATGCCTAATATTGAAAAACTAAGGTCTTGTGGCACA
CACTCTCCCTACATGAGGCCGGTGTACCCAACTAAAACCTTTCCTAACTTATACACTTTGGCCAC
TGGGCTATATCCAGAATCACATGGAATTGTTGGCAATTCAATGTATGATCCTGTATTTGATGCCA
CTTTTCATCTGCGAGGGCGAGAGAAATTTAATCATAGATGGTGGGGAGGTCAACCGCTATGGATT
ACAGCCACCAAGCAAGGGGTGAAAGCTGGAACATTCTTTTGGTCTGTTGTCATCCCTCACGAGCG
GAGAATATTAACCATATTGCAGTGGCTCACCCTGCCAGATCATGAGAGGCCTTCGGTCTATGCCT
TCTATTCTGAGCAACCTGATTTCTCTGGACACAAATATGGCCCTTTCGGCCCTGAGATGACAAAT
CCTCTGAGGGAAATCGACAAAATTGTGGGGCAATTAATGGATGGACTGAAACAACTAAAACTGCA
TCGGTGTGTCAACGTCATCTTTGTCGGAGACCATGGAATGGAAGATGTCACATGTGATAGAACTG
AGTTCTTGAGTAATTACCTAACTAATGTGGATGATATTACTTTAGTGCCTGGAACTCTAGGAAGA
ATTCGATCCAAATTTAGCAACAATGCTAAATATGACCCCAAAGCCATTATTGCCAATCTCACGTG
TAAAAAACCAGATCAGCACTTTAAGCCTTACTTGAAACAGCACCTTCCCAAACGTTTGCACTATG
CCAACAACAGAAGAATTGAGGATATCCATTTATTGGTGGAACGCAGATGGCATGTTGCAAGGAAA
CCTTTGGATGTTTATAAGAAACCATCAGGAAAATGCTTTTTCCAGGGAGACCACGGATTTGATAA
CAAGGTCAACAGCATGCAGACTGTTTTTGTAGGTTATGGCCCAACATTTAAGTACAAGACTAAAG
TGCCTCCATTTGAAAACATTGAACTTTACAATGTTATGTGTGATCTCCTGGGATTGAAGCCAGCT
CCTAATAATGGGACCCATGGAAGTTTGAATCATCTCCTGCGCACTAATACCTTCAGGCCAACCAT
GCCAGAGGAAGTTACCAGACCCAATTATCCAGGGATTATGTACCTTCAGTCTGATTTTGACCTGG
GCTGCACTTGTGATGATAAGGTAGAGCCAAAGAACAAGTTGGATGAACTCAACAAACGGCTTCAT
ACAAAAGGGTCTACAGAAGAGAGACACCTCCTCTATGGGCGACCTGCAGTGCTTTATCGGACTAG
ATATGATATCTTATATCACACTGACTTTGAAAGTGGTTATAGTGAAATATTCCTAATGCCACTCT
GGACATCATATACTGTTTCCAAACAGGCTGAGGTTTCCAGCGTTCCTGACCATCTGACCAGTTGC
GTCCGGCCTGATGTCCGTGTTTCTCCGAGTTTCAGTCAGAACTGTTTGGCCTACAAAAATGATAA
GCAGATGTCCTACGGATTCCTCTTTCCTCCTTATCTGAGCTCTTCACCAGAGGCTAAATATGATG
CATTCCTTGTAACCAATATGGTTCCAATGTATCCTGCTTTCAAACGGGTCTGGAATTATTTCCAA
AGGGTATTGGTGAAGAAATATGCTTCGGAAAGAAATGGAGTTAACGTGATAAGTGGACCAATCTT
CGACTATGACTATGATGGCTTACATGACACAGAAGACAAAATAAAACAGTACGTGGAAGGCAGTT
CCATTCCTGTTCCAACTCACTACTACAGCATCATCACCAGCTGTCTGGATTTCACTCAGCCTGCC
GACAAGTGTGACGGCCCTCTCTCTGTGTCCTCCTTCATCCTGCCTCACCGGCCTGACAACGAGGA
GAGCTGCAATAGCTCAGAGGACGAATCAAAATGGGTAGAAGAACTCATGAAGATGCACACAGCTA
GGGTGCGTGACATTGAACATCTCACCAGCCTGGACTTCTTCCGAAAGACCAGCCGCAGCTACCCA
GAAATCCTGACACTCAAGACATACCTGCATACATATGAGAGCGAGATTTAACTTTCTGAGCATCT
GCAGTACAGTCTTATCAACTGGTTGTATATTTTTATATTGTTTTTGTATTTATTAATTTGAAACC
AGGACATTAAAAATGTTAGTATTTTAATCCTGTACCAAATCTGACATATTATGCCTGAATGACTC
CACTGTTTTTCTCTAATGCTTGATTTAGGTAGCCTTGTGTTCTGAGTAGAGCTTGTAATAAATAC
TGCAGCTTGAGTTTTTAGTGGAAGCTTCTAAATGGTGCTGCAGATTTGATATTTGCATTGAGGAA
ATATTAATTTTCCAATGCACAGTTGCCACATTTAGTCCTGTACTGTATGGAAACACTGATTTTGT
AAAGTTGCCTTTATTTGCTGTTAACTGTTAACTATGACAGATATATTTAAGCCTTATAAACCAAT
CTTAAACATAATAAATCACACATTCAGTTTTTCTGGTAAAAAAAAAAAAAAAA

FIG. 8D. Amino acid sequence of the human autotaxin-t (GenBank Accession Number AAB00855.1; SEQ ID NO: 24)

MARRSSFQSCQIISLFTFAVGVNICLGFTAHRIKRAEGWEEGPPTVLSDSPWTNISGSCKGRCFE
LQEAGPPDCRCDNLCKSYTSCCHDFDELCLKTARAWECTKDRCGEVRNEENACHCSEDCLARGDC
CTNYQVVCKGESHWVDDDCEEIKAAECPAGFVRPPLIIFSVDGFRASYMKKGSKVMPNIEKLRSC
GTHSPYMRPVYPTKTFPNLYTLATGLYPESHGIVGNSMYDPVFDATFHLRGREKFNHRWWGGQPL
WITATKQGVKAGTFFWSVVIPHERRILTILQWLTLPDHERPSVYAFYSEQPDFSGHKYGPFGPEM
TNPLREIDKIVGQLMDGLKQLKLHRCVNVIFVGDHGMEDVTCDRTEFLSNYLTNVDDITLVPGTL
GRIRSKFSNNAKYDPKAIIANLTCKKPDQHFKPYLKQHLPKRLHYANNRRIEDIHLLVERRWHVA
RKPLDVYKKPSGKCFFQGDHGFDNKVNSMQTVFVGYGPTFKYKTKVPPFENIELYNVMCDLLGLK
PAPNNGTHGSLNHLLRTNTFRPTMPEEVTRPNYPGIMYLQSDFDLGCTCDDKVEPKNKLDELNKR
LHTKGSTEERHLLYGRPAVLYRTRYDILYHTDFESGYSEIFLMPLWTSYTVSKQAEVSSVPDHLT
SCVRPDVRVSPSFSQNCLAYKNDKQMSYGFLFPPYLSSSPEAKYDAFLVTNMVPMYPAFKRVWNY
FQRVLVKKYASERNGVNVISGPIFDYDYDGLHDTEDKIKQYVEGSSIPVPTHYYSIITSCLDFTQ
PADKCDGPLSVSSFILPHRPDNEESCNSSEDESKWVEELMKMHTARVRDIEHLTSLDFFRKTSRS
YPEILTLKTYLHTYESEI

FIG. 8S: Nucleic sequence of Mus musculus, ectonucleotide pyrophosphatase/phosphodiesterase 2, clone MGC:6865 (GenBank Accession Number BC003264.1; SEQ ID NO: 25).

CCCACGCGTCCGCCCACGCGTCCGGAGAACACCCTGCAGAGGTTTTCCAAGAATCCCTCGGCATG
GCAAGACAAGGCTGTTTCGGGTCATACCAGGTAATATCCTTGTTCACTTTTGCCATCGGCGTCAA
TCTCTGCTTAGGATTCACAGCAAGTCGAATTAAGAGGGCCGAATGGGATGAAGGACCTCCCACAG
TGTTATCTGACTCTCCATGGACCAACACATCTGGATCCTGCAAAGGTAGATGCTTTGAGCTTCAA
GAGGTTGGACCTCCTGACTCTCGGTGTGACAACCTATGTAAGAGCTACAGCAGCTGCTGCCATGA
TTTTGATGAGCTCTGTTTGAAAACAGCTCGAGGCTGGGAGTGCACCAAAGACAGATGTGGGGAAG
TACGAAATGAGGAAAATGCCTGTCACTGCTCAGAAGACTGCTTGTCCCGGGGAGACTGCTGTACC
AACTATCAAGTGGTCTGCAAAGGAGAATCACACTGGGTAGATGATGACTGTGAAGAAATAAGAGT
CCCTGAATGCCCTGCAGGGTTTGTCCGCCCTCCGTTAATCATCTTCTCTGTGGATGGATTCCGTG
CATCGTACATGAAGAAAGGCAGCAAGGTTATGCCCAACATTGAGAAACTGCGGTCCTGTGGCACC
CATGCTCCCTACATGAGGCCTGTGTACCCTACAAAAACCTTCCCTAATCTGTATACGCTGGCCAC
TGGTTTATATCCAGAATCCCATGGAATCGTTGGCAATTCAATGTATGACCCTGTCTTTGATGCTA
CTTTCCATCTTCGAGGGCGAGAGAAGTTTAACCATAGATGGTGGGGAGGCCAACCGCTATGGATT
ACAGCCACCAAGCAAGGGGTGAGAGCCGGGACATTCTTTTGGTCTGTGAGCATCCCTCACGAGCG
GAGAATCCTAACTATCCTTCAGTGGCTTTCCCTGCCAGACAATGAGAGGCCTTCAGTTTATGCCT
TCTACTCCGAGCAGCCTGATTTTTCTGGACACAAGTACGGCCCTTTTGGCCCTGAGATGACAAAT
CCTCTGAGGGAGATTGACAAGACCGTGGGGCAGTTAATGGACGGACTGAAACAACTCAAGCTGCA
CCGTTGTGTGAATGTTATCTTTGTTGGAGACCATGGAATGGAAGACGTGACATGTGACAGAACTG
AGTTCTTGAGCAACTATCTGACTAACGTGGATGATATTACTTTAGTACCTGGAACTCTAGGAAGA
ATTCGACCCAAGATTCCCAATAATCTTAAATATGACCCTAAAGCCATTATTGCTAACCTCACGTG
TAAAAAACCAGATCAGCACTTTAAGCCTTACATGAAACAGCACCTTCCCAAACGTTTGCACTATG
CCAACAATCGGAGAATCGAGGATCTCCATTTATTGGTGGAACGCAGATGGCATGTTGCAAGGAAA
CCTTTGGACGTTTATAAGAAGCCGTCAGGAAAATGTTTTTTCCAGGGTGACCACGGCTTTGATAA
CAAGGTCAATAGCATGCAGACTGTTTTTGTAGGTTATGGCCCAACTTTTAAGTACAGGACTAAAG
TGCCTCCATTTGAAAACATTGAACTTTATAATGTTATGTGCGATCTCCTAGGCTTGAAGCCAGCT
CCCAATAATGGAACACATGGAAGTTTGAATCACCTGCTACGCACAAATACCTTTAGGCCAACCCT
ACCAGAGGAAGTCAGCAGACCCAATTACCCAGGGATTATGTACCTTCAGTCTGATTTTGACCTGG
GCTGCACCTGTGATGATAAGGTAGAGCCAAAGAACAAATTGGAAGAACTAAATAAACGCCTTCAT
ACCAAAGGATCTACAGAAGAGAGACATCTCCTGTATGGACGACCTGCAGTGCTTTATCGGACTAG
CTATGATATCTTATACCATACGGACTTTGAAAGTGGTTACAGTGAAATATTCTTAATGCCTCTCT
GGACTTCTTATACCATTTCTAAGCAGGCTGAGGTCTCTAGCATCCCAGAGCACCTGACCAACTGT
GTTCGCCCTGATGTCCGTGTATCTCCTGGATTCAGTCAGAACTGTTTAGCCTATAAAAATGATAA
ACAGATGTCCTATGGATTCCTTTTTCCTCCCTATCTGAGCTCTTCCCCAGAAGCGAAATATGATG
CATTCCTTGTAACCAACATGGTTCCAATGTACCCTGCCTTCAAACGTGTTTGGACTTATTTCCAA
AGGGTCTTGGTGAAGAAATATGCGTCAGAAAGGAATGGGGTCAACGTAATAAGTGGACCGATCTT
TGACTACAATTACGATGGCTTACGTGACATTGAGGATGAAATTAAACAGTATGTGGAAGGCAGCT
CTATTCCTGTCCCTACCCACTACTACAGCATCATCACCAGCTGCCTGGACTTCACTCAGCCTGCA
GACAAGTGTGATGGTCCTCTCTCTGTGTCTTCTTTCATCCTTCCTCACCGACCTGACAATGATGA
GAGCTGTAATAGTTCCGAGGATGAGTCGAAGTGGGTAGAGGAACTCATGAAGATGCACACAGCTC
GGGTGAGGGACATCGAGCATCTCACCGGTCTGGATTTCTACCGGAAGACTAGCCGTAGCTATTCG
GAAATTCTGACCCTCAAGACATACCTGCATACATATGAGAGCGAGATTTAACTTCCTGGGCCTGG
GCAGTGTAGTCTTAGCAACTGGTGTATATTTTTATATGGTGTTTGTATTTATTAATTTGAAACCA
GGACATAAACAAACAAAGAAACAAATGAAAAAAAAAAAAAA

FIG. 8F. Amino acid sequence of the mouse ectonucleotide pyrophosphatase/phosphodiesterase 2 (GenBank Accession Number AAH03264.1; SEQ ID NO: 26)

MARQGCFGSYQVISLFTFAIGVNLCLGFTASRIKRAEWDEGPPTVLSDSPWTNTSGSCKGRCFEL
QEVGPPDCRCDNLCKSYSSCCHDFDELCLKTARGWECTKDRCGEVRNEENACHCSEDCLSRGDCC
TNYQVVCKGESHWVDDDCEEIRVPECPAGFVRPPLIIFSVDGFRASYMKKGSKVMPNIEKLRSCG
THAPYMRPVYPTKTFPNLYTLATGLYPESHGIVGNSMYDPVFDATFHLRGREKFNHRWWGGQPLW
ITATKQGVRAGTFFWSVSIPHERRILTILQWLSLPDNERPSVYAFYSEQPDFSGHKYGPFGPEMT
NPLREIDKTVGQLMDGLKQLKLHRCVNVIFVGDHGMEDVTCDRTEFLSNYLTNVDDITLVPGTLG
RIRPKIPNNLKYDPKAIIANLTCKKPDQHFKPYMKQHLPKRLHYANNRRIEDLHLLVERRWHVAR
KPLDVYKKPSGKCFFQGDHGFDNKVNSMQTVFVGYGPTFKYRTKVPPFENIELYNVMCDLLGLKP
APNNGTHGSLNHLLRTNTFRPTLPEEVSRPNYPGIMYLQSDFDLGCTCDDKVEPKNKLEELNKRL
HTKGSTEERHLLYGRPAVLYRTSYDILYHTDFESGYSEIFLMPLWTSYTISKQAEVSSIPEHLTN
CVRPDVRVSPGFSQNCLAYKNDKQMSYGFLFPPYLSSSPEAKYDAFLVTNMVPMYPAFKRVWTYF
QRVLVKKYASERNGVNVISGPIFDYNYDGLRDIEDEIKQYVEGSSIPVPTHYYSIITSCLDFTQP
ADKCDGPLSVSSFILPHRPDNDESCNSSEDESKWVEELMKMHTARVRDIEHLTGLDFYRKTSRSY
SEILTLKTYLHTYESEI

Fig. 9. EXPRESSION OF WE474
WE474
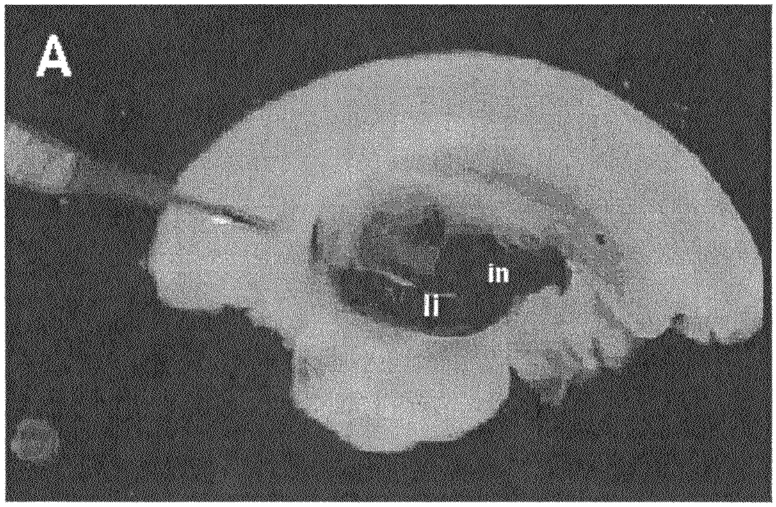

FIG. 10: WE474 sequences

FIG. 10A: Nucleic acid sequence (SEQ ID NO:27) encoding the collectin-like protein of chicken collectin sub-family member 10/collectin liver-1/collectin 43.

CCACGCGTCCGGCTCTCAATCTTTGCACTGCTTCAGTTAGCAGAGCATTTATTTTTGATTCAGCT
GCATTTGTTAAGACTGTAACAACGAAAGGCATTTCCTGAGAAGCTGCAAGGATGAGCAGAAAGAA
AGAACAACAGCTAAGGAAATATGGGACCCTAGTAGTGCTTTTCATCTTCCAAGTTCAGATTTTTG
GTTTTGATGTTGACAATCGACCTACAACAGATGTCTGCTCGACACACACTATTTTACCTGGACCA
AAAGGGGATGATGGTGAAAAAGGAGATAGAGGAGAAGTGGGCAAACAAGGAAAAGTTGGACCAAA
AGGACCTAAAGGAAACAAAGGAACTGTGGGGGATGTCGGTGACCAGGGAATGCTTGGGAAAATCG
GTCCGATTGGAGGAAAAGGTGACAAAGGAGCCAAAGGCATATCAGGGGTATCTGGAAAAAAAGGA
AAAGCAGGCACAGTCTGTGACTGTGGAANGTCCGCANAGTTGTTGGACAACTGAATATCAATGTT
GCTCGGCTTAACACATNCATCAAGTTTGTAAAAGAATGGTTTTTGCNGGCCTTNAGGGGGACCGG
TGGAAAAATTCTTCCTTTTTTTGGC

FIG. 10B: Protein sequence (one-letter-code) of chicken WE474 (SEQ ID NO:28)

MSRKKEQQLRKYGTLVVLFIFQVQIFGFDVDNRPTTDVCSTHTILPGPKGDDGEKGDRGEVGKQG
KVGPKGPKGNKGTVGDVGDQGMLGKIGPIGGKGDKGAKGISGVSGKKGKAGTVCDCG

FIG. 10C: Nucleic acid sequence encoding the Homo sapiens collectin sub-family member 10 (C-type lectin) (COLEC10)(GenBank Accession Number NM_006438.2; SEQ ID NO: 29)

AAGCAGGAGGTTTTATTTAAAATAAAGCTGTTTATTTGGCATTTCTGGGAGACCCTTTTCTGAGG
AACCACAGCAATGAATGGCTTTGCATCCTTGCTTCGAAGAAACCAATTTATCCTCCTGGTACTAT
TTCTTTTGCAAATTCAGAGTCTGGGTCTGGATATTGATAGCCGTCCTACCGCTGAAGTCTGTGCC
ACACACACAATTTCACCAGGACCCAAAGGAGATGATGGTGAAAAAGGAGATCCAGGAGAAGAGGG
AAAGCATGGCAAAGTGGGACGCATGGGGCCGAAAGGAATTAAAGGAGAACTGGGTGATATGGGAG
ATCGGGGCAATATTGGCAAGACTGGGCCCATTGGGAAGAAGGGTGACAAAGGGGAAAAAGGTTTG
CTTGGAATACCTGGAGAAAAAGGCAAAGCAGGTACTGTCTGTGATTGTGGAAGATACCGGAAATT
TGTTGGACAACTGGATATTAGTATTGCCCGGCTCAAGACATCTATGAAGTTTGTCAAGAATGTGA
TAGCAGGGATTAGGGAAACTGAAGAGAAATTCTACTACATCGTGCAGGAAGAGAAGAACTACAGG
GAATCCCTAACCCACTGCAGGATTCGGGGTGGAATGCTAGCCATGCCCAAGGATGAAGCTGCCAA
CACACTCATCGCTGACTATGTTGCCAAGAGTGGCTTCTTTCGGGTGTTCATTGGCGTGAATGACC
TTGAAAGGGAGGGACAGTACATGTTCACAGACAACACTCCACTGCAGAACTATAGCAACTGGAAT
GAGGGGGAACCCAGCGACCCCTATGGTCATGAGGACTGTGTGGAGATGCTGAGCTCTGGCAGATG
GAATGACACAGAGTGCCATCTTACCATGTACTTTGTCTGTGAGTTCATCAAGAAGAAAAAGTAAC
TTCCCTCATCCTACGTATTTGCTATTTTCCTGTGACCGTCATTACAGTTATTGTTATCCATCCTT
TTTTTCCTGATTGTACTACATTTGATCTGAGTCAACATAGCTAGAAAATGCTAAACTGAGGTATG
GAGCCTCCATCATCATGCTCTTTTGTGATGATTTTCATATTTTCACACATGGTATGTTATTGACC
CAATAACTCGCCAGGTTACATGGGTCTTGAGAGAGAATTTTAATTACTAATTGTGCACGAGATAG
TTGGTTGTCTATATGTCAAATGAGTTGTTCTCTTGGTATTTGCTCTACCATCTCTCCCTAGAGCA
CTCTGTGTCTATCCCAGTGGATAATTTCCCAGTTTACTGGTGATGATTAGGAAGGTTGTTGATGG
TTAGGCTAACCTGCCCTGGCCCAAAGCCAGACATGTACAAGGGCTTTCTGTGAGCAATGATAAGA
TCTTTGAATCCAAGATGCCCAGATGTTTTACCAGTCACACCCTATGGCCATGGCTATACTTGGAA
GTTCTCCTTGTTGGCACAGACATAGAAATGCTTTAACCCCAAGCCTTTATATGGGGGACTTCTAG
CTTTGTGTCTTGTTTCAGACCATGTGGAATGATAAATACTCTTTTTGTGCTTCTGATCTATCGAT
TTCACTAACATATACCAAGTAGGTGCTTTGAACCCCTTTCTGTAGGCTCACACCTTAATCTCAGG
CCCCTATATAGTCACACTTTGATTTAAGAAAAATGGAGCTCTTGAAATCAAAAGAAAAAAA

FIG. 10D: Amino acid sequence encoding the Homo sapiens collectin sub-family member 10 (also referred to as collectin liver 1; collectin 34) (GenBank Accession Number NP_006429.1; SEQ ID NO: 30)

MNGFASLLRRNQFILLVLFLLQIQSLGLDIDSRPTAEVCATHTISPGPKGDDGEKGDPGEEGKHG
KVGRMGPKGIKGELGDMGDRGNIGKTGPIGKKGDKGEKGLLGIPGEKGKAGTVCDCGRYRKFVGQ
LDISIARLKTSMKFVKNVIAGIRETEEKFYYIVQEEKNYRESLTHCRIRGGMLAMPKDEAANTLI
ADYVAKSGFFRVFIGVNDLEREGQYMFTDNTPLQNYSNWNEGEPSDPYGHEDCVEMLSSGRWNDT
ECHLTMYFVCEFIKKKK

Fig. 11. Expression of DP160
DP160
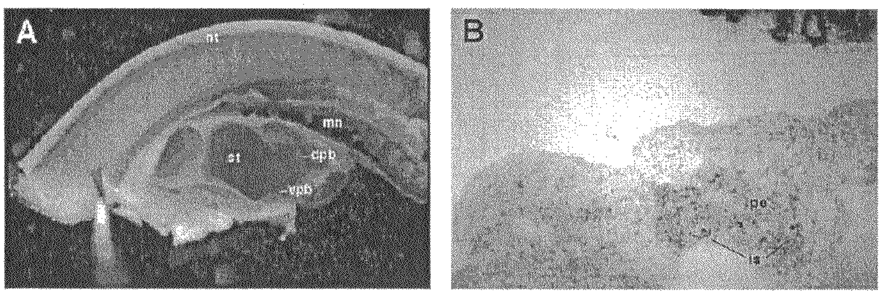

FIG. 12: DP160 sequences

FIG. 12A: . Nucleic acid sequence (SEQ ID NO: 31) encoding the DP160-like protein of chicken. NOTE: The entire sequence is translated and encodes a central part of chicken DP160/Nocturnin TGCAGCTTGTTCCATGGGAAACAGCACCAGCCGGCTCTACAGCGCGCTCGCCAAGACGCTGAGCA
GCAGTGCCGTGTCCCAGCACCAGGACTGCCTGGAGCAGCCCAACTCGGCGCAGCTGGAGCCCATA
GACCCCAAGGACCTACTGGAGGAATGCCAGCTCGTTCTGCAGAAACGGCCACCTCGCTTCCAGAG
GAACTTCGTGGACCTGAAGAAAAACACAGCCAGTAACCACCGCCCCATCCGGGTCATGCAGTGGA
ACATNCTCGCCCAAGCTCTCGGAGAAGGCAAAGACAACTTCGTTCAGTGCCCCATGGAAGCTCTG
AAGTGGGAGGAAAGGAAGTGCCTCATCCTGGAGGAAATCCTTGCCTACAAGCCGGATATCTTGTG
CCTGCAAGAAGTCGACCACTACTTTTACACCTT FIG. 12B: Amino acid sequence of chicken DP160 (SEQ ID NO: 32).

AACSMGNSTSRLYSALAKTLSSSAVSQHQDCLEQPNSAQLEPIDPKDLLEECQLVLQKRPPRFQR
NFVDLKKNTASNHRPIRVMQWNXLAQALGEGKDNFVQCPMEALKWEERKCLILEEILAYKPDILC
LQEVDHYFYT

FIG. 12C: Nucleic sequence of Homo sapiens CCR4 carbon catabolite repression 4-like (S. cerevisiae) (CCRN4L) (GenBank Accession Number NM_003343.2; SEQ ID NO: 33).

CCGACGCAGCGGTGTTGCACCTCCCTCTCCGGCTCTGCTGCCCGGGATTTCCCCAGAACCTGCGC
CGCGCGAGAAGGAGCCTGGGAGCATCCGCCCACACTGCCCGGACAGTCGGCTCGACTCGGTGCCC
TCGGCCCCAGCCGGGCTCCGCTCCTCGGGCGCGCGAGGGGCCGTGGTGGCGGCGGCGCCCGGCAT
GTTTCATAGTCCGCGGCGGCTCTGCTCGGCCCTGCTGCAGAGGGACGCGCCCGGCCTGCGCCGCC
TGCCCGCCCCAGGGCTGCGCCGCCCGTTGTCCCCGCCGGCTGCTGTTCCCAGGCCCGCATCCCCC
CGGCTGCTGGCGGCGGCCTCGGCGGCCTCGGGCGCCGCGAGGTCGTGTTCCCGAACAGTGTGTTC
CATGGGAACCGGTACAAGCAGACTCTATAGTGCTCTCGCCAAGACACTGAACAGCAGCGCTGCCT
CCCAGCACCCAGAGTATTTGGTGTCACCTGACCCAGAGCATCTGGAGCCCATTGATCCTAAAGAG
CTTCTTGAGGAATGCAGGGCCGTCCTGCACACCCGACCTCCCCGGTTCCAGAGGGATTTTGTGGA
TCTGAGGACAGATTGCCCTAGTACCCACCCACCTATCAGGGTTATGCAATGGAACATCCTCGCCC
AAGCTCTTGGAGAAGGCAAAGACAACTTTGTACAGTGCCCTGTTGAAGCACTCAAATGGGAAGAA
AGGAAATGTCTCATCCTGGAAGAAATCCTGGCCTACCAGCCTGATATATTGTGCCTCCAAGAGGT
GGACCACTATTTTGACACCTTCCAGCCACTCCTCAGTAGACTAGGCTATCAAGGCACGTTTTTCC
CCAAACCCTGGTCACCTTGTCTAGATGTAGAACACAACAATGGACCAGATGGTTGTGCCTTATTT
TTTCTTCAAAACCGATTCAAGCTAGTCAACAGTGCCAATATTAGGCTGACAGCCATGACATTGAA
AACCAACCAGGTGGCCATTGCACAGACCCTGGAGTGCAAGGAGTCAGGCCGACAGTTCTGCATCG
CTGTTACCCATCTAAAAGCACGCACTGGCTGGGAGCGGTTTCGATCAGCTCAAGGCTGTGACCTC
CTTCAGAACCTGCAAAACATCACCCAAGGAGCCAAGATTCCCCTTATTGTGTGTGGGGACTTCAA
TGCAGAGCCAACAGAAGAGGTCTACAAACACTTTGCTTCCTCCAGCCTCAACCTGAACAGCGCCT
ACAAGCTGCTGAGTGCTGATGGGCAGTCAGAACCCCCATACACTACCTGGAAGATCCGGACCTCA
GGGGAGTGCAGGCACACCCTGGATTACATCTGGTATTCTAAACATGCTCTAAATGTAAGGTCAGC
TCTCGATCTGCTCACTGAAGAACAGATTGGACCCAACAGGTTACCTTCCTTCAATTATCCTTCAG
ACCACCTGTCTCTAGTGTGTGACTTCAGCTTTACTGAGGAATCTGATGGACTTTCATAAATACTT
GCTTTTGTCTTTTTAATCACAGGAGTCTATTTTTTTTTTTTTTTTTTTTTTTTTGAGACAGAGTC
TCGCTCTGTTGCCTAGGCTGGAGTACAGTGGCCTGATCTCGGCTCACTGCAAGATCCGCCTCCCG
GGTTCATGGCATTCTCCTGCCTCAGCCTCCAGAGCAACTGGGACAACAGGCGCCCGTCACCACGC
CCAGCTAATTTTTTGTATTTTTAGTAGAGACGGGGTTTCACCGTGTTAGCCAGGATGGTCTCGAT
CTCCTGACCTTG

FIG. 12D. Amino acid sequence of the human similar to Nocturnin (CCR4 protein homolog) (GenBank Accession Number XP_003343.3; SEQ ID NO: 34).
Note: Derived from a GeneScan prediction and identical to the published sequence of Nocturnin except for a single amino acid exchange. Both sequences are derived from the same gene.

MFHSPRRLCSALLQRDAPGLRRLPAPGLRRPLSPPAAVPRPASPRLLAAASAASGAARSCSRTVC
SMGTGTSRLYSALAKTLNSSAASQHPEYLVSPDPEHLEPIDPKELLEECRAVLHTRPPRFQRDFV
DLRTDCPSTHPPIRVMQWNILAQALGEGKDNFVQCPVEALKWEERKCLILEEILAYQPDILCLQE
VDHYFDTFQPLLSRLGYQGTFFPKPWSPCLDVEHNNGPDGCALFFLQNRFKLVNSANIRLTAMTL
KTNQVAIAQTLECKESGRQFCIAVTHLKARTGWERFRSAQGCDLLQNLQNITQGAKIPLIVCGDF
NAEPTEEVYKHFASSSLNLNSAYKLLSADGQSEPPYTTWKIRTSGECRHTLDYIWYSKHALNVRS
ALDLLTEEQIGPNRLPSFNYPSDHLSLVCDFSFTEESDGLS

Fig. 13. EXPRESSION OF RA977
RA977
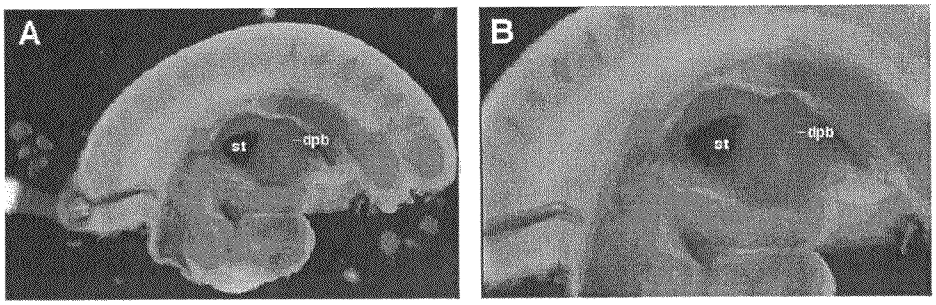

FIG. 14: RA977 SEQUENCES

FIG. 14A: Nucleic acid sequence (SEQ ID NO: 35) OF RA977. Stop and start codons are in bold and the UTRs are underlined.

ACGCACGCACCTCTGCCTCTGCAGGCGGATGAGGGGCACTTTTGAAAATTATTTTCTTTCCACAC
CCAACCCTCGTCTGACATCACTTCTGCAGGAGGGAGGGCGGGAACAGCCCCGCTGCCAGAAGGTC
GCGGAGAGCTCCGCCGGCCCCCGCGCACCATTTGTCTCAAACTAAATACTCTTCAAATCAAGGAT
GTTGATTCTTCTGGCTTTCATTATTATATTTCACATAACTTCAGCAGCGCTGTTGTTCATCTCAA
CTATTGACAATGCCTGGTGGGTAGGAGATAACTTTTCTACAGATGTCTGGAGTGCATGTGCCACA
AATAATAGCACCTGCACACCTATTACTGTTCAATTCAGAGAATATCAATCAATTCAGGCTGTTCA
GGCCTGCATGGTCCTATCTACTATTTTCTGTTGTGTGGCATTTCTGGTTTTCATTCTTCAACTTT
TCCGTCTAAAGCAAGGAGAAAGATTTGTGTTAACCTCTATTATCCAGCTCCTGTCATGTCTGTGC
GTTATGATTGCAGCTTCCATTTACACAGATAGGCATGAGGAACTGCACAAGAGCATTGAATATGC
CATTGAAGTTTCTAAAGGCCAATATGGCTATTCCTTCGTCTTAGCCTGGATTGCATTCGCCTTTA
CTCTGATCAGTGGTGTTATGTACCTAGTATTAAGGAAACGTAAATAAATGTTGGCAGCTAGTTAT
TACTGTCACGGCAGTACAAAACCAAATTCCAGTAACTATTTTGTATNNNNNNNNNNNNNNNGGTTT
TGTAGTAAAGGTATTGTTTCTCTAAAAATGTACTGTGTTCTTAATATGAAACAGAATACAAAACA
AAAAACAACCAACAGCAGGTTTAATGGAATGCCTGGCATTCGGTCTGAGCAAGACTGACCCAAGT
TTTCTTTTACTTATTTCACCATCATCAGTGGTGAAATGGTGTCTTTCCTTTTCTAGACATTAACA
GTTCTTGGCCTCTGTCAGATTACTATTAAAGTCTTTGTAAATTAATTTGGAAGCAATGTGCTAAG
CATACTCCTGGCCTGGATCTAGCCCTTTGGGATGGATAAATACAGGGNNNNNNNNNNNNNNNGGCC
AGGATCGTGATGCAAAAGCAAACAAGTATAAAAGCCCAAAGCTGCACTCAATGTTGCTGTTCTAG
CAGAGGACGAATGTTCTGCTATTTATAATGTGCAGTAAGTGTCATCAAGCTTTTATTAAAACCAC
TTGCTCTGCAAAAGTAAACAACTCCTTTTTGTACTCCAGCAACTGATTCTCTTTATCCTTCTTCA
CGTTTAATTTAAGCATACAGAGCCTTTGGCAGGAAAAGTTACAATCAAATTCGAAATTCAGTGCA
CAACTTGAGACAGGAGTAGTCTGAGCAGAAAGAGGTACTCCACTCAAGTCCTGCAGCCCTTTATT
TTTGCATTGTGCAGTACCAAATTTAACACTTTTTTTTCAGCCAAACTCAGTATGTTTATTACATT
GGGCTCTGGCTAGATATATCATGTTGGCTAATATATGATTTAGAAAGGCTCTTCTTTTTTGTTT
TTCCTGTGTCTGCTCACTAGGAAATTGGCCTTTACAAAATTCATTCTAAGTTCCTATGTGGATTT
GACTTGAATAAGAATTCCTACTAAAGAAATCAGAGTGTAACTATTATGCATAGGAGTTCCAGGAT
AGTTTTAAGAATTTTTGGTGATTCTTTCTTTTCAATAATTCTGTGAGAGAATTACTGTAATACCA
GATTTAACTGCTCAGCAATATAATACTGGCTTTGGCTGGTGGTGATTTCAGGGTTTGGAGACCAG
TGTGGGGAATGAATTAAGTGGCTTTTTCTGGTTAGTCACACTTCTGATGTTAAAATGTAGATTTG
ACTTTGTAAAAGCATTAACCCTGTATTCATTTCATGATACTCACTGCAGCTGACCCAATATATAG
GCAATAAAAATAAATGAATTTTAAATGAGATTTTACACTTAATGTAGAACAAAATTCCTATTACA
AAATAATGTAGCTCTACTAATGTTGATAACTTACCCTATTACACAGCAGCTGATAGTCTGACCCA
TTGCTGCAGGTAGTTCATCCTTGAGTTCTCACGGAACTGTATAGGAATTGTGTCGGACATGAGTA
ATGGGTCATGCTGTTCCATCTCCATTCCCTGAACATCCTAAAATGCACTAACGAGTAATACTTCT
ATTAGGCAGCAAAGAAAGCACAACAGGACTGGCAAGAAGTTAATTAGACAACTAAGCAGAACAGC
AAATTAATAGTAAAAATAACAGCAGTTAAAAAAAACCCTCAATAAATCAGTCTGAGCGAAATGCA
TTCTCACCTTCCCAGTCTTGCATGATGCTAATCTTCTGTTAGTCTTTTTTCTCTTAGTGGAACA
CTCTGAATTTCAGGCATTACTACCCTACTTTTTAAAAAAGTGTTTCTGCTGTTTGCTGAATACAT
TTCAGATTCAAAACGTGAATTTTGCTAGCAAGCAGGATTTGTTTTAAATAAACAGATGTAGGTTT
AAGGCTGAAAGTAGATAGTCTGTAAGTTGGGTGTTTGGCTAGTCTTATTCAAACATGAAATATTA
AGGGTGAAATTCTAAAACAAATGTGCATTGAAGCTATTTTATATCTAGAAGATAATCCTATAACA
CTGTAAATTAAGCTGAAATGCCACTGACTTGAAGAGATGCTTCTTCAGTTTCTTGCCTTAATAAT
GCTTAGGTCATTTATAGAGCAAATATTTAAGATAAAGATGTATATATACATGAACTCAGCTTACT
TCTACAGTAAAAGCTCTGTCACTTTAGTTAGAAGTGAAAAGCACACACAGCAGCATATACGTGGT
GCCACACAGAGAACATACGTCAATATTCGAAGTACCAAGAAAATAAATGCCAAAAAGTTTGGACA
AGAGTTTTAACAGGACAAACATATTTTAGAATATTCTTTTTATCTGATATGCTTTTAAAATATAC
CATTTTCTATGCTCTATATATTCTGAAATTGTACATGAAAATAAAGTTAAAATGAATTCTTGTAT
TGTAAAAAAAAAAAAAAAA

FIG. 14B: Amino acid sequence of RA977 (SEQ ID NO:36).

MLILLAFIIIFHITSAALLFISTIDNAWWVGDNFSTDVWSACATNNSTCTPITVQFREYQSIQAV
QACMVLSTIFCCVAFLVFILQLFRLKQGERFVLTSIIQLLSCLCVMIAASIYTDRHEELHKSIEY
AIEVSKGQYGYSFVLAWIAFAFTLISGVMYLVLRKRK

FIG. 14C. Nucleic acid sequence of Homo sapiens epithelial membrane protein 2 (EMP2), mRNA (GENBANK ACCESSION NUMBER XM_030218.1; SEQ ID NO: 37)

CAGCACATCCCGCTCTGGGCTTTAAACGTGACCCCTCGCCTCGACTCGCCCTGCCCTGTGAAAAT
GTTGGTGCTTCTTGCTTTCATCATCGCCTTCCACATCACCTCTGCAGCCTTGCTGTTCATTGCCA
CCGTCGACAATGCCTGGTGGGTAGGAGATGAGTTTTTTGCAGATGTCTGGAGAATATGTACCAAC
AACACGAATTGCACAGTCATCAATGACAGCTTTCAAGAGTACTCCACGCTGCAGGCGGTCCAGGC
CACCATGATCCTCTCCACCATTCTCTGCTGCATCGCCTTCTTCATCTTCGTGCTCCAGCTCTTCC
GCCTGAAGCAGGGAGAGAGGTTTGTCCTAACCTCCATCATCCAGCTAATGTCATGTCTGTGTGTC
ATGATTGCGGCCTCCATTTATACAGACAGGCGTGAAGACATTCACGACAAAAACGCGAAATTCTA
TCCCGTGACCAGAGAAGGCAGCTACGGCTACTCCTACATCCTGGCGTGGGTGGCCTTCGCCTGCA
CCTTCATCAGCGGCATGATGTACCTGATACTGAGGAAGCGCAAATAGAGTTCCGGAGCTGGGTTG
CTTCTGCTGCAGTACAGAATCCACATTCAGATAACCATTTTGTATATAATCATTATTTTTTGAGG
TTTTTCTAGCAAACGTATTGTTTCCTTTAAAAGCCCAAAA

FIG. 14D. Amino acid sequence of EMP2_HUMAN Epithelial membrane protein-2 (EMP-2) (XMP protein)(GenBank Accession Number P54851; SEQ ID NO: 38)

MLVLLAFIIAFHITSAALLFIATVDNAWWVGDEFFADVWRICTNNTNCTVINDSFQEYSTLQAVQ
ATMILSTILCCIAFFIFVLQLFRLKQGERFVLTSIIQLMSCLCVMIAASIYTDRREDIHDKNAKF
YPVTREGSYGYSYILAWVAFACTFISGMMYLILRKRK

Fig. 15. Expression of RA770/neurturin
RA770
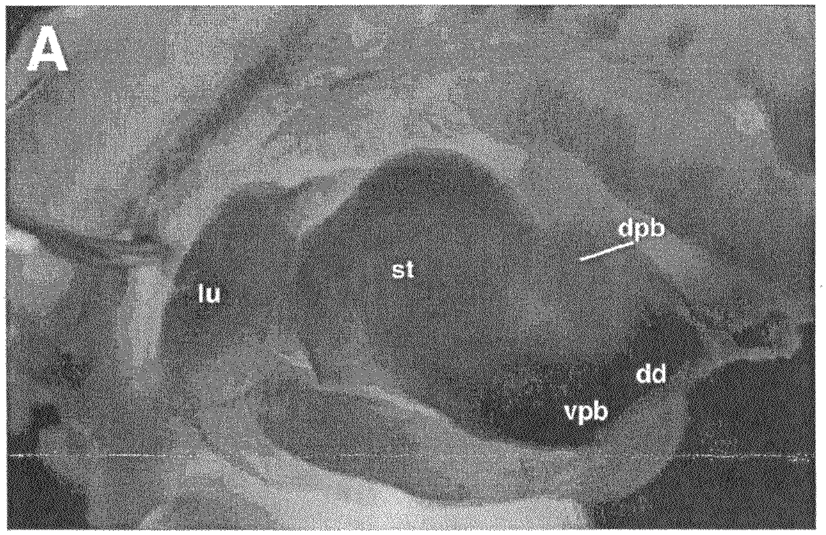

FIG. 16: RA770 sequences

FIG. 16A: Nucleic acid sequence (SEQ ID NO: 39) encoding the RA770-like protein of chicken.

GGTCGACCCACGCGTCCGGGTGAGCGTCAGCGAGTTGGGCCTGGGCTACGAGTCGGACGAGACCG
TGTTGTTCCGCTACTGCAGCGGCACCTGCGACGCGGCCGTCAGGAACTACGACCTCTCGCTGAAG
AGCGTGCGCAGCCGGAAGAAGATCAGGAAGGAGAAGGTGCGCGCGCGGCCCTGCTGCAGGCCGCT
GGCCTACGATGATGACGTCTCCTTCTTGGATGCCTACAACCGCTACTACACCGTCAATGAGCTGT
CGGCCAAAGAGTGTGGCTGTGTGTGAAGGGCCGGGTTGGGGGGTGGCTCAATGGGGCCGAAGCCC
GTGGTGGGGATGGGGATGGACCCCGCACCGCTGCCCGCCCCATGGACCTCCCGTGTCCAGTTGGA
GGAGGAGAGACGACCCATGGACCTACCATGTCCATTGGGAAGAGGAAAGATGCCCCATGGACCCT
CCGTGTCCATTGGGAGGAGGAGAAATGCCCCACAGACCCCCCATGTCCATTGGGAAGAGGAGAGA
TGCCCCATGGACCCTTCGTGTCTAGTGGGAA

FIG. 16B: Amino acid sequence of chicken RA770 (SEQ ID NO: 40).

VDPRVRVSVSELGLGYESDETVLFRYCSGTCDAAVRNYDLSLKSVRSRKKIRKEKVRARPCCRPL
AYDDDVSFLDAYNRYYTVNELSAKECGCV

FIG. 16C: Nucleic sequence of Homo sapiens neurturin (GenBank Accession Number NM_004558.1; SEQ ID NO: 41).

ATGCAGCGCTGGAAGGCGGCGGCCTTGGCCTCAGTGCTCTGCAGCTCCGTGCTGTCCATCTGGAT
GTGTCGAGAGGGCCTGCTTCTCAGCCACCGCCTCGGACCTGCGCTGGTCCCCCTGCACCGCCTGC
CTCGAACCCTGGACGCCCGGATTGCCCGCCTGGCCCAGTACCGTGCACTCCTGCAGGGGGCCCCG
GATGCGATGGAGCTGCGCGAGCTGACGCCCTGGGCTGGGCGGCCCCCAGGTCCGCGCCGTCGGGC
GGGGCCCCGGCGGCGGCGCGCGCGTGCGCGGTTGGGGGCGCGGCCTTGCGGGCTGCGCGAGCTGG
AGGTGCGCGTGAGCGAGCTGGGCCTGGGCTACGCGTCCGACGAGACGGTGCTGTTCCGCTACTGC
GCAGGCGCCTGCGAGGCTGCCGCGCGCGTCTACGACCTCGGGCTGCGACGACTGCGCCAGCGGCG
GCGCCTGCGGCGGGAGCGGGTGCGCGCGCAGCCCTGCTGCCGCCCGACGGCCTACGAGGACGAGG
TGTCCTTCCTGGACGCGCACAGCCGCTACCACACGGTGCACGAGCTGTCGGCGCGCGAGTGCGCC
TGCGTGTGA

FIG. 16D. Amino acid sequence of the human neurturin precursor (GenBank Accession Number NP_004549.1; SEQ ID NO: 42)

MQRWKAAALASVLCSSVLSIWMCREGLLLSHRLGPALVPLHRLPRTLDARIARLAQYRALLQGAP
DAMELRELTPWAGRPPGPRRRAGPRRRRARARLGARPCGLRELEVRVSELGLGYASDETVLFRYC
AGACEAAARVYDLGLRRLRQRRRLRRERVRAQPCCRPTAYEDEVSFLDAHSRYHTVHELSARECA
CV

FIG. 16E: Nucleic sequence of Mus musculus neurturin (GenBank Accession Number NM_008738.1; SEQ ID NO: 43).

GGAGGGAGAGCGCGCGGTGGTTTCGTCCGTGTGCCCCGCGCCCGGCGCTCCTCGCGTGGCCCCGC
GTCCTGAGCGCGCTCCAGCCTCCCACGCGCGCCACCCCGGGGTTCACTGAGCCCGGCGAGCCCGG
GGAAGACAGAGAAAGAGAGGCCAGGGGGGGAACCCCATGGCCCGGCCCGTGTCCCGCACCCTGTG
CGGTGGCCTCCTCCGGCACGGGGTCCCCGGGTCGCCTCCGGTCCCCGCGATCCGGATGGCGCACG
CAGTGGCTGGGGCCGGGCCGGGCTCGGGTGGTCGGAGGAGTCACCACTGACCGGGTCATCTGGAG
CCCGTGGCAGGCCGAGGCCCAGGATGAGGCGCTGGAAGGCAGCGGCCCTGGTGTCGCTCATCTGC
AGCTCCCTGCTATCTGTCTGGATGTGCCAGGAGGGTCTGCTCTTGGGCCACCGCCTGGGACCCGC
GCTTGCCCCGCTACGACGCCCTCCACGCACCCTGGACGCCCGCATCGCCCGCCTGGCCCAGTATC
GCGCTCTGCTCCAGGGCGCCCCCGACGCGGTGGAGCTTCGAGAACTTTCTCCCTGGGCTGCCCGC
ATCCCGGGACCGCGCCGTCGAGCGGGTCCCCGGCGTCGGCGGGCGCGGCCGGGGGCTCGGCCTTG
TGGGCTGCGCGAGCTCGAGGTGCGCGTGAGCGAGCTGGGCCTGGGCTACACGTCGGATGAGACCG
TGCTGTTCCGCTACTGCGCAGGCGCGTGCGAGGCGGCCATCCGCATCTACGACCTGGGCCTTCGG
CGCCTGCGCCAGCGGAGGCGCGTGCGCAGAGAGCGGGCGCGGGCGCACCCGTGTTGTCGCCCGAC
GGCCTATGAGGACGAGGTGTCCTTCCTGGACGTGCACAGCCGCTACCACACGCTGCAAGAGCTGT
CGGCGCGGGAGTGCGCGTGCGTGTGATGCTACCTCACGCCCCCCGACCTGCGAAAGGGCCCTCCC
TGCCGACCCTCGCTGAGAACTGACTTCACATAAAGTGTGGGAACTCCC

FIG. 16F. Amino acid sequence of the mouse neurturin precursor (GenBank Accession Number NP_032764.1; SEQ ID NO: 44)

MRRWKAAALVSLICSSLLSVWMCQEGLLLGHRLGPALAPLRRPPRTLDARIARLAQYRALLQGAP
DAVELRELSPWAARIPGPRRRAGPRRRRARPGARPCGLRELEVRVSELGLGYTSDETVLFRYCAG
ACEAAIRIYDLGLRRLRQRRRVRRERARAHPCCRPTAYEDEVSFLDVHSRYHTLQELSARECACV

SEQUENCE LISTING

<160> NUMBER OF SEQ ID NOS: 61

<210> SEQ ID NO 1
<211> LENGTH: 1350
<212> TYPE: DNA
<213> ORGANISM: Gallus gallus

<400> SEQUENCE: 1
acgtcgtcta caacgggtcc ttctactaca accgggcctt caccccgcaac atcatcaaat 60 acgacctgaa gcagcggtac gtggccgcct gggccatgct gcacgacgtg gcctacgagg 120
agtccacccc gtggcgatgg cgcggccatt ccgatgtgga cttcgccgtg gacgagaacg 180
gcctgtgggt catttacccg gccatcagct acgagggctt caatcaggag gtgatcgtgc 240
tgagcaagct gaacgcagcc gacctcagca cccagaaaga gacgacgtgg aggacgggcc 300
tgcggaagaa cttctatggg aactgcttcg tcatctgcgg ggtcctgtac gcggtcgaca 360
gctacaacaa gaggaacgcc aacatctcct acgcctttga cacgcacacc aacactcaga 420
tcatcccccg gctgctcttt gagaatgagt acgcctacac cacgcagata gactataacc 480
ccaaggaccg cctgctctac gcttgggaca atggccacca ggtcacctac cacgtcatct 540
ttgcctactg agcgccccgg gatggggcac tgcgagcgag gggccaccag cacctttcat 600
tgttgttatt tttattatta ttattattat tattttgtac aaatcaaaga gtacgtgatg 660
ggtttttgtc tcaggctgtt tagatggcgg attgtagatc gatccccagg ccaggaccac 720
ccctttgtcc ccggtgtgac cttgcctctg tgctcgaggg cagtgcggcg gggcccgtgg 780
cagcagggct gctcctttgg ggggacgctg aggaggaggt ggccctgaca taaccctgct 840
gatgtttttt tagatgaaag ccatcagcgc ttaaccccag gcccagtgca aagctggcct 900
ttctgctgca ggcaccggct cctgtggcag gacggtggtg tccacccgtc cccgtggagg 960
ggtgcattgt cccctcgggg ggccaccctc ccacccgaca gtcagcgggt gcttgggaga 1020
tcctgctgta caacacgcac agccccggtg ctggcactta gctgaggact gtcccctctc 1080
cccctgactc tgccctttgc agcctgccct gggggctcca tctggcctgg ggggggggctg 1140 tgggtgccgg gctgggtgct ggcagtggga ggggggcact gtaaatatgt gtagatgact 1200
tctgtttgtg cgttttgtaa ccaaaatagt ccccatttgg tatctgcctc gcggaggtcc 1260
cagcctccgt ccctccagcc tggcaccgcc ttgtatttac ccgctgttaa taataaaaga 1320
tcaagtacct ttgcaaaaaa aaaaaaaaaa 1350

<210> SEQ ID NO 2
<211> LENGTH: 182
<212> TYPE: PRT
<213> ORGANISM: Gallus gallus

<400> SEQUENCE: 2

Val Val Tyr Asn Gly Ser Phe Tyr Tyr Asn Arg Ala Phe Thr Arg Asn
1 5 10 15

-continued

```
Ile Ile Lys Tyr Asp Leu Lys Gln Arg Tyr Val Ala Ala Trp Ala Met
            20                  25                  30

Leu His Asp Val Ala Tyr Glu Glu Ser Thr Pro Trp Arg Trp Arg Gly
        35                  40                  45

His Ser Asp Val Asp Phe Ala Val Asp Glu Asn Gly Leu Trp Val Ile
    50                  55                  60

Tyr Pro Ala Ile Ser Tyr Glu Gly Phe Asn Gln Glu Val Ile Val Leu
65                  70                  75                  80

Ser Lys Leu Asn Ala Ala Asp Leu Ser Thr Gln Lys Glu Thr Thr Trp
                85                  90                  95

Arg Thr Gly Leu Arg Lys Asn Phe Tyr Gly Asn Cys Phe Val Ile Cys
            100                 105                 110

Gly Val Leu Tyr Ala Val Asp Ser Tyr Asn Lys Arg Asn Ala Asn Ile
        115                 120                 125

Ser Tyr Ala Phe Asp Thr His Thr Asn Thr Gln Ile Ile Pro Arg Leu
    130                 135                 140

Leu Phe Glu Asn Glu Tyr Ala Tyr Thr Thr Gln Ile Asp Tyr Asn Pro
145                 150                 155                 160

Lys Asp Arg Leu Leu Tyr Ala Trp Asp Asn Gly His Gln Val Thr Tyr
                165                 170                 175

His Val Ile Phe Ala Tyr
            180
```

```
<210> SEQ ID NO 3
<211> LENGTH: 1801
<212> TYPE: DNA
<213> ORGANISM: Homo sapiens

<400> SEQUENCE: 3

gtgagttttt cagcggtgac aatggagtgg atttgctgat tgaagatcag ctcctgagac      60

acaacggcct gatgaccagt gtcacccgga ggcctgcagc cacccgtcag ggacacagca     120

ctgctgtgac aagcgacctg aacgctcgga ccgcaccctg gtcctcagca ctgccacagc     180

cctcgacctc agatcccagc atcgccaacc atgcctcagt gggaccaaca ctccaaacaa     240

cctcggtgtc tccagatccc acaagggagt cagtcctgca gccttctcct caggtaccag     300

ccaccactgt ggcccacaca gccacccagc aaccagcagc cccagctcct ccggcagtgt     360

ctcccaggga ggcattgatg gaagctatgc acacagtccc agtgcctccc accacagtca     420

gaacagactc gctggggaaa gatgctcctg ctgggcgggg aacaacccct gccagcccca     480

cgctgagccc cgaagaagaa gatgacatcc ggaatgtcat aggaaggtgc aaggacactc     540

tctccacaat cacggggccg accacccaga acacatatgg gcggaatgaa ggggcctgga     600

tgaaggaccc cctggccaag gatgagcgga tttacgtaac caactattac tacggcaaca     660

ccctggtaga gttccggaac ctggagaact tcaaacaagg tcgctggagc aattcctaca     720

agctcccgta cagctggatc ggcacaggcc acgtggtata caatggcgcc ttctactaca     780

atcgcgcctt cacccgcaac atcatcaagt acgacctgaa gcagcgctac gtggctgcct     840

gggccatgct gcatgacgtg gcctacgagg aggccacccc ctggcgatgg cagggccact     900

cagacgtgga ctttgctgtg gacgagaatg gcctatggct catctacccg gccctggacg     960

atgagggctt cagccaggag gtcattgtcc tgagcaagct caatgccgcg gacctgagca    1020

cacagaagga gaccacatgg cgcacggggc tccggaggaa tttctacggc aactgcttcg    1080

tcatctgtgg ggtgctgtat gccgtggata gctacaacca gcggaatgcc aacatctcct    1140
```

-continued

```
acgctttcga cacccacacc aacacacaga tcgtccccag gctgctgttc gagaatgagt   1200

attcctatac gacccagata gactacaacc ccaaggaccg cctgctctat gcctgggaca   1260

atggccacca ggtcacttac catgtcatct ttgcctactg acacccttgt ccccacaagc   1320

agaagcacag aggggtcact agcaccttgt gtgtatgtgt gtgcgtgcac gtgtgtgtag   1380

gtgggtatgt gttgtttaaa aatatatatt attttgtata atattgcaaa tgtaaaatga   1440

caatttgggt ctattttttt atatggattg tagatcaatc catacgtgta tgtgctggtc   1500

tcatcctccc cagtttatat ttttgtgcaa atgaacttct ccttttgacc agtaaccacc   1560

ttccttcaag ccttcagccc ctccagctcc aagtctcaga tctcgaccat tgaaaaggtt   1620

tcttcatctg ggtcttgcag gaggcaggca acaccaggag cagaaatgaa agaggcaaga   1680

aagaagtgct atgtggcgag aaaaaaagtt ttaatgtatt ggagaagttt taaaaaaccc   1740

agaaaaacgc tttttttttt ttaataaaga agaaatttaa aatcaaaaaa aaaaaaaaaa   1800

a                                                                   1801


<210> SEQ ID NO 4
<211> LENGTH: 432
<212> TYPE: PRT
<213> ORGANISM: Homo sapiens

<400> SEQUENCE: 4

Glu Phe Phe Ser Gly Asp Asn Gly Val Asp Leu Leu Ile Glu Asp Gln
1               5                   10                  15

Leu Leu Arg His Asn Gly Leu Met Thr Ser Val Thr Arg Arg Pro Ala
            20                  25                  30

Ala Thr Arg Gln Gly His Ser Thr Ala Val Thr Ser Asp Leu Asn Ala
        35                  40                  45

Arg Thr Ala Pro Trp Ser Ser Ala Leu Pro Gln Pro Ser Thr Ser Asp
    50                  55                  60

Pro Ser Ile Ala Asn His Ala Ser Val Gly Pro Thr Leu Gln Thr Thr
65                  70                  75                  80

Ser Val Ser Pro Asp Pro Thr Arg Glu Ser Val Leu Gln Pro Ser Pro
                85                  90                  95

Gln Val Pro Ala Thr Thr Val Ala His Thr Ala Thr Gln Gln Pro Ala
            100                 105                 110

Ala Pro Ala Pro Pro Ala Val Ser Pro Arg Glu Ala Leu Met Glu Ala
        115                 120                 125

Met His Thr Val Pro Val Pro Pro Thr Thr Val Arg Thr Asp Ser Leu
    130                 135                 140

Gly Lys Asp Ala Pro Ala Gly Arg Gly Thr Thr Pro Ala Ser Pro Thr
145                 150                 155                 160

Leu Ser Pro Glu Glu Glu Asp Asp Ile Arg Asn Val Ile Gly Arg Cys
                165                 170                 175

Lys Asp Thr Leu Ser Thr Ile Thr Gly Pro Thr Thr Gln Asn Thr Tyr
            180                 185                 190

Gly Arg Asn Glu Gly Ala Trp Met Lys Asp Pro Leu Ala Lys Asp Glu
        195                 200                 205

Arg Ile Tyr Val Thr Asn Tyr Tyr Tyr Gly Asn Thr Leu Val Glu Phe
    210                 215                 220

Arg Asn Leu Glu Asn Phe Lys Gln Gly Arg Trp Ser Asn Ser Tyr Lys
225                 230                 235                 240

Leu Pro Tyr Ser Trp Ile Gly Thr Gly His Val Val Tyr Asn Gly Ala
                245                 250                 255
```

Phe Tyr Tyr Asn Arg Ala Phe Thr Arg Asn Ile Ile Lys Tyr Asp Leu
260 265 270

Lys Gln Arg Tyr Val Ala Ala Trp Ala Met Leu His Asp Val Ala Tyr
275 280 285

Glu Glu Ala Thr Pro Trp Arg Trp Gln Gly His Ser Asp Val Asp Phe
290 295 300

Ala Val Asp Glu Asn Gly Leu Trp Leu Ile Tyr Pro Ala Leu Asp Asp
305 310 315 320

Glu Gly Phe Ser Gln Glu Val Ile Val Leu Ser Lys Leu Asn Ala Ala
325 330 335

Asp Leu Ser Thr Gln Lys Glu Thr Thr Trp Arg Thr Gly Leu Arg Arg
340 345 350

Asn Phe Tyr Gly Asn Cys Phe Val Ile Cys Gly Val Leu Tyr Ala Val
355 360 365

Asp Ser Tyr Asn Gln Arg Asn Ala Asn Ile Ser Tyr Ala Phe Asp Thr
370 375 380

His Thr Asn Thr Gln Ile Val Pro Arg Leu Leu Phe Glu Asn Glu Tyr
385 390 395 400

Ser Tyr Thr Thr Gln Ile Asp Tyr Asn Pro Lys Asp Arg Leu Leu Tyr
405 410 415

Ala Trp Asp Asn Gly His Gln Val Thr Tyr His Val Ile Phe Ala Tyr
420 425 430

<210> SEQ ID NO 5
<211> LENGTH: 2863
<212> TYPE: DNA
<213> ORGANISM: Mus musculus

<400> SEQUENCE: 5
ccacgcgtcc gagtgaagcc gccttccagc ctgtctttgc tgagacctcc gacccaaggt 60
ggtctctgta gggactaaag tccctactgt cgcatctctc atggcctatc ccctgccatt 120
ggttctctgc tttgctctgg tggtggcaca ggtctggggg tccactacac ctcccacagg 180
gacaagcgag ccccctgatg tgcaaacagt ggagcccacg gaagatgaca ttctgcaaaa 240
cgaggcggac aaccaggaga acgttttatc tcagctgctg ggagactatg acaaggtcaa 300
ggctgtgtct gagggctctg actgtcagtg caaatgtgtg gtgagaccgc tgggccgaga 360
tgcctgccag aggatcaacc agggggcttc caggaaggaa gacttctaca ctgtggaaac 420
catcacctcg ggctcatcct gtaaatgtgc ttgtgttgct cctccgtctg ccgtcaatcc 480
ctgtgaggga gacttcaggc tccagaagct tcgggaggct gacagccgag atttgaagct 540
gtctacaatt atagacatgt tggaaggtgc tttctacggc ctggacctcc taaagctgca 600
ttcggttacc actaaactcg tggggcgagt ggataaactg gaggaggaag tctctaagaa 660
cctcaccaag gagaatgagc aaatcaaaga ggacgtggaa gaaatccgaa cggagctgaa 720
caagcgaggc aaggagaact gctctgacaa caccctagag agcatgccag acatccgctc 780
agccctgcag agggatgcgg ctgcagccta cgcccaccca gagtatgaag aacggtttct 840
gcaggaggaa actgtgtcac agcagatcaa ctccatcgaa ctcctgagga cgcagccact 900
ggtccctcct gcagcgatga agccgcagcg gcccctgcag agacaggtgc acctgagagg 960
tcggctggcc tccaagccca ccgtcatcag gggaatcacc tactataaag ccaaggtctc 1020
tgaggaggaa aatgacatag aagagcagca cgatgagctt ttcagtggcg acagtggagt 1080
ggacttgctg atagaagatc agcttctaag acaggaagac ctactgacaa gtgccacccg 1140

```
gaggccagca accactcgtc acactgctgc tgtcacgact gatgcgagca ttcaggccgc   1200

agcctcatcc tcagagcctg cacaggcctc tgcctcagca tccagctttg ttgagcctgc   1260

tcctcaggcc tccgatagag agctcttggc aaccccacag actaccacag tgtttccaga   1320

gcccacgggg gtgatgcctt ctacccaagt ctcacccacc accgtggccc acacagctgt   1380

ccagccactt ccagcaatgg ttcctgggga catatttgtg gaagctctac ccttggtccc   1440

tctgttacct gacacagttg ggacagacat gccagaggaa gaggggactg cagggcagga   1500

agcaacctct gctggtccca tcctgagccc tgaagaagaa gatgacattc ggaatgtgat   1560

aggaaggtgc aaggacaccc tctctacaat cacaggaccg accacccaga acacatatgg   1620

acggaatgaa ggggcctgga tgaaggaccc cctagccaag gacgaccgca tttacgtaac   1680

caactattac tatggcaaca cactggtcga gttccgaaac ctggagaact tcaaacaagg   1740

tcgctggagc aattcctaca agcttccata cagctggatc ggcacgggtc acgtggtcta   1800

caacggcgcc ttctactata accgggcctt cacccgaaac atcatcaagt atgacctgaa   1860

gcagcgttat gtggctgcct gggccatgct gcacgatgtg gcctatgagg aggccactcc   1920

ttggcggtgg cagggtcact cggatgtgga ctttgctgtg gatgagaatg gcctgtggct   1980

tatctaccca gctctggatg atgaaggttt caaccaggag gtcattgtcc tgagcaagct   2040

caatgccgtg gacctgagca cgcagaagga gaccacgtgg cgcactgggc tccggaggaa   2100

tttctatggc aactgctttg tcatctgtgg ggtactatat gctgtggaca gctataacca   2160

gaggaatgcc aacatctcct atgcctttga cacacacacc aacacacaga ttgtccctag   2220

gctgctgttt gagaatgaat attcgtacac cacccagata gactacaacc ccaaggaccg   2280

cctcctctat gcctgggaca atggccacca ggtcacctac catgtcatct ttgcctactg   2340

acacacttga ccctgcaaaa agaagcacag tggggccact agcaccttgt gtgtgtctgt   2400

gtgcatgtct gtctgtgaga ttgtgcaggt gggtgtgtgt tgttttaaaa tatattattt   2460

tgtataatat tacaagtgta aaatgacagt ttgggtctat ttttttata tggattgtag   2520

atcaatccat atgtgtatgt gctggtctca tccttcacaa tttatatttt tgtgcaaatg   2580

aacttctcct tctgaccagt aactaccttc tttcgtgctc tgaacctctg gctcctgagg   2640

tcaagggctg gagggtttct tcctccaggt cttgcagcca ggagcaggag tgtggggctc   2700

aggaaaaagt gctaagtggc ggcaaagttt ttatgtatta gagaagttct taaaactcag   2760

aaaaaaatac tttttttaaa taaaggagat attttaagac ccttaaaaaa aaaaaaaaaa   2820

aaaaaaaaaa aaaaaaaaaa aaaaaaaaaa aaaaaaaaaa aaa                     2863
```

<210> SEQ ID NO 6
<211> LENGTH: 746
<212> TYPE: PRT
<213> ORGANISM: Mus musculus

<400> SEQUENCE: 6

```
Met Ala Tyr Pro Leu Pro Leu Val Leu Cys Phe Ala Leu Val Val Ala
1               5                   10                  15

Gln Val Trp Gly Ser Thr Thr Pro Pro Thr Gly Thr Ser Glu Pro Pro
            20                  25                  30

Asp Val Gln Thr Val Glu Pro Thr Glu Asp Asp Ile Leu Gln Asn Glu
        35                  40                  45

Ala Asp Asn Gln Glu Asn Val Leu Ser Gln Leu Leu Gly Asp Tyr Asp
    50                  55                  60
```

-continued

```
Lys Val Lys Ala Val Ser Glu Gly Ser Asp Cys Gln Cys Lys Cys Val
65                  70                  75                  80

Val Arg Pro Leu Gly Arg Asp Ala Cys Gln Arg Ile Asn Gln Gly Ala
                85                  90                  95

Ser Arg Lys Glu Asp Phe Tyr Thr Val Glu Thr Ile Thr Ser Gly Ser
            100                 105                 110

Ser Cys Lys Cys Ala Cys Val Ala Pro Pro Ser Ala Val Asn Pro Cys
        115                 120                 125

Glu Gly Asp Phe Arg Leu Gln Lys Leu Arg Glu Ala Asp Ser Arg Asp
    130                 135                 140

Leu Lys Leu Ser Thr Ile Ile Asp Met Leu Glu Gly Ala Phe Tyr Gly
145                 150                 155                 160

Leu Asp Leu Leu Lys Leu His Ser Val Thr Thr Lys Leu Val Gly Arg
                165                 170                 175

Val Asp Lys Leu Glu Glu Glu Val Ser Lys Asn Leu Thr Lys Glu Asn
            180                 185                 190

Glu Gln Ile Lys Glu Asp Val Glu Glu Ile Arg Thr Glu Leu Asn Lys
        195                 200                 205

Arg Gly Lys Glu Asn Cys Ser Asp Asn Thr Leu Glu Ser Met Pro Asp
    210                 215                 220

Ile Arg Ser Ala Leu Gln Arg Asp Ala Ala Ala Ala Tyr Ala His Pro
225                 230                 235                 240

Glu Tyr Glu Glu Arg Phe Leu Gln Glu Glu Thr Val Ser Gln Gln Ile
                245                 250                 255

Asn Ser Ile Glu Leu Leu Arg Thr Gln Pro Leu Val Pro Pro Ala Ala
            260                 265                 270

Met Lys Pro Gln Arg Pro Leu Gln Arg Gln Val His Leu Arg Gly Arg
        275                 280                 285

Leu Ala Ser Lys Pro Thr Val Ile Arg Gly Ile Thr Tyr Tyr Lys Ala
    290                 295                 300

Lys Val Ser Glu Glu Glu Asn Asp Ile Glu Glu Gln His Asp Glu Leu
305                 310                 315                 320

Phe Ser Gly Asp Ser Gly Val Asp Leu Leu Ile Glu Asp Gln Leu Leu
                325                 330                 335

Arg Gln Glu Asp Leu Leu Thr Ser Ala Thr Arg Arg Pro Ala Thr Thr
            340                 345                 350

Arg His Thr Ala Ala Val Thr Thr Asp Ala Ser Ile Gln Ala Ala Ala
        355                 360                 365

Ser Ser Ser Glu Pro Ala Gln Ala Ser Ala Ser Ala Ser Ser Phe Val
    370                 375                 380

Glu Pro Ala Pro Gln Ala Ser Asp Arg Glu Leu Leu Ala Thr Pro Gln
385                 390                 395                 400

Thr Thr Thr Val Phe Pro Glu Pro Thr Gly Val Met Pro Ser Thr Gln
                405                 410                 415

Val Ser Pro Thr Thr Val Ala His Thr Ala Val Gln Pro Leu Pro Ala
            420                 425                 430

Met Val Pro Gly Asp Ile Phe Val Glu Ala Leu Pro Leu Val Pro Leu
        435                 440                 445

Leu Pro Asp Thr Val Gly Thr Asp Met Pro Glu Glu Glu Gly Thr Ala
    450                 455                 460

Gly Gln Glu Ala Thr Ser Ala Gly Pro Ile Leu Ser Pro Glu Glu Glu
465                 470                 475                 480

Asp Asp Ile Arg Asn Val Ile Gly Arg Cys Lys Asp Thr Leu Ser Thr
```

-continued

```
                485                 490                 495

Ile Thr Gly Pro Thr Thr Gln Asn Thr Tyr Gly Arg Asn Glu Gly Ala
            500                 505                 510

Trp Met Lys Asp Pro Leu Ala Lys Asp Asp Arg Ile Tyr Val Thr Asn
        515                 520                 525

Tyr Tyr Tyr Gly Asn Thr Leu Val Glu Phe Arg Asn Leu Glu Asn Phe
    530                 535                 540

Lys Gln Gly Arg Trp Ser Asn Ser Tyr Lys Leu Pro Tyr Ser Trp Ile
545                 550                 555                 560

Gly Thr Gly His Val Val Tyr Asn Gly Ala Phe Tyr Tyr Asn Arg Ala
                565                 570                 575

Phe Thr Arg Asn Ile Ile Lys Tyr Asp Leu Lys Gln Arg Tyr Val Ala
            580                 585                 590

Ala Trp Ala Met Leu His Asp Val Ala Tyr Glu Glu Ala Thr Pro Trp
        595                 600                 605

Arg Trp Gln Gly His Ser Asp Val Asp Phe Ala Val Asp Glu Asn Gly
    610                 615                 620

Leu Trp Leu Ile Tyr Pro Ala Leu Asp Asp Glu Gly Phe Asn Gln Glu
625                 630                 635                 640

Val Ile Val Leu Ser Lys Leu Asn Ala Val Asp Leu Ser Thr Gln Lys
                645                 650                 655

Glu Thr Thr Trp Arg Thr Gly Leu Arg Arg Asn Phe Tyr Gly Asn Cys
            660                 665                 670

Phe Val Ile Cys Gly Val Leu Tyr Ala Val Asp Ser Tyr Asn Gln Arg
        675                 680                 685

Asn Ala Asn Ile Ser Tyr Ala Phe Asp Thr His Thr Asn Thr Gln Ile
    690                 695                 700

Val Pro Arg Leu Leu Phe Glu Asn Glu Tyr Ser Tyr Thr Thr Gln Ile
705                 710                 715                 720

Asp Tyr Asn Pro Lys Asp Arg Leu Leu Tyr Ala Trp Asp Asn Gly His
                725                 730                 735

Gln Val Thr Tyr His Val Ile Phe Ala Tyr
            740                 745
```

```
<210> SEQ ID NO 7
<211> LENGTH: 2317
<212> TYPE: DNA
<213> ORGANISM: Gallus gallus

<400> SEQUENCE: 7

ccacgcgtcc gcccacgcgt ccggaaagag ttttggtaga gaacaagctt catggacttt     60

ctccagctct ctctgaagcc atccagagca tttctcgctg ggaacttgtc caggctgcgc    120

tcccacatgt gctacactgc actgcaacat tgctctccaa ccgaaacaag ctaggtcatc    180

aggataaact tggagtagct gaaacaaagc ttcttcacac tcttcactgg atgctgttgg    240

aggcccctca ggactgcagc aatgaccgat ttggaggaga cagaggttct agctggggag    300

ggagcagtag tgcctttatc caccaggctg aaaaccaggg atcaccggga catccccgac    360

ccagcaccac gaatgatgag gacgagaaca acagaaggaa gttctttcag aactccatgg    420

ccaccgtgga gctctttgtg ttcctctttg ctcctctggt tcacaggatt aaagaatctg    480

acctgacgtt tcgattggct agtggccttg ttatttggca gcctatgtgg gaacacaggc    540

aacctgaagt gtctgccttc aatgccctcg taaaaccaat caggaacatt gttacagcta    600

aaagaagttc tcctaccaac aatcagagtg tgacttgtga atccctaaat ctggacagtg    660
```

```
gtcatacaga gggactgcag gtggtctgtg agacgaccct gcccgattct gtaccttcaa    720
agcccactgt ttcagcatgt catcgtggaa attccttgga aggaagcgtg tcctctcaaa    780
cctctcagga gagaggtact ccacatccca gagtgtccat ggtgatccca ccatgccaga    840
agtctcgcta tgccacttac tttgatgtgg cagtactgcg ctgcttgctg cagcctcact    900
ggtctgagga gggcacacag tggtcactga tgtattacct gcagagactg aggcatatgc    960
tacaggaaaa gcccgagaaa ccacctgagc cagagatcac ccctttgcca agacttcgca   1020
gtagctccat ggtggctgct gcaccctctc tggtgaatac ccacaaaact caggatctca   1080
caatgaaatg taatgaggaa gaaaaatcac taagcacaga agcgttttcc aaggtttcac   1140
tgaccaactt gcgtaggcca gcggttccag atctctccac agatctgggg atgaacatct   1200
tcaaaaagtt taaaagccgc aaagaggaca gagagcgtga acgcaaaggg tcaattcctt   1260
tccaccatac tgggaagaag cgtcaacgga gaatggggat gcccttcctt ctccatgagg   1320
accatttgga tgtttcaccc actcggagca ctttttcatt tggcagtttt tctggcattg   1380
gagaggaccg acgtggcatt gagagaggag gatggcaaac caccatattg ggaaagttca   1440
ccagacgggg gagctctgac acagcaacgg agatggaaag cctgagcgct aggcactcac   1500
actctcacca cactcttgtc tctgatatgc cagaccactc aaacagccat ggagagaaca   1560
cagtcaaaga agttcggtcc cagatctcta ccatcactgt ggccaccttc aacactaccc   1620
tggcttcgtt caatgtgggc tatgctgatt tcttcagtga gcacatgagg aagctttgca   1680
atcaggtgcc catccctgag atgccccacg agcctcttgc gtgtgccaac ctcccacgga   1740
gcctgacaga ctcatgcatc aattacagtt gcttggagga tacggatcac attgatggaa   1800
ccaacaactt tgtccacaag aacggcatgc tggatctctc ggtaaatggc aaggaatgag   1860
gaaagccagg tccctcttct gtcaatatag tggtaccatt gagatcaggg tgttgatggg   1920
cttttcctcc acctctttat atgacttctc tcagcagtac ataaaggtag tcctgaaggc   1980
tgtttacttg gtcctgaacc atgacatcag ctccaggatt tgtgatgtgg cactgaacat   2040
tgtggagtgc ttgcttcagc ttggagtggt gccatctgta gagaaagtcc ggaggaagag   2100
cgagaacaaa gaaaatgaag cccctgaaaa gagaccaaat gagggatctt ttcaactcaa   2160
agcttctgga ggttcggctt gtggatttgg gcctcctcca gtcagtggaa ctggagatgg   2220
aggagaagaa ggaggcggtg gaagtggtgg aggaggaagc gatggaggtg gtggaggagg   2280
agggccgtat gagaagaatg acaaaaaaaa aaaaaaa                            2317
```

<210> SEQ ID NO 8
<211> LENGTH: 618
<212> TYPE: PRT
<213> ORGANISM: Gallus gallus

<400> SEQUENCE: 8

```
Thr Arg Pro Pro Thr Arg Pro Glu Arg Val Leu Val Glu Asn Lys Leu
1               5                   10                  15

His Gly Leu Ser Pro Ala Leu Ser Glu Ala Ile Gln Ser Ile Ser Arg
            20                  25                  30

Trp Glu Leu Val Gln Ala Ala Leu Pro His Val Leu His Cys Thr Ala
        35                  40                  45

Thr Leu Leu Ser Asn Arg Asn Lys Leu Gly His Gln Asp Lys Leu Gly
    50                  55                  60

Val Ala Glu Thr Lys Leu Leu His Thr Leu His Trp Met Leu Leu Glu
65                  70                  75                  80
```

```
Ala Pro Gln Asp Cys Ser Asn Asp Arg Phe Gly Gly Asp Arg Gly Ser
                85                  90                  95

Ser Trp Gly Gly Ser Ser Ser Ala Phe Ile His Gln Ala Glu Asn Gln
            100                 105                 110

Gly Ser Pro Gly His Pro Arg Pro Ser Thr Thr Asn Asp Glu Asp Glu
        115                 120                 125

Asn Asn Arg Arg Lys Phe Phe Gln Asn Ser Met Ala Thr Val Glu Leu
    130                 135                 140

Phe Val Phe Leu Phe Ala Pro Leu Val His Arg Ile Lys Glu Ser Asp
145                 150                 155                 160

Leu Thr Phe Arg Leu Ala Ser Gly Leu Val Ile Trp Gln Pro Met Trp
                165                 170                 175

Glu His Arg Gln Pro Glu Val Ser Ala Phe Asn Ala Leu Val Lys Pro
            180                 185                 190

Ile Arg Asn Ile Val Thr Ala Lys Arg Ser Ser Pro Thr Asn Asn Gln
        195                 200                 205

Ser Val Thr Cys Glu Ser Leu Asn Leu Asp Ser Gly His Thr Glu Gly
    210                 215                 220

Leu Gln Val Val Cys Glu Thr Thr Leu Pro Asp Ser Val Pro Ser Lys
225                 230                 235                 240

Pro Thr Val Ser Ala Cys His Arg Gly Asn Ser Leu Glu Gly Ser Val
                245                 250                 255

Ser Ser Gln Thr Ser Gln Glu Arg Gly Thr Pro His Pro Arg Val Ser
            260                 265                 270

Met Val Ile Pro Pro Cys Gln Lys Ser Arg Tyr Ala Thr Tyr Phe Asp
        275                 280                 285

Val Ala Val Leu Arg Cys Leu Leu Gln Pro His Trp Ser Glu Glu Gly
    290                 295                 300

Thr Gln Trp Ser Leu Met Tyr Tyr Leu Gln Arg Leu Arg His Met Leu
305                 310                 315                 320

Gln Glu Lys Pro Glu Lys Pro Pro Glu Pro Glu Ile Thr Pro Leu Pro
                325                 330                 335

Arg Leu Arg Ser Ser Ser Met Val Ala Ala Ala Pro Ser Leu Val Asn
            340                 345                 350

Thr His Lys Thr Gln Asp Leu Thr Met Lys Cys Asn Glu Glu Glu Lys
        355                 360                 365

Ser Leu Ser Thr Glu Ala Phe Ser Lys Val Ser Leu Thr Asn Leu Arg
    370                 375                 380

Arg Pro Ala Val Pro Asp Leu Ser Thr Asp Leu Gly Met Asn Ile Phe
385                 390                 395                 400

Lys Lys Phe Lys Ser Arg Lys Glu Asp Arg Glu Arg Glu Arg Lys Gly
                405                 410                 415

Ser Ile Pro Phe His His Thr Gly Lys Lys Arg Gln Arg Arg Met Gly
            420                 425                 430

Met Pro Phe Leu Leu His Glu Asp His Leu Asp Val Ser Pro Thr Arg
        435                 440                 445

Ser Thr Phe Ser Phe Gly Ser Phe Ser Gly Ile Gly Glu Asp Arg Arg
    450                 455                 460

Gly Ile Glu Arg Gly Gly Trp Gln Thr Thr Ile Leu Gly Lys Phe Thr
465                 470                 475                 480

Arg Arg Gly Ser Ser Asp Thr Ala Thr Glu Met Glu Ser Leu Ser Ala
                485                 490                 495
```

-continued

```
Arg His Ser His Ser His His Thr Leu Val Ser Asp Met Pro Asp His
            500                 505                 510

Ser Asn Ser His Gly Glu Asn Thr Val Lys Glu Val Arg Ser Gln Ile
        515                 520                 525

Ser Thr Ile Thr Val Ala Thr Phe Asn Thr Thr Leu Ala Ser Phe Asn
    530                 535                 540

Val Gly Tyr Ala Asp Phe Phe Ser Glu His Met Arg Lys Leu Cys Asn
545                 550                 555                 560

Gln Val Pro Ile Pro Glu Met Pro His Glu Pro Leu Ala Cys Ala Asn
                565                 570                 575

Leu Pro Arg Ser Leu Thr Asp Ser Cys Ile Asn Tyr Ser Cys Leu Glu
            580                 585                 590

Asp Thr Asp His Ile Asp Gly Thr Asn Asn Phe Val His Lys Asn Gly
        595                 600                 605

Met Leu Asp Leu Ser Val Asn Gly Lys Glu
    610                 615


<210> SEQ ID NO 9
<211> LENGTH: 383
<212> TYPE: DNA
<213> ORGANISM: Homo sapiens

<400> SEQUENCE: 9

ggaaattgac ccggcgaggc agttcagatg cagccactga gatggagagt ctgagcgcca      60

ggcattccca ctcccatcac accctggtaa gcgacctgcc ggacccctcc gacagccatg     120

gagaaaacac cgtcaaggaa gtgcgatctc agatctccac catcacagtt gcgaccttca     180

ataccacttt ggcgtcattc aacgtaggct atgcagactt tttcaatgag catatgagga     240

aactctgcaa ccaggtgcct atcccggaga tgccacatga acctctggca tgtgctaacc     300

tacctcgaag cctcacagac tcctgcataa actacagcta cctagaggac acagaacata     360

ttgacgggac caataacttt gtc                                             383


<210> SEQ ID NO 10
<211> LENGTH: 127
<212> TYPE: PRT
<213> ORGANISM: Homo sapiens

<400> SEQUENCE: 10

Lys Leu Thr Arg Arg Gly Ser Ser Asp Ala Ala Thr Glu Met Glu Ser
1               5                   10                  15

Leu Ser Ala Arg His Ser His Ser His His Thr Leu Val Ser Asp Leu
            20                  25                  30

Pro Asp Pro Ser Asp Ser His Gly Glu Asn Thr Val Lys Glu Val Arg
        35                  40                  45

Ser Gln Ile Ser Thr Ile Thr Val Ala Thr Phe Asn Thr Thr Leu Ala
    50                  55                  60

Ser Phe Asn Val Gly Tyr Ala Asp Phe Phe Asn Glu His Met Arg Lys
65                  70                  75                  80

Leu Cys Asn Gln Val Pro Ile Pro Glu Met Pro His Glu Pro Leu Ala
                85                  90                  95

Cys Ala Asn Leu Pro Arg Ser Leu Thr Asp Ser Cys Ile Asn Tyr Ser
            100                 105                 110

Tyr Leu Glu Asp Thr Glu His Ile Asp Gly Thr Asn Asn Phe Val
        115                 120                 125
```

<210> SEQ ID NO 11
<211> LENGTH: 593
<212> TYPE: DNA
<213> ORGANISM: Homo sapiens

<400> SEQUENCE: 11

```
tcggtaccgg gtcagtacgg atgtgaggtc agattccttg atcctggtac cagtggagca     60

aacagaaaca cgaagagctc cacagtagcc atggagttct ggaagatctt tcttcggttg    120

ttctcttctt cgtcattaga gctgctttgg caaggctgcc ctggagaacc ctggttttca    180

acctggtgga tgaaagcact gctgcttcca ccccagctgg agcctcggtc tgtaccccca    240

aaccgctcat tgttgcagtc ctgggggggcc tccagaagca tccagtgtag agtgtgaagg    300

agctttgtct cagcaacacc caatttatcc tggtggccta gcttgtttcg gtttgaaagc    360

agggttgcag tgcagtggag gacatgaggc aaagcagctt gcaccagttc ccatccggaa    420

atgctctgga tggcttcaga gagagctgga gagaggccat gcagcttgtt ttctaccaac    480

actcgctcaa aggacacaca agaagcttca tattgcttcc ccagtttggg cctcaaaaat    540

gcactggttt gccggcacag gaaggtctgg atgggcaggg ggatgccgcg ggc           593
```

<210> SEQ ID NO 12
<211> LENGTH: 418
<212> TYPE: DNA
<213> ORGANISM: Homo sapiens

<400> SEQUENCE: 12

```
tgcccatcca gaccttcctg tggcggcaaa ccagtccttt gagcgagtgt tggtagaaaa     60

caagctgcat ggcctctctc cagctctctc tgaagccatc cagagcattt ccagatggga    120

actggtgcaa gctgctttgc ctcatgtcct ccactgcact gcaaccctgc tttcaaaccg    180

aaacaagcta ggccaccagg ataaattggg tgttgctgag acaaagctcc ttcacactct    240

acactggatg cttctggagg ccccccagga ctgcaacaat gagcggtttg ggggtacaga    300

ccgaggctcc agctggggtg gaagcagcag tgctttcatc caccaggttg aaaaccaggg    360

ttctccaggg cagccttgcc aaagcagctc taatgacgaa gaagagaaca accgaaga      418
```

<210> SEQ ID NO 13
<211> LENGTH: 738
<212> TYPE: DNA
<213> ORGANISM: Homo sapiens

<400> SEQUENCE: 13

```
atggtgaaga ggaagagctc cgagggccag gagcaggacg gcggccgcgg catccccctg     60

cccatccaga ccttcctgtg gcggcaaacc agtttttatt atgactgtac acgccaccag    120

gataaattgg gtgttgctga gacaaagctc cttcacactc tacactggat gcttctggag    180

gccccccagg actgcaacaa tgagcggttt gggggtacag accgaggctc cagctggggt    240

ggaagcagca gtgctttcat ccaccaggtt gaaaaccagg gttctccagg gcagccttgc    300

caaagcagct ctaatgacga agaagagaac aaccgaagaa agatcttcca gaactccatg    360

gctactgtgg agctcttcgt gtttctgttt gctcccctgg tacacaggat caaggaatct    420

gacctcacct tccgtctggc cagtgggctt gttatatggc agcccatgtg ggaacacaga    480

cagcccggag tctctggctt taccgcactg gtgaagccca tcaggaacat cattacagct    540

aagagaagtt ctcctatcaa cagtcaaagc cggacctgtg aatcaccaaa tcaagatgca    600

agacacttag aggtactact aacctggtgc ttctatttta gcctcatgct tctattcagt    660
```

tcacctctgt atgatgaatt cttgatgtgt aactctccta tagatactgg gtatggagat 720
gaaaaagaaa ataattaa 738

<210> SEQ ID NO 14
<211> LENGTH: 245
<212> TYPE: PRT
<213> ORGANISM: Homo sapiens

<400> SEQUENCE: 14

```
Met Val Lys Arg Lys Ser Ser Glu Gly Gln Glu Gln Asp Gly Gly Arg
1               5                   10                  15

Gly Ile Pro Leu Pro Ile Gln Thr Phe Leu Trp Arg Gln Thr Ser Phe
            20                  25                  30

Tyr Tyr Asp Cys Thr Arg His Gln Asp Lys Leu Gly Val Ala Glu Thr
        35                  40                  45

Lys Leu Leu His Thr Leu His Trp Met Leu Leu Glu Ala Pro Gln Asp
    50                  55                  60

Cys Asn Asn Glu Arg Phe Gly Gly Thr Asp Arg Gly Ser Ser Trp Gly
65                  70                  75                  80

Gly Ser Ser Ser Ala Phe Ile His Gln Val Glu Asn Gln Gly Ser Pro
                85                  90                  95

Gly Gln Pro Cys Gln Ser Ser Ser Asn Asp Glu Glu Glu Asn Asn Arg
            100                 105                 110

Arg Lys Ile Phe Gln Asn Ser Met Ala Thr Val Glu Leu Phe Val Phe
        115                 120                 125

Leu Phe Ala Pro Leu Val His Arg Ile Lys Glu Ser Asp Leu Thr Phe
    130                 135                 140

Arg Leu Ala Ser Gly Leu Val Ile Trp Gln Pro Met Trp Glu His Arg
145                 150                 155                 160

Gln Pro Gly Val Ser Gly Phe Thr Ala Leu Val Lys Pro Ile Arg Asn
                165                 170                 175

Ile Ile Thr Ala Lys Arg Ser Ser Pro Ile Asn Ser Gln Ser Arg Thr
            180                 185                 190

Cys Glu Ser Pro Asn Gln Asp Ala Arg His Leu Glu Val Leu Leu Thr
        195                 200                 205

Trp Cys Phe Tyr Phe Ser Leu Met Leu Leu Phe Ser Ser Pro Leu Tyr
    210                 215                 220

Asp Glu Phe Leu Met Cys Asn Ser Pro Ile Asp Thr Gly Tyr Gly Asp
225                 230                 235                 240

Glu Lys Glu Asn Asn
                245
```

<210> SEQ ID NO 15
<211> LENGTH: 6702
<212> TYPE: DNA
<213> ORGANISM: Homo sapiens

<400> SEQUENCE: 15
atgctgtgct gcccctctga aagcttgatt gtcagtataa ttatcttctt tctgccatgg 60
aacagggcct ctcttgtgat acctccgtgc caaaggtccc gctatgccac ctactttgac 120
gttgctgttc tgcgctgcct acttcagccc cattggtctg aggaaggcac tcagtggtct 180
ctgatgtact atctacaaag gctgcgacac atgttggaag agaagccaga aaagcctccg 240
gagccagata ttcctctcct gcccagaccc aggagtagct ccatggtggc agcagctccc 300
tcactagtga acacccacaa aacccaagat ctcaccatga agtgtaacga ggaggaaaaa 360

-continued

```
tctcttagct ctgaggcctt ttccaaggtt tcactgacca atctgcgtag atctgcagtc    420
ccagatcttt cttcagacct gggcatgaat atttttaaaa agttcaagag ccgcaaagaa    480
gaccgagaga ggaaaggctc cattccattc caccacacag gcaagaggag gccacggaga    540
atgggagtgc ccttcctgct tcacgaggac cacctggatg tgtcccccac gcgcagcaca    600
ttctcctttg gaagtttctc tgggctggga gaagacaggc gaggaattga gaaaggaggc    660
tggcaaacca ccattttagg gaaattgacc cggcgaggca gttcagatgc agccactgag    720
atggagagtc tgagcgccag gcattcccac tcccatcaca ccctggtaag cgacctgccg    780
gacccctcca acagccatgg agaaaacacc gtcaaggaag tgcgatctca gatctccacc    840
atcacagttg cgaccttcaa taccactttg gcgtcattca acgtaggcta tgcagacttt    900
ttcaatgagc atatgaggaa actctgcaac caggtgccta tcccggagat gccacatgaa    960
cctctggcat gtgctaacct acctcgaagc ctcacagact cctgcataaa ctacagctac   1020
ctagaggaca cagaacatat tgacgggacc aataactttg tccacaagaa tggaatgctt   1080
gatctttctg tagttctgaa ggctgtttat cttgtcctta atcatgacat cagctctcgt   1140
atctgtgacg tggcgctaaa cattgtggaa tgcttgcttc aacttggtgt ggtgccctgt   1200
gtagaaaaga atagaaagaa gagtgaaaac aaggaaaatg agaccttgga aaagaggcca   1260
agtgagggag ctttccaatt caaaggagta tctggaagtt ccacctgtgg attcggaggc   1320
cctgctgatg aaagtacacc tgtaagcaac catagggttg ctctaacaat gctcatcaaa   1380
atagtgaagt ctttgggatg tgcctatggt tgtggtgaag gacaccgagg gctctctgga   1440
gatcgtctga gacaccaggt attccgagag aatgcccaga actgcctcac taagctatac   1500
aagctagata agatgcagtt ccgacaaacc atgagggact atgtgaacaa ggactctctc   1560
aataatgtag tggacttctt gcatgctttg ctaggatttt gtatggagcc ggtcactgac   1620
aacaaggctg ggtttggaaa taacttcacc acagtggaca acaaatccac agcccaaaat   1680
gtggaaggca ttatcgtcag cgccatgttt aaatccctca tcacacgctg cgcttcaacc   1740
acacatgaat tgcacagccc tgagaatctg ggactgtatt gtgacattcg tcagctggtc   1800
cagtttatca aagaggctca tgggaatgtc ttcaggagag tggccctcag cgctctgctt   1860
gacagtgccg agaagttagc accagggaaa aaggtggagg agaatgaaca ggaatctaag   1920
cctgcaggca gtaaaagcga tgaacaaatg caaggagcca acttggggcg gaaagatttc   1980
tggcgtaaga tgttcaagtc ccagagtgca gcaagtgaca ccagcagcca gtctgaacag   2040
gacacttcag aatgcacgac tgcccactca gggaccacct ctgaccgacg tgcccgctca   2100
cgatcccgca gaatttccct ccgaaagaag cttaaactcc ccatagggaa ctggctgaag   2160
agatcatccc tctcaggcct ggcagatggt gtggaggacc tcctggacat tagctctgtg   2220
gaccgactct ctttcatcag gcaaagctcc aaggtcaaat tcactagtgc tgtgaagctt   2280
tctgaaggtg ggccaggaag tggcatggaa aatggaagag atgaagagga gaatttcttc   2340
aagcgtcttg gttgccacag ttttgatgat catctctctc ccaaccaaga tggtggaaaa   2400
agcaaaaacg tggtgaatct tggagcaatc cgacaaggca tgaaacgctt ccaatttctg   2460
ttaaactgct gtgagccagg gacaattcct gatgcctcca tcctagcagc tgccttggat   2520
ctagaagccc ctgtggtggc cagagcagcc ttgttcctgg aatgtgctcg ttttgttcac   2580
cgctgcaacc gtggcaactg gccagagtgg atgaaagggc accacgtgaa catcaccaag   2640
aaaggacttt cccggggacg ctctcccatt gtgggcaaca agcgaaacca gaagctgcag   2700
```

-continued

```
tggaatgcag ccaagctctt ctaccaatgg ggagacgcaa ttggcgtccg attgaatgag   2760
ctgtgccacg gggaaagtga gagcccagcc aacctgctgg gtctcattta cgatgaagag   2820
accaagagga gacttagaaa ggaggatgag gaggaagact ttttagatga cagtaaggag   2880
actcccttta ctacaagaac ccctgcttgt actgtgaacc cctctaaatg cggttgcccc   2940
tttgccttga agatggcagc atgtcagctt cttctggaga ttaccacctt cctgcgagag   3000
accttttctt gcctgcccag acctcgcact gagcctctgg tggacttgga gagctgcaga   3060
cttcgtttgg atcccgagtt ggaccggcac agatatgaga ggaagatcag ctttgctggg   3120
gtcctggacg aaaatgaaga ctcaaaagat tctctccaca gcagcagcca cactctcaaa   3180
tcagatgcag gagtcgagga gaagaaagtt cccagcagga agatcaggat aggaggttct   3240
cgcctgctcc agattaaagg aacccgcagt ttccaggtga agaagggggg ttccttgtcc   3300
agcattcgcc gggtcggcag cttaaagagc agcaagttat cacggcagga ctcagagtct   3360
gaggctgagg agctgcagct gtcccagagc agggacactg tcactgacct agaagggagt   3420
ccttggagtg caagcgagcc cagcattgag ccagagggaa tgagtaatgc cggcgcggag   3480
gagaattacc acagaaacat gtcgtggctt catgtgatga tcttgctgtg caatcagcag   3540
agtttcatct gcactcacgt tgactactgc catccccact gctacctgca ccacagccgc   3600
tcctgtgccc gactggtcag agccatcaag ctactctatg gagacagtgt ggactccctg   3660
agggaaagca gcaacatcag cagtgtggct ctccggggca agaaacagaa agaatgctca   3720
gataagtcat gcctgaggac accttctcta aagaagagag tttcagatgc caatctggaa   3780
ggaaaaaaag attccggaat gctgaagtac atcagacttc aggtattgtt acctggatca   3840
gaaggattca tggaactttt aacagggagg ggactccaga cagcctattt actaatgttt   3900
gggacataca acatcagttg gtacagtgtt ggcataaagc cccttcagtt ggtgatgagc   3960
ttgtcgcctg ctcccttatc tctgttaatc aaggcagcac caattctgac agaggagatg   4020
tacggagaca tccagccagc tgcctgggag ctcctgctca gcatggatga gcacatggca   4080
ggggcagcag tgaaggtgcc tgaggccgtg tccgacatgc tgatgtcaga gttccaccac   4140
ccggagactg tgcagaggct gaacgctgtc ctcaagttcc acacgctctg gaggtttcgc   4200
tatcaggtct ggccccggat ggaggaaggg gcacagcaga tttttaagaa atccttttca   4260
gcccgggctg tgtcccgctc ccatcaaagg gcagaacaca tcttaaagaa cttgcagcag   4320
gaggaagaaa agaaacgact tggtagagaa gccagcctca tcactgccat ccccatcacc   4380
caggaggctt gctatgagcc cacatgcacg cccaactcag aaccggaaga agaagtagaa   4440
gaagtcacca atctggcatc ccgtcgactg tctgtgagtc catcctgcac ctccagcact   4500
tcccacagga attattcctt ccgccgcggg tcagtctggt cagtgcgttc agccgtcagt   4560
gctgaagatg aggaacatac cactgaacac acgccgaacc accatgtgcc tcagcccccca   4620
caagcagtgt tcccagcatg catctgtgca gcagtacttc ccattgttca tctgatggag   4680
gatggtgagg tgcgggaaga tggagtagca gtgagtgctg tggctcaaca agtcttatgg   4740
aactgtctaa ttgaagatcc atcaacggtt cttcgacatt ttctggaaaa actgaccatc   4800
agcaatagac aagatgagtt aatgtacatg ctgcgcaaac ttctcttgaa tattggagac   4860
tttcctgctc agacatctca catcctattc aactatttgg taggattaat catgtacttt   4920
gtgcggaccc cctgcgagtg gggatggat gccatttcag ccaccctgac attcctgtgg   4980
gaggtggtgg gttacgtgga gggcctcttc ttcaaggatc tcaagcagac gatgaagaag   5040
gagcagtgtg aggtgaagct cctggtgacc gcttcaatgc caggtactaa aaccttggta   5100
```

-continued

```
gttcatggac agaatgagtg cgatatccca acccagttac cagtccatga agacactcaa   5160

tttgaagccc tgttgaagga gtgtctggag ttttttaata tcccagaatc ccagtcaaca   5220

cattattttc ttatggataa acgatggaac cttatccact acaataagac ctatgttcga   5280

gatatttatc ctttccggag gtcagtatct ccccagctga atcttgtaca tatgcatcca   5340

gagaagggac aggagctcat tcagaaacag gtgttcaccc gaaagctgga agaagtaggg   5400

cgggtgttgt ttctcatctc cctaacccag aagatcccca cagcccacaa acagtcccac   5460

gtctccatgc ttcaggaaga cctcctccgc ctgccctcat tccctcgtag tgctattgat   5520

gctgagtttt cactcttcag tgatcctcaa gctggaaagg aactgtttgg cctcgacact   5580

cttcagaaaa gcttgtggat ccagctgctg gaggaaatgt tcctgggcat gccgagcgag   5640

tttccatggg gagacgaaat catgcttttc ctcaacgttt ttaacggggc tctgatcctc   5700

cacccggaag acagtgccct gctcaggcag tatgctgcca ccgtcatcaa caccgcggtg   5760

cacttcaacc acctcttctc tctcagcggc taccagtgga ttctccccac catgctgcag   5820

gtgtactccg actatgaaag caatccccag ctgcgtcaag ccatcgaatt tgcctgtcac   5880

cagttctata ttctacaccg gaagcccttt gtgctccagc tgtttgctag tgtggcccct   5940

ctcctggaat ttcctgatgc tgccaataat gggcccagca aaggtgtgtc agctcagtgc   6000

ctgtttgact tgctgcagtc cctagaggga gagaccaccg acatattaga catcttagag   6060

ctggtcaaag ctgagaagcc tctcaagtca ttagatttct gctatggaaa cgaagatctg   6120

acattttcta tcagtgaagc cattaagctc tgtgtcactg tggtggcgta tgctcccgaa   6180

tcattcagaa gtcttcagat gctgatggtc ttagaagcct tagttccatg ttacctacaa   6240

aagctaaaga ggcagacatc acaggtggag acagtacctg ctgcccgaga ggagattgcg   6300

gccactgctg ctcttgcgac gtccctacag gccctttgt acagtgtaga ggtcctcacc   6360

agggaaaacc ttcatttact ggaggaaggg caaggcattc ccagagagga actggatgaa   6420

cgaattgctc gggaagagtt cagaagaccc cgggagtcct tactgaatat ttgcactgag   6480

ttctataagc actgtgggcc acggctgaag atcttgcaaa atctggctgg ggagcctcgg   6540

gtcattgcct tggaactgct ggatgtgaag tctcacatga gtgtgctagg gaaaggcccc   6600

agaattactt ccctgtgcac tcgtatttcg tcttcctaca gagatgccat ttcacttgaa   6660

attcatgcta aaggccgtat ttgtgtttca aaaggaacgt ga                       6702
```

<210> SEQ ID NO 16
<211> LENGTH: 2233
<212> TYPE: PRT
<213> ORGANISM: Homo sapiens

<400> SEQUENCE: 16

```
Met Leu Cys Cys Pro Ser Glu Ser Leu Ile Val Ser Ile Ile Ile Phe
1               5                   10                  15

Phe Leu Pro Trp Asn Arg Ala Ser Leu Val Ile Pro Pro Cys Gln Arg
            20                  25                  30

Ser Arg Tyr Ala Thr Tyr Phe Asp Val Ala Val Leu Arg Cys Leu Leu
        35                  40                  45

Gln Pro His Trp Ser Glu Glu Gly Thr Gln Trp Ser Leu Met Tyr Tyr
    50                  55                  60

Leu Gln Arg Leu Arg His Met Leu Glu Glu Lys Pro Glu Lys Pro Pro
65                  70                  75                  80

Glu Pro Asp Ile Pro Leu Leu Pro Arg Pro Arg Ser Ser Ser Met Val
```

```
                85                  90                  95

Ala Ala Ala Pro Ser Leu Val Asn Thr His Lys Thr Gln Asp Leu Thr
            100                 105                 110

Met Lys Cys Asn Glu Glu Glu Lys Ser Leu Ser Ser Glu Ala Phe Ser
        115                 120                 125

Lys Val Ser Leu Thr Asn Leu Arg Arg Ser Ala Val Pro Asp Leu Ser
    130                 135                 140

Ser Asp Leu Gly Met Asn Ile Phe Lys Lys Phe Lys Ser Arg Lys Glu
145                 150                 155                 160

Asp Arg Glu Arg Lys Gly Ser Ile Pro Phe His His Thr Gly Lys Arg
                165                 170                 175

Arg Pro Arg Arg Met Gly Val Pro Phe Leu Leu His Glu Asp His Leu
            180                 185                 190

Asp Val Ser Pro Thr Arg Ser Thr Phe Ser Phe Gly Ser Phe Ser Gly
        195                 200                 205

Leu Gly Glu Asp Arg Arg Gly Ile Glu Lys Gly Gly Trp Gln Thr Thr
    210                 215                 220

Ile Leu Gly Lys Leu Thr Arg Arg Gly Ser Ser Asp Ala Ala Thr Glu
225                 230                 235                 240

Met Glu Ser Leu Ser Ala Arg His Ser His Ser His His Thr Leu Val
                245                 250                 255

Ser Asp Leu Pro Asp Pro Ser Asn Ser His Gly Glu Asn Thr Val Lys
            260                 265                 270

Glu Val Arg Ser Gln Ile Ser Thr Ile Thr Val Ala Thr Phe Asn Thr
        275                 280                 285

Thr Leu Ala Ser Phe Asn Val Gly Tyr Ala Asp Phe Phe Asn Glu His
    290                 295                 300

Met Arg Lys Leu Cys Asn Gln Val Pro Ile Pro Glu Met Pro His Glu
305                 310                 315                 320

Pro Leu Ala Cys Ala Asn Leu Pro Arg Ser Leu Thr Asp Ser Cys Ile
                325                 330                 335

Asn Tyr Ser Tyr Leu Glu Asp Thr Glu His Ile Asp Gly Thr Asn Asn
            340                 345                 350

Phe Val His Lys Asn Gly Met Leu Asp Leu Ser Val Val Leu Lys Ala
        355                 360                 365

Val Tyr Leu Val Leu Asn His Asp Ile Ser Ser Arg Ile Cys Asp Val
    370                 375                 380

Ala Leu Asn Ile Val Glu Cys Leu Leu Gln Leu Gly Val Val Pro Cys
385                 390                 395                 400

Val Glu Lys Asn Arg Lys Lys Ser Glu Asn Lys Glu Asn Glu Thr Leu
                405                 410                 415

Glu Lys Arg Pro Ser Glu Gly Ala Phe Gln Phe Lys Gly Val Ser Gly
            420                 425                 430

Ser Ser Thr Cys Gly Phe Gly Gly Pro Ala Asp Glu Ser Thr Pro Val
        435                 440                 445

Ser Asn His Arg Leu Ala Leu Thr Met Leu Ile Lys Ile Val Lys Ser
    450                 455                 460

Leu Gly Cys Ala Tyr Gly Cys Gly Glu Gly His Arg Gly Leu Ser Gly
465                 470                 475                 480

Asp Arg Leu Arg His Gln Val Phe Arg Glu Asn Ala Gln Asn Cys Leu
                485                 490                 495

Thr Lys Leu Tyr Lys Leu Asp Lys Met Gln Phe Arg Gln Thr Met Arg
            500                 505                 510
```

```
Asp Tyr Val Asn Lys Asp Ser Leu Asn Asn Val Val Asp Phe Leu His
        515                 520                 525

Ala Leu Leu Gly Phe Cys Met Glu Pro Val Thr Asp Asn Lys Ala Gly
    530                 535                 540

Phe Gly Asn Asn Phe Thr Thr Val Asp Asn Lys Ser Thr Ala Gln Asn
545                 550                 555                 560

Val Glu Gly Ile Ile Val Ser Ala Met Phe Lys Ser Leu Ile Thr Arg
            565                 570                 575

Cys Ala Ser Thr Thr His Glu Leu His Ser Pro Glu Asn Leu Gly Leu
            580                 585                 590

Tyr Cys Asp Ile Arg Gln Leu Val Gln Phe Ile Lys Glu Ala His Gly
        595                 600                 605

Asn Val Phe Arg Arg Val Ala Leu Ser Ala Leu Leu Asp Ser Ala Glu
    610                 615                 620

Lys Leu Ala Pro Gly Lys Lys Val Glu Glu Asn Glu Gln Glu Ser Lys
625                 630                 635                 640

Pro Ala Gly Ser Lys Ser Asp Glu Gln Met Gln Gly Ala Asn Leu Gly
            645                 650                 655

Arg Lys Asp Phe Trp Arg Lys Met Phe Lys Ser Gln Ser Ala Ala Ser
            660                 665                 670

Asp Thr Ser Ser Gln Ser Glu Gln Asp Thr Ser Glu Cys Thr Thr Ala
        675                 680                 685

His Ser Gly Thr Thr Ser Asp Arg Arg Ala Arg Ser Arg Ser Arg Arg
    690                 695                 700

Ile Ser Leu Arg Lys Lys Leu Lys Leu Pro Ile Gly Asn Trp Leu Lys
705                 710                 715                 720

Arg Ser Ser Leu Ser Gly Leu Ala Asp Gly Val Glu Asp Leu Leu Asp
            725                 730                 735

Ile Ser Ser Val Asp Arg Leu Ser Phe Ile Arg Gln Ser Ser Lys Val
            740                 745                 750

Lys Phe Thr Ser Ala Val Lys Leu Ser Glu Gly Gly Pro Gly Ser Gly
        755                 760                 765

Met Glu Asn Gly Arg Asp Glu Glu Glu Asn Phe Phe Lys Arg Leu Gly
    770                 775                 780

Cys His Ser Phe Asp Asp His Leu Ser Pro Asn Gln Asp Gly Gly Lys
785                 790                 795                 800

Ser Lys Asn Val Val Asn Leu Gly Ala Ile Arg Gln Gly Met Lys Arg
            805                 810                 815

Phe Gln Phe Leu Leu Asn Cys Cys Glu Pro Gly Thr Ile Pro Asp Ala
            820                 825                 830

Ser Ile Leu Ala Ala Ala Leu Asp Leu Glu Ala Pro Val Val Ala Arg
        835                 840                 845

Ala Ala Leu Phe Leu Glu Cys Ala Arg Phe Val His Arg Cys Asn Arg
    850                 855                 860

Gly Asn Trp Pro Glu Trp Met Lys Gly His His Val Asn Ile Thr Lys
865                 870                 875                 880

Lys Gly Leu Ser Arg Gly Arg Ser Pro Ile Val Gly Asn Lys Arg Asn
            885                 890                 895

Gln Lys Leu Gln Trp Asn Ala Ala Lys Leu Phe Tyr Gln Trp Gly Asp
            900                 905                 910

Ala Ile Gly Val Arg Leu Asn Glu Leu Cys His Gly Glu Ser Glu Ser
        915                 920                 925
```

```
Pro Ala Asn Leu Leu Gly Leu Ile Tyr Asp Glu Glu Thr Lys Arg Arg
    930                 935                 940

Leu Arg Lys Glu Asp Glu Glu Glu Asp Phe Leu Asp Asp Ser Lys Glu
945                 950                 955                 960

Thr Pro Phe Thr Thr Arg Thr Pro Ala Cys Thr Val Asn Pro Ser Lys
                965                 970                 975

Cys Gly Cys Pro Phe Ala Leu Lys Met Ala Ala Cys Gln Leu Leu Leu
            980                 985                 990

Glu Ile Thr Thr Phe Leu Arg Glu  Thr Phe Ser Cys Leu  Pro Arg Pro
        995                 1000                 1005

Arg Thr  Glu Pro Leu Val Asp  Leu Glu Ser Cys Arg  Leu Arg Leu
    1010                 1015                 1020

Asp Pro  Glu Leu Asp Arg His  Arg Tyr Glu Arg Lys  Ile Ser Phe
    1025                 1030                 1035

Ala Gly  Val Leu Asp Glu Asn  Glu Asp Ser Lys Asp  Ser Leu His
    1040                 1045                 1050

Ser Ser  Ser His Thr Leu Lys  Ser Asp Ala Gly Val  Glu Glu Lys
    1055                 1060                 1065

Lys Val  Pro Ser Arg Lys Ile  Arg Ile Gly Gly Ser  Arg Leu Leu
    1070                 1075                 1080

Gln Ile  Lys Gly Thr Arg Ser  Phe Gln Val Lys Lys  Gly Gly Ser
    1085                 1090                 1095

Leu Ser  Ser Ile Arg Arg Val  Gly Ser Leu Lys Ser  Ser Lys Leu
    1100                 1105                 1110

Ser Arg  Gln Asp Ser Glu Ser  Glu Ala Glu Glu Leu  Gln Leu Ser
    1115                 1120                 1125

Gln Ser  Arg Asp Thr Val Thr  Asp Leu Glu Gly Ser  Pro Trp Ser
    1130                 1135                 1140

Ala Ser  Glu Pro Ser Ile Glu  Pro Glu Gly Met Ser  Asn Ala Gly
    1145                 1150                 1155

Ala Glu  Glu Asn Tyr His Arg  Asn Met Ser Trp Leu  His Val Met
    1160                 1165                 1170

Ile Leu  Leu Cys Asn Gln Gln  Ser Phe Ile Cys Thr  His Val Asp
    1175                 1180                 1185

Tyr Cys  His Pro His Cys Tyr  Leu His His Ser Arg  Ser Cys Ala
    1190                 1195                 1200

Arg Leu  Val Arg Ala Ile Lys  Leu Leu Tyr Gly Asp  Ser Val Asp
    1205                 1210                 1215

Ser Leu  Arg Glu Ser Ser Asn  Ile Ser Ser Val Ala  Leu Arg Gly
    1220                 1225                 1230

Lys Lys  Gln Lys Glu Cys Ser  Asp Lys Ser Cys Leu  Arg Thr Pro
    1235                 1240                 1245

Ser Leu  Lys Lys Arg Val Ser  Asp Ala Asn Leu Glu  Gly Lys Lys
    1250                 1255                 1260

Asp Ser  Gly Met Leu Lys Tyr  Ile Arg Leu Gln Val  Leu Leu Pro
    1265                 1270                 1275

Gly Ser  Glu Gly Phe Met Glu  Leu Leu Thr Gly Arg  Gly Leu Gln
    1280                 1285                 1290

Thr Ala  Tyr Leu Leu Met Phe  Gly Thr Tyr Asn Ile  Ser Trp Tyr
    1295                 1300                 1305

Ser Val  Gly Ile Lys Pro Leu  Gln Leu Val Met Ser  Leu Ser Pro
    1310                 1315                 1320

Ala Pro  Leu Ser Leu Leu Ile  Lys Ala Ala Pro Ile  Leu Thr Glu
```

```
    1325                1330                1335

Glu Met  Tyr Gly Asp Ile Gln  Pro Ala Ala Trp Glu  Leu Leu Leu
    1340                1345                1350

Ser Met  Asp Glu His Met Ala  Gly Ala Ala Val Lys  Val Pro Glu
    1355                1360                1365

Ala Val  Ser Asp Met Leu Met  Ser Glu Phe His His  Pro Glu Thr
    1370                1375                1380

Val Gln  Arg Leu Asn Ala Val  Leu Lys Phe His Thr  Leu Trp Arg
    1385                1390                1395

Phe Arg  Tyr Gln Val Trp Pro  Arg Met Glu Glu Gly  Ala Gln Gln
    1400                1405                1410

Ile Phe  Lys Lys Ser Phe Ser  Ala Arg Ala Val Ser  Arg Ser His
    1415                1420                1425

Gln Arg  Ala Glu His Ile Leu  Lys Asn Leu Gln Gln  Glu Glu Glu
    1430                1435                1440

Lys Lys  Arg Leu Gly Arg Glu  Ala Ser Leu Ile Thr  Ala Ile Pro
    1445                1450                1455

Ile Thr  Gln Glu Ala Cys Tyr  Glu Pro Thr Cys Thr  Pro Asn Ser
    1460                1465                1470

Glu Pro  Glu Glu Glu Val Glu  Glu Val Thr Asn Leu  Ala Ser Arg
    1475                1480                1485

Arg Leu  Ser Val Ser Pro Ser  Cys Thr Ser Ser Thr  Ser His Arg
    1490                1495                1500

Asn Tyr  Ser Phe Arg Arg Gly  Ser Val Trp Ser Val  Arg Ser Ala
    1505                1510                1515

Val Ser  Ala Glu Asp Glu Glu  His Thr Thr Glu His  Thr Pro Asn
    1520                1525                1530

His His  Val Pro Gln Pro Pro  Gln Ala Val Phe Pro  Ala Cys Ile
    1535                1540                1545

Cys Ala  Ala Val Leu Pro Ile  Val His Leu Met Glu  Asp Gly Glu
    1550                1555                1560

Val Arg  Glu Asp Gly Val Ala  Val Ser Ala Val Ala  Gln Gln Val
    1565                1570                1575

Leu Trp  Asn Cys Leu Ile Glu  Asp Pro Ser Thr Val  Leu Arg His
    1580                1585                1590

Phe Leu  Glu Lys Leu Thr Ile  Ser Asn Arg Gln Asp  Glu Leu Met
    1595                1600                1605

Tyr Met  Leu Arg Lys Leu Leu  Leu Asn Ile Gly Asp  Phe Pro Ala
    1610                1615                1620

Gln Thr  Ser His Ile Leu Phe  Asn Tyr Leu Val Gly  Leu Ile Met
    1625                1630                1635

Tyr Phe  Val Arg Thr Pro Cys  Glu Trp Gly Met Asp  Ala Ile Ser
    1640                1645                1650

Ala Thr  Leu Thr Phe Leu Trp  Glu Val Val Gly Tyr  Val Glu Gly
    1655                1660                1665

Leu Phe  Phe Lys Asp Leu Lys  Gln Thr Met Lys Lys  Glu Gln Cys
    1670                1675                1680

Glu Val  Lys Leu Leu Val Thr  Ala Ser Met Pro Gly  Thr Lys Thr
    1685                1690                1695

Leu Val  Val His Gly Gln Asn  Glu Cys Asp Ile Pro  Thr Gln Leu
    1700                1705                1710

Pro Val  His Glu Asp Thr Gln  Phe Glu Ala Leu Leu  Lys Glu Cys
    1715                1720                1725
```

```
Leu Glu  Phe Phe Asn Ile Pro  Glu Ser Gln Ser Thr  His Tyr Phe
    1730                 1735                 1740

Leu Met  Asp Lys Arg Trp Asn  Leu Ile His Tyr Asn  Lys Thr Tyr
    1745                 1750                 1755

Val Arg  Asp Ile Tyr Pro Phe  Arg Arg Ser Val Ser  Pro Gln Leu
    1760                 1765                 1770

Asn Leu  Val His Met His Pro  Glu Lys Gly Gln Glu  Leu Ile Gln
    1775                 1780                 1785

Lys Gln  Val Phe Thr Arg Lys  Leu Glu Glu Val Gly  Arg Val Leu
    1790                 1795                 1800

Phe Leu  Ile Ser Leu Thr Gln  Lys Ile Pro Thr Ala  His Lys Gln
    1805                 1810                 1815

Ser His  Val Ser Met Leu Gln  Glu Asp Leu Leu Arg  Leu Pro Ser
    1820                 1825                 1830

Phe Pro  Arg Ser Ala Ile Asp  Ala Glu Phe Ser Leu  Phe Ser Asp
    1835                 1840                 1845

Pro Gln  Ala Gly Lys Glu Leu  Phe Gly Leu Asp Thr  Leu Gln Lys
    1850                 1855                 1860

Ser Leu  Trp Ile Gln Leu Leu  Glu Glu Met Phe Leu  Gly Met Pro
    1865                 1870                 1875

Ser Glu  Phe Pro Trp Gly Asp  Glu Ile Met Leu Phe  Leu Asn Val
    1880                 1885                 1890

Phe Asn  Gly Ala Leu Ile Leu  His Pro Glu Asp Ser  Ala Leu Leu
    1895                 1900                 1905

Arg Gln  Tyr Ala Ala Thr Val  Ile Asn Thr Ala Val  His Phe Asn
    1910                 1915                 1920

His Leu  Phe Ser Leu Ser Gly  Tyr Gln Trp Ile Leu  Pro Thr Met
    1925                 1930                 1935

Leu Gln  Val Tyr Ser Asp Tyr  Glu Ser Asn Pro Gln  Leu Arg Gln
    1940                 1945                 1950

Ala Ile  Glu Phe Ala Cys His  Gln Phe Tyr Ile Leu  His Arg Lys
    1955                 1960                 1965

Pro Phe  Val Leu Gln Leu Phe  Ala Ser Val Ala Pro  Leu Leu Glu
    1970                 1975                 1980

Phe Pro  Asp Ala Ala Asn Asn  Gly Pro Ser Lys Gly  Val Ser Ala
    1985                 1990                 1995

Gln Cys  Leu Phe Asp Leu Leu  Gln Ser Leu Glu Gly  Glu Thr Thr
    2000                 2005                 2010

Asp Ile  Leu Asp Ile Leu Glu  Leu Val Lys Ala Glu  Lys Pro Leu
    2015                 2020                 2025

Lys Ser  Leu Asp Phe Cys Tyr  Gly Asn Glu Asp Leu  Thr Phe Ser
    2030                 2035                 2040

Ile Ser  Glu Ala Ile Lys Leu  Cys Val Thr Val Val  Ala Tyr Ala
    2045                 2050                 2055

Pro Glu  Ser Phe Arg Ser Leu  Gln Met Leu Met Val  Leu Glu Ala
    2060                 2065                 2070

Leu Val  Pro Cys Tyr Leu Gln  Lys Leu Lys Arg Gln  Thr Ser Gln
    2075                 2080                 2085

Val Glu  Thr Val Pro Ala Ala  Arg Glu Glu Ile Ala  Ala Thr Ala
    2090                 2095                 2100

Ala Leu  Ala Thr Ser Leu Gln  Ala Leu Leu Tyr Ser  Val Glu Val
    2105                 2110                 2115
```

Leu Thr Arg Glu Asn Leu His Leu Leu Glu Glu Gly Gln Gly Ile
2120 2125 2130

Pro Arg Glu Glu Leu Asp Glu Arg Ile Ala Arg Glu Glu Phe Arg
2135 2140 2145

Arg Pro Arg Glu Ser Leu Leu Asn Ile Cys Thr Glu Phe Tyr Lys
2150 2155 2160

His Cys Gly Pro Arg Leu Lys Ile Leu Gln Asn Leu Ala Gly Glu
2165 2170 2175

Pro Arg Val Ile Ala Leu Glu Leu Leu Asp Val Lys Ser His Met
2180 2185 2190

Ser Val Leu Gly Lys Gly Pro Arg Ile Thr Ser Leu Cys Thr Arg
2195 2200 2205

Ile Ser Ser Ser Tyr Arg Asp Ala Ile Ser Leu Glu Ile His Ala
2210 2215 2220

Lys Gly Arg Ile Cys Val Ser Lys Gly Thr
2225 2230

<210> SEQ ID NO 17
<211> LENGTH: 3962
<212> TYPE: DNA
<213> ORGANISM: Gallus gallus
<220> FEATURE:
<221> NAME/KEY: misc_feature
<222> LOCATION: (832)..(846)
<223> OTHER INFORMATION: n is a, c, g, or t

<400> SEQUENCE: 17
gaattcggca cgaggatcac ccacgtcata gtactcgggg acaacttcaa ctgtgagcac 60
aaacatcact ttgtcatgtg tagaaggcta cactctggtg ggagcaagca catccacgtg 120
caaggagagt ggcgtttgga tgccagagtt ttctgatgac atttgcattc ctgtgtcatg 180
tgggatccca gaatctccag agcacggatt tgtggttggc accaaattca gttacaaaga 240
tgtggttctt tataaatgtg atcctggcta cgaactacaa ggtgatacag aacggacttg 300
ccaagaagac aagctttgga gtggctcagt gccaacatgc agaagagtat cttgtgggcc 360
cccagaggtg atcgaaaatg gatctgttca aggagaagag ttcctgtttg gcagcgaggc 420
tttttacagc tgtgaccctg gtttcgaact gcagggacca agccgaagaa tttgccacgt 480
tgacaagaag tggagcccct ctgctcctgt gtgtaggcga attacttgcg ggctgcctcc 540
ttcaatagaa aaagcagagg ccatttctac aggaaacaca tacaaaagta atgtaacctt 600
tgtgtgcagc tctggttacc accttgttgg accgcagaat atcacatgtc ttgccaatgg 660
gagctggagt aagccattac cactgtgtga agagaccaga tgcaaactgc cactttcttt 720
gctgaatggg aaggcaattt atgaaaataa tacagttggc agtactgtag catatttctg 780
caagagcgga tacagtttgg aaggagaacc tacagcagag tgcacaaggg annnnnnnnn 840
nnnnnntcct ttgcctctct gtaaaccaaa cccttgtccc gtgcctttca taatcccaga 900
gaatgccctt ctctctgagg tggattttta cgtcgggcag aatgtgtcca tcaggtgcag 960
ggaaggctac cagttgaaag ggcaggctgt gatcacttgt aatgctgatg agacttggac 1020
tccaacaaca gctaagtgtg aaaagatatc ttgcgggccc ccagctcaca tagagaatgc 1080
tttcatccgt ggtagcttct atcagtatgg agatatgatc acctactcat gctacagtgg 1140
ttatatgctg gagggacccc tgcggagcat ttgcttagaa aatggaacgt ggacaacacc 1200
acctacatgc aaagctgtct gtcggttccc atgtcagaat ggtggagtct gtgagcgacc 1260
aaatgcctgc tcgtgtccag atggctggat gggtcgtctc tgtgaagagc caatatgcat 1320

```
tttgccatgt ctcaatggag gtcgctgtgt ggctccttac aagtgtgact gcccccctgg   1380
atggactgga tcgcggtgcc atacagctgt ttgccagtca ccttgcttaa atggtgggaa   1440
gtgcatacga ccaaatcgat gttactgtcc ctcatcatgg actggacatg attgctcaag   1500
aaaacggaag gctggattct accacttcta acagcagagc aacagtttta cactcagaaa   1560
cctttcttca gcctagacag cggggctcag aatctaatgc attgtaaatc acatccattg   1620
cttcccttcc ccccacctcc tttgttttgt attttatttt gtgatatatt ttttctatac   1680
ctttcaattt ttaaagaaaa cctctgtatt ttccatttac aaaagtatta tcaaatatat   1740
gctgctatat acacaccata cacatacaaa agtgaagatc cctactgttc actgagaaag   1800
tggctgtgta cggtgaagtc cctcccattt cttacacccg gtaagctaat taaaacatgc   1860
tatactgcca gccatgatta aacmsamtgy kkcmgttctg cttatcatct gccaaagcat   1920
actgaaatcc agcaacttaa tggtaaggaa taattatgta aagctaattg aaccaccgaa   1980
ctttgcattg ggcttgtgtc atggttgtat aaattagaag tacatctgat aaagtcccaa   2040
ttgtagccag agttcctggt ggacgtaagt agattctgta atgttcatta tgtgacatta   2100
acgtcattgg aaagcgactt agatggaagg cagtggcaag aattttagcc atcagtaaaa   2160
tactcaaaag catgaaagag ttgagacaat gtctaggcaa taacagcctc tgaggatttt   2220
tggcatacag gcatttcagg tgtcatgatc agtctggata atccagaatg cagcagcgga   2280
cagcacagac cactgaaaac ttccccctgg taatggaact caccactact tgcctgcaac   2340
cagtagccct ttcctgtgtg atgatcaaat acacatccaa catcctcctg ccaggcaaat   2400
gtttttgaga catggggttt gggtcccaat gttttggccc tgcagtaggg agagaaggtg   2460
aagctttgct gtttgcttgc agaagagtgg tatttatgtt atgctgaacc ctcagagaac   2520
tggaaaaggc ctctcttgtg tacatgcaca ggcagaaata cctagctgag taagaaatgc   2580
tgagagcaca catgctgtcc gatttctctt tcgcacattg ttgatcccag tgcatctgag   2640
agtcacacat ggttgagtgc catcattcag ttgtgctcta atgagctgag atgctgagat   2700
ttaccgatgg gtacgtggtg tggcggaatt acaaggtgga aatcccagtc atgtgctgag   2760
gtcaaatgtt tgctaattat catcagatag taatgaagtc tagtctgtga aagaagattt   2820
tagagtgaga accattgatc gggagctcca tttttcccag tagcagcaga aaagcatgac   2880
tgtcagccca cactaggaaa gaagaaggaa tatgctctac actctgcagc attactgcgt   2940
agttaccctc ggggtcatga gcgtgcacac gctgccccca cctcccccct tccctcttta   3000
taaatataca ttccctttat gaatgcatga taggacaata aaaggagcta atggagggac   3060
tagggcgcta gtgaagactg acacatagct aatggctgtt aacccaagac cagaaatggg   3120
gaacaaacaa gtgaagctgt gaaccaggaa aagctggaag aaaaacaaac aggtgaagaa   3180
tatttgtcaa gggacgagct gaattcgaat gcagattcct tcccactggg agctgcaacc   3240
ggctgaagag ttgttctttc aactcccgta aatatatttt ttctgatgga ttctgctgac   3300
atgtaccaac agccatcagt gtttacagct ttggttcaag ttagcattca gtaaataata   3360
acacgtttca acccacggtc actgccatgt gtaggcactt tgttccctga ctcctgctgc   3420
tgtgcacagt ggggtgtaca gatgctgtag tgagcagctc gggatacctg aagggaaaga   3480
gtgcatcagt gggagaagtg gatttttatt tatatgtcat tctcatcttt tacaaagtag   3540
tcccattttc agtgtgcttc tctggtacgt gccctcacag ccctggcaat ctccagagca   3600
gagcagcagt gctttggaag gcgagcaggg ctggcaggag actgctgagc cttgggggcg   3660
```

agggccggct tttagcactg cagcttcaca ctagtgacta gtacatggag tttggggata 3720
tactcagtca atacgtttca taagctgatg tggtagaaag agtagctgaa actataggct 3780
gttatattag tgctgtgtat gatgctttga tacttgctgg aatattatcc cttccccatt 3840
ctgtgcggta ttgtcattta tgtcactgct tgttgtgtgt tttaaaggac ttctgtgtga 3900
tgcactttac actgtaaata aagttgcacc ctgtttagta ccwaaaaaaa aaaaaaaaaa 3960
aa 3962

<210> SEQ ID NO 18
<211> LENGTH: 499
<212> TYPE: PRT
<213> ORGANISM: Gallus gallus

<400> SEQUENCE: 18

Tyr Ser Gly Thr Thr Ser Thr Val Ser Thr Asn Ile Thr Leu Ser Cys
1 5 10 15

Val Glu Gly Tyr Thr Leu Val Gly Ala Ser Thr Ser Thr Cys Lys Glu
20 25 30

Ser Gly Val Trp Met Pro Glu Phe Ser Asp Asp Ile Cys Ile Pro Val
35 40 45

Ser Cys Gly Ile Pro Glu Ser Pro Glu His Gly Phe Val Val Gly Thr
50 55 60

Lys Phe Ser Tyr Lys Asp Val Val Leu Tyr Lys Cys Asp Pro Gly Tyr
65 70 75 80

Glu Leu Gln Gly Asp Thr Glu Arg Thr Cys Gln Glu Asp Lys Leu Trp
85 90 95

Ser Gly Ser Val Pro Thr Cys Arg Arg Val Ser Cys Gly Pro Pro Glu
100 105 110

Val Ile Glu Asn Gly Ser Val Gln Gly Glu Glu Phe Leu Phe Gly Ser
115 120 125

Glu Ala Phe Tyr Ser Cys Asp Pro Gly Phe Glu Leu Gln Gly Pro Ser
130 135 140

Arg Arg Ile Cys His Val Asp Lys Lys Trp Ser Pro Ser Ala Pro Val
145 150 155 160

Cys Arg Arg Ile Thr Cys Gly Leu Pro Pro Ser Ile Glu Lys Ala Glu
165 170 175

Ala Ile Ser Thr Gly Asn Thr Tyr Lys Ser Asn Val Thr Phe Val Cys
180 185 190

Ser Ser Gly Tyr His Leu Val Gly Pro Gln Asn Ile Thr Cys Leu Ala
195 200 205

Asn Gly Ser Trp Ser Lys Pro Leu Pro Leu Cys Glu Glu Thr Arg Cys
210 215 220

Lys Leu Pro Leu Ser Leu Leu Asn Gly Lys Ala Ile Tyr Glu Asn Asn
225 230 235 240

Thr Val Gly Ser Thr Val Ala Tyr Phe Cys Lys Ser Gly Tyr Ser Leu
245 250 255

Glu Gly Glu Pro Thr Ala Glu Cys Thr Arg Asn Asn Asn Asn Asn Asn
260 265 270

Pro Leu Pro Leu Cys Lys Pro Asn Pro Cys Pro Val Pro Phe Ile Ile
275 280 285

Pro Glu Asn Ala Leu Leu Ser Glu Val Asp Phe Tyr Val Gly Gln Asn
290 295 300

Val Ser Ile Arg Cys Arg Glu Gly Tyr Gln Leu Lys Gly Gln Ala Val
305 310 315 320

```
Ile Thr Cys Asn Ala Asp Glu Thr Trp Thr Pro Thr Thr Ala Lys Cys
                325                 330                 335

Glu Lys Ile Ser Cys Gly Pro Pro Ala His Ile Glu Asn Ala Phe Ile
            340                 345                 350

Arg Gly Ser Phe Tyr Gln Tyr Gly Asp Met Ile Thr Tyr Ser Cys Tyr
        355                 360                 365

Ser Gly Tyr Met Leu Glu Gly Pro Leu Arg Ser Ile Cys Leu Glu Asn
    370                 375                 380

Gly Thr Trp Thr Thr Pro Pro Thr Cys Lys Ala Val Cys Arg Phe Pro
385                 390                 395                 400

Cys Gln Asn Gly Gly Val Cys Glu Arg Pro Asn Ala Cys Ser Cys Pro
                405                 410                 415

Asp Gly Trp Met Gly Arg Leu Cys Glu Glu Pro Ile Cys Ile Leu Pro
            420                 425                 430

Cys Leu Asn Gly Gly Arg Cys Val Ala Pro Tyr Lys Cys Asp Cys Pro
        435                 440                 445

Pro Gly Trp Thr Gly Ser Arg Cys His Thr Ala Val Cys Gln Ser Pro
    450                 455                 460

Cys Leu Asn Gly Gly Lys Cys Ile Arg Pro Asn Arg Cys Tyr Cys Pro
465                 470                 475                 480

Ser Ser Trp Thr Gly His Asp Cys Ser Arg Lys Arg Lys Ala Gly Phe
                485                 490                 495

Tyr His Phe


<210> SEQ ID NO 19
<211> LENGTH: 1969
<212> TYPE: DNA
<213> ORGANISM: Homo sapiens

<400> SEQUENCE: 19

tatgaatgca cagcttgccc atcggggaca tacaaacctg aagcctcacc aggaggaatc     60

agcagttgca ttccatgtcc cgatgaaaat cacacctctc cacctggaag cacatcccct    120

gaagactgtg tctgcagaga gggatacagg gcatctggcc agacctgtga acttgtccac    180

tgccctgccc tgaagcctcc cgaaaatggt tactttatcc aaaacacttg caacaaccac    240

ttcaatgcag cctgtggggt ccgatgtcac cctggatttg atcttgtggg aagcagcatc    300

atcttatgtc tacccaatgg tttgtggtcc ggttcagaga gctactgcag agtaagaaca    360

tgtcctcatc tccgccagcc gaaacatggc cacatcagct gttctacaag ggaaatgtta    420

tataagacaa catgtttggt tgcctgtgat gaagggtaca gactagaagg cagtgataag    480

cttacttgtc aaggaaacag ccagtgggat gggccagaac cccggtgtgt ggagcgccac    540

tgttccacct ttcagatgcc caaagatgtc atcatatccc cccacaactg tggcaagcag    600

ccagccaaat ttgggacgat ctgctatgta agttgccgcc aagggttcat tttatctgga    660

gtcaaagaaa tgctgagatg taccacttct ggaaaatgga atgtcggagt tcaggcagct    720

gtgtgtaaag acgtggaggc tcctcaaatc aactgtccta aggacataga ggctaagact    780

ctggaacagc aagattctgc caatgttacc tggcagattc caacagctaa agacaactct    840

ggtgaaaagg tgtcagtccg cgttcatcca gctttcaccc caccttacct tttcccaatt    900

ggagatgttg ctatcgtata cacggcaact gacctatccg gcaaccaggc cagctgcatt    960

ttccatatca aggttattga tgcagaacca cctgtcatag actggtgcag atctccacct   1020

cccgtccagg tctcggagaa ggtacatgcc gcaagctggg atgagcctca gttctcagac   1080
```

```
aactcagggg ctgaattggt cattaccaga agtcatacac aaggagacct tttccctcaa   1140

ggggagacta tagtacagta tacagccact gacccctcag gcaataacag gacatgtgat   1200

atccatattg tcataaaagg ttctccctgt gaaatcccat tcacacctgt aaatggggat   1260

tttatatgca ctccagataa tactggagtc aactgtacat taacttgctt ggagggctat   1320

gatttcacag aagggtctac tgacaagtat tattgtgctt atgaagatgg cgtctggaaa   1380

ccaacatata ccactgaatg gccagactgt gccaaaaaac gttttgcaaa ccacgggttc   1440

aagtcctttg agatgttcta caaagcagct cgttgtgatg acacagatct gatgaagaag   1500

ttttctgaag cattggagac gaccctggga aaaatggtcc catcattttg tagtgatgca   1560

gaggacattg actgcagact ggaggagaac ctgaccaaaa aatattgcct agaatataat   1620

tatgactatg aaaatggctt tgcaattggt aattaaattc tgtggcatcg gtagttggca   1680

agactaatct gcaaaataag aataattcca gaaaagtgag gcaaactaga aacattaact   1740

tctattaatt tattcatcaa gtattttagg atggctaaat aatttgataa tgtgctgaaa   1800

gatcattaag gttatatcaa attttagtaa caaataaatt atttaaaatt atttgccagg   1860

attcttaaaa atgacaaaaa ctaagaaaac taagtcacat atgctggtaa aattcaaatg   1920

ttgatgtatc ctaaaagaga atagtaataa agtcctaaca gcaactttt                1969
```

<210> SEQ ID NO 20
<211> LENGTH: 413
<212> TYPE: PRT
<213> ORGANISM: Homo sapiens

<400> SEQUENCE: 20

```
Met Leu Tyr Lys Thr Thr Cys Leu Val Ala Cys Asp Glu Gly Tyr Arg
1               5                   10                  15

Leu Glu Gly Ser Asp Lys Leu Thr Cys Gln Gly Asn Ser Gln Trp Asp
            20                  25                  30

Gly Pro Glu Pro Arg Cys Val Glu Arg His Cys Ser Thr Phe Gln Met
        35                  40                  45

Pro Lys Asp Val Ile Ile Ser Pro His Asn Cys Gly Lys Gln Pro Ala
    50                  55                  60

Lys Phe Gly Thr Ile Cys Tyr Val Ser Cys Arg Gln Gly Phe Ile Leu
65                  70                  75                  80

Ser Gly Val Lys Glu Met Leu Arg Cys Thr Thr Ser Gly Lys Trp Asn
                85                  90                  95

Val Gly Val Gln Ala Ala Val Cys Lys Asp Val Glu Ala Pro Gln Ile
            100                 105                 110

Asn Cys Pro Lys Asp Ile Glu Ala Lys Thr Leu Glu Gln Gln Asp Ser
        115                 120                 125

Ala Asn Val Thr Trp Gln Ile Pro Thr Ala Lys Asp Asn Ser Gly Glu
    130                 135                 140

Lys Val Ser Val Arg Val His Pro Ala Phe Thr Pro Pro Tyr Leu Phe
145                 150                 155                 160

Pro Ile Gly Asp Val Ala Ile Val Tyr Thr Ala Thr Asp Leu Ser Gly
                165                 170                 175

Asn Gln Ala Ser Cys Ile Phe His Ile Lys Val Ile Asp Ala Glu Pro
            180                 185                 190

Pro Val Ile Asp Trp Cys Arg Ser Pro Pro Pro Val Gln Val Ser Glu
        195                 200                 205

Lys Val His Ala Ala Ser Trp Asp Glu Pro Gln Phe Ser Asp Asn Ser
```

```
    210                 215                 220

Gly Ala Glu Leu Val Ile Thr Arg Ser His Thr Gln Gly Asp Leu Phe
225                 230                 235                 240

Pro Gln Gly Glu Thr Ile Val Gln Tyr Thr Ala Thr Asp Pro Ser Gly
                245                 250                 255

Asn Asn Arg Thr Cys Asp Ile His Ile Val Ile Lys Gly Ser Pro Cys
            260                 265                 270

Glu Ile Pro Phe Thr Pro Val Asn Gly Asp Phe Ile Cys Thr Pro Asp
        275                 280                 285

Asn Thr Gly Val Asn Cys Thr Leu Thr Cys Leu Glu Gly Tyr Asp Phe
    290                 295                 300

Thr Glu Gly Ser Thr Asp Lys Tyr Tyr Cys Ala Tyr Glu Asp Gly Val
305                 310                 315                 320

Trp Lys Pro Thr Tyr Thr Thr Glu Trp Pro Asp Cys Ala Lys Lys Arg
                325                 330                 335

Phe Ala Asn His Gly Phe Lys Ser Phe Glu Met Phe Tyr Lys Ala Ala
            340                 345                 350

Arg Cys Asp Asp Thr Asp Leu Met Lys Lys Phe Ser Glu Ala Leu Glu
        355                 360                 365

Thr Thr Leu Gly Lys Met Val Pro Ser Phe Cys Ser Asp Ala Glu Asp
    370                 375                 380

Ile Asp Cys Arg Leu Glu Glu Asn Leu Thr Lys Lys Tyr Cys Leu Glu
385                 390                 395                 400

Tyr Asn Tyr Asp Tyr Glu Asn Gly Phe Ala Ile Gly Asn
                405                 410


<210> SEQ ID NO 21
<211> LENGTH: 2693
<212> TYPE: DNA
<213> ORGANISM: Gallus gallus
<220> FEATURE:
<221> NAME/KEY: misc_feature
<222> LOCATION: (2651)..(2651)
<223> OTHER INFORMATION: n is a, c, g, or t

<400> SEQUENCE: 21

cttaagtaga ggagactgtt gcactaatta ccaggtcgtt tgcaaaggag aaacccactg      60

ggtcgatgat gactgtgaag agataaaaac tcctgaatgt ccagcaggct ttgttcgtcc     120

tcctttgatc atcttctctg ttgatggttt ccgtgcatca tatatgaaga aagggaacaa     180

ggtcatgccc aatattgaaa agctgagatc ttgtggaaca cattctcctt acatgaggcc     240

ggtctaccct acaaaaacct tccccaactt gtacaccctt gctactggac tctatcctga     300

atcacatgga atcgttggca attcaatgta tgacccagtg tttgatgcca gcttcagtct     360

tcgagggcga gagaaattca atcacagatg gtggggaggt caaccaattt ggattactgc     420

agccaagcaa ggggtgaaag ctggcacatt cttctggtct gttgtcatcc cccacgagcg     480

tagaatacta acaatactgc agtggctgac ccttccggat aacgaaaggc cttatgttta     540

tgctttctac tctgagcaac cagatgctgc tggccacaga tatggtcctt tcaactcaga     600

gatgatggta aatcccctga gagagattga caagacagta ggacaactaa tggatggact     660

gaaacagctg aaactgcatc gatgtgtcaa tgtcatattt gttggtgatc atgggatgga     720

agatactact tgtgaaagaa ctgaattttt gagcaactac ctgaccaacg tggaagatat     780

cattctgctg cctggatctt tagggagaat tcgccctagg tctagcaata acctgaaata     840

tgaccccaaa gtgattgttg ccaaccttac atgcaggaag ccagaccagc actttaagcc     900
```

```
atacttgaag catcaccttt ctaaacgctt gcactatgct tacaataggc gaattgagga    960
tgtccattta ctggttgagc gcaagtggca tgtagcaagg aaagctgtgg atgtttacaa   1020
gaaaccaaca ggaaagtgtt tcttccatgg agaccatggc tatgacaaca agataaacag   1080
catgcagact gtcttcatag gttatggacc tacattcaaa tacaagacca aagtaccgcc   1140
ttttgaaaac attgaacttt acaatgtcat gtgtgatctg cttggattaa agcctgctcc   1200
caataatggt acccacggaa gtttgaatca cctgctaaga gccaatgttt ataaaccaac   1260
tgtgccagat gaagttgcta agccacttta tcctgtagca ctaccttctg catcagattt   1320
tgatatagga tgtacatgtg atgataagaa caagttggat gaactcaaca agcgctttca   1380
tgtcaaggga acggaagaga agcatcttct gtacgggcgc cctgcagtgc tgtaccgcac   1440
gaagtacaat atcttgcacc accatgactt tgaaagtggc tacagtgaaa cattcctgat   1500
gcctctctgg acatcctaca ctatttccaa acaggcagag gtatccggtg tcccagaaca   1560
cctggccagc tgcgtcaggc ccgatctccg catatctcca ggaaacagcc agagctgctc   1620
agcctacaga ggtgacaagc agctctccta cagcttcctc ttccctcctc aactaagttc   1680
ctctgcagaa gcaaagtatg atgcttttct aataacaaat atcattccaa tgtatcctgc   1740
tttcaaaaag gtatggaact atttccaaag ggttttagtg aagagatatg ccactgaacg   1800
aaatggagtc aatgttataa gtggaccaat ctttgactat gactatgatg gtttacatga   1860
cacacctgaa aaaatcaaac agtttgtgga aggcagtgcc atccctgttc ctactcatta   1920
ctatgccatc ataaccagct gtttagattt cactcagcca gccgacaagt gtgatggacc   1980
actctctgtt ctctcgtaca tccttcccca ccggcctgac aacgatgaga gctgcaatag   2040
catggaagat gaatcaaagt gggttgaaga tcttcttaag atgcacactg cacgggtgcg   2100
ggacattgag cagctcacaa gcttggactt cttccgaaag acgagtcgca gctacacaga   2160
aatcctctcc ctaaagacat acctgcatac atttgaaagt gaaatttagc tttctaacct   2220
tgctcagtgc attcttttat caactggtgt atatttttat attggtttta tatttattaa   2280
tttgaaacca ggacattaaa aatattagta ttttaatctt gtatcaaatc ttaaatatta   2340
aacccttgtg tcatttgttt tgtttctcta atgtttaata taggtatgtc tcttggttta   2400
tttagtagcg cttgtaatac tgcagcttaa gtccttactc caagctttta tctggtgctg   2460
cagaatttga tacgtgattc gaggaaatat taatttccca tgctccttta ccacactttt   2520
agtcctgtac tgtgtatcaa aatactgaac atgtaaaatt acattcattt actgttgact   2580
atgtgacaga catatttaaa ccctatagac aaatagcatc ttaaatataa taaaccacac   2640
attcagtttt naaaaaaaaa aaaaaaaaaa aaaaaaaaaa aaaaaaaaaa aaa          2693
```

<210> SEQ ID NO 22
<211> LENGTH: 735
<212> TYPE: PRT
<213> ORGANISM: Gallus gallus

<400> SEQUENCE: 22

```
Leu Ser Arg Gly Asp Cys Cys Thr Asn Tyr Gln Val Val Cys Lys Gly
1               5                   10                  15

Glu Thr His Trp Val Asp Asp Asp Cys Glu Glu Ile Lys Thr Pro Glu
            20                  25                  30

Cys Pro Ala Gly Phe Val Arg Pro Pro Leu Ile Ile Phe Ser Val Asp
        35                  40                  45

Gly Phe Arg Ala Ser Tyr Met Lys Lys Gly Asn Lys Val Met Pro Asn
```

-continued

```
    50                  55                  60

Ile Glu Lys Leu Arg Ser Cys Gly Thr His Ser Pro Tyr Met Arg Pro
65                  70                  75                  80

Val Tyr Pro Thr Lys Thr Phe Pro Asn Leu Tyr Thr Leu Ala Thr Gly
                85                  90                  95

Leu Tyr Pro Glu Ser His Gly Ile Val Gly Asn Ser Met Tyr Asp Pro
            100                 105                 110

Val Phe Asp Ala Ser Phe Ser Leu Arg Gly Arg Glu Lys Phe Asn His
        115                 120                 125

Arg Trp Trp Gly Gly Gln Pro Ile Trp Ile Thr Ala Ala Lys Gln Gly
    130                 135                 140

Val Lys Ala Gly Thr Phe Phe Trp Ser Val Val Ile Pro His Glu Arg
145                 150                 155                 160

Arg Ile Leu Thr Ile Leu Gln Trp Leu Thr Leu Pro Asp Asn Glu Arg
                165                 170                 175

Pro Tyr Val Tyr Ala Phe Tyr Ser Glu Gln Pro Asp Ala Ala Gly His
            180                 185                 190

Arg Tyr Gly Pro Phe Asn Ser Glu Met Met Val Asn Pro Leu Arg Glu
        195                 200                 205

Ile Asp Lys Thr Val Gly Gln Leu Met Asp Gly Leu Lys Gln Leu Lys
    210                 215                 220

Leu His Arg Cys Val Asn Val Ile Phe Val Gly Asp His Gly Met Glu
225                 230                 235                 240

Asp Thr Thr Cys Glu Arg Thr Glu Phe Leu Ser Asn Tyr Leu Thr Asn
                245                 250                 255

Val Glu Asp Ile Ile Leu Leu Pro Gly Ser Leu Gly Arg Ile Arg Pro
            260                 265                 270

Arg Ser Ser Asn Asn Leu Lys Tyr Asp Pro Lys Val Ile Val Ala Asn
        275                 280                 285

Leu Thr Cys Arg Lys Pro Asp Gln His Phe Lys Pro Tyr Leu Lys His
    290                 295                 300

His Leu Ser Lys Arg Leu His Tyr Ala Tyr Asn Arg Arg Ile Glu Asp
305                 310                 315                 320

Val His Leu Leu Val Glu Arg Lys Trp His Val Ala Arg Lys Ala Val
                325                 330                 335

Asp Val Tyr Lys Lys Pro Thr Gly Lys Cys Phe Phe His Gly Asp His
            340                 345                 350

Gly Tyr Asp Asn Lys Ile Asn Ser Met Gln Thr Val Phe Ile Gly Tyr
        355                 360                 365

Gly Pro Thr Phe Lys Tyr Lys Thr Lys Val Pro Pro Phe Glu Asn Ile
    370                 375                 380

Glu Leu Tyr Asn Val Met Cys Asp Leu Leu Gly Leu Lys Pro Ala Pro
385                 390                 395                 400

Asn Asn Gly Thr His Gly Ser Leu Asn His Leu Leu Arg Ala Asn Val
                405                 410                 415

Tyr Lys Pro Thr Val Pro Asp Glu Val Ala Lys Pro Leu Tyr Pro Val
            420                 425                 430

Ala Leu Pro Ser Ala Ser Asp Phe Asp Ile Gly Cys Thr Cys Asp Asp
        435                 440                 445

Lys Asn Lys Leu Asp Glu Leu Asn Lys Arg Phe His Val Lys Gly Thr
    450                 455                 460

Glu Glu Lys His Leu Leu Tyr Gly Arg Pro Ala Val Leu Tyr Arg Thr
465                 470                 475                 480
```

```
Lys Tyr Asn Ile Leu His His His Asp Phe Glu Ser Gly Tyr Ser Glu
                485                 490                 495

Thr Phe Leu Met Pro Leu Trp Thr Ser Tyr Thr Ile Ser Lys Gln Ala
            500                 505                 510

Glu Val Ser Gly Val Pro Glu His Leu Ala Ser Cys Val Arg Pro Asp
        515                 520                 525

Leu Arg Ile Ser Pro Gly Asn Ser Gln Ser Cys Ser Ala Tyr Arg Gly
    530                 535                 540

Asp Lys Gln Leu Ser Tyr Ser Phe Leu Phe Pro Pro Gln Leu Ser Ser
545                 550                 555                 560

Ser Ala Glu Ala Lys Tyr Asp Ala Phe Leu Ile Thr Asn Ile Ile Pro
                565                 570                 575

Met Tyr Pro Ala Phe Lys Lys Val Trp Asn Tyr Phe Gln Arg Val Leu
            580                 585                 590

Val Lys Arg Tyr Ala Thr Glu Arg Asn Gly Val Asn Val Ile Ser Gly
        595                 600                 605

Pro Ile Phe Asp Tyr Asp Tyr Asp Gly Leu His Asp Thr Pro Glu Lys
    610                 615                 620

Ile Lys Gln Phe Val Glu Gly Ser Ala Ile Pro Val Pro Thr His Tyr
625                 630                 635                 640

Tyr Ala Ile Ile Thr Ser Cys Leu Asp Phe Thr Gln Pro Ala Asp Lys
                645                 650                 655

Cys Asp Gly Pro Leu Ser Val Leu Ser Tyr Ile Leu Pro His Arg Pro
            660                 665                 670

Asp Asn Asp Glu Ser Cys Asn Ser Met Glu Asp Glu Ser Lys Trp Val
        675                 680                 685

Glu Asp Leu Leu Lys Met His Thr Ala Arg Val Arg Asp Ile Glu Gln
    690                 695                 700

Leu Thr Ser Leu Asp Phe Phe Arg Lys Thr Ser Arg Ser Tyr Thr Glu
705                 710                 715                 720

Ile Leu Ser Leu Lys Thr Tyr Leu His Thr Phe Glu Ser Glu Ile
                725                 730                 735
```

<210> SEQ ID NO 23
<211> LENGTH: 3110
<212> TYPE: DNA
<213> ORGANISM: Homo sapiens

<400> SEQUENCE: 23

```
agtgcactcc gtgaaggcaa agagaacacg ctgcaaaagg ctttccaata atcctcgaca     60

tggcaaggag gagctcgttc cagtcgtgtc agataatatc cctgttcact tttgccgttg    120

gagtcaatat ctgcttagga ttcactgcac atcgaattaa gagagcagaa ggatgggagg    180

aaggtcctcc tacagtgcta tcagactccc cctggaccaa catctccgga tcttgcaagg    240

gcaggtgctt tgaacttcaa gaggctggac ctcctgattg tcgctgtgac aacttgtgta    300

agagctatac cagttgctgc catgactttg atgagctgtg tttgaagaca gcccgtgcgt    360

gggagtgtac taaggacaga tgtggggaag tcagaaatga agaaaatgcc tgtcactgct    420

cagaggactg cttggccagg ggagactgct gtaccaatta ccaagtggtt tgcaaaggag    480

agtcgcattg ggttgatgat gactgtgagg aaataaaggc cgcagaatgc cctgcagggt    540

ttgttcgccc tccattaatc atcttctccg tggatggctt ccgtgcatca tacatgaaga    600

aaggcagcaa agtcatgcct aatattgaaa aactaaggtc ttgtggcaca cactctccct    660
```

-continued

```
acatgaggcc ggtgtaccca actaaaacct ttcctaactt atacactttg gccactgggc    720
tatatccaga atcacatgga attgttggca attcaatgta tgatcctgta tttgatgcca    780
cttttcatct gcgagggcga gagaaattta atcatagatg gtggggaggt caaccgctat    840
ggattacagc caccaagcaa ggggtgaaag ctggaacatt cttttggtct gttgtcatcc    900
ctcacgagcg gagaatatta accatattgc agtggctcac cctgccagat catgagaggc    960
cttcggtcta tgccttctat tctgagcaac ctgatttctc tggacacaaa tatggccctt   1020
tcggccctga gatgacaaat cctctgaggg aaatcgacaa aattgtgggg caattaatgg   1080
atggactgaa acaactaaaa ctgcatcggt gtgtcaacgt catctttgtc ggagaccatg   1140
gaatggaaga tgtcacatgt gatagaactg agttcttgag taattaccta actaatgtgg   1200
atgatattac tttagtgcct ggaactctag gaagaattcg atccaaattt agcaacaatg   1260
ctaaatatga ccccaaagcc attattgcca atctcacgtg taaaaaacca gatcagcact   1320
ttaagcctta cttgaaacag caccttccca aacgtttgca ctatgccaac aacagaagaa   1380
ttgaggatat ccatttattg gtggaacgca gatggcatgt tgcaaggaaa cctttggatg   1440
tttataagaa accatcagga aaatgctttt tccagggaga ccacggattt gataacaagg   1500
tcaacagcat gcagactgtt tttgtaggtt atggcccaac atttaagtac aagactaaag   1560
tgcctccatt tgaaaacatt gaactttaca atgttatgtg tgatctcctg ggattgaagc   1620
cagctcctaa taatgggacc catggaagtt tgaatcatct cctgcgcact aataccttca   1680
ggccaaccat gccagaggaa gttaccagac ccaattatcc agggattatg taccttcagt   1740
ctgattttga cctgggctgc acttgtgatg ataaggtaga gccaaagaac aagttggatg   1800
aactcaacaa acggcttcat acaaaagggt ctacagaaga gagacacctc ctctatgggc   1860
gacctgcagt gctttatcgg actagatatg atatcttata tcacactgac tttgaaagtg   1920
gttatagtga aatattccta atgccactct ggacatcata tactgtttcc aaacaggctg   1980
aggtttccag cgttcctgac catctgacca gttgcgtccg gcctgatgtc cgtgtttctc   2040
cgagtttcag tcagaactgt ttggcctaca aaaatgataa gcagatgtcc tacggattcc   2100
tctttcctcc ttatctgagc tcttcaccag aggctaaata tgatgcattc cttgtaacca   2160
atatggttcc aatgtatcct gctttcaaac gggtctggaa ttatttccaa agggtattgg   2220
tgaagaaata tgcttcggaa agaaatggag ttaacgtgat aagtggacca atcttcgact   2280
atgactatga tggcttacat gacacagaag acaaaataaa acagtacgtg gaaggcagtt   2340
ccattcctgt tccaactcac tactacagca tcatcaccag ctgtctggat ttcactcagc   2400
ctgccgacaa gtgtgacggc cctctctctg tgtcctcctt catcctgcct caccggcctg   2460
acaacgagga gagctgcaat agctcagagg acgaatcaaa atgggtagaa gaactcatga   2520
agatgcacac agctagggtg cgtgacattg aacatctcac cagcctggac ttcttccgaa   2580
agaccagccg cagctaccca gaaatcctga cactcaagac atacctgcat acatatgaga   2640
gcgagattta actttctgag catctgcagt acagtcttat caactggttg tatattttta   2700
tattgttttt gtatttatta atttgaaacc aggacattaa aaatgttagt attttaatcc   2760
tgtaccaaat ctgacatatt atgcctgaat gactccactg tttttctcta atgcttgatt   2820
taggtagcct tgtgttctga gtagagcttg taataaatac tgcagcttga gtttttagtg   2880
gaagcttcta aatggtgctg cagatttgat atttgcattg aggaaatatt aattttccaa   2940
tgcacagttg ccacatttag tcctgtactg tatggaaaca ctgattttgt aaagttgcct   3000
ttatttgctg ttaactgtta actatgacag atatatttaa gccttataaa ccaatcttaa   3060
```

acataataaa tcacacattc agttttttct ggtaaaaaaa aaaaaaaaaa 3110

<210> SEQ ID NO 24
<211> LENGTH: 863
<212> TYPE: PRT
<213> ORGANISM: Homo sapiens

<400> SEQUENCE: 24

```
Met Ala Arg Arg Ser Ser Phe Gln Ser Cys Gln Ile Ile Ser Leu Phe
1               5                   10                  15

Thr Phe Ala Val Gly Val Asn Ile Cys Leu Gly Phe Thr Ala His Arg
            20                  25                  30

Ile Lys Arg Ala Glu Gly Trp Glu Glu Gly Pro Pro Thr Val Leu Ser
        35                  40                  45

Asp Ser Pro Trp Thr Asn Ile Ser Gly Ser Cys Lys Gly Arg Cys Phe
    50                  55                  60

Glu Leu Gln Glu Ala Gly Pro Pro Asp Cys Arg Cys Asp Asn Leu Cys
65                  70                  75                  80

Lys Ser Tyr Thr Ser Cys Cys His Asp Phe Asp Glu Leu Cys Leu Lys
                85                  90                  95

Thr Ala Arg Ala Trp Glu Cys Thr Lys Asp Arg Cys Gly Glu Val Arg
            100                 105                 110

Asn Glu Glu Asn Ala Cys His Cys Ser Glu Asp Cys Leu Ala Arg Gly
        115                 120                 125

Asp Cys Cys Thr Asn Tyr Gln Val Val Cys Lys Gly Glu Ser His Trp
    130                 135                 140

Val Asp Asp Asp Cys Glu Glu Ile Lys Ala Ala Glu Cys Pro Ala Gly
145                 150                 155                 160

Phe Val Arg Pro Pro Leu Ile Ile Phe Ser Val Asp Gly Phe Arg Ala
                165                 170                 175

Ser Tyr Met Lys Lys Gly Ser Lys Val Met Pro Asn Ile Glu Lys Leu
            180                 185                 190

Arg Ser Cys Gly Thr His Ser Pro Tyr Met Arg Pro Val Tyr Pro Thr
        195                 200                 205

Lys Thr Phe Pro Asn Leu Tyr Thr Leu Ala Thr Gly Leu Tyr Pro Glu
    210                 215                 220

Ser His Gly Ile Val Gly Asn Ser Met Tyr Asp Pro Val Phe Asp Ala
225                 230                 235                 240

Thr Phe His Leu Arg Gly Arg Glu Lys Phe Asn His Arg Trp Trp Gly
                245                 250                 255

Gly Gln Pro Leu Trp Ile Thr Ala Thr Lys Gln Gly Val Lys Ala Gly
            260                 265                 270

Thr Phe Phe Trp Ser Val Val Ile Pro His Glu Arg Arg Ile Leu Thr
        275                 280                 285

Ile Leu Gln Trp Leu Thr Leu Pro Asp His Glu Arg Pro Ser Val Tyr
    290                 295                 300

Ala Phe Tyr Ser Glu Gln Pro Asp Phe Ser Gly His Lys Tyr Gly Pro
305                 310                 315                 320

Phe Gly Pro Glu Met Thr Asn Pro Leu Arg Glu Ile Asp Lys Ile Val
                325                 330                 335

Gly Gln Leu Met Asp Gly Leu Lys Gln Leu Lys Leu His Arg Cys Val
            340                 345                 350

Asn Val Ile Phe Val Gly Asp His Gly Met Glu Asp Val Thr Cys Asp
        355                 360                 365
```

```
Arg Thr Glu Phe Leu Ser Asn Tyr Leu Thr Asn Val Asp Asp Ile Thr
    370                 375                 380

Leu Val Pro Gly Thr Leu Gly Arg Ile Arg Ser Lys Phe Ser Asn Asn
385                 390                 395                 400

Ala Lys Tyr Asp Pro Lys Ala Ile Ile Ala Asn Leu Thr Cys Lys Lys
                405                 410                 415

Pro Asp Gln His Phe Lys Pro Tyr Leu Lys Gln His Leu Pro Lys Arg
            420                 425                 430

Leu His Tyr Ala Asn Asn Arg Arg Ile Glu Asp Ile His Leu Leu Val
        435                 440                 445

Glu Arg Arg Trp His Val Ala Arg Lys Pro Leu Asp Val Tyr Lys Lys
    450                 455                 460

Pro Ser Gly Lys Cys Phe Phe Gln Gly Asp His Gly Phe Asp Asn Lys
465                 470                 475                 480

Val Asn Ser Met Gln Thr Val Phe Val Gly Tyr Gly Pro Thr Phe Lys
                485                 490                 495

Tyr Lys Thr Lys Val Pro Pro Phe Glu Asn Ile Glu Leu Tyr Asn Val
            500                 505                 510

Met Cys Asp Leu Leu Gly Leu Lys Pro Ala Pro Asn Asn Gly Thr His
        515                 520                 525

Gly Ser Leu Asn His Leu Leu Arg Thr Asn Thr Phe Arg Pro Thr Met
    530                 535                 540

Pro Glu Glu Val Thr Arg Pro Asn Tyr Pro Gly Ile Met Tyr Leu Gln
545                 550                 555                 560

Ser Asp Phe Asp Leu Gly Cys Thr Cys Asp Asp Lys Val Glu Pro Lys
                565                 570                 575

Asn Lys Leu Asp Glu Leu Asn Lys Arg Leu His Thr Lys Gly Ser Thr
            580                 585                 590

Glu Glu Arg His Leu Leu Tyr Gly Arg Pro Ala Val Leu Tyr Arg Thr
        595                 600                 605

Arg Tyr Asp Ile Leu Tyr His Thr Asp Phe Glu Ser Gly Tyr Ser Glu
    610                 615                 620

Ile Phe Leu Met Pro Leu Trp Thr Ser Tyr Thr Val Ser Lys Gln Ala
625                 630                 635                 640

Glu Val Ser Ser Val Pro Asp His Leu Thr Ser Cys Val Arg Pro Asp
                645                 650                 655

Val Arg Val Ser Pro Ser Phe Ser Gln Asn Cys Leu Ala Tyr Lys Asn
            660                 665                 670

Asp Lys Gln Met Ser Tyr Gly Phe Leu Phe Pro Pro Tyr Leu Ser Ser
        675                 680                 685

Ser Pro Glu Ala Lys Tyr Asp Ala Phe Leu Val Thr Asn Met Val Pro
    690                 695                 700

Met Tyr Pro Ala Phe Lys Arg Val Trp Asn Tyr Phe Gln Arg Val Leu
705                 710                 715                 720

Val Lys Lys Tyr Ala Ser Glu Arg Asn Gly Val Asn Val Ile Ser Gly
                725                 730                 735

Pro Ile Phe Asp Tyr Asp Tyr Asp Gly Leu His Asp Thr Glu Asp Lys
            740                 745                 750

Ile Lys Gln Tyr Val Glu Gly Ser Ser Ile Pro Val Pro Thr His Tyr
        755                 760                 765

Tyr Ser Ile Ile Thr Ser Cys Leu Asp Phe Thr Gln Pro Ala Asp Lys
    770                 775                 780
```

-continued

```
Cys Asp Gly Pro Leu Ser Val Ser Ser Phe Ile Leu Pro His Arg Pro
785                 790                 795                 800

Asp Asn Glu Glu Ser Cys Asn Ser Ser Glu Asp Glu Ser Lys Trp Val
                805                 810                 815

Glu Glu Leu Met Lys Met His Thr Ala Arg Val Arg Asp Ile Glu His
            820                 825                 830

Leu Thr Ser Leu Asp Phe Phe Arg Lys Thr Ser Arg Ser Tyr Pro Glu
        835                 840                 845

Ile Leu Thr Leu Lys Thr Tyr Leu His Thr Tyr Glu Ser Glu Ile
    850                 855                 860


<210> SEQ ID NO 25
<211> LENGTH: 2772
<212> TYPE: DNA
<213> ORGANISM: Mus musculus

<400> SEQUENCE: 25

cccacgcgtc cgcccacgcg tccggagaac accctgcaga ggttttccaa gaatccctcg      60

gcatggcaag acaaggctgt ttcgggtcat accaggtaat atccttgttc acttttgcca     120

tcggcgtcaa tctctgctta ggattcacag caagtcgaat taagagggcc gaatgggatg     180

aaggacctcc cacagtgtta tctgactctc catggaccaa cacatctgga tcctgcaaag     240

gtagatgctt tgagcttcaa gaggttggac ctcctgactg tcggtgtgac aacctatgta     300

agagctacag cagctgctgc catgattttg atgagctctg tttgaaaaca gctcgaggct     360

gggagtgcac caaagacaga tgtggggaag tacgaaatga ggaaaatgcc tgtcactgct     420

cagaagactg cttgtcccgg ggagactgct gtaccaacta tcaagtggtc tgcaaaggag     480

aatcacactg ggtagatgat gactgtgaag aaataagagt ccctgaatgc cctgcagggt     540

ttgtccgccc tccgttaatc atcttctctg tggatggatt ccgtgcatcg tacatgaaga     600

aaggcagcaa ggttatgccc aacattgaga aactgcggtc ctgtggcacc catgctccct     660

acatgaggcc tgtgtaccct acaaaaacct tccctaatct gtatacgctg gccactggtt     720

tatatccaga atcccatgga atcgttggca attcaatgta tgaccctgtc tttgatgcta     780

ctttccatct tcgagggcga gagaagttta accatagatg gtggggaggc caaccgctat     840

ggattacagc caccaagcaa ggggtgagag ccgggacatt cttttggtct gtgagcatcc     900

ctcacgagcg gagaatccta actatccttc agtggctttc cctgccagac aatgagaggc     960

cttcagttta tgccttctac tccgagcagc ctgatttttc tggacacaag tacggccctt    1020

ttggccctga gatgacaaat cctctgaggg agattgacaa gaccgtgggg cagttaatgg    1080

acggactgaa acaactcaag ctgcaccgtt gtgtgaatgt tatctttgtt ggagaccatg    1140

gaatggaaga cgtgacatgt gacagaactg agttcttgag caactatctg actaacgtgg    1200

atgatattac tttagtacct ggaactctag gaagaattcg acccaagatt cccaataatc    1260

ttaaatatga ccctaaagcc attattgcta acctcacgtg taaaaaacca gatcagcact    1320

ttaagcctta catgaaacag caccttccca aacgtttgca ctatgccaac aatcggagaa    1380

tcgaggatct ccatttattg gtggaacgca gatggcatgt tgcaaggaaa cctttggacg    1440

tttataagaa gccgtcagga aaatgttttt tccagggtga ccacggcttt gataacaagg    1500

tcaatagcat gcagactgtt tttgtaggtt atggcccaac ttttaagtac aggactaaag    1560

tgcctccatt tgaaaacatt gaactttata atgttatgtg cgatctccta ggcttgaagc    1620

cagctcccaa taatggaaca catggaagtt tgaatcacct gctacgcaca aataccttta    1680
```

```
ggccaaccct accagaggaa gtcagcagac ccaattaccc agggattatg taccttcagt   1740

ctgattttga cctgggctgc acctgtgatg ataaggtaga gccaaagaac aaattggaag   1800

aactaaataa acgccttcat accaaaggat ctacagaaga gagacatctc ctgtatggac   1860

gacctgcagt gctttatcgg actagctatg atatcttata ccatacggac tttgaaagtg   1920

gttacagtga aatattctta atgcctctct ggacttctta taccatttct aagcaggctg   1980

aggtctctag catcccagag cacctgacca actgtgttcg ccctgatgtc cgtgtatctc   2040

ctggattcag tcagaactgt ttagcctata aaaatgataa acagatgtcc tatggattcc   2100

tttttcctcc ctatctgagc tcttccccag aagcgaaata tgatgcattc cttgtaacca   2160

acatggttcc aatgtaccct gccttcaaac gtgtttggac ttatttccaa agggtcttgg   2220

tgaagaaata tgcgtcagaa aggaatgggg tcaacgtaat aagtggaccg atctttgact   2280

acaattacga tggcttacgt gacattgagg atgaaattaa acagtatgtg gaaggcagct   2340

ctattcctgt ccctacccac tactacagca tcatcaccag ctgcctggac ttcactcagc   2400

ctgcagacaa gtgtgatggt cctctctctg tgtcttcttt catccttcct caccgacctg   2460

acaatgatga gagctgtaat agttccgagg atgagtcgaa gtgggtagag gaactcatga   2520

agatgcacac agctcgggtg agggacatcg agcatctcac cggtctggat ttctaccgga   2580

agactagccg tagctattcg gaaattctga ccctcaagac atacctgcat acatatgaga   2640

gcgagattta acttcctggg cctgggcagt gtagtcttag caactggtgt atatttttat   2700

atggtgtttg tatttattaa tttgaaacca ggacataaac aaacaaagaa acaaatgaaa   2760

aaaaaaaaaa aa                                                       2772
```

<210> SEQ ID NO 26
<211> LENGTH: 862
<212> TYPE: PRT
<213> ORGANISM: Mus musculus

<400> SEQUENCE: 26

```
Met Ala Arg Gln Gly Cys Phe Gly Ser Tyr Gln Val Ile Ser Leu Phe
1               5                   10                  15

Thr Phe Ala Ile Gly Val Asn Leu Cys Leu Gly Phe Thr Ala Ser Arg
            20                  25                  30

Ile Lys Arg Ala Glu Trp Asp Glu Gly Pro Pro Thr Val Leu Ser Asp
        35                  40                  45

Ser Pro Trp Thr Asn Thr Ser Gly Ser Cys Lys Gly Arg Cys Phe Glu
    50                  55                  60

Leu Gln Glu Val Gly Pro Pro Asp Cys Arg Cys Asp Asn Leu Cys Lys
65                  70                  75                  80

Ser Tyr Ser Ser Cys Cys His Asp Phe Asp Glu Leu Cys Leu Lys Thr
                85                  90                  95

Ala Arg Gly Trp Glu Cys Thr Lys Asp Arg Cys Gly Glu Val Arg Asn
            100                 105                 110

Glu Glu Asn Ala Cys His Cys Ser Glu Asp Cys Leu Ser Arg Gly Asp
        115                 120                 125

Cys Cys Thr Asn Tyr Gln Val Val Cys Lys Gly Glu Ser His Trp Val
    130                 135                 140

Asp Asp Asp Cys Glu Glu Ile Arg Val Pro Glu Cys Pro Ala Gly Phe
145                 150                 155                 160

Val Arg Pro Pro Leu Ile Ile Phe Ser Val Asp Gly Phe Arg Ala Ser
                165                 170                 175
```

```
Tyr Met Lys Lys Gly Ser Lys Val Met Pro Asn Ile Glu Lys Leu Arg
            180                 185                 190

Ser Cys Gly Thr His Ala Pro Tyr Met Arg Pro Val Tyr Pro Thr Lys
        195                 200                 205

Thr Phe Pro Asn Leu Tyr Thr Leu Ala Thr Gly Leu Tyr Pro Glu Ser
    210                 215                 220

His Gly Ile Val Gly Asn Ser Met Tyr Asp Pro Val Phe Asp Ala Thr
225                 230                 235                 240

Phe His Leu Arg Gly Arg Glu Lys Phe Asn His Arg Trp Trp Gly Gly
                245                 250                 255

Gln Pro Leu Trp Ile Thr Ala Thr Lys Gln Gly Val Arg Ala Gly Thr
            260                 265                 270

Phe Phe Trp Ser Val Ser Ile Pro His Glu Arg Arg Ile Leu Thr Ile
        275                 280                 285

Leu Gln Trp Leu Ser Leu Pro Asp Asn Glu Arg Pro Ser Val Tyr Ala
    290                 295                 300

Phe Tyr Ser Glu Gln Pro Asp Phe Ser Gly His Lys Tyr Gly Pro Phe
305                 310                 315                 320

Gly Pro Glu Met Thr Asn Pro Leu Arg Glu Ile Asp Lys Thr Val Gly
                325                 330                 335

Gln Leu Met Asp Gly Leu Lys Gln Leu Lys Leu His Arg Cys Val Asn
            340                 345                 350

Val Ile Phe Val Gly Asp His Gly Met Glu Asp Val Thr Cys Asp Arg
        355                 360                 365

Thr Glu Phe Leu Ser Asn Tyr Leu Thr Asn Val Asp Asp Ile Thr Leu
    370                 375                 380

Val Pro Gly Thr Leu Gly Arg Ile Arg Pro Lys Ile Pro Asn Asn Leu
385                 390                 395                 400

Lys Tyr Asp Pro Lys Ala Ile Ile Ala Asn Leu Thr Cys Lys Lys Pro
                405                 410                 415

Asp Gln His Phe Lys Pro Tyr Met Lys Gln His Leu Pro Lys Arg Leu
            420                 425                 430

His Tyr Ala Asn Asn Arg Arg Ile Glu Asp Leu His Leu Leu Val Glu
        435                 440                 445

Arg Arg Trp His Val Ala Arg Lys Pro Leu Asp Val Tyr Lys Lys Pro
    450                 455                 460

Ser Gly Lys Cys Phe Phe Gln Gly Asp His Gly Phe Asp Asn Lys Val
465                 470                 475                 480

Asn Ser Met Gln Thr Val Phe Val Gly Tyr Gly Pro Thr Phe Lys Tyr
                485                 490                 495

Arg Thr Lys Val Pro Pro Phe Glu Asn Ile Glu Leu Tyr Asn Val Met
            500                 505                 510

Cys Asp Leu Leu Gly Leu Lys Pro Ala Pro Asn Asn Gly Thr His Gly
        515                 520                 525

Ser Leu Asn His Leu Leu Arg Thr Asn Thr Phe Arg Pro Thr Leu Pro
    530                 535                 540

Glu Glu Val Ser Arg Pro Asn Tyr Pro Gly Ile Met Tyr Leu Gln Ser
545                 550                 555                 560

Asp Phe Asp Leu Gly Cys Thr Cys Asp Asp Lys Val Glu Pro Lys Asn
                565                 570                 575

Lys Leu Glu Glu Leu Asn Lys Arg Leu His Thr Lys Gly Ser Thr Glu
            580                 585                 590

Glu Arg His Leu Leu Tyr Gly Arg Pro Ala Val Leu Tyr Arg Thr Ser
```

```
        595                 600                 605

Tyr Asp Ile Leu Tyr His Thr Asp Phe Glu Ser Gly Tyr Ser Glu Ile
    610                 615                 620

Phe Leu Met Pro Leu Trp Thr Ser Tyr Thr Ile Ser Lys Gln Ala Glu
625                 630                 635                 640

Val Ser Ser Ile Pro Glu His Leu Thr Asn Cys Val Arg Pro Asp Val
                645                 650                 655

Arg Val Ser Pro Gly Phe Ser Gln Asn Cys Leu Ala Tyr Lys Asn Asp
            660                 665                 670

Lys Gln Met Ser Tyr Gly Phe Leu Phe Pro Pro Tyr Leu Ser Ser Ser
        675                 680                 685

Pro Glu Ala Lys Tyr Asp Ala Phe Leu Val Thr Asn Met Val Pro Met
    690                 695                 700

Tyr Pro Ala Phe Lys Arg Val Trp Thr Tyr Phe Gln Arg Val Leu Val
705                 710                 715                 720

Lys Lys Tyr Ala Ser Glu Arg Asn Gly Val Asn Val Ile Ser Gly Pro
                725                 730                 735

Ile Phe Asp Tyr Asn Tyr Asp Gly Leu Arg Asp Ile Glu Asp Glu Ile
            740                 745                 750

Lys Gln Tyr Val Glu Gly Ser Ser Ile Pro Val Pro Thr His Tyr Tyr
        755                 760                 765

Ser Ile Ile Thr Ser Cys Leu Asp Phe Thr Gln Pro Ala Asp Lys Cys
    770                 775                 780

Asp Gly Pro Leu Ser Val Ser Ser Phe Ile Leu Pro His Arg Pro Asp
785                 790                 795                 800

Asn Asp Glu Ser Cys Asn Ser Ser Glu Asp Glu Ser Lys Trp Val Glu
                805                 810                 815

Glu Leu Met Lys Met His Thr Ala Arg Val Arg Asp Ile Glu His Leu
            820                 825                 830

Thr Gly Leu Asp Phe Tyr Arg Lys Thr Ser Arg Ser Tyr Ser Glu Ile
        835                 840                 845

Leu Thr Leu Lys Thr Tyr Leu His Thr Tyr Glu Ser Glu Ile
    850                 855                 860
```

<210> SEQ ID NO 27
<211> LENGTH: 610
<212> TYPE: DNA
<213> ORGANISM: Gallus gallus
<220> FEATURE:
<221> NAME/KEY: misc_feature
<222> LOCATION: (484)..(484)
<223> OTHER INFORMATION: n is a, c, g, or t
<220> FEATURE:
<221> NAME/KEY: misc_feature
<222> LOCATION: (492)..(492)
<223> OTHER INFORMATION: n is a, c, g, or t
<220> FEATURE:
<221> NAME/KEY: misc_feature
<222> LOCATION: (537)..(537)
<223> OTHER INFORMATION: n is a, c, g, or t
<220> FEATURE:
<221> NAME/KEY: misc_feature
<222> LOCATION: (567)..(567)
<223> OTHER INFORMATION: n is a, c, g, or t
<220> FEATURE:
<221> NAME/KEY: misc_feature
<222> LOCATION: (574)..(574)
<223> OTHER INFORMATION: n is a, c, g, or t

<400> SEQUENCE: 27

```
ccacgcgtcc ggctctcaat ctttgcactg cttcagttag cagagcattt atttttgatt     60
```

```
cagctgcatt tgttaagact gtaacaacga aaggcatttc ctgagaagct gcaaggatga    120

gcagaaagaa agaacaacag ctaaggaaat atgggaccct agtagtgctt ttcatcttcc    180

aagttcagat ttttggtttt gatgttgaca atcgacctac aacagatgtc tgctcgacac    240

acactatttt acctggacca aaaggggatg atggtgaaaa aggagataga ggagaagtgg    300

gcaaacaagg aaaagttgga ccaaaaggac ctaaaggaaa caaaggaact gtgggggatg    360

tcggtgacca gggaatgctt gggaaaatcg gtccgattgg aggaaaaggt gacaaaggag    420

ccaaaggcat atcaggggta tctggaaaaa aaggaaaagc aggcacagtc tgtgactgtg    480

gaangtccgc anagttgttg gacaactgaa tatcaatgtt gctcggctta acacatncat    540

caagtttgta aaagaatggt ttttgcnggc cttnaggggg accggtggaa aaattcttcc    600

tttttttggc                                                           610


<210> SEQ ID NO 28
<211> LENGTH: 122
<212> TYPE: PRT
<213> ORGANISM: Gallus gallus

<400> SEQUENCE: 28

Met Ser Arg Lys Lys Glu Gln Gln Leu Arg Lys Tyr Gly Thr Leu Val
1               5                   10                  15

Val Leu Phe Ile Phe Gln Val Gln Ile Phe Gly Phe Asp Val Asp Asn
            20                  25                  30

Arg Pro Thr Thr Asp Val Cys Ser Thr His Thr Ile Leu Pro Gly Pro
        35                  40                  45

Lys Gly Asp Asp Gly Glu Lys Gly Asp Arg Gly Glu Val Gly Lys Gln
    50                  55                  60

Gly Lys Val Gly Pro Lys Gly Pro Lys Gly Asn Lys Gly Thr Val Gly
65                  70                  75                  80

Asp Val Gly Asp Gln Gly Met Leu Gly Lys Ile Gly Pro Ile Gly Gly
                85                  90                  95

Lys Gly Asp Lys Gly Ala Lys Gly Ile Ser Gly Val Ser Gly Lys Lys
            100                 105                 110

Gly Lys Ala Gly Thr Val Cys Asp Cys Gly
        115                 120


<210> SEQ ID NO 29
<211> LENGTH: 1686
<212> TYPE: DNA
<213> ORGANISM: Homo sapiens

<400> SEQUENCE: 29

aagcaggagg ttttatttaa aataaagctg tttatttggc atttctggga gacccttttc     60

tgaggaacca cagcaatgaa tggctttgca tccttgcttc gaagaaacca atttatcctc    120

ctggtactat ttcttttgca aattcagagt ctgggtctgg atattgatag ccgtcctacc    180

gctgaagtct gtgccacaca cacaatttca ccaggaccca aaggagatga tggtgaaaaa    240

ggagatccag gagaagaggg aaagcatggc aaagtgggac gcatggggcc gaaaggaatt    300

aaaggagaac tgggtgatat gggagatcgg ggcaatattg gcaagactgg gcccattggg    360

aagaagggtg acaaagggga aaaaggtttg cttggaatac ctggagaaaa aggcaaagca    420

ggtactgtct gtgattgtgg aagataccgg aaatttgttg gacaactgga tattagtatt    480

gcccggctca agacatctat gaagtttgtc aagaatgtga tagcagggat tagggaaact    540
```

```
gaagagaaat tctactacat cgtgcaggaa gagaagaact acagggaatc cctaacccac    600

tgcaggattc ggggtggaat gctagccatg cccaaggatg aagctgccaa cacactcatc    660

gctgactatg ttgccaagag tggcttcttt cgggtgttca ttggcgtgaa tgaccttgaa    720

agggagggac agtacatgtt cacagacaac actccactgc agaactatag caactggaat    780

gagggggaac ccagcgaccc ctatggtcat gaggactgtg tggagatgct gagctctggc    840

agatggaatg acacagagtg ccatcttacc atgtactttg tctgtgagtt catcaagaag    900

aaaaagtaac ttccctcatc ctacgtattt gctattttcc tgtgaccgtc attacagtta    960

ttgttatcca tcctttttt cctgattgta ctacatttga tctgagtcaa catagctaga   1020

aaatgctaaa ctgaggtatg gagcctccat catcatgctc ttttgtgatg attttcatat   1080

tttcacacat ggtatgttat tgacccaata actcgccagg ttacatgggt cttgagagag   1140

aattttaatt actaattgtg cacgagatag ttggttgtct atatgtcaaa tgagttgttc   1200

tcttggtatt tgctctacca tctctcccta gagcactctg tgtctatccc agtggataat   1260

ttcccagttt actggtgatg attaggaagg ttgttgatgg ttaggctaac ctgccctggc   1320

ccaaagccag acatgtacaa gggctttctg tgagcaatga taagatcttt gaatccaaga   1380

tgcccagatg ttttaccagt cacaccctat ggccatggct atacttggaa gttctccttg   1440

ttggcacaga catagaaatg ctttaacccc aagcctttat atgggggact tctagctttg   1500

tgtcttgttt cagaccatgt ggaatgataa atactctttt tgtgcttctg atctatcgat   1560

ttcactaaca tataccaagt aggtgctttg aacccctttc tgtaggctca caccttaatc   1620

tcaggcccct atatagtcac actttgattt aagaaaaatg gagctcttga aatcaaaaga   1680

aaaaaa                                                               1686
```

<210> SEQ ID NO 30
<211> LENGTH: 277
<212> TYPE: PRT
<213> ORGANISM: Homo sapiens

<400> SEQUENCE: 30

```
Met Asn Gly Phe Ala Ser Leu Leu Arg Arg Asn Gln Phe Ile Leu Leu
1               5                   10                  15

Val Leu Phe Leu Leu Gln Ile Gln Ser Leu Gly Leu Asp Ile Asp Ser
            20                  25                  30

Arg Pro Thr Ala Glu Val Cys Ala Thr His Thr Ile Ser Pro Gly Pro
        35                  40                  45

Lys Gly Asp Asp Gly Glu Lys Gly Asp Pro Gly Glu Glu Gly Lys His
    50                  55                  60

Gly Lys Val Gly Arg Met Gly Pro Lys Gly Ile Lys Gly Glu Leu Gly
65                  70                  75                  80

Asp Met Gly Asp Arg Gly Asn Ile Gly Lys Thr Gly Pro Ile Gly Lys
                85                  90                  95

Lys Gly Asp Lys Gly Glu Lys Gly Leu Leu Gly Ile Pro Gly Glu Lys
            100                 105                 110

Gly Lys Ala Gly Thr Val Cys Asp Cys Gly Arg Tyr Arg Lys Phe Val
        115                 120                 125

Gly Gln Leu Asp Ile Ser Ile Ala Arg Leu Lys Thr Ser Met Lys Phe
    130                 135                 140

Val Lys Asn Val Ile Ala Gly Ile Arg Glu Thr Glu Glu Lys Phe Tyr
145                 150                 155                 160

Tyr Ile Val Gln Glu Glu Lys Asn Tyr Arg Glu Ser Leu Thr His Cys
```

```
                165                 170                 175

Arg Ile Arg Gly Gly Met Leu Ala Met Pro Lys Asp Glu Ala Ala Asn
            180                 185                 190

Thr Leu Ile Ala Asp Tyr Val Ala Lys Ser Gly Phe Phe Arg Val Phe
        195                 200                 205

Ile Gly Val Asn Asp Leu Glu Arg Glu Gly Gln Tyr Met Phe Thr Asp
    210                 215                 220

Asn Thr Pro Leu Gln Asn Tyr Ser Asn Trp Asn Glu Gly Glu Pro Ser
225                 230                 235                 240

Asp Pro Tyr Gly His Glu Asp Cys Val Glu Met Leu Ser Ser Gly Arg
                245                 250                 255

Trp Asn Asp Thr Glu Cys His Leu Thr Met Tyr Phe Val Cys Glu Phe
            260                 265                 270

Ile Lys Lys Lys Lys
        275


<210> SEQ ID NO 31
<211> LENGTH: 423
<212> TYPE: DNA
<213> ORGANISM: Gallus gallus
<220> FEATURE:
<221> NAME/KEY: misc_feature
<222> LOCATION: (265)..(265)
<223> OTHER INFORMATION: n is a, c, g, or t

<400> SEQUENCE: 31

tgcagcttgt tccatgggaa acagcaccag ccggctctac agcgcgctcg ccaagacgct      60

gagcagcagt gccgtgtccc agcaccagga ctgcctggag cagcccaact cggcgcagct     120

ggagcccata gaccccaagg acctactgga ggaatgccag ctcgttctgc agaaacggcc     180

acctcgcttc cagaggaact tcgtggacct gaagaaaaac acagccagta accaccgccc     240

catccgggtc atgcagtgga acatnctcgc ccaagctctc ggagaaggca aagacaactt     300

cgttcagtgc cccatggaag ctctgaagtg ggaggaaagg aagtgcctca tcctggagga     360

aatccttgcc tacaagccgg atatcttgtg cctgcaagaa gtcgaccact acttttacac     420

ctt                                                                   423


<210> SEQ ID NO 32
<211> LENGTH: 140
<212> TYPE: PRT
<213> ORGANISM: Gallus gallus
<220> FEATURE:
<221> NAME/KEY: misc_feature
<222> LOCATION: (88)..(88)
<223> OTHER INFORMATION: Xaa can be any naturally occurring amino acid

<400> SEQUENCE: 32

Ala Ala Cys Ser Met Gly Asn Ser Thr Ser Arg Leu Tyr Ser Ala Leu
1               5                   10                  15

Ala Lys Thr Leu Ser Ser Ser Ala Val Ser Gln His Gln Asp Cys Leu
            20                  25                  30

Glu Gln Pro Asn Ser Ala Gln Leu Glu Pro Ile Asp Pro Lys Asp Leu
        35                  40                  45

Leu Glu Glu Cys Gln Leu Val Leu Gln Lys Arg Pro Pro Arg Phe Gln
    50                  55                  60

Arg Asn Phe Val Asp Leu Lys Lys Asn Thr Ala Ser Asn His Arg Pro
65                  70                  75                  80

Ile Arg Val Met Gln Trp Asn Xaa Leu Ala Gln Ala Leu Gly Glu Gly
```

```
                85                  90                  95

Lys Asp Asn Phe Val Gln Cys Pro Met Glu Ala Leu Lys Trp Glu Glu
            100                 105                 110

Arg Lys Cys Leu Ile Leu Glu Glu Ile Leu Ala Tyr Lys Pro Asp Ile
        115                 120                 125

Leu Cys Leu Gln Glu Val Asp His Tyr Phe Tyr Thr
    130                 135                 140


<210> SEQ ID NO 33
<211> LENGTH: 1767
<212> TYPE: DNA
<213> ORGANISM: Homo sapiens

<400> SEQUENCE: 33

ccgacgcagc ggtgttgcac ctccctctcc ggctctgctg cccgggattt ccccagaacc     60

tgcgccgcgc gagaaggagc ctgggagcat ccgcccacac tgcccggaca gtcggctcga    120

ctcggtgccc tcggccccag ccgggctccg ctcctcgggc gcgcgagggg ccgtggtggc    180

ggcggcgccc ggcatgtttc atagtccgcg gcggctctgc tcggccctgc tgcagaggga    240

cgcgcccggc ctgcgccgcc tgcccgcccc agggctgcgc cgcccgttgt ccccgccggc    300

tgctgttccc aggcccgcat ccccccggct gctggcggcg gcctcggcgg cctcgggcgc    360

cgcgaggtcg tgttcccgaa cagtgtgttc catgggaacc ggtacaagca gactctatag    420

tgctctcgcc aagacactga acagcagcgc tgcctcccag cacccagagt atttggtgtc    480

acctgaccca gagcatctgg agcccattga tcctaaagag cttcttgagg aatgcagggc    540

cgtcctgcac acccgacctc cccggttcca gagggatttt gtggatctga ggacagattg    600

ccctagtacc cacccaccta tcagggttat gcaatggaac atcctcgccc aagctcttgg    660

agaaggcaaa gacaactttg tacagtgccc tgttgaagca ctcaaatggg aagaaaggaa    720

atgtctcatc ctggaagaaa tcctggccta ccagcctgat atattgtgcc tccaagaggt    780

ggaccactat tttgacacct tccagccact cctcagtaga ctaggctatc aaggcacgtt    840

tttccccaaa ccctggtcac cttgtctaga tgtagaacac aacaatggac cagatggttg    900

tgccttattt tttcttcaaa accgattcaa gctagtcaac agtgccaata ttaggctgac    960

agccatgaca ttgaaaacca accaggtggc cattgcacag accctggagt gcaaggagtc   1020

aggccgacag ttctgcatcg ctgttaccca tctaaaagca cgcactggct gggagcggtt   1080

tcgatcagct caaggctgtg acctccttca gaacctgcaa aacatcaccc aaggagccaa   1140

gattcccctt attgtgtgtg gggacttcaa tgcagagcca acagaagagg tctacaaaca   1200

ctttgcttcc tccagcctca acctgaacag cgcctacaag ctgctgagtg ctgatgggca   1260

gtcagaaccc ccatacacta cctggaagat ccggacctca ggggagtgca ggcacaccct   1320

ggattacatc tggtattcta aacatgctct aaatgtaagg tcagctctcg atctgctcac   1380

tgaagaacag attggaccca acaggttacc ttccttcaat tatccttcag accacctgtc   1440

tctagtgtgt gacttcagct ttactgagga atctgatgga ctttcataaa tacttgcttt   1500

tgtcttttta atcacaggag tctatttttt tttttttttt tttttttttg agacagagtc   1560

tcgctctgtt gcctaggctg gagtacagtg gcctgatctc ggctcactgc aagatccgcc   1620

tcccgggttc atggcattct cctgcctcag cctccagagc aactgggaca acaggcgccc   1680

gtcaccacgc ccagctaatt ttttgtattt ttagtagaga cggggtttca ccgtgttagc   1740

caggatggtc tcgatctcct gaccttg                                       1767
```

<210> SEQ ID NO 34
<211> LENGTH: 431
<212> TYPE: PRT
<213> ORGANISM: Homo sapiens

<400> SEQUENCE: 34

Met Phe His Ser Pro Arg Arg Leu Cys Ser Ala Leu Leu Gln Arg Asp
1 5 10 15

Ala Pro Gly Leu Arg Arg Leu Pro Ala Pro Gly Leu Arg Arg Pro Leu
20 25 30

Ser Pro Pro Ala Ala Val Pro Arg Pro Ala Ser Pro Arg Leu Leu Ala
35 40 45

Ala Ala Ser Ala Ala Ser Gly Ala Ala Arg Ser Cys Ser Arg Thr Val
50 55 60

Cys Ser Met Gly Thr Gly Thr Ser Arg Leu Tyr Ser Ala Leu Ala Lys
65 70 75 80

Thr Leu Asn Ser Ser Ala Ala Ser Gln His Pro Glu Tyr Leu Val Ser
85 90 95

Pro Asp Pro Glu His Leu Glu Pro Ile Asp Pro Lys Glu Leu Leu Glu
100 105 110

Glu Cys Arg Ala Val Leu His Thr Arg Pro Pro Arg Phe Gln Arg Asp
115 120 125

Phe Val Asp Leu Arg Thr Asp Cys Pro Ser Thr His Pro Pro Ile Arg
130 135 140

Val Met Gln Trp Asn Ile Leu Ala Gln Ala Leu Gly Glu Gly Lys Asp
145 150 155 160

Asn Phe Val Gln Cys Pro Val Glu Ala Leu Lys Trp Glu Glu Arg Lys
165 170 175

Cys Leu Ile Leu Glu Glu Ile Leu Ala Tyr Gln Pro Asp Ile Leu Cys
180 185 190

Leu Gln Glu Val Asp His Tyr Phe Asp Thr Phe Gln Pro Leu Leu Ser
195 200 205

Arg Leu Gly Tyr Gln Gly Thr Phe Phe Pro Lys Pro Trp Ser Pro Cys
210 215 220

Leu Asp Val Glu His Asn Asn Gly Pro Asp Gly Cys Ala Leu Phe Phe
225 230 235 240

Leu Gln Asn Arg Phe Lys Leu Val Asn Ser Ala Asn Ile Arg Leu Thr
245 250 255

Ala Met Thr Leu Lys Thr Asn Gln Val Ala Ile Ala Gln Thr Leu Glu
260 265 270

Cys Lys Glu Ser Gly Arg Gln Phe Cys Ile Ala Val Thr His Leu Lys
275 280 285

Ala Arg Thr Gly Trp Glu Arg Phe Arg Ser Ala Gln Gly Cys Asp Leu
290 295 300

Leu Gln Asn Leu Gln Asn Ile Thr Gln Gly Ala Lys Ile Pro Leu Ile
305 310 315 320

Val Cys Gly Asp Phe Asn Ala Glu Pro Thr Glu Glu Val Tyr Lys His
325 330 335

Phe Ala Ser Ser Ser Leu Asn Leu Asn Ser Ala Tyr Lys Leu Leu Ser
340 345 350

Ala Asp Gly Gln Ser Glu Pro Pro Tyr Thr Thr Trp Lys Ile Arg Thr
355 360 365

Ser Gly Glu Cys Arg His Thr Leu Asp Tyr Ile Trp Tyr Ser Lys His
370 375 380

```
Ala Leu Asn Val Arg Ser Ala Leu Asp Leu Leu Thr Glu Glu Gln Ile
385                 390                 395                 400

Gly Pro Asn Arg Leu Pro Ser Phe Asn Tyr Pro Ser Asp His Leu Ser
                405                 410                 415

Leu Val Cys Asp Phe Ser Phe Thr Glu Glu Ser Asp Gly Leu Ser
            420                 425                 430


<210> SEQ ID NO 35
<211> LENGTH: 3075
<212> TYPE: DNA
<213> ORGANISM: Gallus gallus
<220> FEATURE:
<221> NAME/KEY: misc_feature
<222> LOCATION: (762)..(775)
<223> OTHER INFORMATION: n is a, c, g, or t
<220> FEATURE:
<221> NAME/KEY: misc_feature
<222> LOCATION: (1088)..(1101)
<223> OTHER INFORMATION: n is a, c, g, or t

<400> SEQUENCE: 35

acgcacgcac ctctgcctct gcaggcggat gaggggcact tttgaaaatt attttctttc     60

cacacccaac cctcgtctga catcacttct gcaggaggga gggcgggaac agccccgctg    120

ccagaaggtc gcggagagct ccgccggccc ccgcgcacca tttgtctcaa actaaatact    180

cttcaaatca aggatgttga ttcttctggc tttcattatt atatttcaca taacttcagc    240

agcgctgttg ttcatctcaa ctattgacaa tgcctggtgg gtaggagata actttctac     300

agatgtctgg agtgcatgtg ccacaaataa tagcacctgc acacctatta ctgttcaatt    360

cagagaatat caatcaattc aggctgttca ggcctgcatg gtcctatcta ctattttctg    420

ttgtgtggca tttctggttt tcattcttca acttttccgt ctaaagcaag gagaaagatt    480

tgtgttaacc tctattatcc agctcctgtc atgtctgtgc gttatgattg cagcttccat    540

ttacacagat aggcatgagg aactgcacaa gagcattgaa tatgccattg aagtttctaa    600

aggccaatat ggctattcct tcgtcttagc ctggattgca ttcgccttta ctctgatcag    660

tggtgttatg tacctagtat taaggaaacg taaataaatg ttggcagcta gttattactg    720

tcacggcagt acaaaaccaa attccagtaa ctattttgta tnnnnnnnnn nnnnnggttt    780

tgtagtaaag gtattgtttc tctaaaaatg tactgtgttc ttaatatgaa acagaataca    840

aaacaaaaaa caaccaacag caggtttaat ggaatgcctg gcattcggtc tgagcaagac    900

tgacccaagt tttcttttac ttatttcacc atcatcagtg gtgaaatggt gtctttcctt    960

ttctagacat taacagttct tggcctctgt cagattacta ttaaagtctt tgtaaattaa   1020

tttggaagca atgtgctaag catactcctg gcctggatct agccctttgg gatggataaa   1080

tacagggnnn nnnnnnnnnn nggccaggat cgtgatgcaa aagcaaacaa gtataaaagc   1140

ccaaagctgc actcaatgtt gctgttctag cagaggacga atgttctgct atttataatg   1200

tgcagtaagt gtcatcaagc ttttattaaa accacttgct ctgcaaaagt aaacaactcc   1260

tttttgtact ccagcaactg attctcttta tccttcttca cgtttaattt aagcatacag   1320

agcctttggc aggaaaagtt acaatcaaat tcgaaattca gtgcacaact tgagacagga   1380

gtagtctgag cagaaagagg tactccactc aagtcctgca gccctttatt tttgcattgt   1440

gcagtaccaa atttaacact ttttttcag ccaaactcag tatgtttatt acattgggct    1500

ctggctagat atatcatgtt ggctaatata tgatttagaa aaggctcttc ttttttgttt   1560

ttcctgtgtc tgctcactag gaaattggcc tttacaaaat tcattctaag ttcctatgtg   1620
```

```
gatttgactt gaataagaat tcctactaaa gaaatcagag tgtaactatt atgcatagga   1680

gttccaggat agttttaaga atttttggtg attctttctt ttcaataatt ctgtgagaga   1740

attactgtaa taccagattt aactgctcag caatataata ctggctttgg ctggtggtga   1800

tttcagggtt tggagaccag tgtggggaat gaattaagtg gctttttctg gttagtcaca   1860

cttctgatgt taaaatgtag atttgacttt gtaaaagcat taaccctgta ttcatttcat   1920

gatactcact gcagctgacc caatatatag gcaataaaaa taaatgaatt ttaaatgaga   1980

ttttacactt aatgtagaac aaaattccta ttacaaaata atgtagctct actaatgttg   2040

ataacttacc ctattacaca gcagctgata gtctgaccca ttgctgcagg tagttcatcc   2100

ttgagttctc acggaactgt ataggaattg tgtcggacat gagtaatggg tcatgctgtt   2160

ccatctccat tccctgaaca tcctaaaatg cactaacgag taatacttct attagggagc   2220

aaagaaagca caacaggact ggcaagaagt taattagaca actaagcaga acagcaaatt   2280

aatagtaaaa ataacagcag ttaaaaaaaa ccctcaataa atcagtctga gcgaaatgca   2340

ttctcacctt cccagtcttg catgatgcta atcttctgtt agtctttttt ctcttagtgg   2400

gaacactctg aatttcaggc attactaccc tactttttaa aaaagtgttt ctgctgtttg   2460

ctgaatacat ttcagattca aaacgtgaat tttgctagca agcaggattt gttttaaata   2520

aacagatgta ggtttaaggc tgaaagtaga tagtctgtaa gttgggtgtt tggctagtct   2580

tattcaaaca tgaaatatta agggtgaaat tctaaaacaa atgtgcattg aagctatttt   2640

atatctagaa gataatccta taacactgta aattaagctg aaatgccact gacttgaaga   2700

gatgcttctt cagtttcttg ccttaataat gcttaggtca tttatagagc aaatatttaa   2760

gataaagatg tatatataca tgaactcagc ttacttctac agtaaaagct ctgtcacttt   2820

agttagaagt gaaaagcaca cacagcagca tatacgtggt gccacacaga gaacatacgt   2880

caatattcga agtaccaaga aaataaatgc caaaaagttt ggacaagagt tttaacagga   2940

caaacatatt ttagaatatt ctttttatct gatatgcttt taaaatatac cattttctat   3000

gctctatata ttctgaaatt gtacatgaaa ataaagttaa aatgaattct tgtattgtaa   3060

aaaaaaaaaa aaaaa                                                    3075
```

```
<210> SEQ ID NO 36
<211> LENGTH: 167
<212> TYPE: PRT
<213> ORGANISM: Gallus gallus

<400> SEQUENCE: 36

Met Leu Ile Leu Leu Ala Phe Ile Ile Ile Phe His Ile Thr Ser Ala
1               5                   10                  15

Ala Leu Leu Phe Ile Ser Thr Ile Asp Asn Ala Trp Trp Val Gly Asp
            20                  25                  30

Asn Phe Ser Thr Asp Val Trp Ser Ala Cys Ala Thr Asn Asn Ser Thr
        35                  40                  45

Cys Thr Pro Ile Thr Val Gln Phe Arg Glu Tyr Gln Ser Ile Gln Ala
    50                  55                  60

Val Gln Ala Cys Met Val Leu Ser Thr Ile Phe Cys Cys Val Ala Phe
65                  70                  75                  80

Leu Val Phe Ile Leu Gln Leu Phe Arg Leu Lys Gln Gly Glu Arg Phe
                85                  90                  95

Val Leu Thr Ser Ile Ile Gln Leu Leu Ser Cys Leu Cys Val Met Ile
            100                 105                 110
```

```
Ala Ala Ser Ile Tyr Thr Asp Arg His Glu Glu Leu His Lys Ser Ile
        115                 120                 125

Glu Tyr Ala Ile Glu Val Ser Lys Gly Gln Tyr Gly Tyr Ser Phe Val
    130                 135                 140

Leu Ala Trp Ile Ala Phe Ala Phe Thr Leu Ile Ser Gly Val Met Tyr
145                 150                 155                 160

Leu Val Leu Arg Lys Arg Lys
                165

<210> SEQ ID NO 37
<211> LENGTH: 690
<212> TYPE: DNA
<213> ORGANISM: Homo sapiens

<400> SEQUENCE: 37

cagcacatcc cgctctgggc tttaaacgtg acccctcgcc tcgactcgcc ctgccctgtg     60

aaaatgttgg tgcttcttgc tttcatcatc gccttccaca tcacctctgc agccttgctg    120

ttcattgcca ccgtcgacaa tgcctggtgg gtaggagatg agttttttgc agatgtctgg    180

agaatatgta ccaacaacac gaattgcaca gtcatcaatg acagctttca agagtactcc    240

acgctgcagg cggtccaggc caccatgatc ctctccacca ttctctgctg catcgccttc    300

ttcatcttcg tgctccagct cttccgcctg aagcagggag agaggtttgt cctaacctcc    360

atcatccagc taatgtcatg tctgtgtgtc atgattgcgg cctccattta tacagacagg    420

cgtgaagaca ttcacgacaa aaacgcgaaa ttctatcccg tgaccagaga aggcagctac    480

ggctactcct acatcctggc gtgggtggcc ttcgcctgca ccttcatcag cggcatgatg    540

tacctgatac tgaggaagcg caaatagagt tccggagctg ggttgcttct gctgcagtac    600

agaatccaca ttcagataac cattttgtat ataatcatta ttttttgagg tttttctagc    660

aaacgtattg tttcctttaa aagcccaaaa                                     690

<210> SEQ ID NO 38
<211> LENGTH: 167
<212> TYPE: PRT
<213> ORGANISM: Homo sapiens

<400> SEQUENCE: 38

Met Leu Val Leu Leu Ala Phe Ile Ile Ala Phe His Ile Thr Ser Ala
1               5                   10                  15

Ala Leu Leu Phe Ile Ala Thr Val Asp Asn Ala Trp Trp Val Gly Asp
            20                  25                  30

Glu Phe Phe Ala Asp Val Trp Arg Ile Cys Thr Asn Asn Thr Asn Cys
        35                  40                  45

Thr Val Ile Asn Asp Ser Phe Gln Glu Tyr Ser Thr Leu Gln Ala Val
    50                  55                  60

Gln Ala Thr Met Ile Leu Ser Thr Ile Leu Cys Cys Ile Ala Phe Phe
65                  70                  75                  80

Ile Phe Val Leu Gln Leu Phe Arg Leu Lys Gln Gly Glu Arg Phe Val
                85                  90                  95

Leu Thr Ser Ile Ile Gln Leu Met Ser Cys Leu Cys Val Met Ile Ala
            100                 105                 110

Ala Ser Ile Tyr Thr Asp Arg Arg Glu Asp Ile His Asp Lys Asn Ala
        115                 120                 125

Lys Phe Tyr Pro Val Thr Arg Glu Gly Ser Tyr Gly Tyr Ser Tyr Ile
    130                 135                 140
```

```
Leu Ala Trp Val Ala Phe Ala Cys Thr Phe Ile Ser Gly Met Met Tyr
145                 150                 155                 160

Leu Ile Leu Arg Lys Arg Lys
                165
```

<210> SEQ ID NO 39
<211> LENGTH: 551
<212> TYPE: DNA
<213> ORGANISM: Gallus gallus

<400> SEQUENCE: 39

```
ggtcgaccca cgcgtccggg tgagcgtcag cgagttgggc ctgggctacg agtcggacga     60

gaccgtgttg ttccgctact gcagcggcac ctgcgacgcg gccgtcagga actacgacct    120

ctcgctgaag agcgtgcgca gccggaagaa gatcaggaag gagaaggtgc gcgcgcggcc    180

ctgctgcagg ccgctggcct acgatgatga cgtctccttc ttggatgcct acaaccgcta    240

ctacaccgtc aatgagctgt cggccaaaga gtgtggctgt gtgtgaaggg ccgggttggg    300

gggtggctca atggggccga agcccgtggt ggggatgggg atggaccccg caccgctgcc    360

cgccccatgg acctcccgtg tccagttgga ggaggagaga cgacccatgg acctaccatg    420

tccattggga agaggaaaga tgccccatgg accctccgtg tccattggga ggaggagaaa    480

tgccccacag accccccatg tccattggga agaggagaga tgccccatgg acccttcgtg    540

tctagtggga a                                                         551
```

<210> SEQ ID NO 40
<211> LENGTH: 94
<212> TYPE: PRT
<213> ORGANISM: Gallus gallus

<400> SEQUENCE: 40

```
Val Asp Pro Arg Val Arg Val Ser Val Ser Glu Leu Gly Leu Gly Tyr
1               5                   10                  15

Glu Ser Asp Glu Thr Val Leu Phe Arg Tyr Cys Ser Gly Thr Cys Asp
            20                  25                  30

Ala Ala Val Arg Asn Tyr Asp Leu Ser Leu Lys Ser Val Arg Ser Arg
        35                  40                  45

Lys Lys Ile Arg Lys Glu Lys Val Arg Ala Arg Pro Cys Cys Arg Pro
    50                  55                  60

Leu Ala Tyr Asp Asp Asp Val Ser Phe Leu Asp Ala Tyr Asn Arg Tyr
65                  70                  75                  80

Tyr Thr Val Asn Glu Leu Ser Ala Lys Glu Cys Gly Cys Val
                85                  90
```

<210> SEQ ID NO 41
<211> LENGTH: 594
<212> TYPE: DNA
<213> ORGANISM: Homo sapiens

<400> SEQUENCE: 41

```
atgcagcgct ggaaggcggc ggccttggcc tcagtgctct gcagctccgt gctgtccatc     60

tggatgtgtc gagagggcct gcttctcagc caccgcctcg gacctgcgct ggtccccctg    120

caccgcctgc ctcgaaccct ggacgcccgg attgcccgcc tggcccagta ccgtgcactc    180

ctgcaggggg ccccggatgc gatggagctg cgcgagctga cgccctgggc tgggcggccc    240

ccaggtccgc gccgtcgggc ggggccccgg cggcggcgcg cgcgtgcgcg gttgggggcg    300
```

-continued cggccttgcg ggctgcgcga gctggaggtg cgcgtgagcg agctgggcct gggctacgcg 360
tccgacgaga cggtgctgtt ccgctactgc gcaggcgcct gcgaggctgc cgcgcgcgtc 420
tacgacctcg ggctgcgacg actgcgccag cggcggcgcc tgcggcggga gcgggtgcgc 480
gcgcagccct gctgccgccc gacggcctac gaggacgagg tgtccttcct ggacgcgcac 540
agccgctacc acacggtgca cgagctgtcg gcgcgcgagt gcgcctgcgt gtga 594

<210> SEQ ID NO 42
<211> LENGTH: 197
<212> TYPE: PRT
<213> ORGANISM: Homo sapiens

<400> SEQUENCE: 42

Met Gln Arg Trp Lys Ala Ala Ala Leu Ala Ser Val Leu Cys Ser Ser
1 5 10 15

Val Leu Ser Ile Trp Met Cys Arg Glu Gly Leu Leu Leu Ser His Arg
20 25 30

Leu Gly Pro Ala Leu Val Pro Leu His Arg Leu Pro Arg Thr Leu Asp
35 40 45

Ala Arg Ile Ala Arg Leu Ala Gln Tyr Arg Ala Leu Leu Gln Gly Ala
50 55 60

Pro Asp Ala Met Glu Leu Arg Glu Leu Thr Pro Trp Ala Gly Arg Pro
65 70 75 80

Pro Gly Pro Arg Arg Arg Ala Gly Pro Arg Arg Arg Arg Ala Arg Ala
85 90 95

Arg Leu Gly Ala Arg Pro Cys Gly Leu Arg Glu Leu Glu Val Arg Val
100 105 110

Ser Glu Leu Gly Leu Gly Tyr Ala Ser Asp Glu Thr Val Leu Phe Arg
115 120 125

Tyr Cys Ala Gly Ala Cys Glu Ala Ala Ala Arg Val Tyr Asp Leu Gly
130 135 140

Leu Arg Arg Leu Arg Gln Arg Arg Arg Leu Arg Arg Glu Arg Val Arg
145 150 155 160

Ala Gln Pro Cys Cys Arg Pro Thr Ala Tyr Glu Asp Glu Val Ser Phe
165 170 175

Leu Asp Ala His Ser Arg Tyr His Thr Val His Glu Leu Ser Ala Arg
180 185 190

Glu Cys Ala Cys Val
195

<210> SEQ ID NO 43
<211> LENGTH: 1023
<212> TYPE: DNA
<213> ORGANISM: Mus musculus

<400> SEQUENCE: 43
ggagggagag cgcgcggtgg tttcgtccgt gtgccccgcg cccggcgctc ctcgcgtggc 60
cccgcgtcct gagcgcgctc cagcctccca cgcgcgccac cccggggttc actgagcccg 120
gcgagcccgg ggaagacaga gaaagagagg ccaggggggg aaccccatgg cccggcccgt 180
gtcccgcacc ctgtgcggtg gcctcctccg gcacggggtc cccgggtcgc ctccggtccc 240
cgcgatccgg atggcgcacg cagtggctgg ggccgggccg ggctcgggtg gtcggaggag 300
tcaccactga ccgggtcatc tggagcccgt ggcaggccga ggcccaggat gaggcgctgg 360
aaggcagcgg ccctggtgtc gctcatctgc agctccctgc tatctgtctg gatgtgccag 420

-continued gagggtctgc tcttgggcca ccgcctggga cccgcgcttg ccccgctacg acgccctcca 480
cgcaccctgg acgcccgcat cgcccgcctg gcccagtatc gcgctctgct ccagggcgcc 540
cccgacgcgg tggagcttcg agaactttct ccctgggctg cccgcatccc gggaccgcgc 600
cgtcgagcgg gtccccggcg tcggcgggcg cggccggggg ctcggccttg tgggctgcgc 660
gagctcgagg tgcgcgtgag cgagctgggc ctgggctaca cgtcggatga gaccgtgctg 720
ttccgctact gcgcaggcgc gtgcgaggcg gccatccgca tctacgacct gggccttcgg 780
cgcctgcgcc agcggaggcg cgtgcgcaga gagcgggcgc gggcgcaccc gtgttgtcgc 840
ccgacggcct atgaggacga ggtgtccttc ctggacgtgc acagccgcta ccacacgctg 900
caagagctgt cggcgcggga gtgcgcgtgc gtgtgatgct acctcacgcc ccccgacctg 960
cgaaagggcc ctccctgccg accctcgctg agaactgact tcacataaag tgtgggaact 1020
ccc 1023

<210> SEQ ID NO 44
<211> LENGTH: 195
<212> TYPE: PRT
<213> ORGANISM: Mus musculus

<400> SEQUENCE: 44

Met Arg Arg Trp Lys Ala Ala Ala Leu Val Ser Leu Ile Cys Ser Ser
1 5 10 15

Leu Leu Ser Val Trp Met Cys Gln Glu Gly Leu Leu Leu Gly His Arg
20 25 30

Leu Gly Pro Ala Leu Ala Pro Leu Arg Arg Pro Pro Arg Thr Leu Asp
35 40 45

Ala Arg Ile Ala Arg Leu Ala Gln Tyr Arg Ala Leu Leu Gln Gly Ala
50 55 60

Pro Asp Ala Val Glu Leu Arg Glu Leu Ser Pro Trp Ala Ala Arg Ile
65 70 75 80

Pro Gly Pro Arg Arg Arg Ala Gly Pro Arg Arg Arg Arg Ala Arg Pro
85 90 95

Gly Ala Arg Pro Cys Gly Leu Arg Glu Leu Glu Val Arg Val Ser Glu
100 105 110

Leu Gly Leu Gly Tyr Thr Ser Asp Glu Thr Val Leu Phe Arg Tyr Cys
115 120 125

Ala Gly Ala Cys Glu Ala Ala Ile Arg Ile Tyr Asp Leu Gly Leu Arg
130 135 140

Arg Leu Arg Gln Arg Arg Arg Val Arg Arg Glu Arg Ala Arg Ala His
145 150 155 160

Pro Cys Cys Arg Pro Thr Ala Tyr Glu Asp Glu Val Ser Phe Leu Asp
165 170 175

Val His Ser Arg Tyr His Thr Leu Gln Glu Leu Ser Ala Arg Glu Cys
180 185 190

Ala Cys Val
195

<210> SEQ ID NO 45
<211> LENGTH: 261
<212> TYPE: PRT
<213> ORGANISM: Danio rerio

<400> SEQUENCE: 45

Ile Phe Gly Glu Pro Glu Pro Val Lys Met Ile Ser Glu Gly Ser Asp
1 5 10 15

```
Cys Arg Cys Lys Cys Val Met Arg Pro Leu Ser Ile Glu Ala Cys Ser
            20                  25                  30

Arg Leu Arg Asp Gly Ser Leu Arg Val Asp Asp Phe Tyr Thr Val Glu
        35                  40                  45

Thr Val Ser Ser Gly Ser Asp Cys Lys Cys Ser Cys Thr Ala Pro Pro
    50                  55                  60

Ser Ser Leu Asn Pro Cys Glu Asn Glu Trp Arg Thr Glu Lys Leu Met
65                  70                  75                  80

Lys Gln Ala Pro Glu Leu Leu Lys Leu His Ser Met Val Asp Leu Leu
                85                  90                  95

Glu Gly Thr Leu Tyr Ser Met Asp Leu Met Lys Val His Ala Tyr Met
            100                 105                 110

Asn Lys Val Val Ser Gln Met Asn Thr Leu Glu Glu Thr Ile Lys Thr
        115                 120                 125

Asn Leu Thr Arg Glu Asn Glu Phe Val Arg Asp Ser Val Val Asn Leu
    130                 135                 140

Ser Asn Gln Leu Lys Arg Tyr Glu Asn Tyr Ser Asp Ile Met Val Ser
145                 150                 155                 160

Ile Lys Lys Glu Ile Ser Ser Leu Gly Leu Gln Leu Leu Gln Lys Asp
                165                 170                 175

Ala Ala Ser Asp Ser Lys Ala Gln Gly Thr Glu Ser Lys Lys Ser Lys
            180                 185                 190

Glu Ala Ile Lys Pro Pro Asn Lys Lys Pro Pro Ala Val Lys Pro Pro
        195                 200                 205

Pro Lys Gln Pro Lys Glu Lys Pro Val Lys Pro Lys Lys Glu Ala Pro
    210                 215                 220

Ala Lys Ala Ala Lys Pro Ala Lys Pro Asp Pro Thr Thr Lys Thr Lys
225                 230                 235                 240

Thr Ser Val His Gln Thr Gly Val Ile Arg Gly Ile Thr Tyr Tyr Lys
                245                 250                 255

Ala Ser Lys Ser Glu
            260


<210> SEQ ID NO 46
<211> LENGTH: 146
<212> TYPE: PRT
<213> ORGANISM: Danio rerio

<400> SEQUENCE: 46

Met Trp Arg Ile Val Glu Leu Val Ala Cys Leu Leu Met Met Ser Ser
1               5                   10                  15

His Val Ser Ser Gln Ser Lys Ile Phe Gly Glu Glu Gln Val Arg Met
            20                  25                  30

Thr Ser Glu Gly Ser Asp Cys Arg Cys Lys Cys Ile Met Arg Pro Leu
        35                  40                  45

Thr Arg Asp Ala Cys Ala Arg Leu Arg Thr Gly Ser Val Arg Val Glu
    50                  55                  60

Asp Phe Tyr Thr Val Glu Thr Val Ser Ser Gly Ala Asp Cys Lys Cys
65                  70                  75                  80

Ser Cys Thr Ala Pro Pro Ser Ser Leu Asn Pro Cys Glu Asn Glu Trp
                85                  90                  95

Lys Arg Glu Lys Leu Lys Lys Gln Ala Pro Glu Leu Leu Lys Leu Gln
            100                 105                 110

Ser Met Val Asp Leu Leu Glu Gly Thr Leu Phe Ser Met Asp Leu Leu
```

```
        115                 120                 125

Lys Val His Ser Tyr Ile Asn Lys Val Val Ser Gln Met Asn Asn Leu
    130                 135                 140

Glu Glu
145


<210> SEQ ID NO 47
<211> LENGTH: 681
<212> TYPE: PRT
<213> ORGANISM: Mus musculus

<400> SEQUENCE: 47

Met Glu Ala Ala Ala Val Leu Pro Arg Tyr Leu Gln Leu Arg Leu Leu
1               5                   10                  15

Leu Val Leu Leu Leu Leu Val Leu Leu Arg Ala Gly Pro Val Trp Pro
            20                  25                  30

Asp Ser Lys Val Phe Ser Asp Leu Asp Gln Val Arg Met Thr Ser Glu
        35                  40                  45

Gly Ser Asp Cys Arg Cys Lys Cys Ile Met Arg Pro Leu Ser Lys Asp
    50                  55                  60

Ala Cys Ser Arg Val Arg Ser Gly Arg Ala Arg Val Glu Asp Phe Tyr
65                  70                  75                  80

Thr Val Glu Thr Val Ser Ser Gly Ala Asp Cys Arg Cys Ser Cys Thr
                85                  90                  95

Ala Pro Pro Ser Ser Leu Asn Pro Cys Glu Asn Glu Trp Lys Met Glu
            100                 105                 110

Lys Leu Lys Lys Gln Ala Pro Glu Leu Leu Lys Leu Gln Ser Met Val
        115                 120                 125

Asp Leu Leu Glu Gly Ala Leu Tyr Ser Met Asp Leu Met Lys Val His
    130                 135                 140

Ala Tyr Ile Gln Lys Val Ala Ser Gln Met Asn Thr Leu Glu Glu Ser
145                 150                 155                 160

Ile Lys Ala Asn Leu Ser Leu Glu Asn Lys Val Val Lys Asp Ser Val
                165                 170                 175

His His Leu Ser Glu Gln Leu Lys Ser Tyr Glu Asn Gln Ser Ala Ile
            180                 185                 190

Met Met Ser Ile Lys Lys Glu Leu Ser Ser Leu Gly Leu Gln Leu Leu
        195                 200                 205

Gln Arg Asp Ala Ala Ala Val Pro Ala Thr Ala Pro Ala Ser Ser Pro
    210                 215                 220

Asp Ser Lys Ala Gln Asp Thr Ala Gly Gly Gln Gly Arg Asp Leu Asn
225                 230                 235                 240

Lys Tyr Gly Ser Ile Gln Lys Ser Phe Ser Asp Lys Gly Leu Ala Lys
                245                 250                 255

Pro Pro Lys Glu Lys Leu Leu Lys Val Glu Lys Leu Arg Lys Glu Ser
            260                 265                 270

Ile Lys Gly Arg Ile Pro Gln Pro Thr Ala Arg Pro Arg Ala Leu Ala
        275                 280                 285

Gln Gln Gln Ala Val Ile Arg Gly Phe Thr Tyr Tyr Lys Ala Gly Arg
    290                 295                 300

Gln Glu Ala Arg Gln Glu Ala Arg Gln Glu Ala Pro Lys Ala Ala Ala
305                 310                 315                 320

Asp Ser Thr Leu Lys Gly Thr Ser Trp Leu Glu Lys Leu Pro Pro Lys
                325                 330                 335
```

```
Ile Glu Ala Lys Leu Pro Glu Pro Asn Ser Ala Lys His Asp Asp Val
            340                 345                 350

Arg Leu Gln Ala Ser Glu Gly Gly Asn Leu Thr Pro Asp Ile Thr Thr
        355                 360                 365

Thr Thr Thr Ser Thr Ser Ser Ser Thr Thr Thr Thr Thr Gly Thr Thr
    370                 375                 380

Ser Thr Thr Ser Thr Thr Ser Thr Thr Ser Thr Thr Thr Pro Ser Pro
385                 390                 395                 400

Ile Thr Thr Pro Trp Pro Thr Glu Pro Pro Leu His Pro Glu Val Pro
                405                 410                 415

Ser Gln Gly Arg Glu Asp Ser Cys Glu Gly Thr Leu Arg Ala Val Asp
            420                 425                 430

Pro Pro Val Lys His His Ser Tyr Gly Arg His Glu Gly Ala Trp Met
        435                 440                 445

Lys Asp Pro Ala Ala Leu Asp Asp Arg Ile Tyr Val Thr Asn Tyr Tyr
    450                 455                 460

Tyr Gly Asn Ser Leu Val Glu Phe Arg Asn Leu Glu Asn Phe Lys Gln
465                 470                 475                 480

Gly Arg Trp Ser Asn Met Tyr Lys Leu Pro Tyr Asn Trp Ile Gly Thr
                485                 490                 495

Gly His Val Val Tyr Gln Gly Ala Phe Tyr Tyr Asn Arg Ala Phe Thr
            500                 505                 510

Lys Asn Ile Ile Lys Tyr Asp Leu Arg Gln Arg Phe Val Ala Ser Trp
        515                 520                 525

Ala Leu Leu Pro Asp Val Val Tyr Glu Asp Thr Thr Pro Trp Lys Trp
    530                 535                 540

Arg Gly His Ser Asp Ile Asp Phe Ala Val Asp Glu Ser Gly Leu Trp
545                 550                 555                 560

Val Ile Tyr Pro Ala Val Asp Glu His Asp Glu Thr Gln His Glu Val
                565                 570                 575

Ile Val Leu Ser Arg Leu Asp Pro Ala Asp Leu Ser Val His Arg Glu
            580                 585                 590

Thr Thr Trp Lys Thr Arg Leu Arg Arg Asn Ser Tyr Gly Asn Cys Phe
        595                 600                 605

Leu Val Cys Gly Ile Leu Tyr Thr Val Asp Thr Tyr Asn Gln His Glu
    610                 615                 620

Gly Gln Val Ala Tyr Ala Phe Asp Thr His Thr Gly Thr Asp Ala His
625                 630                 635                 640

Pro Gln Leu Pro Phe Leu Asn Glu Tyr Ser Tyr Thr Thr Gln Val Asp
                645                 650                 655

Tyr Asn Pro Lys Glu Arg Val Leu Tyr Ala Trp Asp Asn Gly His Gln
            660                 665                 670

Leu Thr Tyr Thr Leu His Phe Val Val
        675                 680
```

<210> SEQ ID NO 48
<211> LENGTH: 704
<212> TYPE: PRT
<213> ORGANISM: Homo sapiens

<400> SEQUENCE: 48

```
Met Ala Ala Ala Ala Leu Pro Pro Arg Pro Leu Leu Leu Leu Pro Leu
1               5                   10                  15

Val Leu Leu Leu Ser Gly Arg Pro Thr Arg Ala Asp Ser Lys Val Phe
            20                  25                  30
```

```
Gly Asp Leu Asp Gln Val Arg Met Thr Ser Glu Gly Ser Asp Cys Arg
        35                  40                  45

Cys Lys Cys Ile Met Arg Pro Leu Ser Lys Asp Ala Cys Ser Arg Val
    50                  55                  60

Arg Ser Gly Arg Ala Arg Val Glu Asp Phe Tyr Thr Val Glu Thr Val
65                  70                  75                  80

Ser Ser Gly Thr Asp Cys Arg Cys Ser Cys Thr Ala Pro Pro Ser Ser
                85                  90                  95

Leu Asn Pro Cys Glu Asn Glu Trp Lys Met Glu Lys Leu Lys Lys Gln
            100                 105                 110

Ala Pro Glu Leu Leu Lys Ser Ile Lys Ala Asn Leu Ser Arg Glu Asn
        115                 120                 125

Glu Val Val Lys Asp Ser Val Arg His Leu Ser Glu Gln Leu Arg His
    130                 135                 140

Tyr Glu Asn His Ser Ala Ile Met Leu Gly Ile Lys Lys Glu Leu Ser
145                 150                 155                 160

Arg Leu Gly Leu Gln Leu Leu Gln Lys Asp Ala Ala Ala Ala Pro Ala
                165                 170                 175

Thr Pro Ala Thr Gly Thr Gly Ser Lys Ala Gln Asp Thr Ala Arg Gly
            180                 185                 190

Lys Gly Lys Asp Ile Ser Lys Tyr Gly Ser Val Gln Lys Ser Phe Ala
        195                 200                 205

Asp Arg Gly Leu Pro Lys Pro Pro Lys Glu Lys Leu Leu Gln Val Glu
    210                 215                 220

Lys Leu Arg Lys Glu Ser Gly Lys Gly Ser Phe Leu Gln Pro Thr Ala
225                 230                 235                 240

Lys Pro Arg Ala Leu Ala Gln Gln Gln Ala Val Ile Arg Gly Phe Thr
                245                 250                 255

Tyr Tyr Lys Ala Gly Lys Gln Glu Val Thr Glu Ala Val Ala Asp Asn
            260                 265                 270

Ala Leu Gln Gly Thr Ser Trp Leu Glu Gln Leu Pro Pro Lys Val Glu
        275                 280                 285

Gly Arg Ser Asn Ser Ala Glu Pro Asn Ser Ala Glu Gln Asp Glu Ala
    290                 295                 300

Glu Pro Arg Ser Ser Glu Arg Val Asp Leu Ala Ser Gly Thr Thr His
305                 310                 315                 320

Leu Ile Leu Pro Pro His Ser Leu His His His Ser Thr Pro Val Leu
                325                 330                 335

Ala Thr Pro Ala Pro Phe His Leu Gln Cys His Asn Lys Pro Val Pro
            340                 345                 350

Ser Pro Arg Arg Trp Gln Thr Thr Pro Ser Arg Ala Leu Pro Gly Trp
        355                 360                 365

Ser Asn Cys Arg Pro Arg Trp Arg Ala Gly Pro Thr Pro Gln Ser Pro
    370                 375                 380

Thr Pro Gln Ser Arg Met Arg Leu Ser Pro Gly Pro Pro Ser Glu Trp
385                 390                 395                 400

Thr Trp Leu Leu Ala Pro His Phe Asn Pro Cys His His His His Arg
                405                 410                 415

His Pro His Pro Gln Pro Pro Thr Thr Ser Leu Leu Pro Thr Glu Pro
            420                 425                 430

Pro Ser Gly Pro Glu Val Ser Ser Gln Gly Arg Glu Ala Ser Cys Glu
        435                 440                 445
```

Gly Thr Leu Arg Ala Val Asp Pro Pro Val Arg His His Ser Tyr Gly
450 455 460

Arg His Glu Gly Ala Trp Met Lys Asp Pro Ala Ala Arg Asp Asp Arg
465 470 475 480

Ile Tyr Val Thr Asn Tyr Tyr Tyr Gly Asn Ser Leu Val Glu Phe Arg
485 490 495

Asn Leu Glu Asn Phe Lys Gln Gly Arg Trp Ser Asn Met Tyr Lys Leu
500 505 510

Pro Tyr Asn Trp Ile Gly Thr Gly His Val Val Tyr Gln Gly Ala Phe
515 520 525

Tyr Tyr Asn Arg Ala Phe Thr Lys Asn Ile Ile Lys Tyr Asp Leu Arg
530 535 540

Gln Arg Phe Val Ala Ser Trp Ala Leu Leu Pro Asp Val Val Tyr Glu
545 550 555 560

Asp Thr Thr Pro Trp Lys Trp Arg Gly His Ser Asp Ile Asp Phe Ala
565 570 575

Val Asp Glu Ser Gly Leu Trp Val Ile Tyr Pro Ala Val Asp Asp Arg
580 585 590

Asp Glu Ala Gln Pro Glu Val Ile Val Leu Ser Arg Leu Asp Pro Gly
595 600 605

Asp Leu Ser Val His Arg Glu Thr Thr Trp Lys Thr Arg Leu Arg Arg
610 615 620

Asn Ser Tyr Gly Asn Cys Phe Leu Val Cys Gly Ile Leu Tyr Ala Val
625 630 635 640

Asp Thr Tyr Asn Gln Gln Glu Gly Gln Val Ala Tyr Ala Phe Asp Thr
645 650 655

His Thr Gly Thr Asp Ala Arg Pro Gln Leu Pro Phe Leu Asn Glu His
660 665 670

Ala Tyr Thr Thr Gln Ile Asp Tyr Asn Pro Lys Glu Arg Val Leu Tyr
675 680 685

Ala Trp Asp Asn Gly His Gln Leu Thr Tyr Thr Leu His Phe Val Val
690 695 700

<210> SEQ ID NO 49
<211> LENGTH: 831
<212> TYPE: PRT
<213> ORGANISM: Rattus norvegicus

<400> SEQUENCE: 49

Met Ala Tyr Pro Leu Pro Leu Val Leu Cys Phe Ala Leu Val Val Ala
1 5 10 15

Arg Val Trp Gly Ser Ser Thr Pro Pro Thr Gly Thr Ser Glu Pro Pro
20 25 30

Asp Val Gln Thr Val Ala Pro Thr Glu Asp Asp Val Leu Gln Asn Glu
35 40 45

Ala Asp Asn Gln Glu Asn Val Leu Ser Gln Leu Leu Gly Asp Tyr Asp
50 55 60

Lys Val Lys Ala Val Ser Glu Gly Ser Asp Cys Gln Cys Lys Cys Val
65 70 75 80

Val Arg Pro Leu Gly Arg Asp Ala Cys Gln Arg Ile Asn Glu Gly Ala
85 90 95

Ser Arg Lys Glu Asp Phe Tyr Thr Val Glu Thr Ile Thr Ser Gly Ser
100 105 110

Ser Cys Lys Cys Ala Cys Val Ala Pro Pro Ser Ala Val Asn Pro Cys
115 120 125

-continued

```
Glu Gly Asp Phe Arg Leu Gln Lys Leu Arg Glu Ala Asp Ser Arg Asp
    130                 135                 140

Leu Lys Leu Ser Thr Ile Ile Asp Met Leu Glu Gly Ala Phe Tyr Gly
145                 150                 155                 160

Leu Asp Leu Leu Lys Leu His Ser Val Thr Thr Lys Leu Val Gly Arg
                165                 170                 175

Val Asp Lys Leu Glu Glu Glu Val Ser Lys Asn Leu Thr Lys Glu Asn
            180                 185                 190

Glu Gln Ile Lys Glu Asp Val Glu Glu Ile Arg Thr Glu Leu Asn Lys
        195                 200                 205

Arg Gly Lys Glu Asn Cys Ser Asp Asn Ile Leu Gly Asn Met Pro Asp
    210                 215                 220

Ile Arg Ser Ala Leu Gln Arg Asp Ala Ala Ala Ala Tyr Ala His Pro
225                 230                 235                 240

Glu Glu Gln Tyr Glu Glu Arg Phe Leu Gln Glu Glu Thr Val Ser Gln
                245                 250                 255

Gln Ile Asn Ser Ile Glu Leu Leu Arg Thr Gln Pro Leu Ala Pro Pro
            260                 265                 270

Thr Val Met Lys Pro Arg Gln Pro Ser Gln Arg Gln Val His Leu Arg
        275                 280                 285

Gly Arg Leu Ala Ser Lys Pro Thr Val Ile Arg Gly Ile Thr Tyr Tyr
    290                 295                 300

Lys Ala Lys Val Ser Glu Glu Glu Asn Asp Ile Glu Asp Gln His Asp
305                 310                 315                 320

Glu Leu Phe Ser Gly Asp Ser Gly Val Asp Leu Leu Ile Glu Asp Gln
                325                 330                 335

Leu Leu Arg Gln Glu Asp Leu Leu Met Ser Ala Thr Arg Arg Pro Ala
            340                 345                 350

Thr Thr Arg His Ala Ala Ala Val Ser Thr Asp Ala Ser Val Gln Ala
        355                 360                 365

Thr Ala Leu Ser Ser Glu Pro Ala Gln Ala Ser Ala Ser Ala Pro Ser
    370                 375                 380

Leu Val Asp Pro Ala Ser Gln Ala Pro Asp Arg Gln Leu Leu Ala Ser
385                 390                 395                 400

Pro Gln Thr Thr Thr Val Ser Pro Glu Thr Met Gly Val Met Pro Ser
                405                 410                 415

Thr Gln Val Ser Pro Thr Thr Val Ala His Thr Ala Ile Gln Pro Pro
            420                 425                 430

Pro Ala Met Ile Pro Gly Asp Ile Phe Val Glu Ala Leu His Leu Val
        435                 440                 445

Pro Met Ser Pro Asp Thr Val Gly Thr Asp Met Ala Glu Glu Glu Gly
    450                 455                 460

Thr Ala Arg Gln Glu Ala Thr Ser Ala Ser Pro Ile Leu Ser Pro Glu
465                 470                 475                 480

Glu Glu Asp Asp Ile Arg Asn Val Ile Gly Val Phe Lys Cys Ser Glu
                485                 490                 495

Ala Pro His Ile Ser Ala Ala Phe Leu His Gly Leu Lys His Ser Val
            500                 505                 510

Gly Phe Ser Val Pro Trp Arg His Val Glu Ile Cys Leu Lys Ile Arg
        515                 520                 525

Val Ser Val Leu Leu Ser Leu Val Trp Gln Gly Leu Pro Gly Tyr Gln
    530                 535                 540
```

-continued

```
Ala Ile Pro Lys Arg Tyr Phe Glu Glu Asn Gly Trp Ile Pro Ala Pro
545                 550                 555                 560

Pro Arg Lys Thr Gly Val Leu Lys Glu Ala Leu Gln Leu Glu Cys Lys
                565                 570                 575

Asp Thr Leu Ser Thr Ile Thr Gly Pro Thr Thr Gln Asn Thr Tyr Gly
            580                 585                 590

Arg Asn Glu Gly Ala Trp Met Lys Asp Pro Leu Ala Lys Asp Asp Arg
        595                 600                 605

Ile Tyr Val Thr Asn Tyr Tyr Tyr Gly Asn Thr Leu Val Glu Phe Arg
    610                 615                 620

Asn Leu Glu Asn Phe Lys Gln Gly Arg Trp Ser Asn Ser Tyr Lys Leu
625                 630                 635                 640

Pro Tyr Ser Trp Ile Gly Thr Gly His Val Val Tyr Asn Gly Ala Phe
                645                 650                 655

Tyr Tyr Asn Arg Ala Phe Thr Arg Asn Ile Ile Lys Tyr Asp Leu Lys
            660                 665                 670

Gln Arg Tyr Val Ala Ala Trp Ala Met Leu His Asp Val Ala Tyr Glu
        675                 680                 685

Glu Thr Thr Pro Trp Arg Trp Gln Gly His Ser Asp Val Asp Phe Ala
    690                 695                 700

Val Asp Glu Asn Gly Leu Trp Leu Ile Tyr Pro Ala Leu Asp Asp Glu
705                 710                 715                 720

Gly Phe Ser Gln Glu Val Ile Val Leu Ser Lys Leu Asn Ala Val Asp
                725                 730                 735

Leu Ser Thr Gln Lys Glu Thr Thr Trp Arg Thr Gly Leu Arg Arg Asn
            740                 745                 750

Phe Tyr Gly Asn Cys Phe Val Ile Cys Gly Val Leu Tyr Ala Val Asp
        755                 760                 765

Ser Tyr Asn Gln Arg Asn Ala Asn Ile Ser Tyr Ala Phe Asp Thr His
    770                 775                 780

Thr Asn Thr Gln Ile Val Pro Arg Leu Leu Phe Glu Asn Glu Tyr Ser
785                 790                 795                 800

Tyr Thr Thr Gln Ile Asp Tyr Asn Pro Lys Asp Arg Leu Leu Tyr Ala
                805                 810                 815

Trp Asp Asn Gly His Gln Val Thr Tyr His Val Ile Phe Ala Tyr
            820                 825                 830


<210> SEQ ID NO 50
<211> LENGTH: 860
<212> TYPE: PRT
<213> ORGANISM: Homo sapiens

<400> SEQUENCE: 50

Met Ala Lys Pro Arg Leu Leu Val Leu Tyr Phe Ala Leu Ile Val Val
1               5                   10                  15

Pro Ala Trp Val Ser Ser Ile Val Leu Thr Gly Thr Ser Glu Pro Pro
            20                  25                  30

Asp Ala Gln Thr Val Ala Pro Ala Glu Asp Glu Thr Leu Gln Asn Glu
        35                  40                  45

Ala Asp Asn Gln Glu Asn Val Leu Ser Gln Leu Leu Gly Asp Tyr Asp
    50                  55                  60

Lys Val Lys Ala Met Ser Glu Gly Ser Asp Cys Gln Cys Lys Cys Val
65                  70                  75                  80

Val Arg Pro Leu Gly Arg Asp Ala Cys Gln Arg Ile Asn Ala Gly Ala
                85                  90                  95
```

```
Ser Arg Lys Glu Asp Phe Tyr Thr Val Glu Thr Ile Thr Ser Gly Ser
            100                 105                 110

Ser Cys Lys Cys Ala Cys Val Ala Pro Pro Ser Ala Leu Asn Pro Cys
        115                 120                 125

Glu Gly Asp Phe Arg Leu Gln Lys Leu Arg Glu Ala Asp Ser Gln Asp
    130                 135                 140

Leu Lys Val Gly Pro Gly Met Gly Gln Cys Leu Gly Arg Glu Gly Thr
145                 150                 155                 160

Phe Glu Ile His Lys Ser Gly Lys Ala Met Val Glu Asp Ser Lys Pro
                165                 170                 175

Phe Glu Glu Gly Leu Ser His Phe Leu Thr Gln Thr Phe Arg Lys Ala
            180                 185                 190

Glu Cys Thr Tyr Thr Ile Val Leu Ala Tyr Ile Pro Val Tyr Thr Asn
        195                 200                 205

Val Phe Leu Thr Ala Thr Ser Gln Phe Leu Ala Ser Gly Phe Pro Val
    210                 215                 220

Glu Pro Pro Leu Ser Thr Ile Ile Asp Met Leu Glu Gly Ala Phe Tyr
225                 230                 235                 240

Gly Leu Asp Leu Leu Lys Leu His Ser Val Thr Thr Lys Leu Val Gly
                245                 250                 255

Arg Val Asp Lys Leu Glu Glu Met Leu Glu Gly Ala Phe Tyr Gly Leu
            260                 265                 270

Asp Leu Leu Lys Leu His Ser Val Thr Thr Lys Leu Val Gly Arg Val
        275                 280                 285

Asp Lys Leu Glu Glu Glu Val Ser Lys Asn Thr Lys Glu Asn Glu Gln
    290                 295                 300

Ile Lys Glu Asp Met Glu Glu Ile Arg Thr Glu Met Asn Lys Arg Gly
305                 310                 315                 320

Lys Glu Asn Cys Ser Glu Asn Ile Leu Asp Ser Met Pro Asp Ile Arg
                325                 330                 335

Ser Ala Leu Gln Arg Asp Ala Ala Ala Ala Tyr Ala His Pro Glu Tyr
            340                 345                 350

Glu Glu Arg Phe Leu Gln Glu Glu Thr Val Ser Gln Gln Ile Asn Ser
        355                 360                 365

Ile Glu Leu Leu Gln Thr Arg Pro Leu Ala Leu Pro Glu Val Val Lys
    370                 375                 380

Ser Gln Arg Pro Leu Gln Arg Gln Val His Leu Arg Gly Arg Pro Ala
385                 390                 395                 400

Ser Gln Pro Thr Val Ile Arg Gly Ile Thr Tyr Tyr Lys Ala Lys Val
                405                 410                 415

Ser Glu Glu Glu Asn Asp Ile Glu Glu Gln Gln Asp Glu Phe Phe Ser
            420                 425                 430

Gly Asp Asn Gly Val Asp Leu Leu Ile Glu Asp Gln Leu Leu Arg His
        435                 440                 445

Asn Gly Leu Met Thr Ser Val Thr Arg Arg Pro Ala Ala Thr Arg Gln
    450                 455                 460

Gly His Ser Thr Ala Val Thr Ser Asp Leu Asn Ala Arg Thr Ala Pro
465                 470                 475                 480

Trp Ser Ser Ala Leu Pro Gln Pro Ser Thr Ser Asp Pro Ser Ile Ala
                485                 490                 495

Asn His Ala Ser Val Gly Pro Thr Leu Gln Thr Thr Ser Val Ser Pro
            500                 505                 510
```

```
Asp Pro Thr Arg Glu Ser Val Leu Gln Pro Ser Pro Gln Val Pro Ala
        515                 520                 525

Thr Thr Val Ala His Thr Ala Thr Gln Gln Pro Ala Ala Pro Ala Pro
    530                 535                 540

Pro Ala Val Ser Pro Arg Glu Ala Leu Met Glu Ala Met His Thr Val
545                 550                 555                 560

Pro Val Pro Pro Thr Thr Val Arg Thr Asp Ser Leu Gly Lys Asp Ala
                565                 570                 575

Pro Ala Gly Trp Gly Thr Thr Pro Ala Ser Pro Thr Leu Ser Pro Glu
            580                 585                 590

Glu Glu Asp Asp Ile Arg Asn Val Ile Gly Arg Cys Lys Asp Thr Leu
        595                 600                 605

Ser Thr Ile Thr Gly Pro Thr Thr Gln Asn Thr Tyr Gly Arg Asn Glu
    610                 615                 620

Gly Ala Trp Met Lys Asp Pro Leu Ala Lys Asp Glu Arg Ile Tyr Val
625                 630                 635                 640

Thr Asn Tyr Tyr Tyr Gly Asn Thr Leu Val Glu Phe Arg Asn Leu Glu
                645                 650                 655

Asn Phe Lys Gln Gly Arg Trp Ser Asn Ser Tyr Lys Leu Pro Tyr Ser
            660                 665                 670

Trp Ile Gly Thr Gly His Val Val Tyr Asn Gly Ala Phe Tyr Tyr Asn
        675                 680                 685

Arg Ala Phe Thr Arg Asn Ile Ile Lys Tyr Asp Leu Lys Gln Arg Tyr
    690                 695                 700

Val Ala Ala Trp Ala Met Leu His Asp Val Ala Tyr Glu Glu Ala Thr
705                 710                 715                 720

Pro Trp Arg Trp Gln Gly His Ser Asp Val Asp Phe Ala Val Asp Glu
                725                 730                 735

Asn Gly Leu Trp Leu Ile Tyr Pro Ala Leu Asp Asp Glu Gly Phe Ser
            740                 745                 750

Gln Glu Val Ile Val Leu Ser Lys Leu Asn Ala Ala Asp Leu Ser Thr
        755                 760                 765

Gln Lys Glu Thr Thr Trp Arg Thr Gly Leu Arg Arg Asn Phe Tyr Gly
    770                 775                 780

Asn Cys Phe Val Ile Cys Gly Val Leu Tyr Ala Val Asp Ser Tyr Asn
785                 790                 795                 800

Gln Arg Asn Ala Asn Ile Ser Tyr Ala Phe Asp Thr His Thr Asn Thr
                805                 810                 815

Gln Ile Val Pro Arg Leu Leu Phe Glu Asn Glu Tyr Ser Tyr Thr Thr
            820                 825                 830

Gln Ile Asp Tyr Asn Pro Lys Asp Arg Leu Leu Tyr Ala Trp Asp Asn
        835                 840                 845

Gly His Gln Val Thr Tyr His Val Ile Phe Ala Tyr
    850                 855                 860


<210> SEQ ID NO 51
<211> LENGTH: 719
<212> TYPE: PRT
<213> ORGANISM: Danio rerio

<400> SEQUENCE: 51

Met Thr Glu Met Lys Ile Trp Cys Val Leu Leu Met Ala Phe Ala Leu
1               5                   10                  15

Thr Ser Ala Ala Pro Lys Ser His Leu Arg Leu Glu Glu Lys Thr Lys
            20                  25                  30
```

-continued

```
Asp Asn Asn Asp Thr Leu Gln Val Glu Ile Asp Asn Gln Glu His Ile
        35                  40                  45

Leu Ser Gln Leu Leu Gly Asp Tyr Asp Lys Val Lys Ala Leu Ser Glu
    50                  55                  60

Gly Ser Asp Cys Gly Cys Lys Cys Val Val Arg Pro Leu Ser Ala Ser
65                  70                  75                  80

Ala Cys Gln Arg Ile Arg Glu Gly His Ala Thr Pro Gln Asp Phe Tyr
                85                  90                  95

Thr Val Glu Thr Ile Thr Ser Gly Pro His Cys Lys Cys Ala Cys Ile
            100                 105                 110

Ala Pro Pro Ser Ala Leu Asn Pro Cys Glu Gly Asp Phe Arg Leu Lys
        115                 120                 125

Lys Leu Arg Gln Ala Gly Lys Asp Asn Ile Lys Leu Ser Thr Ile Leu
    130                 135                 140

Glu Leu Leu Glu Gly Ser Phe Tyr Gly Met Asp Leu Leu Lys Leu His
145                 150                 155                 160

Ser Val Thr Thr Lys Ile Leu Asp Arg Met Asp Thr Ile Glu Lys Met
                165                 170                 175

Val Leu Asn Asn Gln Thr Glu Glu Lys Leu Asn Thr Ile Ser Thr Ser
            180                 185                 190

Pro Asn Pro Gln Leu Ser Thr Ser Ser Pro Thr Thr Leu Pro Ser Val
        195                 200                 205

Ile Gln Glu Lys Ser Thr Ser Leu Arg Gln Gln Asn Asp Glu Ala Ala
    210                 215                 220

Ala Phe Gln His Met Glu Ser Lys Tyr Glu Glu Lys Phe Val Gly Asp
225                 230                 235                 240

Ile Leu Asn Ser Gly Ser Asp Leu Asn Lys Ala Thr Thr Ala Leu Gln
                245                 250                 255

Glu Gln Glu Gln Gln Gly Arg Lys Lys Gln Pro Lys Ile Thr Val Arg
            260                 265                 270

Gly Ile Thr Tyr Tyr Arg Ser Asp Pro Val Asp Glu Met Asp Ser Glu
        275                 280                 285

Lys Asn Leu Lys Glu Thr Ser Ala Ser Ser Val Thr Gln Thr Gly Ala
    290                 295                 300

Leu Ile Lys Glu His Leu Lys Ala Ser Thr Gln Ser Thr Leu Asn Thr
305                 310                 315                 320

Leu Thr Pro Ser Pro Thr Ser His Ser Asn Ala Leu Thr Val Thr Glu
                325                 330                 335

Ser Ser Val Gly Ile Asn Ala His Lys Gly Glu Val Thr Thr Ile Val
            340                 345                 350

Met Thr Ala Ser Val Thr Gly Ser Lys Thr Asp Ser Val Thr Asp Leu
        355                 360                 365

Thr Gln Leu Ser Pro Arg Val Arg Glu Thr Leu Thr Thr Thr Arg Thr
    370                 375                 380

Thr Thr Lys Thr Ala Thr Thr Ser Gln Pro Val Lys Arg Lys Tyr Ser
385                 390                 395                 400

Ile Ser Trp Asp Glu Glu Glu Glu Ala Val Val Pro Glu Gln Val Glu
                405                 410                 415

Glu Glu Lys Ala Val Lys Pro Val Val Glu Asp Lys Val Gly Glu Glu
            420                 425                 430

Pro Gln Arg Lys Pro Gly Thr Ala His His Gln Ala Lys Thr Ile Ser
        435                 440                 445
```

```
Thr Val Lys Gln Gln Ile Lys Phe Ser Leu Gly Met Cys Lys Asp Thr
    450                 455                 460

Leu Ala Thr Ile Ser Glu Pro Ile Thr His Asn Thr Tyr Gly Arg Asn
465                 470                 475                 480

Glu Gly Ala Trp Met Lys Asp Pro Leu Asp Gln Asp Asp Lys Ile Tyr
                485                 490                 495

Val Thr Asn Tyr Tyr Tyr Gly Asn Asn Leu Leu Glu Phe Arg Asn Ile
            500                 505                 510

Asp Val Phe Lys Gln Gly Arg Phe Thr Asn Ser Tyr Lys Leu Pro Tyr
        515                 520                 525

Asn Trp Ile Gly Thr Gly His Val Val Tyr Lys Gly Ala Phe Tyr Tyr
    530                 535                 540

Asn Arg Ala Phe Ser Arg Asp Ile Ile Lys Phe Asp Leu Arg Leu Arg
545                 550                 555                 560

Tyr Val Ala Ala Trp Thr Met Leu His Asp Ala Val Phe Glu Asn Asp
                565                 570                 575

Asp Val Ser Ser Trp Arg Trp Arg Gly Asn Ser Asp Met Asp Leu Ala
            580                 585                 590

Ile Asp Glu Ser Gly Leu Trp Val Ile Tyr Pro Ala Leu Asp Asp Glu
        595                 600                 605

Gly Phe Leu Gln Glu Val Ile Val Leu Ser Arg Leu Asn Pro Thr Asp
    610                 615                 620

Leu Ser Met Lys Arg Glu Thr Thr Trp Arg Thr Gly Leu Arg Arg Asn
625                 630                 635                 640

Arg Tyr Gly Asn Cys Phe Ile Val Cys Gly Val Leu Tyr Ala Thr Asp
                645                 650                 655

Ser Tyr Asn Gln Gln Asp Thr Asn Leu Ser Tyr Ala Phe Asp Thr His
            660                 665                 670

Thr Asn Thr Gln Val Ile Pro His Leu Pro Phe Ser Asn Asn Tyr Thr
        675                 680                 685

Tyr Val Thr Gln Ile Asp Tyr Asn Pro Lys Glu Arg Val Leu Tyr Ala
    690                 695                 700

Trp Asp Asn Gly His Gln Val Thr Tyr Asn Val Gln Phe Ala Tyr
705                 710                 715


<210> SEQ ID NO 52
<211> LENGTH: 656
<212> TYPE: PRT
<213> ORGANISM: Danio rerio

<400> SEQUENCE: 52

Met Gly Leu Leu Leu Tyr Ile Phe Cys Cys Val Phe Cys Leu Thr Arg
1               5                   10                  15

Ala Asn Val Glu Gln Gln Ala Thr Asp Asn Thr Asp Asn Arg Ala Thr
            20                  25                  30

Leu Glu Asp Glu Met Asp Asn Gln Glu Asn Ile Leu Thr Gln Leu Ile
        35                  40                  45

Gly Asp Tyr Asp Lys Val Lys Thr Leu Ser Glu Gly Ser Asp Cys Gln
    50                  55                  60

Cys Lys Cys Val Val Arg Pro Met Ser Arg Ser Ala Cys Lys Arg Ile
65                  70                  75                  80

Glu Glu Ala Gln Ala Lys Ile Glu Asp Phe Tyr Thr Val Glu Pro Val
                85                  90                  95

Thr Ala Gly Pro Asn Cys Lys Lys Cys Ala Cys Ile Ala Pro Pro Ser
            100                 105                 110
```

```
Ala Leu Asn Pro Cys Glu Gly Asp Phe Arg Phe Lys Lys Leu Gln Lys
        115                 120                 125

Thr Gly Gln Tyr Asp Ile Lys Leu Ser Asn Ile Met Asp Leu Leu Glu
    130                 135                 140

Gly Ser Phe Tyr Gly Met Asp Leu Leu Lys Leu His Ser Val Thr Thr
145                 150                 155                 160

Lys Leu Leu Glu Arg Val Asp Asn Ile Glu Lys Ser Phe Ser Gly Asn
                165                 170                 175

Leu Thr Lys Glu Lys Val Ser Val Lys Gly Glu Lys Gly Gln Gly Lys
            180                 185                 190

Gly Ala Arg Ser Asn Gln Arg Gln Glu Lys Lys Lys Arg Leu Ser Val
        195                 200                 205

Leu Glu Pro Ser Leu Gln Lys Asn Ala Ala Ala Ala Phe Ala His Thr
    210                 215                 220

Glu Val Gln Met Gln Gln Phe Ile Pro Asp Gln Arg Lys Tyr Glu Glu
225                 230                 235                 240

Lys Phe Val Gly Asn Gln Gly Pro Ser Lys Pro Val Leu Lys Lys Ser
                245                 250                 255

Lys Ser Glu Gly Gln Glu Glu Gln His Lys Pro Ala Lys Thr Lys Ala
            260                 265                 270

Asp Ala Lys Asn Met Ser Leu Arg Ser Met Thr Phe Tyr Lys Ala Asn
        275                 280                 285

Arg Met Glu Asp Ser Glu Gly Glu Glu Arg Met Asp Leu Ile Ile Glu
    290                 295                 300

Asp Gln Leu His Lys Gln Gly Leu Asn Thr Pro Val Thr Thr Pro Glu
305                 310                 315                 320

Ala Thr Val Thr Val Thr Gln Ser Thr Thr Ile Asn Leu Asn Thr Gln
                325                 330                 335

Asn Phe Thr Thr Ala Arg Met Ser Asn Val Thr Lys Gln Thr Gln Gly
            340                 345                 350

Gln Ser Val Lys Ala Met Met Ser Ser Thr Ile Thr Thr Glu Arg Pro
        355                 360                 365

Thr Met Pro Thr Ser Thr Thr Ser Thr Ser Thr Met Thr Pro Gly Thr
    370                 375                 380

Asn Thr Thr Thr Ile Ala Thr Pro Leu Val Val Pro Lys Gln Leu Ala
385                 390                 395                 400

Arg Ile Cys Lys Asp Thr Leu Ala Ser Ile Ser Asp Pro Val Thr His
                405                 410                 415

Asn Lys Tyr Gly Lys Asn Glu Gly Ala Trp Met Lys Asp Pro Lys Gly
            420                 425                 430

Asn Gly Lys Val Val Tyr Val Thr Asp Tyr Tyr Tyr Gly Asn Gln Leu
        435                 440                 445

Leu Glu Phe Arg Asp Ile Asp Thr Phe Lys Gln Gly Gln Val Ser Asn
    450                 455                 460

Ser Tyr Lys Leu Pro Tyr Asn Trp Ile Gly Thr Gly His Val Val Tyr
465                 470                 475                 480

Ser Gly Ser Phe Phe Tyr Asn Arg Ala Phe Ser Arg Asp Ile Ile Arg
                485                 490                 495

Phe Asp Leu Arg Leu Arg Tyr Val Ala Ala Trp Thr Thr Leu His Asp
            500                 505                 510

Ala Ile Leu Glu Glu Glu Glu Ala Pro Trp Thr Trp Gly Gly His Ser
        515                 520                 525
```

Asp Ile Asp Phe Ser Val Asp Glu Ser Gly Leu Trp Leu Val Tyr Pro
530 535 540

Ala Leu Asp Asp Glu Gly Phe His Gln Glu Val Ile Ile Leu Ser Lys
545 550 555 560

Leu Arg Ala Ser Asp Leu Gln Lys Glu Lys Ser Trp Arg Thr Gly Leu
565 570 575

Arg Arg Asn Tyr Tyr Gly Asn Cys Phe Val Ile Cys Gly Val Leu Tyr
580 585 590

Ala Val Asp Ser Phe Glu Arg Thr His Ala Asn Ile Ser Tyr Ala Phe
595 600 605

Asp Thr His Thr His Thr Gln Met Ile Pro Arg Leu Pro Phe Ile Asn
610 615 620

Asn Tyr Thr Tyr Thr Thr Gln Ile Asp Tyr Asn Pro Lys Glu Arg Met
625 630 635 640

Leu Tyr Ala Trp Asp Asn Gly His Gln Val Thr Tyr Asp Val Ile Phe
645 650 655

<210> SEQ ID NO 53
<211> LENGTH: 699
<212> TYPE: PRT
<213> ORGANISM: Homo sapiens

<400> SEQUENCE: 53

Met Val Lys Arg Lys Ser Ser Glu Gly Gln Glu Gln Asp Gly Gly Arg
1 5 10 15

Gly Ile Pro Leu Pro Ile Gln Thr Phe Leu Trp Arg Gln Thr Ser Ala
20 25 30

Phe Leu Arg Pro Lys Leu Gly Lys Gln Tyr Glu Ala Ser Cys Val Ser
35 40 45

Phe Glu Arg Val Leu Val Glu Asn Lys Leu His Gly Leu Ser Pro Ala
50 55 60

Leu Ser Glu Ala Ile Gln Ser Ile Ser Arg Trp Glu Leu Val Gln Ala
65 70 75 80

Ala Leu Pro His Val Leu His Cys Thr Ala Thr Leu Leu Ser Asn Arg
85 90 95

Asn Lys Leu Gly His Gln Asp Lys Leu Gly Val Ala Glu Thr Lys Leu
100 105 110

Leu His Thr Leu His Trp Met Leu Leu Glu Ala Pro Gln Asp Cys Asn
115 120 125

Asn Glu Arg Phe Gly Gly Thr Asp Arg Gly Ser Ser Trp Gly Gly Ser
130 135 140

Ser Ser Ala Phe Ile His Gln Val Glu Asn Gln Gly Ser Pro Gly Gln
145 150 155 160

Pro Cys Gln Ser Ser Ser Asn Asp Glu Glu Glu Asn Asn Arg Arg Lys
165 170 175

Ile Phe Gln Asn Ser Met Ala Thr Val Glu Leu Phe Val Phe Leu Phe
180 185 190

Ala Pro Leu Val His Arg Ile Lys Glu Ser Asp Leu Thr Phe Arg Leu
195 200 205

Ala Ser Gly Leu Val Ile Trp Gln Pro Met Trp Glu His Arg Gln Pro
210 215 220

Gly Val Ser Gly Phe Thr Ala Leu Val Lys Pro Ile Arg Asn Ile Ile
225 230 235 240

Thr Ala Lys Arg Ser Ser Pro Ile Asn Ser Gln Ser Arg Thr Cys Glu
245 250 255

```
Ser Pro Asn Gln Asp Ala Arg His Leu Glu Gly Leu Gln Val Val Cys
            260                 265                 270

Glu Thr Phe Gln Ser Asp Ser Ile Ser Pro Lys Ala Thr Ile Ser Gly
        275                 280                 285

Cys His Arg Gly Asn Ser Phe Asp Gly Ser Leu Ser Ser Gln Thr Ser
    290                 295                 300

Gln Glu Arg Gly Pro Ser His Ser Arg Ala Ser Leu Val Ile Pro Pro
305                 310                 315                 320

Cys Gln Arg Ser Arg Tyr Ala Thr Tyr Phe Asp Val Ala Val Leu Arg
                325                 330                 335

Cys Leu Leu Gln Pro His Trp Ser Glu Glu Gly Thr Gln Trp Ser Leu
            340                 345                 350

Met Tyr Tyr Leu Gln Arg Leu Arg His Met Leu Glu Glu Lys Pro Glu
        355                 360                 365

Lys Pro Pro Glu Pro Asp Ile Pro Leu Leu Pro Arg Pro Arg Ser Ser
    370                 375                 380

Ser Met Val Ala Ala Ala Pro Ser Leu Val Asn Thr His Lys Thr Gln
385                 390                 395                 400

Asp Leu Thr Met Lys Cys Asn Glu Glu Glu Lys Ser Leu Ser Ser Glu
                405                 410                 415

Ala Phe Ser Lys Val Ser Leu Thr Asn Leu Arg Arg Ser Ala Val Pro
            420                 425                 430

Asp Leu Ser Ser Asp Leu Gly Met Asn Ile Phe Lys Lys Phe Lys Ser
        435                 440                 445

Arg Lys Glu Asp Arg Glu Arg Lys Gly Ser Ile Pro Phe His His Thr
    450                 455                 460

Gly Lys Arg Arg Pro Arg Arg Met Gly Val Pro Phe Leu Leu His Glu
465                 470                 475                 480

Asp His Leu Asp Val Ser Pro Thr Arg Ser Thr Phe Ser Phe Gly Ser
                485                 490                 495

Phe Ser Gly Leu Gly Glu Asp Arg Arg Gly Ile Glu Lys Gly Gly Trp
            500                 505                 510

Gln Thr Thr Ile Leu Gly Lys Leu Thr Arg Arg Gly Ser Ser Asp Ala
        515                 520                 525

Ala Thr Glu Met Glu Ser Leu Ser Ala Arg His Ser His Ser His His
    530                 535                 540

Thr Leu Val Ser Asp Leu Pro Asp Pro Ser Asn Ser His Gly Glu Asn
545                 550                 555                 560

Thr Val Lys Glu Val Arg Ser Gln Ile Ser Thr Ile Thr Val Ala Thr
                565                 570                 575

Phe Asn Thr Thr Leu Ala Ser Phe Asn Val Gly Tyr Ala Asp Phe Phe
            580                 585                 590

Asn Glu His Met Arg Lys Leu Cys Asn Gln Val Pro Ile Pro Glu Met
        595                 600                 605

Pro His Glu Pro Leu Ala Cys Ala Asn Leu Pro Arg Ser Leu Thr Asp
    610                 615                 620

Ser Cys Ile Asn Tyr Ser Tyr Leu Glu Asp Thr Glu His Ile Asp Gly
625                 630                 635                 640

Thr Asn Asn Phe Val His Lys Asn Gly Met Leu Asp Leu Ser Val Val
                645                 650                 655

Leu Lys Ala Val Tyr Leu Val Leu Asn His Asp Ile Ser Ser Arg Ile
            660                 665                 670
```

Cys Asp Val Ala Leu Asn Ile Val Glu Cys Leu Leu Gln Leu Gly Val
675 680 685

Val Pro Cys Val Glu Lys Asn Arg Lys Lys Ser
690 695

<210> SEQ ID NO 54
<211> LENGTH: 700
<212> TYPE: PRT
<213> ORGANISM: Mus musculus

<400> SEQUENCE: 54

Met Val Lys Arg Lys Ser Ser Glu Gly Gln Glu Gln Asp Gly Gly Arg
1 5 10 15

Gly Ile Pro Leu Pro Ile Gln Thr Phe Leu Trp Arg Gln Thr Ser Ala
20 25 30

Phe Leu Arg Pro Lys Leu Gly Lys Gln Tyr Glu Ala Ser Cys Val Ser
35 40 45

Phe Glu Arg Val Leu Val Glu Asn Lys Leu His Gly Leu Ser Pro Ala
50 55 60

Leu Ser Glu Ala Ile Gln Ser Ile Ser Arg Trp Glu Leu Val Gln Ala
65 70 75 80

Ala Leu Pro His Val Leu His Cys Thr Ala Thr Leu Leu Ser Asn Arg
85 90 95

Asn Lys Leu Gly His Gln Asp Lys Leu Gly Val Ala Glu Thr Lys Leu
100 105 110

Leu His Thr Leu His Trp Met Leu Leu Glu Ala Pro Gln Asp Cys Asn
115 120 125

Asn Asp Gln Phe Gly Gly Thr Asp Arg Gly Ser Ser Trp Gly Gly Ser
130 135 140

Ser Ser Ala Phe Ile His Gln Ile Glu Asn Gln Gly Ser Pro Gly Gln
145 150 155 160

Pro Cys Arg Ser Ser Ser His Asp Glu Glu Glu Asn Asn Arg Arg Lys
165 170 175

Thr Phe Gln Asn Ser Met Ala Thr Val Glu Leu Phe Val Phe Leu Phe
180 185 190

Ala Pro Leu Val His Arg Ile Lys Glu Ser Asp Leu Thr Phe Arg Leu
195 200 205

Ala Ser Gly Leu Val Ile Trp Gln Pro Met Trp Glu His Arg Gln Pro
210 215 220

Glu Val Ser Gly Phe Thr Ala Leu Val Lys Pro Ile Arg Asn Ile Ile
225 230 235 240

Thr Ala Lys Arg Ser Ser Pro Ile Asn Ser Gln Ser Gln Thr Cys Glu
245 250 255

Ser Pro Asn Gln Asp Thr Arg Gln Gln Gly Glu Gly Leu Gln Val Val
260 265 270

Ser Glu Ala Leu Gln Ser Asp Ser Ile Ser Pro Lys Ala Thr Ile Ser
275 280 285

Gly Cys His Gln Gly Asn Ser Phe Asp Gly Ser Leu Ser Ser Gln Thr
290 295 300

Ser Gln Glu Arg Gly Pro Ser His Ser Arg Ala Ser Leu Val Ile Pro
305 310 315 320

Pro Cys Gln Arg Ser Arg Tyr Ala Thr Tyr Phe Asp Val Ala Val Leu
325 330 335

Arg Cys Leu Leu Gln Pro His Trp Ser Glu Glu Gly Thr Gln Trp Ser
340 345 350

Leu Met Tyr Tyr Leu Gln Arg Leu Arg His Met Leu Glu Glu Lys Pro
355 360 365

Glu Lys Thr Pro Asp Pro Asp Ile Pro Leu Leu Pro Arg Pro Arg Ser
370 375 380

Ser Ser Met Val Ala Ala Ala Pro Ser Leu Val Asn Thr His Lys Thr
385 390 395 400

Gln Asp Leu Thr Met Lys Cys Asn Glu Glu Glu Lys Ser Leu Ser Pro
405 410 415

Glu Ala Phe Ser Lys Val Ser Leu Thr Asn Leu Arg Arg Ser Ala Val
420 425 430

Pro Asp Leu Ser Ser Asp Leu Gly Met Asn Ile Phe Lys Lys Phe Lys
435 440 445

Ser Arg Lys Glu Asp Arg Glu Arg Lys Gly Ser Ile Pro Phe His His
450 455 460

Thr Gly Lys Arg Arg Pro Arg Arg Met Gly Val Pro Phe Leu Leu His
465 470 475 480

Glu Asp His Leu Asp Val Ser Pro Thr Arg Ser Thr Phe Ser Phe Gly
485 490 495

Ser Phe Ser Gly Leu Gly Glu Asp Arg Arg Gly Ile Glu Lys Gly Gly
500 505 510

Trp Gln Thr Thr Ile Leu Gly Lys Leu Thr Arg Arg Gly Ser Ser Asp
515 520 525

Ala Ala Thr Glu Met Glu Ser Leu Ser Ala Arg His Ser His Ser His
530 535 540

His Thr Leu Val Ser Asp Leu Pro Asp His Ser Asn Ser His Gly Glu
545 550 555 560

Asn Thr Val Lys Glu Val Arg Ser Gln Ile Ser Thr Ile Thr Val Ala
565 570 575

Thr Phe Asn Thr Thr Leu Ala Ser Phe Asn Val Gly Tyr Ala Asp Phe
580 585 590

Phe Ser Glu His Met Arg Lys Leu Cys Ser Gln Val Pro Ile Pro Glu
595 600 605

Met Pro His Glu Pro Leu Ala Cys Ala Asn Leu Pro Arg Ser Leu Thr
610 615 620

Asp Ser Cys Ile Asn Tyr Ser Tyr Leu Glu Asp Thr Glu His Ile Asp
625 630 635 640

Gly Thr Asn Asn Phe Val His Lys Asn Gly Met Leu Asp Leu Ser Val
645 650 655

Val Leu Lys Ala Val Tyr Leu Val Leu Asn His Asp Ile Ser Ser Arg
660 665 670

Ile Cys Asp Val Ala Leu Asn Ile Val Glu Cys Leu Leu Gln Leu Gly
675 680 685

Val Val Pro Cys Val Glu Lys Asn Arg Lys Lys Ser
690 695 700

<210> SEQ ID NO 55
<211> LENGTH: 618
<212> TYPE: PRT
<213> ORGANISM: Gallus gallus

<400> SEQUENCE: 55

Thr Arg Pro Pro Thr Arg Pro Glu Arg Val Leu Val Glu Asn Lys Leu
1 5 10 15

His Gly Leu Ser Pro Ala Leu Ser Glu Ala Ile Gln Ser Ile Ser Arg

```
            20                  25                  30

Trp Glu Leu Val Gln Ala Ala Leu Pro His Val Leu His Cys Thr Ala
        35                  40                  45

Thr Leu Leu Ser Asn Arg Asn Lys Leu Gly His Gln Asp Lys Leu Gly
    50                  55                  60

Val Ala Glu Thr Lys Leu Leu His Thr Leu His Trp Met Leu Leu Glu
65                  70                  75                  80

Ala Pro Gln Asp Cys Ser Asn Asp Arg Phe Gly Gly Asp Arg Gly Ser
                85                  90                  95

Ser Trp Gly Gly Ser Ser Ser Ala Phe Ile His Gln Ala Glu Asn Gln
            100                 105                 110

Gly Ser Pro Gly His Pro Arg Pro Ser Thr Thr Asn Asp Glu Asp Glu
        115                 120                 125

Asn Asn Arg Arg Lys Phe Phe Gln Asn Ser Met Ala Thr Val Glu Leu
    130                 135                 140

Phe Val Phe Leu Phe Ala Pro Leu Val His Arg Ile Lys Glu Ser Asp
145                 150                 155                 160

Leu Thr Phe Arg Leu Ala Ser Gly Leu Val Ile Trp Gln Pro Met Trp
                165                 170                 175

Glu His Arg Gln Pro Glu Val Ser Ala Phe Asn Ala Leu Val Lys Pro
            180                 185                 190

Ile Arg Asn Ile Val Thr Ala Lys Arg Ser Ser Pro Thr Asn Asn Gln
        195                 200                 205

Ser Val Thr Cys Glu Ser Leu Asn Leu Asp Ser Gly His Thr Glu Gly
    210                 215                 220

Leu Gln Val Val Cys Glu Thr Thr Leu Pro Asp Ser Val Pro Ser Lys
225                 230                 235                 240

Pro Thr Val Ser Ala Cys His Arg Gly Asn Ser Leu Glu Gly Ser Val
                245                 250                 255

Ser Ser Gln Thr Ser Gln Glu Arg Gly Thr Pro His Pro Arg Val Ser
            260                 265                 270

Met Val Ile Pro Pro Cys Gln Lys Ser Arg Tyr Ala Thr Tyr Phe Asp
        275                 280                 285

Val Ala Val Leu Arg Cys Leu Leu Gln Pro His Trp Ser Glu Glu Gly
    290                 295                 300

Thr Gln Trp Ser Leu Met Tyr Tyr Leu Gln Arg Leu Arg His Met Leu
305                 310                 315                 320

Gln Glu Lys Pro Glu Lys Pro Pro Glu Pro Glu Ile Thr Pro Leu Pro
                325                 330                 335

Arg Leu Arg Ser Ser Ser Met Val Ala Ala Ala Pro Ser Leu Val Asn
            340                 345                 350

Thr His Lys Thr Gln Asp Leu Thr Met Lys Cys Asn Glu Glu Glu Lys
        355                 360                 365

Ser Leu Ser Thr Glu Ala Phe Ser Lys Val Ser Leu Thr Asn Leu Arg
    370                 375                 380

Arg Pro Ala Val Pro Asp Leu Ser Thr Asp Leu Gly Met Asn Ile Phe
385                 390                 395                 400

Lys Lys Phe Lys Ser Arg Lys Glu Asp Arg Glu Arg Glu Arg Lys Gly
                405                 410                 415

Ser Ile Pro Phe His His Thr Gly Lys Arg Arg Gln Arg Arg Met Gly
            420                 425                 430

Met Pro Phe Leu Leu His Glu Asp His Leu Asp Val Ser Pro Thr Arg
        435                 440                 445
```

```
Ser Thr Phe Ser Phe Gly Ser Phe Ser Gly Leu Gly Glu Asp Arg Arg
    450                 455                 460

Gly Ile Glu Arg Gly Gly Trp Gln Thr Thr Ile Leu Gly Lys Phe Thr
465                 470                 475                 480

Arg Arg Gly Ser Ser Asp Thr Ala Thr Glu Met Glu Ser Leu Ser Ala
                485                 490                 495

Arg His Ser His Ser His His Thr Leu Val Ser Asp Met Pro Asp His
            500                 505                 510

Ser Asn Ser His Gly Glu Asn Thr Val Lys Glu Val Arg Ser Gln Ile
        515                 520                 525

Ser Thr Ile Thr Val Ala Thr Phe Asn Thr Thr Leu Ala Ser Phe Asn
    530                 535                 540

Val Gly Tyr Ala Asp Phe Phe Ser Glu His Met Arg Lys Leu Cys Asn
545                 550                 555                 560

Gln Val Pro Ile Pro Glu Met Pro His Glu Pro Leu Ala Cys Ala Asn
                565                 570                 575

Leu Pro Arg Ser Leu Thr Asp Ser Cys Ile Asn Tyr Ser Cys Leu Glu
            580                 585                 590

Asp Thr Asp His Ile Asp Gly Thr Asn Asn Phe Val His Lys Asn Gly
        595                 600                 605

Met Leu Asp Leu Ser Val Asn Gly Lys Glu
    610                 615


<210> SEQ ID NO 56
<211> LENGTH: 650
<212> TYPE: PRT
<213> ORGANISM: Danio rerio

<400> SEQUENCE: 56

Met Val Lys Arg Lys Ser Leu Asp Asp Ser Asp Gln Glu Asn Cys Arg
1               5                   10                  15

Gly Ile Pro Phe Pro Ile Gln Thr Phe Leu Trp Arg Gln Thr Ser Ala
            20                  25                  30

Phe Leu Arg Pro Lys Leu Gly Lys Gln Tyr Glu Ala Ser Cys Val Ser
        35                  40                  45

Phe Glu Arg Val Leu Val Glu Asn Lys Leu His Gly Leu Ser Pro Ala
    50                  55                  60

Leu Thr Glu Ala Ile Gln Ser Ile Ser Arg Trp Glu Leu Val Gln Ala
65                  70                  75                  80

Ala Leu Pro His Val Leu His Cys Thr Ser Ile Leu Leu Ser Asn Arg
                85                  90                  95

Asn Lys Leu Gly His Gln Asp Lys Leu Gly Val Ala Glu Thr Lys Leu
            100                 105                 110

Leu His Thr Leu His Trp Met Leu Leu Glu Ala Ala Gln Glu Cys His
        115                 120                 125

Gln Glu Pro Gly Leu Ile His Gly Trp Ser Gly Gly Ser Ser Gly Ser
    130                 135                 140

Gly Ser Ala Tyr Leu Gln Pro Met Gly Asn Gln Gly Leu Thr Asp His
145                 150                 155                 160

Asn Gly Ser Thr Pro Glu Glu Thr Glu Tyr Ala Arg Ala Lys Leu Tyr
                165                 170                 175

His Lys Asn Met Ala Thr Val Glu Leu Phe Val Phe Leu Phe Ala Pro
            180                 185                 190

Leu Ile Asn Arg Ile Lys Glu Ser Asp Leu Thr Phe Arg Leu Ala Gly
```

-continued

```
        195                 200                 205

Gly Leu Val Ile Trp Gln Pro Met Trp Glu His Arg Gln Pro Asp Val
    210                 215                 220

Pro Ala Phe Ser Ala Leu Ile Lys Pro Leu Arg Asn Ile Ile Thr Ala
225                 230                 235                 240

Lys Arg Asn Ser Gln Met Asn Asn Gln Cys Ser Pro His Asp Ser Ser
                245                 250                 255

Asn Pro Cys Pro Ala Val Val Cys Glu Ser Ala Leu Ser Asp Ser Ser
            260                 265                 270

Ser Ser Pro Ser Met Thr Gly Gln Ser Cys Arg Arg Gly Asn Ser Leu
        275                 280                 285

Glu Asn Gln Arg Ala Arg Tyr Ala Thr Tyr Phe Asp Val Ala Val Leu
    290                 295                 300

Arg Cys Leu Met Gln Pro His Trp Thr Glu Glu Gly Val His Trp Ala
305                 310                 315                 320

Leu Ile Tyr Tyr Leu Gln Arg Leu Arg Gln Ile Leu Gln Ile Thr Pro
                325                 330                 335

Leu Pro Arg Pro Arg Ser Ser Ser Met Val Ala Ala Thr Pro Ser Leu
            340                 345                 350

Val Asn Thr His Lys Thr Gln Pro His Asn Pro Phe Thr Arg Pro Arg
        355                 360                 365

Ser Ser Ser Met Val Ala Ala Thr Pro Ser Leu Val Asn Thr His Lys
    370                 375                 380

Thr Gln Asp Met Thr Leu Lys Cys Asn Glu Glu Ser Arg Ser Leu Ser
385                 390                 395                 400

Ser Glu Thr Phe Ser Lys Val Ser Val Thr Asn Leu Arg Arg Gln Ala
                405                 410                 415

Val Pro Asp Leu Ser Ser Glu Met Gly Met Asn Ile Phe Lys Lys Phe
            420                 425                 430

Lys Asn Arg Arg Glu Asp Arg Glu Arg Lys Gly Ser Ile Pro Phe His
        435                 440                 445

His Thr Gly Lys Lys Arg Gln Arg Arg Met Gly Val Pro Phe Leu Met
    450                 455                 460

His Glu Asp His Leu Asp Val Ser Pro Thr Arg Ser Thr Phe Ser Phe
465                 470                 475                 480

Gly Ser Phe Ser Gly Leu Gly Asp Asp Arg Arg Thr Leu Asp Arg Gly
                485                 490                 495

Gly Trp Pro Ser Thr Ile Met Gly Lys Leu Thr Arg Arg Gly Ser Ser
            500                 505                 510

Asp Thr Thr Gly Asp Val Asp Ser Leu Gly Ala Lys His Phe His Ser
        515                 520                 525

His His Asn Leu Pro Glu His Ser Asn Ser His Ser Glu Asn Thr Ile
    530                 535                 540

Lys Glu Gly Val Arg Ser Gln Ile Ser Thr Ile Thr Met Ala Thr Phe
545                 550                 555                 560

Asn Thr Thr Val Ala Ser Phe Asn Val Gly Tyr Thr Asp Phe Phe Thr
                565                 570                 575

Glu His Ile Lys Lys Leu Cys Asn Pro Ile Pro Ile Pro Glu Met Pro
            580                 585                 590

Cys Glu Pro Leu Ala Cys Ser Asn Leu Pro Arg Ser Leu Thr Asp Ser
        595                 600                 605

Cys Ile Asn Tyr Thr Ser Leu Glu Asp Arg Asp Thr Ile Glu Gly Thr
    610                 615                 620
```

-continued

```
Asn Asn Phe Ile Leu Lys Asn Gly Met Leu Asp Leu Met Val Arg Gly
625                 630                 635                 640

Lys Asn Tyr Asn Arg Glu Thr Ile Lys Glu
                645                 650


<210> SEQ ID NO 57
<211> LENGTH: 21
<212> TYPE: DNA
<213> ORGANISM: Mus musculus

<400> SEQUENCE: 57

tgctatctgt ctggatgtgc c                                               21


<210> SEQ ID NO 58
<211> LENGTH: 21
<212> TYPE: DNA
<213> ORGANISM: Mus musculus

<400> SEQUENCE: 58

aaggacacct cgtcctcata g                                               21


<210> SEQ ID NO 59
<211> LENGTH: 21
<212> TYPE: DNA
<213> ORGANISM: Mus musculus

<400> SEQUENCE: 59

gcctatgagg acgaggtgtc c                                               21


<210> SEQ ID NO 60
<211> LENGTH: 19
<212> TYPE: DNA
<213> ORGANISM: Mus musculus

<400> SEQUENCE: 60

agctcttgca gcgtgtggt                                                  19


<210> SEQ ID NO 61
<211> LENGTH: 20
<212> TYPE: DNA
<213> ORGANISM: Mus musculus

<400> SEQUENCE: 61

tcctggacgt gcacagccgc                                                 20
```

SCREENING METHODS FOR COMPOUNDS USEFUL FOR TREATING PANCREATIC DYSFUNCTION

This application is a continuation of U.S. application Ser. No. 10/998,197 filed Nov. 29, 2004 now abandoned, which is a continuation-in-part of International Application No. PCT/EP03/05700, filed May 30, 2003, which is based on and claims priority to European Application Serial Number 02020829.4, filed Sep. 17, 2002, and European Application Serial Number 02011963.2, filed May 29, 2002. The disclosures of each of the foregoing applications are herein incorporated by reference in their entirety.

SEQUENCE LISTING

The instant application contains a Sequence Listing which has been submitted via EFS-Web and is hereby incorporated by reference in its entirety. Said ASCII copy, created on Feb. 18, 2011, is named 1027280038302.txt and is 206,951 bytes in size.

This invention relates to the use of nucleic acid and amino acid sequences of proteins specifically expressed in certain tissues including pancreatic tissues and to the use of effectors/modulators in the diagnosis, study, prevention, and treatment of diseases and disorders, for example, but not limited to, of the pancreas including metabolic disorders such as diabetes and related disorders like obesity, adipositas, and/or metabolic syndrome, as well as liver diseases, neurodegenerative disorders, and others. In addition, these sequences can be used for beta cell regeneration.

There are worldwide more than 151 million people having diabetes, 10% of those in the United States and about 20% in Europe (see, for example, Zimmet et al., 2001, Nature 414: 782-787). Diabetes is among the leading causes of death and considered to be one of the main threats to human health in the 21st century. There are two main forms of diabetes. Type I autoimmune diabetes (IDDM) results from the destruction of insulin producing beta-cells in the pancreatic islets of Langerhans. The adult pancreas has very limited regenerative potential, and so these islets are not replaced after they are destroyed. The patient's survival then depends on exogenous administration of insulin. The risk of developing type I diabetes is higher than for virtually all other severe chronic diseases of childhood. Type II diabetes is characterized by a progression from moderate to severe insulin resistance and glucose intolerance, leading eventually to beta cell failure and dependence on exogenous insulin. High body weight and a sedentary live style are major risk factors for type II diabetes. Recently, LADA (latent autoimmune diabetes in adults) has been recognized as a form of diabetes distinct from Type I and Type II diabetes. Patients with LADA are usually first diagnosed later than most Type I diabetics, are initially not dependent on exogenous insulin and are characterized by the presence of islet autoantibodies, particularly against GAD65. It is estimated that about 10% of all patients which are currently diagnosed as Type II diabetics are actually LADA patients.

In about 4% of all pregnancies, elevated blood glucose levels can be observed in the mother. While this type of diabetes ("gestational diabetes") usually resolves after birth it represents a health risk for both mother and baby and therefore needs to be treated.

It should be noted, that not only early phase type II diabetics but also type I and LADA patients retain some beta cell activity. Therefore, in most if not all forms of diabetes, beneficial treatments can be obtained by improving insulin secretion by the beta cells still present in the patient.

Although since the availability of injectable insulin diabetes is no longer an acutely live-threatening disease, it imposes a significant burden on the patient. This is because administration of insulin and other cannot prevent excursions to high or low blood glucose levels. Acute hypoglycemia can lead to coma and death. Frequent hyperglycemia causes complications, including diabetic ketoacidosis, end-stage renal disease, diabetic neuropathy, diabetic retinopathy and amputation. There are also a host of related conditions, such as obesity, hypertension, heart disease, peripheral vascular disease, and infections, for which persons with diabetes are at substantially increased risk. These and other complications account for a major proportion of the high cost of treating diabetic patients and contribute to overall lower quality of life and a reduced life expectancy. In order to cure diabetes, the lost beta cells would have to be replaced. This is currently done during islet or pancreas transplantation. However, donor organs are not available in sufficient numbers to transplant even a significant proportion of insulin dependent diabetic patients. Furthermore, patients have to undergo immunosuppressive therapy after transplantation, leading to a different set of side effects and long term complications.

Transplantable material could be generated from stem cells differentiated in vitro before transplantation into the patient. Progress has been made towards the differentiation of beta cells in vitro, however, additional factors promoting differentiation will have to be identified in order to enhance the performance of the differentiated cells.

A different approach can be regeneration through differentiation of somatic stem cells contained within the patient's body. These stem cells could be those which mediate the normal replacement of lost beta cells within the pancreas. However, it is also possible to treat diabetes by appropriate differentiation of stem cells in other tissues such as the liver, the intestine, or other organs.

Thus, there is a need in the art for the identification of novel factors which can promote the differentiation and/or function of beta cells in vitro and/or in vivo.

The pancreas is an essential organ possessing both an exocrine function involved in the delivery of enzymes into the digestive tract and an endocrine function by which various hormones are secreted into the blood stream. The exocrine function is assured by acinar and centroacinar cells that produce various digestive enzymes (for example, amylase, proteases, nuclease, etc.) and intercalated ducts that transport these enzymes in alkaline solution to the duodenum. The functional unit of the endocrine pancreas is the islet of Langerhans. Islets are scattered throughout the exocrine portion of the pancreas and are composed of four cell types: alpha-, beta-, delta- and PP-cells, reviewed for example in Kim & Hebrok, 2001, Genes & Development 15:111-127, and in Slack, Development 121 (1995), 1569-1580. Beta-cells produce insulin, represent the majority of the endocrine cells and form the core of the islets, while alpha-cells secrete glucagon and are located in the periphery. Delta-cells and PP-cells are less numerous and secrete somatostatin and pancreatic polypeptide, respectively.

Early pancreatic development has been well studied in different species, including chicken, zebrafish, and mice (for an detailed review, see Kim & Hebrock, 2001, supra). The pancreas develops from distinct dorsal and ventral anlagen. Pancreas development requires specification of the pancreas anlage along both anterior-posterior and dorsal-ventral axes. Within the developing anlage, a number of important regulatory factors important for proper organ development have been described, although a recapitulation of the different developmental programs in vitro has so far proven to be difficult.

Later in life, the acinar and ductal cells retain a significant proliferative capacity that can ensure cell renewal and growth, whereas the islet cells become mostly mitotically inactive. During embryonic development, and probably later in life, pancreatic islets of Langerhans originate from differentiating epithelial stem cells. These stem cells are situated in the pancreatic ducts or appear to form duct-like structures during development but are otherwise poorly characterized. The early progenitor cells to the pancreatic islets are multipotential and coactivate an early endocrine gene expression program. As development proceeds, expression of islet-specific hormones becomes restricted to the pattern of expression characteristic for mature islet cells. Pancreatic islet formation is dynamic and responds to changes in insulin demand, such as during pregnancy, or during childhood and adolescence.

Many pancreas diseases are associated with defects in pancreatic architecture or insufficient cellular regeneration, but the molecular mechanisms underlying these defects are basically unknown. However, studies have identified a number of signaling pathways which influence pancreatic cell fate as well as the morphogenesis of pancreatic structures, for example FGF signaling, activin signaling, the Hedgehog pathway, notch signaling, VEGF signaling, and the TGF-beta signaling pathway. There is a need in the prior art for the identification of candidate genes that are specifically expressed in early development in certain pancreatic tissues. These genes and the thereby encoded proteins can provide tools to the diagnosis and treatment of severe pancreatic disorders and related diseases. Therefore, this invention describes proteins that are specifically expressed in pancreatic tissues early in the development. The invention relates to the use of these genes and proteins in the diagnosis, prevention and/or treatment of pancreatic dysfunctions, such as diabetes, and other diseases.

So far, a function in the regulation of metabolic diseases such as diabetes has not been described in the prior art for the proteins of the invention. This invention describes novel functions for the DP119, DP444, DP810, DP685, WE474, DP160, RA977, or RA770 genes and proteins encoded thereby (referred to as proteins of the invention herein) that are involved in the development of the pancreas.

The identification of polynucleotides encoding molecules specifically expressed in the pancreatic tissues such as embryonic pancreatic epithelium, islet cells of the pancreas, pancreatic mesenchyme, as well as other tissues like forebrain, hindbrain, ganglia, branchial arches, stomach, intestinal region, lung, and mesonephrons, and the molecules themselves, presents the opportunity to investigate diseases and disorders of the pancreas, including diabetes. The identification of the proteins of the invention and antibodies against these proteins as well as effector molecules of said polypeptides or proteins, e.g. aptamers or other receptors satisfies a need in the art by providing new compositions useful in diagnosis, treatment, and prognosis of pancreatic diseases, adipositas and other metabolic disorders, as well as neurodegenerative disorders and other diseases.

DP119, DP444, DP810, DP685, WE474, DP160, RA977, or RA770 proteins and nucleic acid molecules coding therefor are obtainable from vertebrate species, e.g. mammals or birds. Particularly preferred are human homolog nucleic acids or polypeptides (see FIG. 2, 4, 6, 8, 10, 12, 14, or 16, respectively). Also particularly preferred are chicken nucleic acids and polypeptides encoded thereby (see. FIG. 2, 4, 6, 8, 10, 12, 14, or 16, respectively).

Accordingly, the invention features a substantially purified protein which has the amino acid sequence shown in SEQ ID NO: 2, 4, 6, 8, 10, 14, 16, 18, 20, 22, 24, 26, 28, 30, 32, 34, 36, 38, 40, 42 or 44 respectively. One aspect of the invention features isolated and substantially purified polynucleotides that encode the proteins of the invention. In a particular aspect, the polynucleotide is the nucleotide sequence of SEQ ID NO: 1, 3, 5, 7, 9, 11, 12, 13, 15, 17, 19, 21, 23, 25, 27, 29, 31, 33, 35, 37, 39, 41 or 43. The invention also relates to a polynucleotide sequence comprising the complement of SEQ ID NO: 1, 3, 5, 7, 9, 11, 12, 13, 15, 17, 19, 21, 23, 25, 27, 29, 31, 33, 35, 37, 39, 41 or 43, or variants thereof. In addition, the invention features polynucleotide sequences which hybridize under stringent conditions to SEQ ID NO: 1, 3, 5, 7, 9, 11, 12, 13, 15, 17, 19, 21, 23, 25, 27, 29, 31, 33, 35, 37, 39, 41 or 43 and/or the complement thereof. The invention additionally features polypeptides or peptides comprising fragments or portions of the above amino acid sequences and polynucleotides or oligonucleotides comprising fragments or portions of the above nucleic acid sequences and nucleic acid analogs, e.g. peptide nucleic acids (PNA), morpholinonucleic acids, locked nucleic acids (LNA), or antisense molecules thereof, and expression vectors and host cells comprising polynucleotides that encode the proteins of the invention. The length of polypeptide or peptide fragments is preferably at least 5, more preferably at least 6 and most preferably at least 8 amino acids. The length of nucleic acid fragments and nucleic acid analogs is preferably at least 10, more preferably at least 15 and most preferably at least 20 nucleotides.

The present invention also features antibodies which bind specifically to the proteins of the invention, and pharmaceutical compositions comprising substantially purified proteins of the invention. The invention also features the use of effectors, e.g. agonists and antagonists of the proteins of the invention. Effectors are preferably selected from antibodies, aptamers, low molecular weight molecules, antisense-molecules, ribozymes capable of modulating the function of the nucleic acids and proteins of the invention. The nucleic acids that encode the proteins of the invention are used in identifying homologous or related genes; in producing compositions that modulate the expression or function of the encoded proteins; for gene therapy; mapping functional regions of the proteins; and in characterizing associated physiological pathways.

Before the present proteins, nucleotide sequences, and methods are described, it is understood that this invention is not limited to the particular methodology, protocols, cell lines, vectors, and reagents described as these may vary. It is also to be understood that the terminology used herein is for the purpose of describing particular embodiments only, and is not intended to limit the scope of the present invention which will be limited only by the appended claims.

It must be noted that as used herein and in the appended claims, the singular forms "a", "an", and "the" include plural reference unless the context clearly dictates otherwise. Thus, for example, reference to "a host cell" includes a plurality of such host cells, reference to the "antibody" is a reference to one or more antibodies and equivalents thereof known to those skilled in the art, and so forth. Unless defined otherwise, all technical and scientific terms used herein have the same meanings as commonly understood by one of ordinary skill in the art to which this invention belongs. Although any methods and materials similar or equivalent to those described herein can be used in the practice or testing of the present invention, the preferred methods, devices, and materials are now described. All publications mentioned herein are incorporated herein by reference for the purpose of describing and disclosing the cell lines, vectors, and methodologies which are reported in the publications which might be used in connection with the invention. Nothing herein is to be construed as an admission that the invention is not entitled to antedate such disclosure by virtue of prior invention.

The invention is based on the finding of novel functions for DP119, DP444, DP810, DP685, WE474, DP160, RA977, or RA770 proteins and particularly based on the finding that these proteins are expressed specifically in early pancreatic tissues and in other tissues.

The invention is further based on polynucleotides encoding the proteins of the invention, functional fragments of said genes, polypeptides encoded by said genes or fragments thereof, and effectors/modulators, e.g. antibodies, biologically active nucleic acids, such as antisense molecules, RNAi molecules or ribozymes, aptamers, peptides or low-molecular weight organic compounds recognizing said polynucleotides or polypeptides, and the use of these compositions for the diagnosis, study, prevention, or treatment of diseases and disorders related to such cells, including metabolic diseases, such as diabetes and obesity, neurodegenerative disorders, heart diseases, intestinal diseases, liver disorders, and others.

Nucleic acids encoding the chicken proteins of the present invention were first identified from the pancreas tissue cDNA library (day 6) through a whole-mount in situ screen for genes expressed in the embryonic pancreatic bud (see EXAMPLES).

Zebrafish have gained importance as model organism during the recent years. The embryos of this species are transparent and available in large numbers, develop quickly outside of their mother and allow both forward and reverse genetic analysis of gene function. Published data on pancreatic development in zebrafish shows that islet formation occurs, extremely rapid (within 24 hrs) and suggest that this process requires the same regulatory genes as in mammals (see Biemar et al., Dev Biol. 2001 Feb. 15; 230(2):189-203). Suppressing gene function in zebrafish embryos using morpholino antisense oligonucleotides (Mos), modified Peptide Nucleic Acids (mPNAs) or other antisense compounds with good efficiency and specificity yields phenotypes which are usually indistinguishable from genetic mutants in the same gene (Nasevicius et al., Nat. Genet. 2000 October; 26(2):216-20; Effimov et al., NAR 26; 566-575; Urtishak et al., 5th international conference on zebrafish development and genetics, Madison/WI 2002, abstr. #17). Therefore, this approach allows rapid assessment of gene function in a model vertebrate.

Microarrays are analytical tools routinely used in bioanalysis. A microarray has molecules distributed over, and stably associated with, the surface of a solid support. The term "microarray" refers to an arrangement of a plurality of polynucleotides, polypeptides, antibodies, or other chemical compounds on a substrate. Microarrays of polypeptides, polynucleotides, and/or antibodies have been developed and find use in a variety of applications, such as monitoring gene expression, drug discovery, gene sequencing, gene mapping, bacterial identification, and combinatorial chemistry. One area in particular in which microarrays find use is in gene expression analysis (see Example 4). Array technology can be used to explore the expression of a single polymorphic gene or the expression profile of a large number of related or unrelated genes. When the expression of a single gene is examined, arrays are employed to detect the expression of a specific gene or its variants. When an expression profile is examined, arrays provide a platform for identifying genes that are tissue specific, are affected by a substance being tested in a toxicology assay, are part of a signaling cascade, carry out housekeeping functions, or are specifically related to a particular genetic predisposition, condition, disease, or disorder.

Microarrays may be prepared, used, and analyzed using methods known in the art (see for example, Brennan, T. M. et al. (1995) U.S. Pat. No. 5,474,796—Schena, M. et al. (1996) Proc. Natl. Acad. Sci. USA 93:10614-10619; Baldeschweiler et al. (1995) PCT application WO95/251116; Shalon, D. et al. (1995) PCT application WO95/35505; Heller, R. A. et al. (1997) Proc. Natl. Acad. Sci. USA 94:21502155; Heller, M. J. et al. (1997) U.S. Pat. No. 5,605,662). Various types of microarrays are well known and thoroughly described in Schena, M., ed. (1999; DNA Microarrays: A Practical Approach, Oxford University Press, London).

In further embodiments, oligonucleotides or longer fragments derived from any of the polynucleotides described herein may be used as elements on a microarray. The microarray can be used in transcript imaging techniques which monitor the relative expression levels of large numbers of genes simultaneously as described below. The microarray may also be used to identify genetic variants, mutations, and polymorphisms. This information may be used to determine gene function, to understand the genetic basis of a disorder, to diagnose a disorder, to monitor progression/regression of disease as a function of gene expression, and to develop and monitor the activities of therapeutic agents in the treatment of disease. In particular, this information may be used to develop a pharmacogenomic profile of a patient in order to select the most appropriate and effective treatment regimen for that patient. For example, therapeutic agents, which are highly effective and display the fewest side effects may be selected for a patient based on his/her pharmacogenomic profile.

DP119: In one embodiment, the invention encompasses the chicken DP119 protein, a polypeptide comprising the amino acid sequence of SEQ ID NO:2, as presented using the one-letter code in FIG. 2B. In situ hybridization experiments using the DP119 protein described in this invention were done on whole mounts of 5-day-old chick embryos (FIG. 1A), on sectioned pancreatic bud tissue (FIG. 1B), and on a cross-section through the dorsal part of a day 5 chicken embryo (FIG. 1C). The hybridizations show that DP119 transcripts are exclusively expressed in the ganglia along the neural tube (nt), on the outside of the developing stomach (st) and in the dorsal and ventral pancreatic buds (dpb, vpb), in pancreatic islets (is), and in some cells of the pancreatic epithelium and duct cells (du) (see FIG. 1).

The predicted amino acid sequence was searched in the publicly available GenBank database. In search of sequence databases, it was found, for example, that DP119 has homology with a human hypothetical protein (Genbank Accession Number AL050137.1 for the cDNA and CAB43286.1 for the protein) and to mouse hypothetical protein (Genbank Accession Number BC025654.1 for the cDNA and AAH25654.1 for the protein, see FIG. 2). Based upon homology, DP119 protein and each homologous protein or peptide may share at least some activity.

The C-terminus of DP119 contains an olfactomedin-like domain; the N-terminus is characterized by a cystein-rich domain reminiscent of certain cytokines. These two domains may represent functional subdomains of the protein.

DP444: In one embodiment, the invention encompasses the chicken DP444 protein, a polypeptide comprising the amino acid sequence of SEQ ID NO: 8, as presented using the one-letter code in FIG. 4B. In situ hybridization experiments using the DP444 protein described in this invention were done on whole mounts of 3.5-(FIG. 3A), 4-(FIG. 3B), and 5-day-old chick embryos (FIG. 3C) and on sectioned pancreatic bud tissue (FIG. 3D). The hybridizations show that DP444 transcripts are exclusively expressed in dorsal and ventral pancreatic buds, along the neural tube, in somites, the developing intestine, in the dorsal hindbrain, the stomach, and in pancreatic islets (see FIG. 3).

The predicted amino acid sequence was searched in the publicly available GenBank database. In search of sequence databases, it was found, for example, that DP444 has homology with the human protein BACO3521, nucleotide GenBank Accession no. AK090815 (see EXAMPLE 10 for more detail). Highly homologous mouse and fish proteins could also be identified (see FIGS. 4M-4N). Search of public domain databases (e.g. SMART at the Heidelberg Computational Services or RPS-BLAST at the NCBI) revealed that there are no known protein domains within DP444. DP444, its human, mouse and fish homologs and the proteins F25C8.3 (*Anopheles gambiae*, gi|19572386), F25C8.3.p (*C. elegans*, gi|17560138) and the CG18437 gene product (*Drosophila melanogaster*, gi|7301616) form a novel family of unknown function (FIGS. 4M-4N).

Knockdown of DP444 gene-function in zebrafish using antisense-Morpholino-oligos specific for DP444 leads to an islet convergence defect in 20-30% of all, injected embryos (see FIG. 3E). A similar defect can be observed, when the zebrafish homolog of the neural-adhesion molecule DM-GRASP/neurolin/BEN/CD166 is functionally suppressed by the same method. Suppression of both genes at the same time does not lead to an additive effect suggesting that CD166 and DP444 might act in the same pathway. The CD166 gene has, besides its role in neural pathfinding and T-cell-activation, been implicated in pancreatic development. A link between CD166 function and expression of the key pancreatic regulatory gene Pdx1 has been suggested (see Stephan et al., Developmental Biology 212, 264-277). Thus, DP444 may be involved in Pdx1 regulation.

Expression analysis in adult mouse tissues reveals that DP444 transcripts are restricted to brain (particularly hypothalamus) and islets, suggesting an important function of DP444 in beta cells.

DP810: In one embodiment, the invention encompasses the chicken DP810-like protein, a polypeptide comprising the amino acid sequence of SEQ ID NO: 18, as presented using the one-letter code in FIG. 6C. In situ hybridization experiments using the DP810 protein described in this invention were done on whole mounts of 5-day-old chick embryos (FIGS. 5A and 5B) and on sectioned pancreatic bud tissue (FIGS. 5C and 5D). The hybridizations show that DP810 transcripts of the invention are exclusively expressed in the periphery of islets (is, FIG. 5) and in the surrounding pancreatic mesenchyme (pm, FIG. 5).

The predicted amino acid sequence was searched in the publicly available GenBank database. In search of sequence databases, it was found, for example, that DP810 has homology with human likely ortholog of mouse polydom protein (GenBank Accession Number NM_024500.1 for the cDNA (FIG. 6D, SEQ ID NO: 19), NP_078776.1 for the protein (FIG. 6E, SEQ ID NO: 20). Based upon homology, DP810 protein and each homologous protein or peptide may share at least some activity.

Polydom was described first in 2000 (Gilges D. et al., 2000, Biochem J. 352 Pt 1:49-59). It was shown that a C-terminally tagged form of the protein is secreted when expressed in Cos 7 cells. Sites for N-glycosylation in the primary sequence and a slightly reduced mobility on SDS-PAGE gels suggest posttranslational modification by glycosylation. Strong expression of polydom was found in human placenta and lung, weaker expression was seen in spleen, skeletal muscle and heart. Pancreatic expression was not analyzed. The human homolog of Polydom was mapped by FISH to chromosome 9q32. Polydom contains a number of protein domains. Most notable are EGF—(epidermal growth factor) like repeats, a von Willebrand factor type A domain, and 34 complement control protein (CCP) modules, suggesting a potential function in cell signalling or cell adhesion.

DP685: In one embodiment, the invention encompasses the chicken DP685 protein, a polypeptide encoded by the nucleic acid sequence of SEQ ID NO: 21, as presented in FIG. 8A. In situ hybridization experiments using the DP685 protein described in this invention were done on whole mounts of 4-(FIG. 7A) and 5-day-old chick embryos (FIG. 7B). The hybridizations show that transcripts are expressed in the dorsal pancreatic bud and in the developing stomach, and in the dorsal neural tube, the dorsal forebrain, hindbrain, branchial arches, hindlimb and forelimb.

The predicted amino acid sequence was searched in the publicly available GenBank database. In search of sequence databases, it was found, for example, that DP685 has homology with a human autotaxin-t (synonym Ectonucleotide pyrophosphatase/Pyrophosphatase 2 (ENPP2); Genbank Accession Number L46720.1 and AAB00855.1; SEQ ID NO: 23 and 24). Based upon homology, DP685 protein and each homologous protein or peptide may share at least some activity.

The bifunctional enzyme phosphodiesterase I (EC 3.1.4.1)/nucleotide pyrophosphatase (EC 3.6.1.9) (referred to as PD-I (alpha)) was cloned from rat brain by Narita et al. (1994) J. Biol. Chem. 269: 28235-28242. The human PD-I alpha homologue is an 863-amino acid protein with 89% identity to the rat protein (Kawagoe et al. (1995) Genomics 30: 380-384). Northern blot analysis detected a 3-kb transcript in brain, placenta, kidney and lung. An apparent splice variant of PD-I (alpha) lacking 52 amino acids, but otherwise identical, has been described as autotaxin, a tumor cell motility-stimulating factor (Murata et al., 1994 J. Biol. Chem. 269: 30479-30484). Kawagoe et al. (1995), supra, obtained a genomic clone for the 5'-end of the gene which contained a variety of potential DNA-binding sites as well as intron 1.

However, two recent publications have identified that autotaxin has lysophospholipase D activity and that it synthesizes lysophosphatidic acid (LPA) (Tokumura et al., 2002, J Biol Chem. 2002 Aug. 9; Umezu-Goto et al., 2002, J Cell Biol. 158(2):227-33; reviewed in Moolenaar, 2002, J Cell Biol. 158(2):197-9). LPA is a potent signalling compound with effects on cytoskeletal organization, cell proliferation and cell migration. Its activity is mediated by a family of G-protein coupled receptors belonging to, the edg-family. The different members of this family show differences in expression and downstream signalling partners (reviewed e.g. in Takuwa et al., 2002, J Biochem (Tokyo). 131(6):767-71).

As shown in this invention, the expression pattern of autotaxin in the day 4 and day 5 chicken embryo suggests that autotaxin and/or LPA synthesized by autotaxin plays an important and up to now unknown role in animal development. This is especially striking when the patterning of the limbs, the central nervous system and growth, differentiation and morphogenesis of the pancreas are considered (see FIG. 3).

The expression of autotaxin in the embryonic pancreatic bud suggests a novel function of insulin secreting cells from other cell types such as stem cells.

The expression of autotaxin in neural tissues, e.g. the neural tube and the brain, and in the limbs suggests a novel function and a use of autotaxin, LPA, or other reaction products generated by autotaxin in the generation of neural cells and cells of the motility apparatus from other cell types such as stem cells.

It also raises the possibility that agonists specific for LPA-receptors expressed in specific cell types or their precursors can modulate the growth, differentiation, or organ-specific organization of these cells. For example, stimulation of an LPA-receptor more or less specifically expressed in certain cell types such as pancreatic stem cells, other stem cells or other cells that can be used to generate new insulin-secreting cells might yield relatively specific responses in spite of the many effects described in the literature for LPA.

WE474: In one embodiment, the invention encompasses the chicken WE474 protein, a polypeptide comprising the amino acid sequence of SEQ ID NO:28, as presented using the one-letter code in FIG. 10B. In situ hybridization experiments using the WE474 protein described in this invention were done on whole mounts of 5-day-old chick embryos. The hybridizations show that WE474 transcripts are exclusively expressed in the liver (li) and in the intestinal region (in) including the developing pancreas (FIG. 9A).

The predicted amino acid sequence was searched in the publicly available GenBank database. In search of sequence databases, it was found, for example, that WE474 has homology with a human collectin sub-family member 10 (Genbank Accession Number NM_006438.2 for the cDNA and NP_006429.1 for the protein; SEQ ID. NO: 29 and 30). Based upon homology, WE474 protein and each homologous protein or peptide may share at least some activity.

Collectins are a C-lectin family with collagen-like sequences and carbohydrate recognition domains. These proteins can bind to carbohydrate antigens of microorganisms and inhibit their infection by direct neutralization and agglutination, the activation of complement through the lectin pathway, and opsonization by collectin receptors (Ohtani K. et al., 1999, J Biol Chem 274(19):13681-13689). A cDNA encoding human collectin from liver (CL-L1 (collectin liver 1)) has typical collectin structural characteristics, consisting of an N-terminal cysteine-rich domain, a collagen-like domain, a neck domain, and a carbohydrate recognition domain. This collectin has a unique repeat of four lysine residues in its C-terminal area. CL-L1 is present mainly in liver as a cytosolic protein and at low levels in placenta. More sensitive analyses showed that most tissues (except skeletal muscle) have CL-L1 mRNA. Zoo-blot analysis indicated that CL-L1 is limited to mammals and birds. A chromosomal localization study indicated that the CL-L1 gene localizes to chromosome 8q23-q24.1. CL-L1 binds mannose weakly (see, for example, Ohtani K. et al., 1999, J Biol Chem 274 (19):13681-13689). Analysis of the WE474 protein sequence using suitable software (such as SignalP, Nielsen et al., Protein Engineering 10, 1-6) reveals the presence of a secretion signal. Thus, WE474 is likely to have a role in cell-cell or autocrine signalling.

DP160: In one embodiment, the invention encompasses the chicken DP160 protein, a polypeptide comprising the amino acid sequence of SEQ ID NO:32, as presented using the one-letter code in FIG. 12B. In situ hybridization experiments using the DP160 protein described in this invention were done on whole mounts of 5-day-old chick embryos (FIG. 11A) and on a cross-section through the developing pancreas of a 5-day-old chick embryo (FIG. 11A). The hybridizations show that DP160 transcripts are exclusively expressed in the ganglia along the neural tube (nt), on the outside of the developing stomach (st), in the mesonephros, in the dorsal and ventral pancreatic buds (dpb, vpb), in pancreatic islets (is), and in some cells of the pancreatic epithelium (see FIG. 11).

The predicted amino acid sequence was searched in the publicly available GenBank database. In search of sequence databases, it was found, for example, that DP160 has homology with a human CCR4 carbon catabolite repression 4-like protein (CCRN4L; Nocturnin) (Genbank Accession Number XP_003343.3 and XP_003343.2; SEQ ID NO: 33 and 34). Based upon homology, or DP160 protein and each homologous protein or peptide may share at least some activity.

Nocturnin was originally identified by differential display as a circadian clock regulated gene with high expression at night in photoreceptors of the African clawed frog, *Xenopus laevis*. Although encoding a novel protein, the nocturnin cDNA had strong sequence similarity with a C-terminal domain of the yeast transcription factor CCR4, and with mouse and human ESTs. Since its original identification several homologues of nocturnin/CCR4 were cloned, including from human and mouse. Northern analysis of mRNA in C3H/He and C57/B16 mice revealed that the mNoc gene is expressed in a broad range of tissues, with greatest abundance in liver, kidney and testis as well as in multiple brain regions. Furthermore, mNoc exhibits circadian rhythmicity of mRNA abundance with peak levels at the time of light offset in the retina, spleen, heart, kidney and liver (Wang et al., 2001, BMC Dev Biol 1(1):9).

RA977: In one embodiment, the invention encompasses the chicken RA977 protein, a polypeptide comprising the amino acid sequence of SEQ ID NO:36, as presented using the one-letter code in FIG. 14B. In situ hybridization experiments using the RA977 protein described in this invention were done on whole mounts of 5-day-old chick embryos. The hybridizations show that RA977 transcripts are exclusively expressed in dorsal pancreatic bud (see FIGS. 13A and 13B).

The predicted amino acid sequence was searched in the publicly available GenBank database. In search of sequence databases, it was found, for example, that RA977 has homology with a human epithelial membrane protein 2 (EMP2; Genbank Accession Number XM_030218.1 for the cDNA and P54851 for the protein; SEQ ID NO: 37 and 38, see FIG. 14). Based upon homology, RA977 protein and each homologous protein or peptide may share at least some activity.

The epithelial membrane protein-2 (EMP-2) is a member of the peripheral myelin protein 22 gene family (PMP22/EMP/MP20 gene family). Mutations affecting the PMP22 gene are associated with hereditary motor and sensory neuropathies. In human, EMP-2 mRNA transcripts are found in most tissues including liver. EMP-2 is most prominently expressed in the adult ovary, heart, lung and intestine and in fetal lung. Since PMP22 has been implicated in the regulation of cell proliferation and apoptosis, it appears likely that EMP-2 is involved in similar regulatory processes in a variety of tissues (Taylor V. and Suter U., 1996, Gene 175(1-2):115-120).

Charcot-Marie-Tooth (CMT) neuropathy represents a genetically heterogeneous group of diseases affecting the peripheral nervous system. Autosomal dominant CMT type 1C (CMT1C). was mapped genetically to chromosome 16p13.1-p12.3. The epithelial membrane protein 2 gene (EMP2), which maps to chromosome 16p13.2, is a candidate gene for CMT1C (Street V. A., 2002, Am J Hum Genet 70(1): 244-250).

Epithelial membrane protein 2, a 4-transmembrane protein, might suppress B-cell lymphoma tumorigenicity through a functional tumor suppressor phenotype (Wang C. X., 2001, Blood 97(12):3890-3895)

RA770: In one embodiment, the invention encompasses the chicken RA770-like protein, a polypeptide comprising the amino acid sequence of SEQ ID NO: 40, as presented using the one-letter code in FIG. 16B. In situ hybridization experiments using the RA770 protein described in this invention were done on whole mounts of 5-day-old chick embryos (FIG. 15A). The hybridizations show that RA770 transcripts of the invention are exclusively expressed in the duodenum (dd) and ventral pancreatic bud (vpd), in the stomach region (st), lung (lu) and dorsal pancreatic bud (dpb) (FIG. 15).

The predicted amino acid sequence was searched in the publicly available GenBank database. In search of sequence databases, it was found, for example, that RA770 has homology with human neurturin precursor (GenBank Accession Number NM_004558 (FIG. 16C, SEQ ID NO: 41, FIG. 16D, SEQ ID NO: 42)) and with mouse neurturin precursor (GenBank Accession Number NM_008738 (FIG. 16E, SEQ ID NO: 43, FIG. 16F, SEQ ID NO: 44)). Based upon homology, RA770 protein and each homologous protein or peptide may share at least some activity.

Neurturin (or NRTN), a potent neurotrophic factor, was purified from Chinese hamster ovary cell-conditioned media by Kotzbauer et al. (1996) Nature 384: 467-470. The protein is closely related to glial cell line-derived neurotrophic factor (GDNF). Neurturin and GDNF form a distinct TGF-beta subfamily, referred to as TRNs (for 'TGF-beta-related neurotrophins'; see review by Takahashi, 2001, Cytokine Growth Factor Rev 12(4):361-73). Members of this protein family signal through a unique multicomponent receptor system consisting of RET tyrosine kinase and glycosyl-phosphatidylinositol-anchored coreceptor (GFRalpha1-4)). These neurotrophic factors promote the survival of various neurons including peripheral autonomic and sensory neurons as well as central motor and dopamine neurons, and have been expected as therapeutic agents for neurodegenerative diseases. In addition, the GDNF/RET signaling plays a crucial role in renal development and regulation of spermatogonia differentiation. RET mutations cause several human diseases such as papillary thyroid carcinoma, multiple endocrine neoplasia types 2A and 2B, and Hirschsprung's disease. The mutations resulted in RET activation or inactivation by various mechanisms and the biological properties of mutant proteins appeared to be correlated with disease phenotypes. The signaling pathways activated by GDNF or mutant RET are being extensively investigated to understand the molecular mechanisms of disease development and the physiological roles of the GDNF family ligands. Heuckeroth et al. (1997) Genomics 44:137-140 stated that inactivating mutations in GDNF or Ret in knockout mice cause intestinal aganglionosis and renal dysplasia. Neurturin also signals through RET and a GPI-linked coreceptor. Like GDNF, neurturin can promote the survival of numerous neuronal populations, including sympathetic, nodose, and dorsal root ganglion sensory neurons. Heuckeroth et al. (1997), supra, isolated mouse and human genomic neurturin clones and showed that preproneurturin is encoded by 2 exons. Mouse and human clones have common intron/exon boundaries. They used interspecific backcross analysis to localize neurturin to mouse chromosome 17 and fluorescence in situ hybridization to localize human neurturin to the syntenic region of 19p13.3.

Considering that RET and glial cell line-derived neurotrophic factor mutations had been reported in Hirschsprung disease, Doray et al. (1998) Hum. Molec. Genet. 7: 1449-1452 regarded the other RET ligand, neurturin, as an attractive candidate gene, especially as it shares large homologies with GDNF. Doray et al. (1998), supra, reported a heterozygous missense Neurturin mutation in a large nonconsanguineous family including 4 children affected with a severe aganglionosis phenotype extending up to the small intestine. It appeared that the Neurturin mutation they found was not sufficient to cause HSCR, and this multiplex family also segregated a RET mutation. This cascade of independent and additive genetic events fits well with the multigenic pattern of inheritance expected in HSCR, and further supports the role of RET ligands in the development of the enteric nervous system.

The invention also encompasses variants of the proteins of the invention. A preferred variant is one having at least 80%, and more preferably 90%, amino acid sequence similarity to the amino acid sequence of the proteins of the invention (SEQ ID NO: 2, 4, 6, 8, 10, 14, 16, 18, 20, 22, 24, 26, 28, 30, 32, 34, 36, 38, 40, 42 or 44 respectively). A most preferred variant is one having at least 95% amino acid sequence similarity to SEQ ID NO: 2, 4, 6, 8, 10, 14, 16, 18, 20, 22, 24, 26, 28, 30, 32, 34, 36, 38, 40, 42 or 44 respectively.

The invention also encompasses polynucleotides which encode the proteins of the invention. Accordingly, any nucleic acid sequence which encodes the amino acid sequence of the proteins of the invention can be used to generate recombinant molecules which express the proteins of the invention. In a particular embodiment, the invention encompasses the polynucleotide comprising the nucleic acid sequence of SEQ ID NO: 1, 3, 5, 7, 9, 11, 12, 13, 15, 17, 19, 21, 23, 25, 27, 29, 31, 33, 35, 37, 39, 41 or 43. It will be appreciated by those skilled in the art that as a result of the degeneracy of the genetic code, a multitude of nucleotide sequences encoding the proteins of the invention, some bearing minimal homology to the nucleotide sequences of any known and naturally occurring gene, may be produced. Thus, the invention contemplates each and every possible variation of nucleotide sequence that could be made by selecting combinations based on possible codon choices.

Also encompassed by the invention are polynucleotide sequences that are capable of hybridizing to the claimed nucleotide sequences, and in particular, those shown in SEQ ID NO: 1, 3, 5, 7, 9, 11, 12, 13, 15, 17, 19, 21, 23, 25, 27, 29, 31, 33, 35, 37, 39, 41 or 43, and/or the complement thereof under various conditions of stringency. Hybridization conditions are based on the melting temperature (Trn) of the nucleic acid binding complex or probe, as taught in Wahl, G. M. and S. L. Berger. (1987, Methods Enzymol. 152:399-407) and Kimmel, A. R. (1987, Methods Enzymol. 152:507-511), and may be used at a defined stringency. Preferably, hybridization under stringent conditions means that after washing for 1 h with 1×SSC and 0.1% SDS at 50° C., preferably at 55° C., more preferably at 62° C. and most preferably at 68° C., particularly for 1 h in 0.2×SSC and 0.1% SDS at 50° C., preferably at 55° C., more preferably at 62° C. and most preferably at 68° C., a positive hybridization signal is observed. Altered nucleic acid sequences encoding the proteins of the invention which are encompassed by the invention include deletions, insertions, or substitutions of different nucleotides resulting in polynucleotides that encode the same or functionally equivalent proteins of the invention. The encoded proteins may also contain deletions, insertions, or substitutions of amino acid residues which produce a silent change and result in a functionally equivalent protein of the invention.

Also included within the scope of the present invention are alleles of the genes encoding the proteins of the invention. As used herein, an "allele" or "allelic sequence" is an alternative form of the gene which may result from at least one mutation in the nucleic acid sequence. Alleles may result in altered mRNAs or polypeptides whose structures or function may or may not be altered. Any given gene may have none, one, or many allelic forms. Common mutational changes which give rise to alleles are generally ascribed to natural deletions, additions, or substitutions of nucleotides. Each of these types of changes may occur alone, or in combination with the others, one or more times in a given sequence. Methods for DNA sequencing which are well known and generally available in the art may be used to practice any embodiments of the invention. The nucleic acid sequences encoding the proteins of the invention may be extended utilizing a partial nucleotide sequence and employing various methods known in the art to detect upstream sequences such as promoters and regulatory elements. For example, one method which may be employed, "restriction-site" PCR, uses universal primers to retrieve unknown sequence adjacent to a known locus (Sarkar, G. (1993) PCR Methods Applic. 2:318-322). In particular, genomic DNA is first amplified in the presence of primer to linker sequence and a primer specific to the known region. The amplified sequences are then subjected to a second round of PCR with the same linker primer and another specific primer internal to the first one. Products of each round of PCR are transcribed with an appropriate RNA polymerase and sequenced using reverse transcriptase. Inverse PCR may also be used to amplify or extend sequences using divergent primers based on a known region (Triglia, T. et al. (1988) Nucleic Acids Res. 16:8186). The primers may be designed using OLIGO 4.06 primer analysis software (National Biosciences Inc., Plymouth, Minn.), or another appropriate program, to 22-30 nucleotides in length, to have a GC content of 50% or more, and to anneal to the target sequence at temperatures about 68° C.-72° C. The method uses several restriction enzymes to generates suitable fragment. The fragment is then circularized by intramolecular ligation and used as a PCR template.

Another method which may be used is capture PCR which involves PCR amplification of DNA fragments adjacent to a known sequence in human and yeast artificial chromosome DNA (Lagerstrom, M. et al. (PCR Methods Applic. 1:111-119). In this method, multiple restriction enzyme digestions and ligations also be used to place an engineered double-stranded sequence into an unknown portion of the DNA molecule before performing PCR. Another method which may be used to retrieve unknown sequences is that of Parker, J. D. et al. (1991; Nucleic Acids Res. 19:3055-3060). Additionally, one may use PCR, nested primers, and PROMOTERFINDER libraries to walk in genomic DNA (Clontech, Palo Alto, Calif.). This process avoids the need to screen libraries and is useful in finding intron/exon junctions. When screening for full-length cDNAs, it is preferable to use libraries that have been size-selected to include larger cDNAs. Also, random-primed libraries are preferable, in that they will contain more sequences which contain the 5' regions of genes. Use of a randomly primed library may be especially preferable for situations in which an oligo d(T) library does not yield a full-length cDNA. Genomic libraries may be useful for extension of sequence into the 5' and 3' non-transcribed regulatory regions. Capillary electrophoresis systems which are commercially available may be used to analyze the size or confirm the nucleotide sequence of sequencing or PCR products. In particular, capillary sequencing may employ flowable polymers for electrophoretic separation, four different fluorescent dyes (one for each nucleotide) which are laser activated, and detection of the emitted wavelengths by a charge coupled devise camera. Output/light intensity may be converted to electrical signal using appropriate software (e.g. GENOTYPER and SEQUENCE NAVIGATOR, Perkin Elmer) and the entire process from loading of samples to computer analysis and electronic data display may be computer controlled. Capillary electrophoresis is especially preferable for the sequencing of small pieces of DNA which might be present in limited amounts in a particular sample.

In another embodiment of the invention, polynucleotide sequences or functional fragments thereof which encode the proteins of the invention, or fusion proteins or functional equivalents thereof, may be used in recombinant DNA molecules to direct expression of the proteins of, the invention in appropriate host cells. Due to the inherent degeneracy of the genetic code, other DNA sequences which encode substantially the same or a functionally equivalent amino acid sequence may be produced and these sequences may be used to clone and express the proteins of the invention. As will be understood by those of skill in the art, it may be advantageous to produce the protein-encoding nucleotide sequences possessing non-naturally occurring codons. For example, codons preferred by a particular prokaryotic or eukaryotic host can be selected to increase the rate of protein expression or to produce a recombinant RNA transcript having desirable properties, such as a half-life which is longer than that of a transcript generated from the naturally occurring sequence. The nucleotide sequences of the present invention can be engineered using methods generally known in the art in order to alter the proteins of the invention encoding sequences for a variety of reasons, including but not limited to, alterations, which modify the cloning, processing, and/or expression of the gene product. DNA shuffling by random fragmentation and PCR reassembly of gene fragments and synthetic oligonucleotides may be used to engineer the nucleotide sequences. For example, site-directed mutagenesis may be used to insert new restriction sites, alter glycosylation patterns, change codon preference, produce splice variants, or introduce mutations, and so forth. Such mutated genes may be used to study structure-function relationships of the proteins of the invention, or to alter properties of the proteins that affect their function or regulation.

In another embodiment of the invention, natural, modified, or recombinant nucleic acid sequences encoding the proteins of the invention may be ligated to a heterologous sequence to encode a fusion protein. For example, to screen peptide libraries for inhibitors of the proteins of the invention activity, it may be useful to encode chimeric proteins of the invention that can be recognized by a commercially available antibody. A fusion protein may also be engineered to contain a cleavage site located between the proteins of the invention encoding sequence and the heterologous protein sequence, so that the proteins of the invention may be cleaved and purified away from the heterologous moiety. A fusion protein between the DP444 protein and a protein transduction peptide (reviewed e.g. in Lindsay, M. A.; Curr Opin Pharmacol 2002 October; 2(5):587-94) may be engineered to allow the uptake of recombinant fusion protein by mammalian cells. In another embodiment, sequences encoding the proteins of the invention may be synthesized, in whole or in part, using chemical methods well known in the art (see Caruthers, M. H. et al. (1980) Nucl. Acids Res. Symp. Ser. 7:215-223, Horn, T. et al. (1980) Nucl. Acids Res. Symp. Ser. 7:225-232). Alternatively, the protein itself may be produced using chemical methods to synthesize the amino acid sequence of the proteins of the invention, or a portion thereof. For example, peptide synthesis can be performed using various solid-phase techniques (Roberge, J. Y. et al. (1995) Science 269:202-204) and automated synthesis may be achieved, for example, using the ABI 431A peptide synthesizer (Perkin Elmer). The newly synthesized peptide may be substantially purified by preparative high performance liquid chromatography (e.g. Creighton, T. (1983) proteins, Structures and Molecular Principles, WH Freeman and Co., New York, N.Y.) The composition of the synthetic peptides may be confirmed by amino acid analysis or sequencing (e.g. the Edman degradation procedure; Creighton, supra). Additionally, the amino acid sequence of the proteins of the invention, or any part thereof, may be altered during direct synthesis and/or combined using chemical methods with sequences from other proteins, or any part thereof, to produce a variant polypeptide.

In order to express a biologically active protein of the invention, the nucleotide sequences encoding the proteins of the invention or functional equivalents, may be inserted into appropriate expression vector, i.e. a vector which contains the necessary elements for the transcription and translation of the inserted coding sequence. Methods which are well known to those skilled in the art may be used to construct expression vectors containing sequences encoding the proteins of the invention and appropriate transcriptional and translational control elements. These methods include in vitro recombinant DNA techniques, synthetic techniques; and in vivo genetic recombination. Such techniques are described in Sambrook, J. et al. (1989) Molecular Cloning, A Laboratory Manual, Cold Spring Harbor Press, Plainview, N.Y., and Ausubel, F. M. et al. (1989) Current Protocols in Molecular Biology, John Wiley & Sons, New York, N.Y.

A variety of expression vector/host systems may be utilized to contain and express sequences encoding the proteins of the invention. These include, but are not limited to, microorganisms such as bacteria transformed with recombinant bacteriophage, plasmid, or cosmid DNA expression vectors; yeast transformed with yeast expression vectors; insect cell systems infected with virus expression vectors (e.g. baculovirus); plant cell systems transformed with virus expression vectors (e.g. cauliflower mosaic virus; CaMV; tobacco mosaic virus, TMV) or with bacterial expression vectors (e.g. Ti or PBR322 plasmids); or animal cell systems.

The presence of polynucleotide sequences encoding the proteins of the invention can be detected by DNA-DNA or DNA-RNA hybridization and/or amplification using probes or portions or functional fragments of polynucleotides encoding the proteins of the invention. Nucleic acid amplification based assays involve the use of oligonucleotides or oligomers based on the sequences encoding the proteins of the invention to detect transformants containing DNA or RNA encoding the proteins of the invention. As used herein “oligonucleotides” or “oligomers” refer to a nucleic acid sequence of at least about 10 nucleotides and as many as about 60 nucleotides, preferably about 15 to 30 nucleotides, and more preferably about 20-25 nucleotides, which can be used as a probe or amplimer.

A variety of protocols for detecting and measuring the expression of the proteins of the invention, using either polyclonal or monoclonal antibodies specific for the protein are known in the art. Examples include enzyme-linked immunosorbent assay (ELISA), radioimmunoassay (RIA), and fluorescence activated cell sorting (FACS). A two-site, monoclonal-based immunoassay utilizing monoclonal antibodies reactive to two non-interfering epitopes on the proteins of the invention is preferred, but a competitive binding assay may be employed. These and other assays are described, among other places, in Hampton, R. et al. (1990; Serological Methods, a Laboratory Manual, APS Press, St Paul, Minn.) and Maddox, D. E. et al. (1983; J. Exp. Med. 158:1211-1216).

Compounds that bind the proteins of the invention, e.g. antibodies, are useful for the identification or enrichment of cells, which are positive for the expression of the proteins of the invention, from complex cell mixtures. Such cell populations are useful in transplantation, for experimental evaluation, and as source of lineage and cell specific products, including mRNA species useful in identifying genes specifically expressed in these cells, and as target for the identification of factors of molecules that can affect them. The pancreatic progenitor cell population, which is positive for the expression of the proteins of the invention, is useful in transplantation to provide a recipient with pancreatic islet cells, including insulin producing beta cells; for drug screening; experimental models of islet differentiation and interaction with other cell types; in vitro screening assays to define growth and differentiation factors, and to additionally characterize genes involved in islet development and regulation; and the like. The native cells may be used for these purposes, or they may be genetically modified to provide altered capabilities. Cells from a regenerating pancreas, from embryonic foregut, stomach and duodenum, or other sources of pancreatic progenitor cells may be used as a starting population. The progenitor cells may be obtained from any mammalian species, e.g. equine, bovine, porcine, canine, feline, rodent, e.g. mice, rats, hamster, primate, etc. particularly human.

A wide variety of labels and conjugation techniques are known by those skilled in the art and may be used in various nucleic acid and amino acid assays. Means for producing labeled hybridization or PCR probes for detecting sequences related to polynucleotides encoding the proteins of the invention include oligolabeling, nick translation, end-labeling or PCR amplification using a labeled nucleotide.

Alternatively, the sequences encoding the proteins of the invention, or any portions thereof may be cloned into a vector for the production of an mRNA probe. Such vectors are known in the art, are commercially available, and may be used to synthesize RNA probes in vitro by addition of an appropriate RNA polymerase such as T7, T3, or SP6 and labeled nucleotides. These procedures may be conducted using a variety of commercially available kits (Pharmacia & Upjohn, (Kalamazoo, Mich.); Promega (Madison Wis.); and U.S. Biochemical Corp., (Cleveland, Ohio). Suitable reporter molecules or labels, which may be used, include radionuclides, enzymes, fluorescent, chemiluminescent, or chromogenic agents as well as substrates, cofactors, inhibitors, magnetic particles, and the like.

Host cells transformed with nucleotide sequences encoding the proteins of the invention may be cultured under conditions suitable for the expression and recovery of the protein from cell culture. The protein produced by a recombinant cell may be secreted or contained intracellularly depending on the sequence and/or the vector used. As will be understood by those of skill in the art, expression vectors containing polynucleotides which encode the proteins of the invention may be designed to contain signal sequences which direct secretion of the proteins of the invention through a prokaryotic or eukaryotic cell membrane. Other recombinant constructions may be used to join sequences encoding the proteins of the invention to nucleotide sequence encoding a polypeptide domain which will facilitate purification of soluble proteins. Such purification facilitating domains include, but are not limited to, metal chelating peptides such as histidine-tryptophan modules that allow purification on immobilized metals, protein A domains that allow purification on immobilized immunoglobulin, and the domain utilized in the FLAG extension/affinity purification system (Immunex Corp., Seattle, Wash.) The inclusion of cleavable linker sequences such as those specific for Factor XA or enterokinase (Invitrogen, San Diego, Calif.) between the purification domain and the proteins of the invention may be used to facilitate purification. One such expression vector provides for expression of a fusion protein containing the proteins of the invention and a nucleic acid encoding 6 histidine residues preceding a thioredoxin or an enterokinase cleavage site. The histidine residues facilitate purification on IMIAC (immobilized metal ion affinity chromotagraphy as described in Porath, J. et al. (1992, Prot. Exp. Purif. 3: 263-281) while the enterokinase cleavage site provides a means for purifying the proteins of the invention from the fusion protein. A discussion of vectors which contain fusion proteins is provided in Kroll, D. J. et al. (1993; DNA Cell Biol. 12:441-453). In addition to recombinant production, fragments of the proteins of the invention may be produced by direct peptide synthesis using solid-phase techniques (Merrifield J. (1963) J. Am. Chem. Soc. 85:2149-2154). protein synthesis may be performed using manual techniques or by automation. Automated synthesis may be achieved, for example, using Applied Biosystems 431A peptide synthesizer (Perkin Elmer). Various fragments of the proteins of the invention may be chemically synthesized separately and combined using chemical methods to produce the full length molecule.

The nucleic acids encoding the proteins of the invention can be used to generate transgenic animal or site specific gene modifications in cell lines. Transgenic animals may be made through homologous recombination, where the normal locus of the genes encoding the proteins of the invention is altered. Alternatively, a nucleic acid construct is randomly integrated into the genome. Vectors for stable integration include plasmids, retrovirusses and other animal virusses, YACs, and the like. The modified cells or animal are useful in the study of the function and regulation of the proteins of the invention. For example, a series of small deletions and/or substitutions may be made in the genes that encode the proteins of the invention to determine the role of particular domains of the protein, functions in pancreatic differentiation, etc. Specific constructs of interest include anti-sense molecules, which will block the expression of the proteins of the invention, or expression of dominant negative mutations. A detectable marker, such as lac Z may be introduced in the locus of the genes of the invention, where upregulation of expression of the genes of the invention will result in an easily detected change in phenotype. One may also provide for expression of the genes of the invention or variants thereof in cells or tissues where it is not normally expressed or at abnormal times of development. In addition, by providing expression of the proteins of the invention in cells in which they are not normally produced, one can induce changes in cell behavior. DNA constructs for homologous recombination will comprise at least portions of the genes of the invention with the desired genetic modification, and will include regions of homology to the target locus. DNA constructs for random integration need not include regions of homology to mediate recombination. Conveniently, markers for positive and negative selection are included. Methods for generating cells having targeted gene modifications through homologous recombination are known in the art. For embryonic stem (ES) cells, an ES cell line may be employed, or embryonic cells may be obtained freshly from a host, e.g. mouse, rat, guinea pig etc. Such cells are grown on an appropriate fibroblast-feeder layer or grown in presence of leukemia inhibiting factor (LIF). When ES or embryonic cells have been transformed, they may be used to produce transgenic animals. After transformation, the cells are plated onto a feeder layer in an appropriate medium. Cells containing the construct may be detected by employing a selective medium. After sufficient time for colonies to grow, they are picked and analyzed for the occurrence of homologous recombination or integration of the construct. Those colonies that are positive may then be used for embryo manipulation and blastocyst injection. Blastocysts are obtained from 4 to 6 week old superovulated females. The ES cells are trypsinized, and the modified cells are injected into the blastocoel of the blastocyst. After injection, the blastocysts are returned to each uterine horn of pseudopregnant females. Females are then allowed to go to term and the resulting offspring screened for the construct. By providing for a different phenotype of the blastocyst and the genetically modified cells, chimeric progeny can be readily detected. The chimeric animals are screened for the presence of the modified gene and males and females having the modification are mated to produce homozygous progeny. If the gene alterations cause lethality at some point in development, tissues or organs can be maintained as allogenic or congenic grafts or transplants, or in vitro culture. The transgenic animals may be any non-human mammal, such as laboratory animal, domestic animals, etc. The transgenic animals may be used in functional studies, drug screening, etc.

Diagnostics and Therapeutics

From the in situ expression patterns obtained by using the proteins of this invention it can be concluded that the proteins described in this invention are specifically expressed in pancreatic cells such as islet cells (for example DP685; DP160; RA770), pancreatic mesenchyme (RA770), cells of the pancreatic epithelium (for example DP685; DP160), pancreatic duct cells (DP160) as well as in other cells such as ganglia along the neural tube (DP160; DP444), somites (DP444), dorsal hindbrain (DP444), liver (DP685), heart (DP685), stomach (DP444) and intestinal cells (DP685; DP444). Therefore, the nucleic acids and proteins of the invention and effectors/modulators thereof are useful in diagnostic and therapeutic applications implicated, for example but not limited to, in metabolic disorders and dysfunctions associated with the above organs or tissues like diabetes and obesity, liver diseases and neural diseases, e.g. neuro-degenerative disorders and other diseases and disorders. Hence the proteins of the invention could be useful as a diagnostic markers or as a target for small molecule screening, and in prevention or treatment of diabetes and/or obesity and other metabolic disorders and other diseases such as neurodegenerative disorders, heart, liver, stomach, or intestinal disorders.

Therapeutic uses for the invention(s) are, for example but not limited to, the following: (i) tissue regeneration in vitro and in vivo (regeneration for all these tissues and cell types composing these tissues and cell types derived from these tissues); (ii) protein therapeutic, (iii) small molecule drug target, (iv) antibody target (therapeutic, diagnostic, drug targeting/cytotoxic antibody), (v) diagnostic and/or prognostic marker, (vi) gene therapy (gene delivery/gene ablation), and (vii) research tools.

The nucleic acids and proteins of the invention are useful in therapeutic applications implicated in various diseases and disorders described below and/or other pathologies and disorders. For example, but not limited to, a cDNA encoding one of the proteins of the invention may be useful in gene therapy, and the proteins of the invention may be useful when administered to a subject in need thereof. By way of non-limiting example, the compositions of the present invention will have efficacy for treatment of patients suffering from, for example, but not limited to, in metabolic disorders like diabetes and obesity, and other diseases and disorders. The novel nucleic acids encoding the proteins of the invention, or functional fragments thereof, may further be useful in diagnostic applications, wherein the presence or amount of the nucleic acid or the protein are to be assessed. These materials are further useful in the generation of antibodies that bind immunospecifically to the novel substances of the invention for use in therapeutic or diagnostic methods. In other embodiments of the invention, the compositions of the invention e.g. the proteins or functional fragments thereof may be used for therapeutic purposes. For example, the compositions, such as the pancreas specific proteins described in this invention, can be used for promoting the differentiation and/or function of beta cells in vitro and/or in vivo. Further, the compositions, such as the proteins, can be used for the regeneration of β-cells, e.g. of partially or completely dysfunctional β-cells in vitro and/or in vivo.

For example, in one aspect, antibodies which are specific for the proteins of the invention may be used directly as an antagonist, or indirectly as a targeting or delivery mechanism for bringing a pharmaceutical agent to cells or tissue which express the proteins of the invention. The antibodies may be generated using methods that are well known in the art. Such antibodies may include, but are not limited to, polyclonal, monoclonal, chimeric, single chain, Fab fragments, and fragments produced by a Fab expression library. Neutralizing antibodies, (i.e. those which inhibit biological function) are especially preferred for therapeutic use.

For the production of antibodies, various hosts including goats, rabbits, rats, mice, humans, and others, may be immunized by injection with the proteins of the invention or any fragment or oligopeptide thereof which has immunogenic properties. Depending on the host species, various adjuvants may be used to increase immunological response. It is preferred that the peptides, fragments or oligopeptides used to induce antibodies to the proteins of the invention have an amino acid sequence consisting of at least five amino acids, and more preferably at least 10 amino acids.

Monoclonal antibodies to the proteins of the invention may be prepared using any technique which provides for the production of antibody molecules by continuous cell lines in culture. These include, but are not limited to, the hybridoma technique, the human B-cell hybridoma technique, and the EBV-hybridoma technique (Köhler, G. et al. (1975) Nature 256:495-497; Kozbor, D. et al. (1985) J. Immunol. Methods 81:31-42; Cote, R. J. et al. (Proc. Natl. Acad. Sci. 80:2026-2030; Cole, S. P. et al. (1984) Mol. Cell Biol. 62:109-120). In addition, techniques developed for the production of "chimeric antibodies", the splicing of mouse antibody genes to human antibody genes to obtain a molecule with appropriate antigen specificity and biological activity can be used (Morrison, S. L. et al. (1984) Proc. Natl. Acad. Sci. 81:6851-6855; Neuberger, M. S. et al. (1984) Nature 312:604-608; Takeda, S. et al. (1985) Nature 314:452-454). Alternatively, techniques described for the production of single chain antibodies may be adapted, using methods known in the art, to produce the proteins of the invention-specific single chain antibodies. Antibodies with related specificity, but of distinct idiotypic composition, may be generated by chain shuffling from random combinatorial immunoglobulin libraries (Burton, D. R. (1991) Proc. Natl. Acad. Sci. 88:11120-3). Antibodies may also be producing by inducing in vivo production in the lymphocyte population or by screening recombinant immunoglobulin libraries or panels of highly specific binding reagents as disclosed in the literature (Orlandi, R. et al. (1989) Proc. Natl. Acad. Sci. 86:3833-3837; Winter, G. et al. (1991) Nature 349:293-299).

Antibody fragments which contain specific binding sites for the proteins of the invention may also be generated. For example; such fragments include, but are not limited to, the $F(ab')_2$ fragments which can be produced by pepsin digestion of the antibody molecule and the Fab fragments which can be generated by reducing the disulfide bridges of $F(ab')_2$ fragments. Alternatively, Fab expression libraries may be constructed to allow rapid and easy identification of monoclonal Fab fragments with the desired specificity (Huse, W. D. et al. (1989) Science 254:1275-1281).

Various immunoassays may be used for screening to identify antibodies having the desired specificity. Numerous protocols for competitive binding and immunoradiometric assays using either polyclonal or monoclonal antibodies with established specificities are well known in the art. Such immunoassays typically involve the measurement of complex formation between the proteins of the invention and its specific antibody. A two-site, monoclonal-based immunoassay utilizing monoclonal antibodies reactive to two non-interfering the proteins of the invention epitopes is preferred, but a competitive binding assay may also be employed (Maddox, supra).

In another embodiment of the invention, the polynucleotides, or any fragment thereof, such as aptamers, antisense molecules, RNAi molecules or ribozymes may be used for therapeutic purposes. In one aspect, aptamers i.e. nucleic acid molecules which are capable of binding to a protein of the invention and modulating its activity, may be generated by a screening and selection, procedure involving the use of combinatorial nucleic acid libraries.

In a further aspect, antisense molecules to the polynucleotide encoding the proteins of the invention may be used in situations in which it would be desirable to block the transcription of the mRNA. In particular, cells may be transformed with sequences complementary to polynucleotides encoding the proteins of the invention. Thus, antisense molecules may be used to modulate the activity of the proteins of the invention, or to achieve regulation of gene function. Such technology is now well know in the art, and sense or antisense oligomers or larger fragments, can be designed from various locations along the coding or control regions of sequences encoding the proteins of the invention. Expression vectors derived from retroviruses, adenoviruses, herpes or vaccinia viruses, or from various bacterial plasmids may be used for delivery of nucleotide sequences to the targeted organ, tissue or cell population. Methods which are well known to those skilled in the art can be used to construct recombinant vectors which will express antisense molecules complementary to the polynucleotides of the gene encoding the proteins of the invention. These techniques are described both in Sambrook et al. (supra) and in Ausubel et al. (supra). Genes encoding the proteins of the invention can be turned off by transforming a cell or tissue with expression vectors which express high levels of a polynucleotide or fragment thereof which encodes the proteins of the invention. Such constructs may be used to introduce untranslatable sense or antisense sequences into a cell. Even in the absence of integration into the DNA, such vectors may continue to transcribe RNA molecules until they are disabled by endogenous nucleases. Transient expression may last for a month or more with a non-replicating vector and even longer if appropriate replication elements are part of the vector system.

As mentioned above, modifications of gene expression can be obtained by designing antisense molecules, DNA, RNA, or nucleic acid analogues such as PNA, to the control regions of the gene encoding the proteins of the invention, i.e., the promoters, enhancers, and introns. Oligonucleotides derived from the transcription initiation site, e.g. between positions −10 and +10 from the start site are preferred. Similarly, inhibition can be achieved using "triple helix" base-pairing methodology. Triple helix pairing is useful because it causes inhibition of the ability of the double helix to open sufficiently for the binding of polymerases, transcription factors, or regulatory molecules. Recent therapeutic advances using triplex DNA have been described in the literature (Gee, J. E. et al. (1994) In; Huber, B. E. and B. I. Carr, Molecular and Immunologic Approaches, Futura Publishing Co., Mt. Kisco, N.Y.). The antisense molecules may also be designed to block translation of mRNA by preventing the transcript from binding to ribosomes.

Ribozymes, enzymatic RNA molecules, may also be used to catalyze the specific cleavage of RNA. The mechanism of ribozyme action involves sequence-specific hybridization of the ribozyme molecule to complementary target RNA, followed by endonucleolytic cleavage. Examples which may be used include engineered hammerhead motif ribozyme molecules that can be specifically and efficiently catalyze endonucleolytic cleavage of sequences encoding the proteins of the invention. Specific ribozyme cleavage sites within any potential RNA target are initially identified by scanning the target molecule for ribozyme cleavage sites which include the following sequences: GUA, GUU, and GUC. Once identified, short RNA sequences of between 15 and 20 ribonucleotides corresponding to the region of the target gene containing the cleavage site may be evaluated for secondary structural features which may render the oligonucleotide inoperable. The suitability of candidate targets may also be evaluated by testing accessibility to hybridization with complementary oligonucleotides using ribonuclease protection assays.

Effector nucleic acid molecules, e.g. antisense molecules and ribozymes of the invention may be prepared by any method known in the art for the synthesis of nucleic acid molecules. These include techniques for chemically synthesizing oligonucleotides such as solid phase phosphoramidite chemical synthesis. Alternatively, RNA molecules may be generated by in vitro and in vivo transcription of DNA sequences encoding the proteins of the invention. Such DNA sequences may be incorporated into a variety of vectors with suitable RNA polymerase promoters such as T7 or SP6. Alternatively, these cDNA constructs that synthesize antisense RNA constitutively or inducibly can be introduced into cell lines, cells, or tissues. RNA molecules may be modified to increase intracellular stability and half-life. Possible modifications include, but are not limited to, the addition of flanking sequences at the 5' and/or 3' ends of the molecule or the use of phosphorothioate or 2' O-methyl rather than phosphodiesterase linkages within the backbone of the molecule. This concept is inherent in the production of PNAs and can be extended in all of these molecules by the inclusion of nontraditional bases such as inosine, queosine, and wybutosine, as well as acetyl-, methyl-, thio- and similarly modified forms of adenine, cytidine, guanine, thymine, and uridine which are not as easily recognized by endogenous endonucleases.

Gene function can also be suppressed using small interfering. RNAs. These are short (18 to 25 bp) RNA duplexes (the RNA may be modified for stabilization). The small interfering RNAs can be made either synthetically, by in vitro transcription procedures or using suitable vectors which express the desired RNA duplex as a hairpin structure inside the target cell. Applications include functional gene suppression in tissue culture, in model organisms such as mice or therapeutically (see e.g. Shi, Y. Trends Genet 19(1):9-12; Shuey, D. J., Drug Discov Today. 7(20):1040-6). The presence of longer (>30 bp) antisense RNAs inside of eukaryotic cells can also lead to gene silencing under certain circumstances.

Many methods for introducing vectors into cells or tissues are available and equally suitable for use in vivo, in vitro, and ex vivo. For ex vivo therapy, vectors may be introduced into stem cells taken from the patient and clonally propagated for autologous transplant back into that same patient. Delivery by transfection and by liposome injections may be achieved using methods which are well known in the art. Any of the therapeutic methods described above may be applied to any suitable subject including, for example, mammals such as dogs, cats, cows, horses, rabbits, monkeys, and most preferably, humans.

An additional embodiment of the invention relates to the administration of a pharmaceutical composition, in conjunction with a pharmaceutically acceptable carrier, for any of the therapeutic effects discussed above. Such pharmaceutical compositions may consist of the proteins of the invention, antibodies to the proteins of the invention, mimetics, agonists, antagonists, or inhibitors of the proteins of the invention. The compositions may be administered alone or in combination with at least one other agent, such as stabilizing compound, which may be administered in any sterile, biocompatible pharmaceutical carrier, including, but not limited to, saline, buffered saline, dextrose, and water. The compositions may be administered to a patient alone, or in combination with other agents, drugs or hormones. The pharmaceutical compositions utilized in this invention may be administered by any number of routes including, but not limited to, oral, intravenous, intramuscular, intra-arterial, intramedullary, intrathecal, intraventricular, transdermal, subcutaneous, intraperitoneal, intranasal, enteral, topical, sublingual, or rectal means.

In addition to the active ingredients, these pharmaceutical compositions may contain suitable pharmaceutically-acceptable carriers comprising excipients and auxiliaries which facilitate processing of the active compounds into preparations which can be used pharmaceutically. Further details on techniques for formulation and administration may be found in the latest edition of Remington's Pharmaceutical Sciences (Maack Publishing Co., Easton, Pa.).

The pharmaceutical compositions of the present invention may be manufactured in a manner that is known in the art, e.g. by means of conventional mixing, dissolving, granulating, dragee-making; levigating, emulsifying, encapsulating, entrapping, or lyophilizing processes. After pharmaceutical compositions have been prepared, they can be placed in an appropriate container and labeled for treatment of an indicated condition. For administration of the proteins of the invention, such labeling would include amount, frequency, and method of administration.

Pharmaceutical compositions suitable for use in the invention include compositions wherein the active ingredients are contained in an effective amount to achieve the intended purpose. The determination of an effective dose is well within the capability of those skilled in the art. For any compounds, the therapeutically effective does can be estimated initially either in cell culture assays, e.g. of preadipoctic cell lines, or in animal models, usually mice, rabbits, dogs, or pigs. The animal model may also be used to determine the appropriate concentration range and route of administration. Such information can then be used to determine useful doses and routes for administration in humans. A therapeutically effective dose refers to that amount of active ingredient, for example the proteins of the invention or fragments thereof, antibodies of the proteins of the invention, which is effective for the treatment of a specific condition. Therapeutic efficacy can toxicity may be determined by standard pharmaceutical procedures in cell cultures or experimental animals, e.g. ED50 (the does therapeutically effective in 50% of the population) and LD50 (the dose lethal to 50% of the population). The dose ratio between therapeutic and toxic effects is the therapeutic index, and it can be expressed as the ratio, LD50/ED50. Pharmaceutical compositions which exhibit large therapeutic indices are preferred. The data obtained from cell culture assays and animal studies is used in formulating a range of dosage for human use. The dosage contained in such compositions is preferably within a range of circulating concentrations that include the ED50 with little or no toxicity. The dosage varies within this range depending upon the dosage from employed, sensitivity of the patient, and the route of administration. The exact dosage will be determined by the practitioner, in light of factors related to the subject that requires treatment. Dosage and administration are adjusted to provide sufficient levels of the active moiety or to maintain the desired effect. Factors which may be taken into account include the severity of the disease state, general health of the subject, age, weight, and gender of the subject, diet, time and frequency of administration, drug combination(s), reaction sensitivities, and tolerance/response to therapy. Long-acting pharmaceutical compositions may be administered every 3 to 4 days, every week, or once every two weeks depending on half-life and clearance rate of the particular formulation. Normal dosage amounts may vary from 0.1 to 100,000 micrograms, up to a total dose of about 1 g, depending upon the route of administration. Guidance as to particular dosages and methods of delivery is provided in the literature and generally available to practitioners in the art. Those skilled in the art employ different formulations for nucleotides than for proteins or their inhibitors. Similarly, delivery of polynucleotides or polypeptides will be specific to particular cells, conditions, locations, etc.

In another embodiment, antibodies which specifically bind the proteins of the invention may be used for the diagnosis of conditions or diseases characterized by expression of the proteins of the invention, or in assays to monitor patients being treated with the proteins of the invention, agonists, antagonists or inhibitors. The antibodies useful for diagnostic purposes may be prepared in the same manner as those described above for therapeutics. Diagnostic assays for the proteins of the invention include methods which utilize the antibody and a label to detect the proteins of the invention in human body fluids or extracts of cells or tissues. The antibodies may be used with or without modification, and may be labeled by joining them, either covalently or non-covalently, with a reporter molecule. A wide variety of reporter molecules which are known in the art may be used several of which are described above.

A variety of protocols including ELISA, RIA, and FACS for measuring the proteins of the invention are known in the art and provide a basis for diagnosing altered or abnormal levels of the proteins of the invention expression. Normal or standard values for the proteins of the invention expression are established by combining body fluids or cell extracts taken from normal mammalian subjects, preferably human, with antibody to the proteins of the invention under conditions suitable for complex formation. The amount of standard complex formation may be quantified by various methods, but preferably by photometric means. Quantities of the proteins of the invention expressed in control and disease samples from biopsied tissues, for example, are compared with the standard values. Deviation between standard and subject values establishes the parameters for diagnosing disease.

In another embodiment of the invention, the polynucleotides of the invention may be used for diagnostic purposes. The polynucleotides which may be used include oligonucleotide sequences, antisense. RNA and DNA molecules, and PNAs. The polynucleotides may be used to detect and quantitate gene expression in biopsied tissues in which expression of the proteins of the invention may be correlated with disease. The diagnostic assay may be used to distinguish between absence, presence, and excess expression of the proteins of the invention, and to monitor regulation of the proteins of the invention levels during therapeutic intervention.

In one aspect, hybridization with PCR probes which are capable of, detecting polynucleotide sequences, including genomic sequences, encoding the proteins of the invention or closely related molecules, may be used to identify nucleic acid sequences which encode the proteins of the invention. The specificity of the probe, whether it is made from a highly specific region, or a less specific region; and the stringency of the hybridization or amplification (maximal, high, intermediate, or low) will determine whether the probe identifies only naturally occurring sequences encoding the proteins of the invention, alleles, or related sequences. Probes may also be used for the detection of related sequences, and should preferably contain at least 50% of the nucleotides from any of the proteins of the invention encoding sequences. The hybridization probes of the subject invention may be DNA or RNA and derived from the nucleotide sequence of SEQ ID NO: 1, 3, 5, 7, 9, 11, 12, 13, 15, 17, 19, 21, 23, 25, 27, 29, 31, 33, 35, 37, 39, 41 or 43, or from a genomic sequence including promoter, enhancer elements, and introns of the naturally occurring the proteins of the invention. Means for producing specific hybridization probes for DNAs encoding the proteins of the invention include the cloning of nucleic acid sequences encoding the proteins of the invention or the proteins of the invention derivatives into vectors for the production of mRNA probes. Such vectors are known in the art, commercially available, and may be used to synthesize RNA probes in vitro by means of the addition of the appropriate RNA polymerases and the appropriate labeled nucleotides. Hybridization probes may be labeled by a variety of reporter groups, for example, radionuclides such as $^{32}P$ or $^{35}S$, or enzymatic labels, such as alkaline phosphatase coupled to the probe via avidin/biotin coupling systems, and the like.

Polynucleotide sequences may be used for the diagnosis of conditions or diseases which are associated with expression of the proteins of the invention. Examples of such conditions or diseases include, but are not limited to, pancreatic diseases and disorders, including diabetes. Polynucleotide sequences may also be used to monitor the progress of patients receiving treatment for pancreatic diseases and disorders, including diabetes. The polynucleotide sequences may be used in Southern or northern analysis, dot, blot, or other membrane-based technologies; in PCR technologies; or in dip stick, pin, ELISA or chip assays utilizing fluids or tissues from patient biopsies to detect altered the proteins of the invention expression. Such, qualitative or quantitative methods are well known in the art.

In a particular aspect, the nucleotide sequences may be useful in assays that detect activation or induction of various pancreatic diseases and disorders, including diabetes, particularly those mentioned above. The nucleotide sequences may be labeled by standard methods, and added to a fluid or tissue sample from a patient under conditions suitable for the formation of hybridization complexes. After a suitable incubation period, the sample is washed and the signal is quantitated and compared with a standard value. The presence of altered levels of nucleotide sequences in the sample compared to the standard, e.g. a control sample indicates the presence of the associated disease. Such assays may also be used to evaluate the efficacy of a particular therapeutic treatment regimen in animal studies, in clinical trials, or in monitoring the treatment of an individual patient.

In order to provide a basis for the diagnosis of disease associated with expression of the proteins of the invention, a normal or standard profile for expression is established. This may be accomplished by combining body fluids or cell extracts taken from normal subjects, either animal or human, with a sequence, or a fragment thereof, which encodes the proteins of the invention, under conditions suitable for hybridization or amplification. Standard hybridization may be quantified by comparing the values obtained from normal subjects with those from an experiment where a known amount of a substantially purified polynucleotide is used. Standard values obtained from normal samples may be compared with values obtained from samples from patients who are symptomatic for disease. Deviation between standard and subject values is used to establish the presence of disease. Once disease is established and a treatment protocol is initiated, hybridization assays may be repeated on a regular basis to evaluate whether the level of expression in the patient begins to approximate that which is observed in the normal patient. The results obtained from successive assays may be used to show the efficacy of treatment over a period ranging from several days to months.

With respect to pancreatic diseases and disorders, including diabetes, the presence of a relatively high amount of transcript in biopsied tissue from an individual may indicate a predisposition for the development of the disease, or may provide a means for detecting the disease prior to the appearance of actual clinical symptoms. A more definitive diagnosis of this type may allow health professionals to employ preventative measures or aggressive treatment earlier thereby preventing the development or further progression of the pancreatic diseases and disorders. Additional diagnostic uses for oligonucleotides designed from the sequences encoding the proteins of the invention may involve the use of PCR. Such oligomers may be chemically synthesized, generated enzymatically, or produced from a recombinant source. Oligomers will preferably consist of two nucleotide sequences, one with sense orientation (5'.fwdarw.3') and another with antisense (3'.rarw.5'), employed under optimized conditions for identification of a specific gene or condition. The same two oligomers, nested sets of oligomers, or even a degenerate pool of oligomers may be employed under less stringent conditions for detection and/or quantitation of closely related DNA or RNA sequences.

Methods, which may also be used to quantitate the expression of the proteins of the invention, include various labels, e.g. radioisotopes, fluorescers, chemiluminescers, enzymes, specific binding, molecules, particles, e.g. magnetic particles or the like. Specific binding molecules include pairs, such as biotin and streptavidin, digoxin and antidigoxin etc. For the specific binding members, the complementary member would normally be labeled with a molecule that provides for detection, in accordance with known procedures. The methods include coamplification of a control nucleic acid, and standard curves onto which the experimental results are interpolated (Melby, P. C. et al. (1993) J. Immunol. Methods, 159:235-244; Duplaa, C. et al. (1993) Anal. Biochem. 212: 229-236. The speed of quantitation of multiple samples may be accelerated by running the assay in an ELISA format where the oligomer of interest is presented in various dilutions and a spectrophotometric or colorimetric response gives rapid quantitation.

In another embodiment of the invention, the nucleic acid sequences which encode the proteins of the invention may also be used to generate hybridization probes which are useful for mapping the naturally occurring genomic sequence. The sequences may be mapped to a particular chromosome or to a specific region of the chromosome using well known techniques. Such techniques include FISH, FACS, or artificial chromosome constructions, such as yeast artificial chromosomes, bacterial artificial chromosomes, bacterial P1 constructions or single chromosomencDNA libraries as reviewed in Price, C. M. (1993) Blood Rev. 7:127-134, and Trask, B. J. (1991) Trends Genet. 7:149-154. FISH (as described in Verma et al. (1988) Human Chromosomes: A Manual of Basic Techniques, Pergamon Press, New York, N.Y.) may be correlated with other physical chromosome mapping techniques and genetic map data Examples of genetic map data can be found in the 1994 Genome Issue of Science (265: 1981f). Correlation between the location of the gene encoding the proteins of the invention on a physical chromosomal map and a specific disease, or predisposition to a specific disease, may help delimit the region of DNA associated with that genetic disease.

The nucleotide sequences of the subject invention may be used to detect differences in gene sequences between normal, carrier, or affected individuals. In situ hybridization of chromosomal preparations and physical mapping techniques such as linkage analysis using established chromosomal markers may be used for extending genetic maps. Often the placement of a gene on the chromosome of another mammalian species, such as mouse, may reveal associated markers even if the number or arm of a particular human chromosome is not known. New sequences can be assigned to chromosomal arms, or parts thereof, by physical mapping. This provides valuable information to investigators searching for disease genes using positional cloning or other gene discovery techniques. Once the disease or syndrome has been crudely localized by genetic linkage to a particular genomic region, for example, AT to 11q22-23 (Gatti, R. A. et al. (1988) Nature 336:577-580), any sequences mapping to that area may represent associated or regulatory genes for further investigation. The nucleotide sequence of the subject invention may also be used to detect differences in the chromosomal location due to translocation, inversion, etc. among normal, carrier, or affected individuals.

In another embodiment of the invention, the proteins of the invention, its catalytic or immunogenic fragments or oligopeptides thereof, an in vitro model, a genetically altered cell or animal, can be used for screening libraries of compounds in any of a variety of drug screening techniques. One can identify ligands or substrates that bind to, modulate or mimic the action of one or more of the proteins of the invention. A protein of the invention or a fragment thereof employed in such screening may be free in solution, affixed to a solid support, borne on a cell surface, or located intracellularly. The formation of binding complexes, between the proteins of the invention and the agent tested, may be measured. Of particular interest are screening assays for agents that have a low toxicity for mammalian cells. The term "agent" as used herein describes any molecule, e.g. protein, peptide or pharmaceutical, with the capability of altering or mimicking the physiological function of one or more of the proteins of the invention. Candidate agents encompass numerous chemical classes, though typically they are organic molecules, preferably small organic compounds having a molecular weight of more than 50 and less than about 2,500 Daltons. Candidate agents comprise functional groups necessary for structural interaction with proteins, particularly hydrogen bonding, and typically include at least an amine, carbonyl, hydroxyl or carboxyl group, preferably at least two of the functional chemical groups. The candidate agents often comprise cyclical carbon or heterocyclic structures and/or aromatic or polyaromatic structures substituted with one or more of the above functional groups. Candidate agents are also found among biomolecules including peptides, saccharides, fatty acids, steroids, purines, pyrimidines, derivatives, structural analogs or combinations thereof. Candidate agents are obtained from a wide variety of sources including libraries of synthetic or natural compounds. For example, numerous means are available for random and directed synthesis of a wide variety of organic compounds and biomolecules, including expression of randomized oligonucleotides and oligopeptides. Alternatively, libraries of natural compounds in the form of bacterial, fungal, plant and animal extracts are available or readily produced. Additionally, natural or synthetically produced libraries and compounds are readily modified through conventional chemical, physical and biochemical means, and may be used to produce combinatorial libraries. Known pharmacological agents may be subjected to directed or random chemical modifications, such as acylation, alkylation, esterification, amidification, etc. to produce structural analogs. Where the screening assay is a binding assay, one or more of the molecules may be joined to a label, where the label, can directly or indirectly provide a detectable signal.

Another technique for drug screening which may be used provides for high throughput screening of compounds having suitable binding affinity to the protein of interest as described in published PCT application WO84/03564. In this method, as applied to the proteins of the invention large numbers of different small test compounds are provided or synthesized on a solid substrate, such as plastic pins or some other surface. The test compounds are reacted with the proteins of the invention, or fragments thereof, and washed. Bound the proteins of the invention is then detected by methods well known in the art. Purified the proteins of the invention can also be coated directly onto plates for use in the aforementioned drug screening techniques. Alternatively, non-neutralizing antibodies can be used to capture the peptide and immobilize it on a solid support. In another embodiment, one may use competitive drug screening assays in which neutralizing antibodies capable of binding the proteins of the invention specifically compete with a test compound for binding the proteins of the invention. In this manner, the antibodies can be used to detect the presence of any peptide which shares one or more antigenic determinants with the proteins of the invention. In additional embodiments, the nucleotide sequences which encode the proteins of the invention may be used in any molecular biology techniques that have yet to be developed, provided the new techniques rely on properties of nucleotide that are currently known, including, but not limited to, such properties as the triplet genetic code and specific base pair interactions.

The nucleic acids encoding the proteins of the invention can be used to generate transgenic cell lines and animals. These transgenic non-human animals are useful in the study of the function and regulation of the proteins of the invention in vivo. Transgenic animals, particularly mammalian transgenic animals, can serve as a model system for the investigation of many developmental and cellular processes common to humans. A variety of non-human models of metabolic disorders can be used to test modulators of the protein of the invention. Misexpression (for example, overexpression or lack of expression) of the protein of the invention, particular feeding conditions, and/or administration of biologically active compounds can create models of metablic disorders.

In one embodiment of the invention, such assays use mouse models of insulin resistance and/or diabetes, such as mice carrying gene knockouts in the leptin pathway (for example, ob (leptin) or db (leptin receptor) mice). Such mice develop typical symptoms of diabetes, show hepatic lipid accumulation and frequently have increased plasma lipid levels (see Bruning et al, 1998, Mol. Cell. 2:449-569). Susceptible wild type mice (for example C57Bl/6) show similiar symptoms if fed a high fat diet. In addition to testing the expression of the proteins of the invention in such mouse strainns, these mice could be used to test whether administration of a candidate modulator alters for example lipid accumulation in the liver, in plasma, or adipose tissues using standard assays well known in the art, such as FPLC, colorimetric assays, blood glucose level tests, insulin tolerance tests and others.

Transgenic animals may be made through homologous recombination in non-human embryonic stem cells, where the normal locus of the gene encoding the protein of the invention is mutated. Alternatively, a nucleic acid construct encoding the protein is injected into oocytes and is randomly integrated into the genome. One may also express the genes of the invention or variants thereof in tissues where they are not normally expressed or at abnormal times of development. Furthermore, variants of the genes of the invention like specific constructs expressing anti-sense molecules or expression of dominant negative mutations, which will block or alter the expression of the proteins of the invention may be randomly integrated into the genome. A detectable marker, such as lac Z or luciferase may be introduced into the locus of the genes of the invention, where upregulation of expression of the genes of the invention will result in an easily detectable change in phenotype. Vectors for stable integration include plasmids, retroviruses and other animal viruses, yeast artificial chromosomes (YACs), and the like.

DNA constructs for homologous recombination will contain at least portions of the genes of the invention with the desired genetic modification, and will include regions of homology to the target locus. Conveniently, markers for positive and negative selection are included. DNA constructs for random integration do not need to contain regions of homology to mediate recombination. DNA constructs for random integration will consist of the nucleic acids encoding the proteins of the invention, a regulatory element (promoter), an intron and a poly-adenylation signal. Methods for generating cells having targeted gene modifications through homologous recombination are known in the field. For embryonic stem (ES) cells, an ES cell line may be employed, or embryonic cells may be obtained freshly from a host, e.g. mouse, rat, guinea pig, etc. Such cells are grown on an appropriate fibroblast-feeder layer and are grown in the presence of leukemia inhibiting factor (LIF).

When ES or embryonic cells or somatic pluripotent stem cells have been transformed, they may be used to produce transgenic animals. After transformation, the cells are plated onto a feeder layer in an appropriate medium. Cells containing the construct may be selected by employing a selective medium. After sufficient time for colonies to grow, they are picked and analyzed for the occurrence of homologous recombination or integration of the construct. Those colonies that are positive may then be used for embryo transfection and blastocyst injection. Blastocysts are obtained from 4 to 6 week old superovulated females. The ES cells are trypsinized, and the modified cells are injected into the blastocoel of the blastocyst. After injection, the blastocysts are returned to each uterine horn of pseudopregnant females. Females are then allowed to go to term and the resulting offspring is screened for the construct. By providing for a different phenotype of the blastocyst and the genetically modified cells, chimeric progeny can be readily detected. The chimeric animals are screened for the presence of the modified gene and males and females having the modification are mated to produce homozygous progeny. If the gene alterations cause lethality at some point in development, tissues or organs can be maintained as allogenic or congenic grafts or transplants, or in vitro culture. The transgenic animals may be any non-human mammal, such as laboratory animal, domestic animals, etc. The transgenic animals may be used in functional studies, drug screening, etc.

Finally, the invention also relates to a kit comprising at least one of (a) a nucleic acid molecule or a functional fragment thereof;
(b) a amino acid molecule or a functional fragment or an isoform thereof;
(c) a vector comprising the nucleic acid of (a);
(d) a host cell comprising the nucleic acid of (a) or the vector of (b);
(e) a polypeptide encoded by the nucleic acid of (a);
(f) a fusion polypeptide encoded by the nucleic acid of (a);
(g) an antibody, an aptamer or another receptor against the nucleic acid of (a) or the polypeptide of (d) or (e) and
(h) an anti-sense oligonucleotide of the nucleic acid of (a).

The kit may be used for diagnostic or therapeutic purposes or for screening applications as described above. The kit may further contain user instructions.

BRIEF DESCRIPTION OF THE FIGURES

FIG. 1: In situ hybridization results for the DP119 protein.

FIG. 1A shows whole-mount in situ hybridizatons on chick embryos (day 5 dpb=dorsal pancreatic bud; vbp=ventral pancreatic bud, st=stomach, nt=neural tube; FIG. 1B shows in situ hybridizations on developing pancreatic tissue sections. DP293 positive cells are shown in blue colour; insulin is stained in brown). Expression can be seen in islets (is) and some cells of the pancreatic epithelium and duct cells (du). FIG. 1C shows a cross-section through the dorsal part of a day 5 chicken embyro stained for DP119 expression by in situ hybridization. Staining is evident in scattered neural tube (nt) cells and in ganglionic cells surrounding the neural tube.

FIG. 1D shows the expression of the human DP119. Shown is the quantitive analysis of DP119 expression in human abdominal adipocyte cells, during the differentiation from preadipocytes to mature adipocytes.

FIG. 2: DP119 sequences

FIG. 2A: Nucleic acid sequence (SEQ ID NO: 1) containing the 3' of a chicken gene homologous to human DKFZp586L151. Underlined is the 3' untranslated region; the stop codon is shown in bold.

FIG. 2B: protein sequence (SEQ ID NO: 2) encoded by the coding sequence shown in FIG. 2A.

FIG. 2C: Nucleic acid sequence (SEQ ID NO: 3) encoding the human homolog protein, (GenBank Accession Number AL050137.1).

FIG. 2D: protein sequence (SEQ ID NO: 4) encoded by the coding sequence shown in FIG. 2C (GenBank Accession Number CAB43286.1).

FIG. 2E: Nucleic acid sequence (SEQ ID NO: 5) encoding the mouse homolog protein, (GenBank Accession Number BC025654.1).

FIG. 2F: protein sequence (SEQ ID NO: 6) encoded by the coding sequence shown in FIG. 8E (GenBank Accession Number Aah25654.1).

FIGS. 2G-2K: Alignment of DP119 from different species (Mm, mouse; Hs, *Homo sapiens*; Dr, Danio rerio; Gg, chicken) [NA73457: SEQ ID NO: 45; NA12640: SEQ ID NO: 46; IPI00221918: SEQ ID NO: 47; FLJ90228: SEQ ID NO: 48; DKFZP586L151-like: SEQ ID NO: 6; CL1BA-like: SEQ ID NO: 49; IPI00178517: SEQ ID NO: 50: ctg11453: SEQ ID NO: 51; ctg30117: SEQ ID NO: 52; DP119: SEQ ID NO: 2].

FIG. 3: Expression of DP444.

FIG. 3A: Whole mount in situ hybridization using a day 3.5 chicken embryo and a DP444 probe. Expression is seen along the neural tube (nt) and in somites, the developing intestine (in) and in branchial arches.

FIG. 3B: Whole mount in situ hybridization using a day 4 chicken embryo and a DP444 probe. Expression is seen along the neural tube (nt) and in somites, the developing intestine (in) and in the dorsal hindbrain (hb).

FIG. 3C: Whole mount in situ hybridization using a day 5 chicken embryo and a DP444 probe. Expression domains in the stomach (st) and the pancreatic buds (dpb, vpb) are indicated.

FIG. 3D: Double labelling on a section through developing pancreas (chicken day 5). Insulin is stained brown, DP444 expression is stained purple. Expression of DP444 can be seen in islets (is) strongly overlapping with insulin expression.

FIG. 3E: Loss of DP444 function leads to islet defects in zebrafish. FIG. 3Ea shows a 24 h old embryo injected with control antisense oligo, FIG. 3Eb shows a 24 h old fish embryo injected with antisense oligo blocking the translation of DP444. Insulin expression is stained purple.

FIG. 4: DP444 sequences.

FIG. 4A: Nucleic acid sequence (SEQ ID NO: 7). The stop codon is in bold and the 3' UTR is underlined.

FIG. 4B: Amino acid sequence of DP444 (SEQ ID NO: 8).

FIG. 4C: Nucleic acid sequence of the human homolog QV2-NN2006-230401-628-d06 NN2006, SEQ ID NO: 9 (GenBank Accession Number BIO35296).

FIG. 4D: Amino acid sequence of the human homolog of DP444 (SEQ ID NO: 10) (Translation of SEQ ID NO: 9).

FIG. 4E: Nucleic acid sequence of GenBank Accession Number BF951817 (QV1-NN0228-091100-436-g05 NN0228 *Homo sapiens*, SEQ ID NO: 11).

FIG. 4F: Nucleic acid sequence of GenBank Accession Number AI1214480.1; (qg69c12.x1 Soares_NFL_T_GBC_S1 *Homo Sapiens*, SEQ ID NO: 12).

FIG. 4G: Genbank Accession Number Hs2__5191__28__4__1 predicted mRNA, SEQ ID NO: 13).

FIG. 4H: GenBank Accession Number Hs2__5191__28__4__1 predicted protein, SEQ ID NO: 14).

FIGS. 4I-4K: GenBank Accession Number Hs2__5191__28__4__3 predicted mRNA, SEQ ID NO: 15).

FIG. 4L: GenBank Accession Number Hs2__5191__28__4__3 predicted protein, SEQ ID NO: 16).

FIGS. 4M-4N: Alignment of DP444 from different species (Dr, zebrafish [SEQ ID NO: 56]; Mm, mouse [SEQ ID NO: 54]; Hs, *Homo sapiens* [SEQ ID NO: 53]; Gg, chicken [SEQ ID NO: 55]).

FIG. 5: In situ hybridization results for the DP810 protein.

FIG. 5A and FIG. 5B show whole-mount in situ hybridizatons on chick embryos (day 5). li=liver, ht=heart, dpb=dorsal pancreatic bud;

FIG. 5C and FIG. 5D show in situ hybridizations on sections through developing pancreas (5-day-old chicken). pe=pancreatic epithelium, is=islet, pm=pancreatic mesenchyme.

FIG. 6: DP810 sequences.

FIGS. 6A-6B: DP810-protein. The 3' untranslated region is underlined and the stop codon is in bold font. (SEQ ID NO: 17)

FIG. 6C: protein sequence (SEQ ID NO: 18) encoded by the coding sequence shown in FIGS. 6A-6B.

FIG. 6D: Nucleic acid sequence (SEQ ID NO:19) encoding the human homolog DP810-protein, (GenBank Accession Number NM__02400.1; polydom).

FIG. 6E: protein sequence (SEQ ID NO:20) encoded by the coding sequence shown in FIG. 6D (GenBank Accession Number NP_078776.1).

FIG. 7: Expression of DP685 protein.

FIG. 7A and FIG. 7B show whole-mount in situ hybridizatons on chick embryos (A: day 4; B: day 5). In FIG. 7A, expression is seen along the dorsal neural tube (nt), in the dorsal forebrain (fb) and hindbrain (hb), in branchial arches (ba) and the anterior part of the developing hindlimb (ahl). A strong signal is also seen in the region of the developing stomach (st). In FIG. 7B, expression is seen in the developing stomach (st) and in the dorsal pancreatic bud (dpb).

FIG. 7C shows the expression of the human DP685. Shown is the quantitative analysis of DP685 expression in human abdominal adipocyte cells, during the differentiation from preadipocytes to mature adipocytes.

FIG. 8: DP685 sequences.

FIG. 8A: Nucleic acid sequence (SEQ ID NO:21) encoding the chicken DP685 protein.

FIG. 8B: Protein sequence (SEQ ID NO: 22) encoded by the coding sequence shown in FIG. 8A.

FIG. 8C: Nucleic acid sequence (SEQ ID NO:23) encoding the human homolog DP685 protein (autotaxin).

FIG. 8D: protein sequence (SEQ ID NO:24) encoded by the coding sequence shown in FIG. 8C.

FIG. 8E: Nucleic acid sequence (SEQ ID NO:25) encoding the mouse homolog DP685 protein.

FIG. 8F: Protein sequence (SEQ ID NO:26) encoded by the coding sequence shown in FIG. 8E.

FIG. 9: In situ hybridization results for the WE474 protein.

FIG. 9A shows whole-mount in situ hybridizatons on chick embryos (day 5). in=intestine, li=liver anlage;

FIG. 10: WE474 sequences.

FIG. 10A: Nucleic acid sequence (SEQ ID NO:27) consisting of the 3' untranslated region of chicken collectin.

FIG. 10B: protein sequence (SEQ ID NO:28) encoded by the coding sequence shown in FIGS. 6A-B.

FIG. 10C: Nucleic acid sequence (SEQ ID NO:29) encoding the human homolog collectin COLEC10-protein, (GenBank Accession Number NM_006438.2).

FIG. 10D: protein sequence (SEQ ID NO:30) encoded by the coding sequence shown in FIG. 10C (GenBank Accession Number NP_006429.1).

FIG. 11: In situ hybridization results for the DP160 protein.

FIG. 11A shows whole-mount in situ hybridizatons on chick embryos (day 5). DP160 is expressed along the neural tube (nt), in the mesonephros (mn) and in the developing gastrointestinal tract (stomach: st; dorsal and ventral pancreatic buds: dpb, vpb).

FIG. 11B. shows a double labelling on a section through developing pancreas (day 5). Insulin is stained in brown, DP160 expression is stained purple. Expression can be seen in islets (is) and in cells of the pancreatic epithelium.

FIG. 12: DP160 sequences.

FIG. 12A: Nucleic acid sequence (SEQ ID NO: 31) encoding the DP 160-like protein of chicken. NOTE: The entire sequence is translated and encodes a central part of chicken DP160/Nocturnin.

FIG. 12B: protein sequence (SEQ ID NO:32) encoded by the coding sequence shown in FIG. 12A.

FIG. 12C: Nucleic acid sequence (SEQ ID NO: 33) encoding the human homolog protein. (Nucleic acid sequence of *Homo sapiens* CCR4 carbon catabolite repression 4-like (*S. cerevisiae*. (CCRN4L) (GenBank Accession Number XM_003343.2.

FIG. 12D: protein sequence (SEQ ID NO: 34) encoded by the coding sequence shown in FIG. 12C. (Amino acid sequence of the human similar to Noctumin (CCR4 protein homolog) (GenBank Accession Number XP_003343.3) NOTE: Derived from a GeneScan prediction and identical to the published sequence of Noctumin except for a single acid exchange. Both sequences are derived from the same gene.

FIG. 13: Expression of RA977.

FIG. 13A and FIG. 13B: Whole mount in situ hybridization using a day 5 chicken embryo and a RA977 probe. Expression of RA977 is observed in the dorsal pancreatic bud (dpb). The strong signal seen in the stomach (st) is due to nonspecific probe trapping. Same embryo is shown at two different magnifications.

FIG. 14: RA977 sequences.

FIG. 14A: Nucleic acid sequence (SEQ ID NO: 35) OF RA977. Stop and start codons are in bold and the UTRs are underlined.

FIG. 14B: Amino acid sequence of RA977 (SEQ ID NO:36).

FIG. 14C: Nucleic acid sequence of *Homo sapiens* epithelial membrane protein 2 (EMP2), mRNA (GENBANK ACCESSION NUMBER XM_030218.1; SEQ ID NO: 37).

FIG. 14D: Amino acid sequence of EMP2 HUMAN Epithelial membrane protein-2 (EMP-2) (XMP protein)(GenBank Accession Number P54851; SEQ ID NO: 38).

FIG. 15: In situ hybridization results for the RA770 protein.

FIG. 15A shows whole-mount in situ hybridizatons on chick embryos (day 5). dpb=dorsal pancreatic bud; vpb=ventral pancreatic bud; lu=lung, st=stomach region; dd=duodenum FIG. 16: RA770 sequences.

FIG. 16A: Nucleic acid sequence (SEQ ID NO:39) encoding the chicken RA770-protein.

FIG. 16B: Protein sequence (SEQ ID NO: 40) encoded by the coding sequence shown in FIG. 16A.

FIG. 16C: Nucleic acid sequence (SEQ ID NO:42) encoding the human homolog RA770 protein (GenBank Accession Number NM_004558.1; Neurturin).

FIG. 16D: protein sequence (SEQ ID NO:43) encoded by the coding sequence shown in FIG. 16C. (GenBank Accession Number NP_004549.1).

FIG. 16E: Nucleic acid sequence (SEQ ID NO:44) encoding the mouse homolog RA770 protein (GenBank Accession Number NM_008738.1; Neurturin).

FIG. 16F: Protein sequence (SEQ ID NO:44) encoded by the coding sequence shown in FIG. 16E (GenBank Accession Number NP_032764.1).

After 4 weeks on HF diet lean and fat body mass of individual male mRA770 transgenic mice (dark grey bars, N=6) and male littermate controls (light grey bars, N=5) was measured using NMR analysis. The data are expressed as mean organ weight as % of bodyweight+/−standard deviation. mRA770 transgenic mice have an increased fat body mass compared to wt mice on HF diet.

Figure 21:
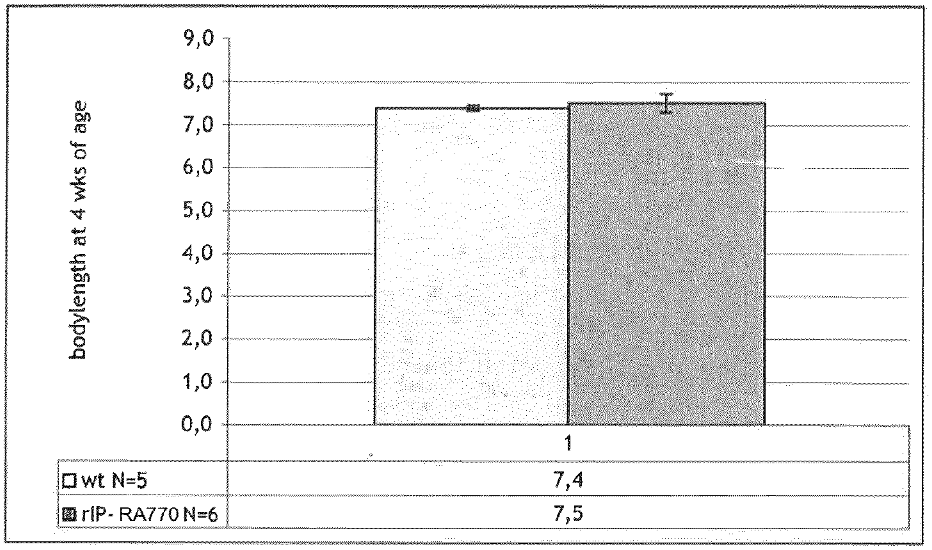

FIG. 21 shows body length of mRA770 transgenic mice compared to wild type mice (wt) on HF diet. Body length of 4 weeks old male wild type mice (light grey bar, N=5) and mRA770 transgenic mice (dark grey bar, N=6). The data are expressed as mean body length in cm+/−standard deviation. mRA770 transgenic mice have a normal body length.

FIG. 22 shows the analysis of RA770 expression in mammalian (mouse) tissues.

Figure 22A:
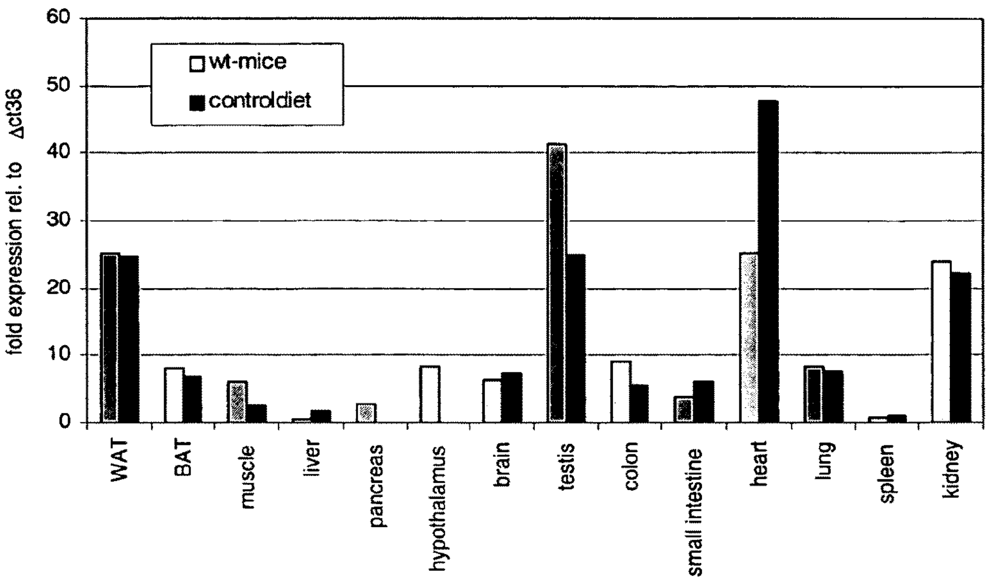

FIG. 22A shows the real-time PCR analysis of RA770 expression in wild type mouse tissues (referred to as wt-mice) and in tissues of mice fed with a control diet (referred to as control diet).

Figure 22B:
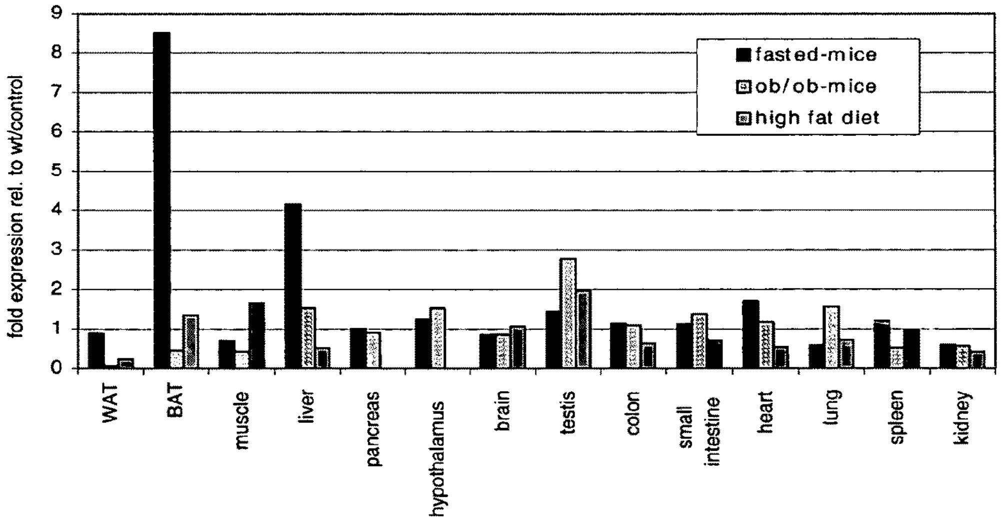

FIG. 22B shows the real-time PCR analysis of RA770 expression in fasted mice (referred to as fasted-mice) and genetically obese mice (referred to as ob/ob-mice) compared to wild-type mice, and in mice fed with a high fat diet (referred to as high fat diet) compared to mice fed with a control diet.

The examples below are provided to illustrate the subject invention and are not included for the purpose of limiting the invention.

EXAMPLES

Example 1

DPd6 Chick cDNA Library Construction

The Chick DPd6 cDNA library was constructed from dorsal pancreatic buds dissected from 6 day old chick embryos. The frozen tissue was homogenized and lysed using a Brinkmann POLYTRON homogenizer PT-3000 (Brinkman Instruments, Westbury, N.J.) in guanidinium isothiocyanate solution. The lysates were centrifuged over a 5.7 M CsCl cushion using as Beckman SW28 rotor in a Beckman L8-70M ultracentrifuge (Beckman Instruments, Fullerton, Calif.) for 18 hours at 25,000 rpm at ambient temperature. The RNA was extracted with acid phenol pH 4.7, precipitated using 0.3 M sodium acetate and 2.5 volumes of ethanol, resuspended in RNase-free water, and DNase treated at 37° C. The RNA extraction was repeated with acid phenol pH 4.7 and precipitated with sodium acetate and ethanol as before. The mRNA was then isolated using the Micro-FastTrack 2.0 mRNA isolation kit (Invitrogen, Groningen, Netherlands) and used to construct the cDNA libraries. The mRNAs were handled according to the recommended protocols in the SUPERSCRIPT cDNA synthesis and plasmid cloning system (Gibco/BRL). Following transformation into DH10B host cells, single colonies were picked and the subjected to PCR in order to amplify the cloned cDNA insert. Amplified PCR fragments representing single cDNA inserts were subsequently in vitro transcribed to generate Digoxygenin labelled RNA probes (Roche). The RNA probes were used in a whole-mount in situ screen to determine the expression of their respective gene products in early chick embryos. Plasmids containing the genes encoding the proteins of the invention were identified because of their high expression in pancreatic tissues.

Example 2

In Situ Hybridizations

Whole-mount in situ hybridizations were performed according to standard protocols as known to those skilled in the art, and as described previously (for example, Pelton, R. W. et al., (1990) Development 110, 609-620; Belo, J. A. et al., (1997) Mech. Dev. 68, 45-57).

Example 3

Isolation and Sequencing of cDNA Clones

Plasmid DNA was released from the cells and purified using the REAL PREP 96-well plasmid isolation kit (QIAGEN). This kit enabled the simultaneous purification of 96 samples in a 96-well block using multi-channel reagent dispensers. The protocol recommended by the manufacturer was employed except for the following changes, as indicated below: (i) the bacteria were cultured in 1 ml of sterile Terrific Broth (LIFE TECHNOLOGIES™, Gaithersburg, Md., USA) with carbenicillin at 25 mg/L and glycerol at 0.4%; (ii) after inoculation, the cultures were incubated for 19 hours and at the end of incubation, the cells were lysed with 0.3 ml of lysis buffer; and (iii) following isopropanol precipitation, the plasmid DNA pellet was resuspended in 0.1 ml of distilled water. After the last step in the protocol, samples were transferred to a 96-well block for storage at 4° C. The cDNAs were sequenced by GATC Biotech AG (Konstanz, Germany) accoding to standard protocols known to those skilled in the art.

Example 4

Homology Searching of cDNA Clones and their Deduced Proteins

After the reading frame was determined, the nucleotide sequences of the invention as well as the amino acid sequences deduced from them were used as query sequences against databases such as GenBank, SwissProt, BLOCKS, and Pima II. These databases, which contain previously identified and annotated sequences, were searched for regions of homology (similarity) using BLAST, which stands for Basic Local Alignment Search Tool (Altschul S. F. (1993) J. Mol. Evol. 36:290-300; Altschul, S. F. et al. (1990) J. Mol. Biol. 215:403-10). BLAST produced alignments of both nucleotide and amino acid sequences to determine sequence similarity. Because of the local nature of the alignments, BLAST was especially useful in determining exact matches or in identifying homologs which may be of prokaryotic (bacterial) or eukaryotic (animal, fungal, or plant) origin. Other algorithms such as the one described in Smith et al. (1992, protein Engineering 5:35-51), incorporated herein by reference, could have been used when dealing with primary sequence patterns and secondary structure gap penalties. The BLAST approach; as detailed in Karlin et al. (supra) and incorporated herein by reference, searched for matches between a query sequence and a database sequence. BLAST evaluated the statistical significance of any matches found, and reported only those matches that satisfy the user-selected threshold of significance. In this application, threshold was set at 10-25 for nucleotides and 10-14 for, peptides. Nucleotide sequences were searched against the GenBank databases for primate, rodent, and other mammalian sequences; and deduced amino acid sequences from the same clones were then searched against GenBank functional protein databases, mammalian, vertebrate, and eukaryote for homology.

Example 5

Extension of Polynucleotides to Full Length or to Recover Regulatory Sequences Full length nucleic acid sequences encoding the proteins of the invention are used to design oligonucleotide primers for extending a partial nucleotide sequence to full length or for obtaining 5' or 3', intron or other control sequences from genomic libraries. One primer is synthesized to initiate extension in the antisense direction and the other is synthesized to extend sequence in the sense direction. Primers are used to facilitate the extension of the known sequence "outward" generating amplicons containing new, unknown nucleotide sequence for the region of interest. The initial primers are designed from the cDNA using OLIGO 4.06 primer analysis software (National Biosciences), or another appropriate program, to be 22-30 nucleotides in length, to have a GC content of 50% or more, and to anneal to the target sequence at temperatures about 68° C.-72° C. Any stretch of nucleotides which would result in hairpin dimerizations is avoided. The original, selected cDNA libraries, or a human genomic library are used to extend the sequence, the latter is most useful to obtain 5' upstream regions. If more extension is necessary or desired, additional sets of primers are designed to further extend the known region. By following the instructions for the XL-PCR kit (Perkin Elmer) and thoroughly mixing the enzyme and reaction mix, high fidelity amplification is obtained. Beginning with 40 pmol of each primer and the recommended concentrations of all other components of the kit, PCR is performed using the Peltier thermal cycler (PTC200; M. J. Research, Watertown, Mass.) and the following parameters:

Step 1 94° C. for 1 min (initial denaturation)
Step 2 65° C. for 1 min
Step 3 68° C. for 6 min
Step 4 94° C. for 15 sec
Step 5 65° C. for 1 min
Step 6 68° C. for 7 min
Step 7 Repeat step 4-6 for 15 additional cycles
Step 8 94° C. for 15 sec
Step 9 65° C. for 1 min
Step 10 68° C. for 7-15 min
Step 11 Repeat step 8-10 for 12 cycles
Step 12 72° C. for 8 min
Step 13 4° C. (and holding)

A 5-10 μl aliquot of the reaction mixture is analyzed by electrophoresis on a low concentration (about 0.6-0.8% agarose mini-gel to determine which reactions were successful in extending the sequence. Bands thought to contain the largest products are selected and removed from the gel. Further purification involves using a commercial gel extraction method such as the QIAQUICK DNA purification kit (QIAGEN). After recovery of the DNA, Klenow enzyme is used to trim single-stranded, nucleotide overhangs creating blunt ends which facilitate religation and cloning. After ethanol precipitation, the products are redissolved in 13 μl of ligation buffer, 1 μl T4-DNA ligase (15 units) and 1 μl T4 polynucleotide kinase are added, and the mixture is incubated at room temperature for 2-3 hours or overnight at 16° C. Competent *E. coli* cells (in 40 μl of appropriate media) are transformed with 3 μl of ligation mixture and cultured in 80 μl of SOC medium (Sambrook et al., supra). After incubation for one hour at 37° C., the whole transformation mixture is plated on Luria Bertani (LB)-agar (Sambrook et al., supra) containing 2× Carb. The following day, several colonies are randomly picked from each plate and cultured in 150 μl of liquid LB/2× Carb medium placed in an individual well of an appropriate, commercially-available, sterile 96-well microtiter plate. The following day, 5 μl of each overnight culture is transferred into a non-sterile 96-well plate and after dilution 1:10 with water, 5 μl of each sample is transferred into a PCR array. For PCR amplification, 18 μl of concentrated PCR reaction mix (3.3×) containing 4 units of rTth DNA polymerase, a vector primer, and one or both of the gene specific primers used for the extension reaction are added to each well. Amplification is performed using the following conditions:

Step 1 94° C. for 60 sec
Step 2 94° C. for 20 sec
Step 3 55° C. for 30 sec
Step 4 72° C. for 90 sec
Step 5 Repeat steps 2-4 for an additional 29 cycles
Step 6 72° C. for 180 sec
Step 7 4° C. (and holding)

Aliquots of the PCR reactions are run on agarose gels together with molecular weight markers. The sizes of the PCR products are compared to the original partial cDNAs, and appropriate clones are selected, ligated into plasmid, and sequenced.

Example 6

Labeling and Use of Hydridization Probes

Hybridization probes derived from nucleic acids described in this invention were employed to screen cDNAs, genomic DNAs, or mRNAs. Although the labeling of oligonucleotides, consisting of about 20 base-pairs, is specifically described, essentially the same procedure is used with larger cDNA fragments. Oligonucleotides are designed using state-of-the-art software such as OLIGO 4.06 primer analysis software (National Biosciences, labeled by combining 50 μmol of each oligomer and 250 μCi of $\gamma$-$^{32}$P adenosine triphosphate (Amersham) and T4 polynucleotide kinase (DuPont Nen(r), Boston, Mass.). The labelled oligonucleotides are substantially purified with SEPHADEX G-25 superfine resin column (Pharmacia & Upjohn). A portion containing 107 counts per minute of each of the sense and antisense oligonucleotides is used in a typical membrane based hybridization analysis of human genomic DNA digested with one of the following membranes (Ase I, Bgl II, EcoRI, Pst I, Xba I, or Pvu II; DuPont NEN(r)). The DNA from each digest is fractionated on a 0.7 percent agarose gel and transferred to nylon membranes (NYTRAN PLUS membrane, Schleicher & Schuell, Durham, N.H.). Hybrization is carried out for 16 hours at 40° C. To remove nonspecific signals, blots are sequentially washed at room temperature under increasingly stringent conditions up to 0.1× saline solution citrate (SSC) and 0.5% sodium dodecyl sulfate. After XOMAI AR Autoradiography film (Kodak Rochester, N.Y.) is exposed to the blots, or the blots are placed in a PHOSPHOIMAGER (Molecular Dynamics, Sunnyvale, Calif.) for several hours, hybridization patterns are compared visually.

Example 7

Antisense Molecules

Antisense molecules to the sequences encoding proteins of the invention, or any part thereof, are used to inhibit in vivo or in vitro expression of naturally occurring the proteins of the invention. Although use of antisense oligonucleotides, comprising about 20 base-pairs, is specifically described, essentially the same procedure is used with larger cDNA fragments. An oligonucleotide is used to inhibit expression of naturally occurring proteins of the invention. Antisense oligonucleotides can inhibit gene function in multiple ways. They can bind to the 5'UTR of a transcript and block translation. Alternatively, binding of the antisense oligonucleotide can induce cleavage of the transcript by RNAseH. Antisense oligos have also been shown to block splicing of a pre-mRNA, thereby either blocking formation of specific splice forms or leading to the accumulation of unspliced messages which cannot give rise to mature protein, are unstable, or both. The mechanism of action of a particular antisense oligonucleotide is determined by the chemical composition of the oligonucleotide and/or by the binding site within the targeted transcript.

Antisense oligonucleotides can be applied to tissue culture cells, used in animals or therapeutically in humans. Injection into early zebrafish or *xenopus* embryos allows convenient analysis of gene function in these species.

Example 8

Expression of the Proteins of the Invention

Expression of the proteins of the invention, such as the proteins of the invention and homologous proteins, is accomplished by subcloning the cDNAs into appropriate vectors and transforming the vectors into host cells. In this case, the cloning vector, PSPORT 1, previously used for the generation of the cDNA library is used to express the proteins of the invention in *E. coli*. Upstream of the cloning site, this vector contains a promoter for β-galactosidase, followed by sequence containing the amino-terminal Met, and the subsequent seven residues of β-galactosidase. Immediately following these eight residues is a bacteriophage promoter useful for transcription and a linker containing a number of unique restriction sites. Induction of an isolated, transformed bacterial strain with IPTG using standard methods produces a fusion protein which consists of the first eight residues of β-galactosidase, about 5 to 15 residues of linker, and the full length protein. The signal residues direct the secretion of the proteins of the invention into the bacterial growth media which can be used directly in the following assay for activity.

Example 9

Production of Antibodies Specific for the Proteins of the Invention

The proteins of the invention that are substantially purified using PAGE electrophoresis (Sambrook, supra), or other purification techniques, is used to immunize rabbits and to produce antibodies using standard protocols. The amino acid sequences are analyzed using DNASTAR software (DNASTAR Inc) to determine regions of high immunogenicity and a corresponding oligopolypeptide is synthesized and used to raise antibodies by means known to those of skill in the art. Selection of appropriate epitopes, such as those near the C-terminus or in hydrophilic regions, is described by Ausubel et al. (supra), and others.

Typically, the oligopeptides are 15 residues in length, synthesized using an Applied Biosystems 431A peptide synthesizer 431A using Fmoc-chemistry, and coupled to keyhole limpet hemocyanin (KLH, Sigma, St. Louis, Mo.) by reaction with N-maleimidobenzoyl-N-hydroxysuccinimide ester (MBS; Ausubel et al., supra). Rabbits are immunized with the oligopeptide-KLH complex in complete Freund's adjuvant. The resulting antisera are tested for antipeptide activity, for example, by binding the peptide to plastic, blocking with 1% BSA, reacting with rabbit antisera, washing, and reacting with radioiodinated, goat anti-rabbit IgG.

The proteins of the invention or biologically active fragments thereof are labeled with $^{125}$I Bolton-Hunter reagent (Bolton et al. (1973) Biochem. J. 133:529). Candidate molecules previously arrayed in the wells of a multi-well plate are incubated with the labeled proteins of the invention, washed and any wells with labeled proteins of the invention complex are assayed. Data obtained using different concentrations of proteins of the invention are used to calculate values for the number, affinity, and association of proteins of the invention with the candidate molecules. All publications and patents mentioned in the above specification are herein incorporated by reference.

Example 10

Identification of Human Homologous Genes and Proteins

Homologous proteins and nucleic acid molecules coding therefore are obtainable from insect or vertebrate species, e.g. mammals or birds. Sequences homologous to the chicken proteins and nucleic acid molecules were identified using the publicly available program BLASTP 2.2.3 of the non-redundant protein data base of the National Center for Biotechnology Information (NCBI) (see, Altschul et al., 1997, Nucleic Acids Res. 25:3389-3402).

Chicken DP119 (SEQ ID NO: 2) showed 93% identities and 98% homologies to amino acids 251 to 432 of human CAB43286.1 (SEQ ID NO: 4; encoded by AL050137.1—SEQ ID NO:3) and 93% identities and 97% homologies to amino acids 565 to 746 of mouse AAH25654.1 (SEQ. ID NO: 5; encoded by BC025654.1; SEQ ID NO: 6). BLAST searches using human in the Derwent GenSeq Database using human CAB43286.1 or mouse AAH25654.1 as querys revealed the following entries: WO200153312-A1 with claimed applications include diseases of the peripheral nervous system and Immune system suppression, and others; WO200018922-A2 describing novel carbohydrate-associated proteins used for the prevention and treatment of autoimmune/inflammatory disorders, the gastrointestinal and reproductive systems; and WO200155320-A2 with uses in prevention and treatment of reproductive system disorders, including cancer.

Chicken DP444 (SEQ ID: 8 encoded by SEQ ID: 7) showed 93% identity and 97% homology to the polypeptide encoded by human BI035296 (SEQ ID: 9, FIG. 4C); 91% identity and 94% homology to the polypeptide encoded by human BF951817 (SEQ ID: 11, FIG. 4E); and 92% identity and 95% homology to the polypeptide encoded by human AI214480.1 (SEQ ID: 12, FIG. 4F). Search of the Derwent GenSeq database revealed no matches.

Chicken DP810 (SEQ ID NO: 17, see. FIG. 6) encodes a polypeptide (SEQ ID NO: 18) showing 55% identities and 66% homologies to amino acids 3082 to 3566 of mouse polydom protein (NP_073725.1). Homology is especially high for amino acids 3346 to 3566 of mouse polydom (84% identities, 94% homology). The partial version of the human homolog of polydom is encoded by NP_078776.1 (SEQ ID NO: 19 and SEQ ID NO: 20). Search of the Derwent GenSeq database revealed no match.

Chicken DP685 (SEQ ID NO:22, see FIG. 8) showed 85% identities and 92% homologies between amino acids 1 to 735 amino acids 125 to 863 of human autotaxin-t (SEQ ID NO:24). BLAST searches in the Derwent GenSeq Database using human autotaxin-t (GenBank Accession Numbers AAB00855.1 and L46720.1) as query identified Accession Number AAR86596, in patent application WO 95/32221 describing an Autotaxin motility stimulating protein, used in cancer diagnosis and therapy.

Chicken WE474 (SEQ ID NO: 27 encoding SEQ ID NO: 28, see FIG. 10) showed 69% identities and 81% homologies to human collectin sub-family member 10 (C-type lectin) Accession Number NM_006438.2 (nucleotide) and NP_006429.1 (amino acids), SEQ ID Nos: 29 and 30, resp., Search of the Derwent GenSeq database using human NP_006429.1 found patent applications WO9946281-A2 targeting blood coagulation disorders, cancers and cellular adhesion disorders and WO200168848-A2 targeting applications in the diagnosis of a wide range of tumours.

Chicken DP160 (SEQ ID NO:32, see FIG. 12) showed 78% identities and 85% homologies between amino acids 3 to 140 to amino acids 386 to 799 of human CCR4 carbon catabolite repression 4-like (CCRN4L) (Genbank Acession Number XM_003343.2) and to amino acids 386 to 799 of human CCR4 carbon catabolite repression 4-like (CCRN4L) (Genbank Acession Number NM_912118.1). BLAST searches in the Derwent GenSeq Database using human CCR4 carbon catabolite repression 4-like (CCRN4L) (GenBank Accession Numbers XP_003343.3 and XM_003343.2) as query identified Accession Number AAZ15795 describing human gene expression product cDNA sequence SEQ ID NO:3264, in patent application WO WO9938972-A2 used in cancer therapy.

Chicken. RA977 (SEQ ID NO: 35; encoded protein SEQ ID NO: 36, see FIG. 14) showed 70% identities and 83% homology to human EMP-2 (XM_030218.1; SEQ ID NO: 37 for nucleotide; P54851; SEQ ID NO: 38 for protein sequence). Search of the Derwent GenSeq database revealed matches to patent applications WO200194629-A2 claiming applications for cancer diagnostics and WO200229086-A2 claiming applications for cancer diagnostics and therapy.

Chicken RA770 (SEQ ID NO:40, see FIG. 16) showed 67% identities and 87% homologies between amino acids 5 to 94 to the C-terminal amino acids 108 to 197 of human neurturin precursor (SEQ ID NO:42). Chicken RA770 (SEQ ID NO:2) showed 64% identities and 84% homologies between amino acids 5 to 94 to the C-terminal amino acids 106 to 195 of mouse neurturin precursor (SEQ ID NO:44). BLAST searches in the Derwent GenSeq Database using human neurturin precursor (GenBank Accession Numbers NP_004549.1 and NM_004558.1) as query identified Accession Number AAY16637, disclosed as SEQ ID NO:7 in patent application WO 99/14235, describing a new isolated persephin growth factor used to promote neuronal growth. The persephin GF polypeptides or polynucleotides can be used for preventing or treating cellular degeneration or insufficiency, and can also be used for treating, e.g. peripheral nerve trauma or injury, exposure to neurotoxins, metabolic diseases such as diabetes or renal dysfunctions and damage caused by infectious agents. In addition, patent application WO 97/08196 describes Accession Number: AAW13716 encoding Human pre-pro-neurturin as novel growth factor Neurturin used to treat neuro-degenerative and haematopoietic cell degeneration diseases. The same protein was also disclosed in WO9906064-A1 as new neurturin neurotrophic factor protein product useful for treating sensorineural hearing loss as well as treating, lesions and disturbances to the vestibular apparatus.

Example 11

Generation of a mRA770 Transgenic Construct

Figure 17:
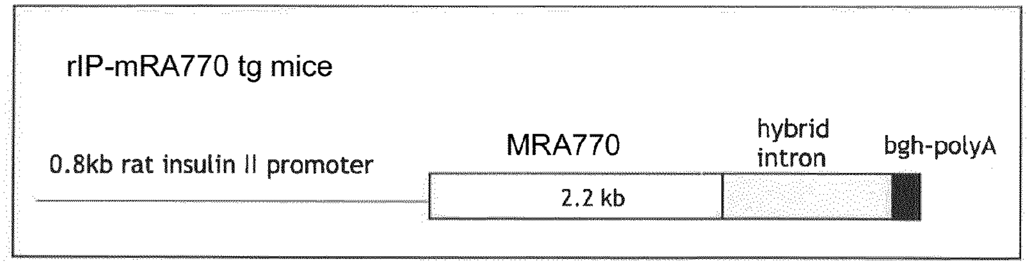
FIG. 17 shows the structure of the mouse mRA770 transgenic construct. Shown is the rIP promoter (0.8 kb rat insulin II promoter) as a thin line, the mouse RA770 cDNA (mRA770) as white box, the hybrid-intron structure (hybrid-intron) as grey box and the polyadenylation signal (bgh-polyA) as black box.
Figure 18:
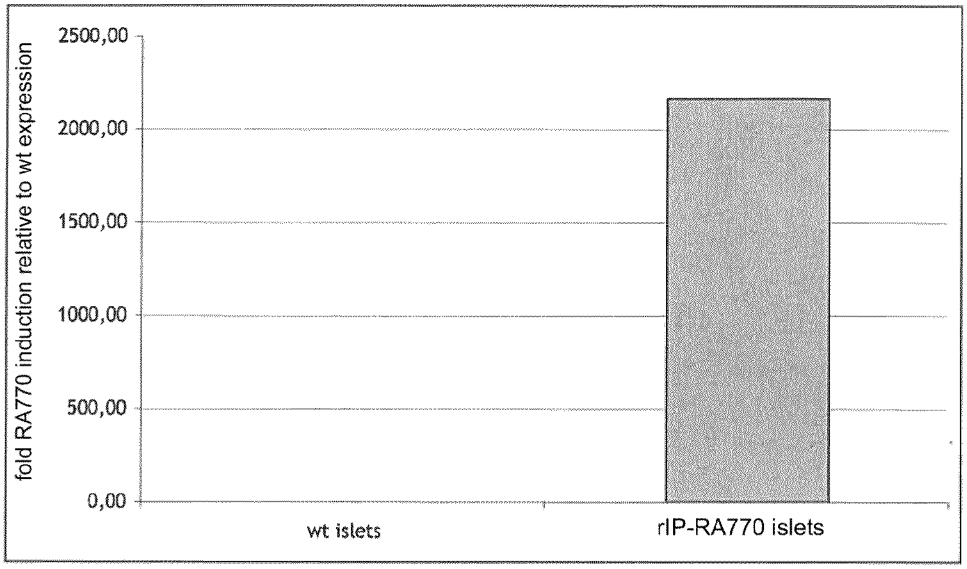
FIG. 18 shows pancreatic islets of mRA770 transgenic mice with ectopic mRA770 expression. Taqman expression analysis on islet cDNA isolated from two wild type and two transgenic littermates using a mRA770 specific primer/probe pair. The data are presented as fold mRA770 induction relative to wild type mRA770 expression in islets.
Figure 19:
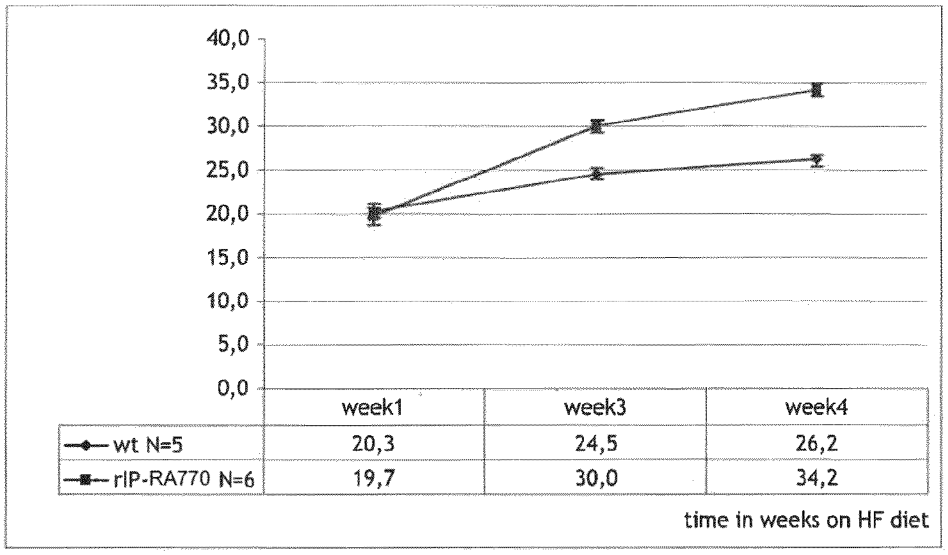
FIG. 19 shows the growth curves of RA770 transgenic mice (rlP-mRA770) compared to wild type mice (wt) on high fat (HF) diet. Data are presented as mean bodyweight in g/over time+/−standard deviation. RA770 transgenic mice have an increased body weight compared to wt mice on HF diet.
Figure 20:
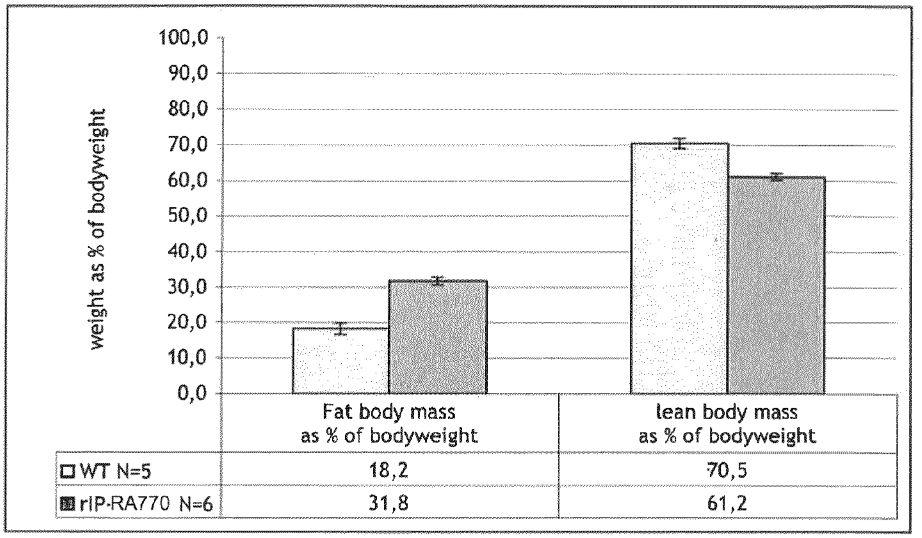
FIG. 20 shows the lean and fat body mass in mRA770 transgenic mice compared to wild type mice (wt) on HF diet.

A complete mRA770 Open Reading Frame (ORF) was cloned under the control of the rat insulin promoter II (Lomedico et al., (1979) Cell 18: 545-558) using the Gateway system (Invitrogen). For the structure of the transgenic construct, see also FIG. 17.

Example 12

Generation of rIP-mRA770 Transgenic Mice

Transgenic construct DNA (see Example 11) was injected into C57/BL6×CBA embryos (Harlan Winkelmann, Borchen, Germany) using standard techniques (see, for example, Brinster et al. (1985), Proc. Natl. Acad. Sci. USA 82: 4438-4442). The mRA770 transgene (see Example 11) was expressed under the control of the rat insulin promoter II (Lomedico et al., supra) using techniques known to those skilled in the art (for example, see, Gunnig et al. (1987), Proc. Natl. Acad. Sci. USA 84:4831-4835). Using this technique, several independent founderlines were generated.

Example 13

Genotype Analysis of rIP-mRA770 Transgenic Mice

Genotyping was performed by PCR using genomic DNA isolated from the tail tip. To detect the mRA770 transgene a transgene specific forward primer (5' tgc tat ctg tct gga tgt gcc 3' [SEQ ID NO: 57] and a mDG770 transgene specific reverse primer (5' aag gac acc tcg tcc tca tag 3' [SEQ ID NO: 58] was used.

Example 14 mRA770 Expression Analysis Via Taqman Analysis

The expression of the mRA770 transgene in islets was monitored by Taqman analysis. For this analysis, 25 ng cDNA derived from pancreatic islet RNA isolated from transgenic mice and their littermates and a mRA770 specific primer/probe pair were used to detect endogenous as well as transgenic mRA770 expression (mRA770-1 forward primer: 5' GCC TAT GAG GAC GAG GTG TCC 3' [SEQ ID NO: 59], mRA770 reverse primer: 5' AGC TCT TGC AGC GTG TGG T 3' [SEQ ID NO: 60], mRA770 probe: 5' TCC TGG ACG TGC ACA GCC GC 3' [SEQ ID NO: 61]). Taqman analysis was performed using standard techniques known to those skilled in the art. Ectopic transgene expression was detected in 3 of 4 rIP-mRA770 transgenic founderlines analysed. The two founderlines showing highest transgene expression levels were used for further analysis.

Example 15

Bodyweight, Body Length and NMR Analysis in mRA770 Transgenic Mice 3 to 6 mice were housed per cage. Growth curves were generated by measuring the bodyweight of individual mRA770 transgenic mice and their wild-type littermates on a weekly basis using a normal balance. The body length was measured from nose to anus placing a ruler along the middle axis of the mouse. On selected time points the lean and fat body mass was measured using non-invasive NMR analysis: to do this individual mice were placed into a Bruker Minispec NMR machine (Bruker, USA) and the lean and body fat content was estimated.

Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in molecular biology or related fields are intended to be within the scope of the following claims.

The invention claimed is:

1. A method for identifying a candidate agent useful for treating pancreatic dysfunction in a pancreatic disease or disorder, comprising:

(a) obtaining a protein encoded by a gene expressed in dorsal pancreatic buds; wherein said protein comprises:

i) the amino acid sequence of amino acid residues 5-94 of SEQ ID NO: 40;

ii) the amino acid sequence of amino acid residues 108-197 of SEQ ID NO: 42; or iii) the amino acid sequence of amino acid residues 106 to 195 of SEQ ID NO: 44;

(b) screening said protein against a compound library; and (c) measuring the effects of a compound from the compound library on said protein, whereby a compound that agonizes or mimics the ability of said protein to activate Rearranged during Transfection (RET) signaling in a pancreatic cell is identified as a candidate agent.

2. The method of claim 1, wherein the disease or disorder is diabetes.

3. The method of claim 2, wherein the diabetes is type I diabetes, type II diabetes, or latent autoimmune diabetes in adults (LADA).

4. The method of claim 2, wherein the diabetes is early-stage diabetes.

5. The method of claim 2, wherein the disease or disorder is hyperglycemia, impaired glucose tolerance, insulin resistance, or decreased beta cell mass.

6. The method of claim 1, wherein said protein comprises the amino acid sequence of SEQ ID NO: 42.

7. The method of claim 1, wherein said protein comprises the amino acid sequence of SEQ ID NO: 44.

8. The method of claim 1, wherein said protein consists of amino acids 5-94 of SEQ ID NO: 40.

9. The method of claim 1, wherein said protein comprises amino acids 108-197 of SEQ ID NO: 42.

10. The method of claim 1, wherein said protein binds to a multicomponent receptor system comprising a Rearranged during Transfection (RET) tyrosine kinase and a Glycosylphosphatidylinositol (GPI)-linked co-receptor.

11. The method of claim 10, wherein the GPI-linked co-receptor is a Glial cell-line derived neurotrophic factor Family Receptor (GFR)-alpha receptor.

12. The method of claim 1, wherein the pancreatic cell is a pancreatic progenitor cell.

13. The method of claim 12, wherein the pancreatic progenitor cell is a human pancreatic progenitor cell.

14. The method of claim 1, wherein said protein comprises amino acids 5-94 of SEQ ID NO: 40.

15. The method of claim 1, wherein said protein consists of amino acids 108-197 of SEQ ID NO: 42.

16. The method of claim 1, wherein said protein consists of amino acids 106-195 of SEQ ID NO: 44.

17. The method of claim 1, wherein said protein comprises amino acids 106-195 of SEQ ID NO: 44.

* * * * *

UNITED STATES PATENT AND TRADEMARK OFFICE

CERTIFICATE OF CORRECTION

PATENT NO. : 9,049,849 B2
APPLICATION NO. : 13/031095
DATED : June 9, 2015
INVENTOR(S) : Dohrmann et al.

It is certified that error appears in the above-identified patent and that said Letters Patent is hereby corrected as shown below:

On the title page, item (63), Line 2, Related U.S. Application Data: delete "Jan. 29, 2004" and replace with --Nov. 29, 2004--

Signed and Sealed this
Seventeenth Day of November, 2015

Michelle K. Lee
*Director of the United States Patent and Trademark Office*